(12) United States Patent
Wang et al.

(10) Patent No.: US 12,258,430 B2
(45) Date of Patent: Mar. 25, 2025

(54) COMPOSITIONS AND METHODS FOR LABELING AND MODULATION OF CELLS IN VITRO AND IN VIVO

(71) Applicant: President and Fellows of Harvard College, Cambridge, MA (US)

(72) Inventors: Hua Wang, Cambridge, MA (US); David J. Mooney, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 930 days.

(21) Appl. No.: 17/206,050

(22) Filed: Mar. 18, 2021

(65) Prior Publication Data
US 2021/0284776 A1    Sep. 16, 2021

Related U.S. Application Data

(63) Continuation of application No. PCT/US2019/051621, filed on Sep. 18, 2019.

(60) Provisional application No. 62/733,378, filed on Sep. 19, 2018.

(51) Int. Cl.
| | | |
|---|---|---|
| C08F 251/00 | (2006.01) | |
| A61K 39/00 | (2006.01) | |
| A61K 49/22 | (2006.01) | |
| A61N 7/00 | (2006.01) | |
| A61P 35/00 | (2006.01) | |
| C08B 37/00 | (2006.01) | |
| G01N 33/543 | (2006.01) | |
| G01N 33/548 | (2006.01) | |

(52) U.S. Cl.
CPC ........ *C08F 251/00* (2013.01); *A61K 39/0011* (2013.01); *A61K 49/221* (2013.01); *A61K 49/222* (2013.01); *A61N 7/00* (2013.01); *A61P 35/00* (2018.01); *C08B 37/0006* (2013.01); *G01N 33/54346* (2013.01); *G01N 33/548* (2013.01); *A61N 2007/0004* (2013.01); *C08F 2438/03* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,465,827 A | 8/1984 | Kawasaki et al. | |
| 4,522,811 A | 6/1985 | Eppstein et al. | |
| 4,946,778 A | 8/1990 | Ladner et al. | |
| 5,091,513 A | 2/1992 | Huston et al. | |
| 5,132,405 A | 7/1992 | Huston et al. | |
| 5,885,829 A | 3/1999 | Mooney et al. | |
| 5,888,987 A | 3/1999 | Haynes et al. | |
| 5,906,826 A | 5/1999 | Emery et al. | |
| 5,951,976 A | 9/1999 | Segal | |
| 6,129,716 A | 10/2000 | Steer | |
| 6,160,084 A | 12/2000 | Langer et al. | |
| 6,187,762 B1 | 2/2001 | Mandeville, III et al. | |
| 6,193,970 B1 | 2/2001 | Pardoll et al. | |
| 6,251,396 B1 | 6/2001 | Gaur et al. | |
| 6,281,256 B1 | 8/2001 | Harris et al. | |
| 6,334,968 B1 | 1/2002 | Shapiro et al. | |
| 6,352,694 B1 | 3/2002 | June et al. | |
| 6,403,374 B1 | 6/2002 | Tsien et al. | |
| 6,429,199 B1 | 8/2002 | Krieg et al. | |
| 6,511,511 B1 | 1/2003 | Slivka et al. | |
| 6,511,650 B1 | 1/2003 | Eiselt et al. | |
| 6,541,022 B1 | 4/2003 | Murphy et al. | |
| 6,642,363 B1 | 11/2003 | Mooney et al. | |
| 6,685,963 B1 | 2/2004 | Taupin et al. | |
| 6,748,954 B2 | 6/2004 | Lee et al. | |
| 6,767,928 B1 | 7/2004 | Murphy et al. | |
| 6,783,712 B2 | 8/2004 | Slivka et al. | |
| 6,790,840 B1 | 9/2004 | Lee et al. | |
| 6,797,738 B2 | 9/2004 | Harris et al. | |
| 6,800,733 B2 | 10/2004 | Tsien et al. | |
| 6,858,222 B2 | 2/2005 | Nelson et al. | |
| 6,974,698 B1 | 12/2005 | Miller et al. | |
| 7,015,205 B1 | 3/2006 | Wallack et al. | |
| 7,157,566 B2 | 1/2007 | Tsien et al. | |
| 7,186,413 B2 | 3/2007 | Bouhadir et al. | |
| 7,192,693 B2 | 3/2007 | Bryant et al. | |
| 7,244,714 B1 | 7/2007 | Gonda et al. | |
| 7,357,936 B1 | 4/2008 | Garcon | |
| 7,410,953 B2 | 8/2008 | Kawasaki | |
| 7,427,602 B1 | 9/2008 | Shea et al. | |
| 7,569,850 B2 | 8/2009 | Noy et al. | |
| 7,575,759 B2 | 8/2009 | Murphy et al. | |

(Continued)

FOREIGN PATENT DOCUMENTS

| | | |
|---|---|---|
| AU | 2014200405 A1 | 2/2014 |
| AU | 2018201930 A1 | 4/2018 |

(Continued)

OTHER PUBLICATIONS

U.S. Appl. No. 15/434,781, filed Feb. 16, 2017, U.S. Pat. No. 10,813,988, Issued.

(Continued)

*Primary Examiner* — Nicole P Babson

(74) *Attorney, Agent, or Firm* — McCarter & English, LLP; Maria Laccotripe Zacharakis; Maneesh Gulati

(57) ABSTRACT

Disclosed herein are compositions and methods for labeling cells using click chemistry reagents. The compositions and methods disclosed herein provide a specific and efficient means of localizing desired agents to a variety of cell types in vivo and in vitro.

18 Claims, 69 Drawing Sheets

Specification includes a Sequence Listing.

(56) References Cited

U.S. PATENT DOCUMENTS

| | | |
|---|---|---|
| 7,687,241 B2 | 3/2010 | Chen |
| 7,709,458 B2 | 5/2010 | Karaolis et al. |
| 7,790,699 B2 | 9/2010 | Melvik et al. |
| 8,067,237 B2 | 11/2011 | Mooney et al. |
| 8,188,058 B2 | 5/2012 | Hackam et al. |
| 8,273,373 B2 | 9/2012 | Alsberg et al. |
| 8,354,119 B2 | 1/2013 | Geistlich et al. |
| 8,367,628 B2 | 2/2013 | Goodwin et al. |
| 8,535,719 B2 | 9/2013 | Badylak et al. |
| 8,709,464 B2 | 4/2014 | Ma et al. |
| 8,728,456 B2 | 5/2014 | Sands et al. |
| 8,883,308 B2 | 11/2014 | Polshettiwar et al. |
| 8,932,583 B2 | 1/2015 | Mooney et al. |
| 9,012,399 B2 | 4/2015 | Cao et al. |
| 9,132,210 B2 | 9/2015 | Mooney et al. |
| 9,139,809 B2 | 9/2015 | Porcelli et al. |
| 9,150,631 B2 | 10/2015 | Super et al. |
| 9,370,558 B2 | 6/2016 | Ali et al. |
| 9,381,235 B2 | 7/2016 | Sands et al. |
| 9,446,107 B2 | 9/2016 | Mooney et al. |
| 9,486,512 B2 | 11/2016 | Kim et al. |
| 9,591,360 B2 | 3/2017 | Jennings et al. |
| 9,610,328 B2 | 4/2017 | Mooney et al. |
| 9,675,561 B2 | 6/2017 | Bencherif et al. |
| 9,770,535 B2 | 9/2017 | Mooney et al. |
| 9,821,045 B2 | 11/2017 | Ali et al. |
| 9,937,249 B2 | 4/2018 | Kim et al. |
| 10,045,947 B2 | 8/2018 | Bencherif et al. |
| 10,080,789 B2 | 9/2018 | Sands et al. |
| 10,137,184 B2 | 11/2018 | Mooney et al. |
| 10,149,897 B2 | 12/2018 | Mooney et al. |
| 10,258,677 B2 | 4/2019 | Mooney et al. |
| 10,328,133 B2 | 6/2019 | Mooney et al. |
| 10,406,216 B2 | 9/2019 | Kim et al. |
| 10,568,949 B2 | 2/2020 | Ali et al. |
| 10,682,400 B2 | 6/2020 | Ali et al. |
| 10,813,988 B2 | 10/2020 | Super et al. |
| 11,059,050 B2 | 7/2021 | Kang et al. |
| 11,096,997 B2 | 8/2021 | Mooney et al. |
| 11,150,242 B2 | 10/2021 | Ali et al. |
| 11,202,759 B2 | 12/2021 | Huebsch et al. |
| 11,278,604 B2 | 3/2022 | Kim et al. |
| 11,555,177 B2 | 1/2023 | Cheung et al. |
| 11,638,748 B2 | 5/2023 | Super et al. |
| 11,684,638 B2 | 6/2023 | Prabha et al. |
| 11,752,238 B2 | 9/2023 | Shah et al. |
| 11,786,457 B2 | 10/2023 | Sandeep et al. |
| 2002/0045672 A1 | 4/2002 | Harris et al. |
| 2002/0131853 A1 | 9/2002 | Nagasawa |
| 2002/0131953 A1 | 9/2002 | Takashima et al. |
| 2002/0150604 A1 | 10/2002 | Yi et al. |
| 2003/0075822 A1 | 4/2003 | Slivka et al. |
| 2003/0082806 A1 | 5/2003 | Berenson et al. |
| 2003/0095994 A1 | 5/2003 | Geistlich et al. |
| 2003/0100527 A1 | 5/2003 | Krieg et al. |
| 2003/0194397 A1 | 10/2003 | Mishra |
| 2003/0232895 A1 | 12/2003 | Omidian et al. |
| 2003/0235557 A1 | 12/2003 | Gaiger et al. |
| 2004/0028745 A1 | 2/2004 | Bouhadir et al. |
| 2004/0043034 A1 | 3/2004 | Jensenius et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0213795 A1 | 10/2004 | Collins et al. |
| 2004/0220111 A1 | 11/2004 | Kleinman et al. |
| 2004/0228858 A1 | 11/2004 | Hanson et al. |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0037330 A1 | 2/2005 | Fischer et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2005/0202394 A1 | 9/2005 | Dobson |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2006/0292134 A1 | 12/2006 | Stohs |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0113929 A1 | 5/2008 | Lipford et al. |
| 2008/0138416 A1 | 6/2008 | Rauh et al. |
| 2008/0152624 A1 | 6/2008 | Paludan et al. |
| 2008/0159993 A1 | 7/2008 | Stauss et al. |
| 2008/0206308 A1 | 8/2008 | Jabbari et al. |
| 2008/0233181 A1 | 9/2008 | Nagy et al. |
| 2008/0268019 A1 | 10/2008 | Badylak et al. |
| 2008/0268052 A1 | 10/2008 | Voytik-Harbin et al. |
| 2008/0279812 A1 | 11/2008 | Boyd et al. |
| 2009/0017096 A1 | 1/2009 | Lowman et al. |
| 2009/0041825 A1 | 2/2009 | Kotov et al. |
| 2009/0192079 A1 | 7/2009 | Santos et al. |
| 2009/0238853 A1 | 9/2009 | Liu et al. |
| 2009/0252752 A1 | 10/2009 | Tahara et al. |
| 2009/0297551 A1 | 12/2009 | Sattentau et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055102 A1 | 3/2010 | Langermann |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0174346 A1 | 7/2010 | Boyden et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0008443 A1 | 1/2011 | Alsberg et al. |
| 2011/0020216 A1 | 1/2011 | Mooney et al. |
| 2011/0117170 A1 | 5/2011 | Cao et al. |
| 2011/0159023 A1 | 6/2011 | Langermann |
| 2011/0207166 A1 | 8/2011 | Vaiselbuh |
| 2011/0223255 A1 | 9/2011 | Thiesen et al. |
| 2011/0253643 A1 | 10/2011 | Polshettiwar et al. |
| 2011/0256184 A1 | 10/2011 | Lei et al. |
| 2011/0300186 A1 | 12/2011 | Hellstrom et al. |
| 2012/0040011 A9 | 2/2012 | Boons et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0294888 A1 | 11/2012 | Kishimoto et al. |
| 2012/0329791 A1 | 12/2012 | Ashwell et al. |
| 2013/0029030 A1 | 1/2013 | Larsen |
| 2013/0035283 A1 | 2/2013 | Super et al. |
| 2013/0045246 A1 | 2/2013 | Edwards et al. |
| 2013/0052117 A1 | 2/2013 | Imai et al. |
| 2013/0072547 A1 | 3/2013 | Hackam et al. |
| 2013/0145488 A1 | 6/2013 | Wang et al. |
| 2013/0202707 A1 | 8/2013 | Ali et al. |
| 2013/0225502 A1 | 8/2013 | Sugiyama et al. |
| 2013/0251784 A1 | 9/2013 | Kim et al. |
| 2013/0302396 A1 | 11/2013 | Mooney et al. |
| 2013/0331343 A1 | 12/2013 | Cao et al. |
| 2014/0072510 A1 | 3/2014 | Shea et al. |
| 2014/0112990 A1 | 4/2014 | Bencherif et al. |
| 2014/0178964 A1 | 6/2014 | Mooney et al. |
| 2014/0227327 A1 | 8/2014 | Bencherif et al. |
| 2014/0227723 A1 | 8/2014 | Ingber et al. |
| 2014/0234423 A1 | 8/2014 | Sands et al. |
| 2015/0024026 A1 | 1/2015 | Mooney et al. |

(56) References Cited

U.S. PATENT DOCUMENTS

| | | |
|---|---|---|
| 2015/0030669 A1 | 1/2015 | Platscher et al. |
| 2015/0072009 A1 | 3/2015 | Kim et al. |
| 2015/0080321 A1 | 3/2015 | Li et al. |
| 2015/0094518 A1 | 4/2015 | Wu et al. |
| 2015/0202291 A1 | 7/2015 | Bosch et al. |
| 2015/0352201 A1 | 12/2015 | Scheinberg et al. |
| 2015/0359928 A1 | 12/2015 | Gu et al. |
| 2015/0366956 A1 | 12/2015 | Mooney et al. |
| 2016/0033511 A1 | 2/2016 | Pannell et al. |
| 2016/0120984 A1 | 5/2016 | Navale et al. |
| 2016/0129053 A1 | 5/2016 | Brass et al. |
| 2016/0220668 A1 | 8/2016 | Mooney et al. |
| 2016/0228543 A1 | 8/2016 | Mooney et al. |
| 2016/0271298 A1 | 9/2016 | Mooney et al. |
| 2016/0279219 A1 | 9/2016 | Mooney et al. |
| 2016/0279220 A1 | 9/2016 | Mooney et al. |
| 2016/0296611 A1 | 10/2016 | Ali et al. |
| 2017/0362307 A1 | 12/2017 | Ingber et al. |
| 2017/0368169 A1 | 12/2017 | Loew et al. |
| 2018/0117171 A1 | 5/2018 | Mooney et al. |
| 2018/0243231 A1 | 8/2018 | Bencherif et al. |
| 2018/0298047 A1 | 10/2018 | Cheng et al. |
| 2018/0320157 A1 | 11/2018 | Super et al. |
| 2018/0326073 A1 | 11/2018 | Mooney et al. |
| 2018/0371058 A1 | 12/2018 | Watters et al. |
| 2019/0076373 A1 | 3/2019 | Bencherif et al. |
| 2019/0183992 A1 | 6/2019 | Sands et al. |
| 2019/0216910 A1 | 7/2019 | Mooney et al. |
| 2019/0290696 A1 | 9/2019 | De Miroschedji |
| 2019/0367550 A1 | 12/2019 | Cheng et al. |
| 2020/0024339 A1 | 1/2020 | Springer et al. |
| 2020/0206333 A1 | 7/2020 | Shah et al. |
| 2020/0276290 A1 | 9/2020 | Ali et al. |
| 2020/0297854 A1 | 9/2020 | Ingber et al. |
| 2021/0205233 A1 | 7/2021 | Bencherif et al. |
| 2022/0047778 A1 | 2/2022 | Shah et al. |
| 2022/0107308 A1 | 4/2022 | Ali et al. |
| 2022/0192986 A1 | 6/2022 | Huebsch et al. |
| 2022/0339274 A1 | 10/2022 | Najibi et al. |
| 2023/0000961 A1 | 1/2023 | Kim et al. |
| 2023/0085214 A1 | 3/2023 | Wang et al. |

FOREIGN PATENT DOCUMENTS

| | | |
|---|---|---|
| CN | 1487839 A | 4/2004 |
| CN | 1527697 A | 9/2004 |
| CN | 1757662 A | 4/2006 |
| CN | 101584612 A | 11/2009 |
| CN | 101655611 A | 2/2010 |
| CN | 101829361 A | 9/2010 |
| CN | 102000689 A | 4/2011 |
| CN | 102006891 A | 4/2011 |
| CN | 102170903 A | 8/2011 |
| CN | 102947341 A | 2/2013 |
| CN | 103237885 A | 8/2013 |
| CN | 104244929 A | 12/2014 |
| CN | 104411331 A | 3/2015 |
| EP | 0562862 A1 | 9/1993 |
| EP | 1452191 A2 | 9/2004 |
| EP | 1561481 A2 | 8/2005 |
| EP | 1712238 A1 | 10/2006 |
| EP | 1975230 A1 | 10/2008 |
| EP | 2254602 A2 | 12/2010 |
| JP | 2000-503884 A | 4/2000 |
| JP | 2001-049018 A | 2/2001 |
| JP | 2001-524136 A | 11/2001 |
| JP | 2003-506401 A | 2/2003 |
| JP | 2003-180815 A | 7/2003 |
| JP | 2004-159849 A | 6/2004 |
| JP | 2004-520043 A | 7/2004 |
| JP | 2005-160669 A | 6/2005 |
| JP | 2005-168760 A | 6/2005 |
| JP | 2005-170816 A | 6/2005 |
| JP | 2005-528401 A | 9/2005 |
| JP | 2007-500673 A | 1/2007 |
| JP | 2007-503881 A | 3/2007 |
| JP | 2007-505827 A | 3/2007 |
| JP | 2007-528848 A | 10/2007 |
| JP | 2008-515503 A | 5/2008 |
| JP | 2008-528114 A | 7/2008 |
| JP | 2009-519042 A | 5/2009 |
| JP | 2009-521406 A | 6/2009 |
| JP | 2009-540921 A | 11/2009 |
| JP | 2010-502824 A | 1/2010 |
| JP | 2010-508976 A | 3/2010 |
| JP | 2010-227012 A | 10/2010 |
| JP | 2010-228961 A | 10/2010 |
| JP | 2011-511684 A | 4/2011 |
| JP | 2011-511834 A | 4/2011 |
| JP | 2012-062236 A | 3/2012 |
| JP | 2013-531043 A | 8/2013 |
| JP | 2015-503626 A | 2/2015 |
| JP | 2015-516398 A | 6/2015 |
| JP | 2015-134766 A | 7/2015 |
| JP | 2018-117680 A | 8/2018 |
| JP | 2019-522486 A | 8/2019 |
| WO | WO-1996/02555 A1 | 2/1996 |
| WO | WO-1996/16086 A1 | 5/1996 |
| WO | WO-1998/012228 A1 | 3/1998 |
| WO | WO-1998/16266 A1 | 4/1998 |
| WO | WO-1999/44583 A2 | 9/1999 |
| WO | WO-1999/51259 A2 | 10/1999 |
| WO | WO-1999/52356 A1 | 10/1999 |
| WO | WO-2008/031525 A1 | 3/2000 |
| WO | WO-2000/50006 A2 | 8/2000 |
| WO | WO-2001/10421 A1 | 2/2001 |
| WO | WO-2001/35932 A2 | 5/2001 |
| WO | WO-2001/37810 A2 | 5/2001 |
| WO | WO-2002/16557 A2 | 2/2002 |
| WO | WO-2002/40071 A1 | 5/2002 |
| WO | WO-2002/058723 A2 | 8/2002 |
| WO | WO-2002/092054 A2 | 11/2002 |
| WO | WO-2003/020161 A2 | 3/2003 |
| WO | WO-2003/020884 A2 | 3/2003 |
| WO | WO-2003/070291 A1 | 8/2003 |
| WO | WO-2003/088905 A2 | 10/2003 |
| WO | WO-2004/006990 A2 | 1/2004 |
| WO | WO-2004/029230 A2 | 4/2004 |
| WO | WO-2004/030706 A2 | 4/2004 |
| WO | WO-2004/031371 A2 | 4/2004 |
| WO | WO-2004/089413 A1 | 10/2004 |
| WO | WO-2005/013896 A2 | 2/2005 |
| WO | WO-2005/013933 A1 | 2/2005 |
| WO | WO-2005/020849 A2 | 3/2005 |
| WO | WO-2005/025614 A2 | 3/2005 |
| WO | WO-2005/026318 A2 | 3/2005 |
| WO | WO-2005/037190 A2 | 4/2005 |
| WO | WO-2005/037293 A1 | 4/2005 |
| WO | WO-2005/046748 A1 | 5/2005 |
| WO | WO-2005/072088 A2 | 8/2005 |
| WO | WO-2005/104755 A2 | 11/2005 |
| WO | WO-2006/039045 A2 | 4/2006 |
| WO | WO-2006/040128 A1 | 4/2006 |
| WO | WO-2006/078987 A2 | 7/2006 |
| WO | WO-2006/113407 A2 | 10/2006 |
| WO | WO-2006/119619 A1 | 11/2006 |
| WO | WO-2006/136905 A2 | 12/2006 |
| WO | WO-2007/001332 A2 | 1/2007 |
| WO | WO-2007/030901 A1 | 3/2007 |
| WO | WO-2007/039150 A2 | 4/2007 |
| WO | WO-2007/042554 A2 | 4/2007 |
| WO | WO-2007/051120 A2 | 5/2007 |
| WO | WO-2007/063075 A1 | 6/2007 |
| WO | WO-2007/064152 A1 | 6/2007 |
| WO | WO-2007/068489 A2 | 6/2007 |
| WO | WO-2007/070660 A2 | 6/2007 |
| WO | WO-2007/078196 A2 | 7/2007 |
| WO | WO-2007/087585 A1 | 8/2007 |
| WO | WO-2007/089870 A2 | 8/2007 |
| WO | WO-2007/107739 A1 | 9/2007 |
| WO | WO-2007/149161 A2 | 12/2007 |
| WO | WO-2007/150020 A1 | 12/2007 |
| WO | WO-2008/008266 A2 | 1/2008 |
| WO | WO-2008/018707 A1 | 2/2008 |

(56) References Cited

FOREIGN PATENT DOCUMENTS

| WO | WO-2008/043157 A1 | 4/2008 |
|---|---|---|
| WO | WO-2008/057600 A2 | 5/2008 |
| WO | WO-2008/109852 A2 | 9/2008 |
| WO | WO-2008/114149 A2 | 9/2008 |
| WO | WO-2008/148761 A1 | 12/2008 |
| WO | WO-2008/157394 A2 | 12/2008 |
| WO | WO-2009/002401 A2 | 12/2008 |
| WO | WO-2009/005769 A2 | 1/2009 |
| WO | WO-2009/018500 A1 | 2/2009 |
| WO | WO-2009/024775 A1 | 2/2009 |
| WO | WO-2009/072767 A2 | 6/2009 |
| WO | WO-2009/074341 A1 | 6/2009 |
| WO | WO-2009/100716 A2 | 8/2009 |
| WO | WO-2009/102465 A2 | 8/2009 |
| WO | WO-2009/146456 A1 | 12/2009 |
| WO | WO-2009/155583 A1 | 12/2009 |
| WO | WO-2010/078209 A2 | 7/2010 |
| WO | WO-2010/120749 A2 | 10/2010 |
| WO | WO-2011/014871 A1 | 2/2011 |
| WO | WO-2011/043834 A1 | 4/2011 |
| WO | WO-2011/043835 A1 | 4/2011 |
| WO | WO-2011/063336 A2 | 5/2011 |
| WO | WO-2011/109834 A2 | 9/2011 |
| WO | WO-2011/130753 A2 | 10/2011 |
| WO | WO-2011/150240 A1 | 12/2011 |
| WO | WO-2011/151431 A1 | 12/2011 |
| WO | WO-2011/163669 A2 | 12/2011 |
| WO | WO-2012/009611 A2 | 1/2012 |
| WO | WO-2012/019049 A1 | 2/2012 |
| WO | WO-2012/048165 A2 | 4/2012 |
| WO | WO-2012/064697 A2 | 5/2012 |
| WO | WO-2012/148684 A1 | 11/2012 |
| WO | WO-2012/149358 A1 | 11/2012 |
| WO | WO-2012/167230 A1 | 12/2012 |
| WO | WO-2013/012924 A2 | 1/2013 |
| WO | WO-2013/106852 A1 | 7/2013 |
| WO | WO-2013/158673 A1 | 10/2013 |
| WO | WO-2013/172967 A1 | 11/2013 |
| WO | WO-2013/190555 A1 | 12/2013 |
| WO | WO-2014/063128 A1 | 4/2014 |
| WO | WO-2014/189805 A1 | 11/2014 |
| WO | WO-2014/190229 A1 | 11/2014 |
| WO | WO-2015/066535 A1 | 5/2015 |
| WO | WO-2015/095811 A2 | 6/2015 |
| WO | WO-2015/148775 A1 | 10/2015 |
| WO | WO-2015/154078 A1 | 10/2015 |
| WO | WO-2015/168379 A2 | 11/2015 |
| WO | WO-2016/004068 A1 | 1/2016 |
| WO | WO-2016/123573 A1 | 8/2016 |
| WO | WO-2016/161372 A1 | 10/2016 |
| WO | WO-2017/136837 A1 | 8/2017 |
| WO | WO-2017/143024 A2 | 8/2017 |
| WO | WO-2018/013797 A1 | 1/2018 |
| WO | WO-2018/026884 A1 | 2/2018 |
| WO | WO-2018/144966 A1 | 8/2018 |
| WO | WO-2018/148650 A1 | 8/2018 |
| WO | WO-2018/170414 A1 | 9/2018 |
| WO | WO-2018/213631 A1 | 11/2018 |
| WO | WO-2018/227205 A1 | 12/2018 |
| WO | WO-2020/061129 A1 | 3/2020 |
| WO | WO-2021/155297 A1 | 8/2021 |

OTHER PUBLICATIONS

U.S. Appl. No. 17/015,177, filed Sep. 9, 2020, U.S. Pat. No. 11,638,748, Issued.
U.S. Appl. No. 18/186,588, filed Mar. 20, 2023, Pending.
U.S. Appl. No. 13/386,950, filed Jan. 25, 2012, U.S. Pat. No. 8,728,456, Issued.
U.S. Appl. No. 14/185,494, filed Feb. 20, 2014, U.S. Pat. No. 9,381,235, Issued.
U.S. Appl. No. 15/147,442, filed May 5, 2016, U.S. Pat. No. 9,381,235, Issued.
U.S. Appl. No. 16/121,988, filed Sep. 5, 2018, 2019-0183992, Abandoned.
U.S. Appl. No. 15/564,905, filed Oct. 6, 2017, U.S. Pat. No. 11,150,242, Issued.
U.S. Appl. No. 17/501,821, filed Oct. 14, 2021, 2022-0107308, Published.
U.S. Appl. No. 16/316,778, filed Jan. 10, 2019, U.S. Pat. No. 11,555,177, Issued.
U.S. Appl. No. 18/072,449, filed Nov. 30, 2022, Pending.
U.S. Appl. No. 11/638,796, filed Dec. 13, 2006, U.S. Pat. No. 8,067,237, Issued.
U.S. Appl. No. 13/305,088, filed Nov. 28, 2011, U.S. Pat. No. 8,932,583, Issued.
U.S. Appl. No. 14/223,759, filed Mar. 24, 2014, U.S. Pat. No. 9,132,210, Issued.
U.S. Appl. No. 14/750,423, filed Jun. 25, 2015, U.S. Pat. No. 9,446,107, Issued.
U.S. Appl. No. 15/085,858, filed Mar. 30, 2016, 2016-0271298, Abandoned.
U.S. Appl. No. 15/135,207, filed Apr. 21, 2016, U.S. Pat. No. 10,149,897, Issued.
U.S. Appl. No. 15/135,213, filed Apr. 21, 2016, U.S. Pat. No. 10,137,184, Issued.
U.S. Appl. No. 16/170,313, filed Oct. 25, 2018, U.S. Pat. No. 11,096,997, Issued.
U.S. Appl. No. 17/381,031, filed Jul. 20, 2021, Abandoned.
U.S. Appl. No. 13/877,572, filed Nov. 19, 2013, U.S. Pat. No. 11,202,759, Issued.
U.S. Appl. No. 17/522,297, filed Nov. 9, 2021, 2022-0192986, Published.
U.S. Appl. No. 14/112,096, filed Dec. 27, 2013, U.S. Pat. No. 10,045,947, Issued.
U.S. Appl. No. 14/166,689, filed Jan. 28, 2014, U.S. Pat. No. 9,675,561, Issued.
U.S. Appl. No. 15/617,837, filed Jun. 8, 2017, 2018-0243231, Abandoned.
U.S. Appl. No. 16/033,025, filed Jul. 11, 2018, 2019-0076373, Abandoned.
U.S. Appl. No. 17/083,720, filed Oct. 29, 2020, 2021-0205233, Published.
U.S. Appl. No. 18/095,488, filed Jan. 10, 2023, Pending.
U.S. Appl. No. 14/394,552, filed Oct. 15, 2014, U.S. Pat. No. 9,937,249, Issued.
U.S. Appl. No. 15/935,392, filed Mar. 26, 2018, U.S. Pat. No. 11,278,604, Issued.
U.S. Appl. No. 17/693,017, filed Mar. 11, 2022, 2023-0000961, Published.
U.S. Appl. No. 15/303,985, filed Oct. 13, 2016, U.S. Pat. No. 10,682,400, Issued.
U.S. Appl. No. 16/877,274, filed May 18, 2020, 2020-0276290, Published.
U.S. Appl. No. 16/263,098, filed Jan. 31, 2019, 2019-0216910, Published.
U.S. Appl. No. 12/867,426, filed Jan. 13, 2012, U.S. Pat. No. 10,328,133, Issued.
U.S. Appl. No. 15/135,255, filed Apr. 21, 2016, U.S. Pat. No. 10,258,677, Issued.
U.S. Appl. No. 15/135,290, filed Apr. 21, 2016, 2016-0228543, Abandoned.
U.S. Appl. No. 15/135,294, filed Apr. 21, 2016, 2016-0220668, Abandoned.
U.S. Appl. No. 13/510,356, filed May 17, 2012, Abandoned.
U.S. Appl. No. 14/123,615, filed Mar. 17, 2014, U.S. Pat. No. 9,486,512, Issued.
U.S. Appl. No. 15/345,131, filed Nov. 7, 2016, U.S. Pat. No. 10,406,216, Issued.
U.S. Appl. No. 13/741,271, filed Jan. 14, 2013, U.S. Pat. No. 9,370,558, Issued.
U.S. Appl. No. 15/135,216, filed Apr. 21, 2016, U.S. Pat. No. 9,821,045, Issued.
U.S. Appl. No. 15/818,509, filed Nov. 20, 2017, U.S. Pat. No. 10,568,949, Issued.

(56) References Cited

OTHER PUBLICATIONS

U.S. Appl. No. 15/563,878, filed Oct. 2, 2017, 2018-0117171, Abandoned.
U.S. Appl. No. 15/546,852, filed Jul. 27, 2017, U.S. Pat. No. 11,786,457, Issued.
U.S. Appl. No. 16/075,937, filed Aug. 6, 2018, U.S. Pat. No. 11,752,238, Issued.
U.S. Appl. No. 18/224,444, filed Jul. 20, 2023, Pending.
U.S. Appl. No. 16/708,218, filed Dec. 9, 2019, 2020-0206333, Published.
U.S. Appl. No. 17/414,037, filed Jun. 15, 2021, 2022-0047778, Published.
U.S. Appl. No. 17/701,270, filed Mar. 22, 2022, 2022-0339274, Published.
U.S. Appl. No. 17/869,611, filed Jul. 20, 2022, 2023-0085214, Published.
Abrahams et al., Expression and secretion of antiviral factors by trophoblast cells following stimulation by the TLR-3 agonist, Poly(I : C). Hum Reprod. Sep. 2006;21(9):2432-9.
Agache et al., Mechanical properties and Young's modulus of human skin in vivo. Arch Dermatol Res. 1980;269(3):221-32.
Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15, 2003;171(10):4984-9.
Aguado et al., Improving viability of stem cells during syringe needle flow through the design of hydrogel cell carriers. Tissue Eng Part A. Apr. 2012; 18(7-8):806-15.
Akira et al., Pathogen recognition and innate immunity. Cell. Feb. 24, 2006;124(4):783-801.
Akira et al., Toll-like receptors: critical proteins linking innate and acquired immunity. Nat Immunol. Aug. 2001;2(8):675-80.
Akpalo et al., Fibrin-polyethylene oxide interpenetrating polymer networks: new self-supported biomaterials combining the properties of both protein gel and synthetic polymer. Acta Biomater. Jun. 2011;7(6):2418-27.
Aldhous, Print Me a Heart and a Set of Arteries. New Scientist. 2006;2547:19.
Ali et al., Biomaterial-based vaccine induces regression of established intracranial glioma in rats. Pharm Res. May 2011;28(5):1074-80.
Ali et al., Controlled Local Delivery of GM-CSF From Polymer-Based Vaccines Enhances Anti-Tumor Immune Responses by Priming Host Dendritic Cells. 2007 AACR Annual Meeting. 2007;48:652, Abstract #2736.
Ali et al., Converging Cell Therapy with Biomaterials. Cell Transplantation from Laboratory to Clinic. 2006:591-609.
Ali et al., Identification of immune factors regulating antitumor immunity using polymeric vaccines with multiple adjuvants. Cancer Res. Mar. 15, 2014;74(6):1670-81.
Ali et al., In situ regulation of DC subsets and T cells mediates tumor regression in mice. Sci Transl Med. Nov. 25, 2009;1(8):8ra19, 1-10.
Ali et al., Infection-mimicking materials to program dendritic cells in situ. Nat Mater. Feb. 2009;8(2):151-8.
Ali et al., Inflammatory cytokines presented from polymer matrices differentially generate and activate DCs in situ. Adv Funct Mater. Aug. 1, 2013;23(36):4621-4628.
Ali et al., Relationship of vaccine efficacy to the kinetics of DC and T-cell responses induced by PLG-based cancer vaccines. Biomater. 2011;1(1):66-75.
Ali et al., Sustained GM-CSF and PEI condensed pDNA presentation increases the level and duration of gene expression in dendritic cells. J Control Release. Dec. 18, 2008;132(3):273-8.
Ali et al., The efficacy of intracranial PLG-based vaccines is dependent on direct implantation into brain tissue. J Control Release. Sep. 25, 2011;154(3):249-57.
Allen et al., Regulation of satellite cells during skeletal muscle growth and development. Proc Soc Exp Biol Med. Jun. 1990;194(2):81-6.
Allen et al., Regulation of skeletal muscle satellite cell proliferation by bovine pituitary fibroblast growth factor. Exp Cell Res. May 1984;152(1):154-60.
Almarza et al., Evaluation of three growth factors in combinations of two for temporomandibular joint disc tissue engineering. Arch Oral Biol. Mar. 2006;51(3):215-21.
Alsberg et al., Cell-interactive alginate hydrogels for bone tissue engineering. J Dent Res. Nov. 2001;80(11):2025-9.
Alsberg et al., Engineering growing tissues. Proc Natl Acad Sci U S A. Sep. 17, 2002;99(19):12025-30.
Alsberg et al., Regulating bone formation via controlled scaffold degradation. J Dent Res. Nov. 2003;82(11):903-8.
Ambrosini et al., Astrocytes produce dendritic cell-attracting chemokines in vitro and in multiple sclerosis lesions. J Neuropathol Exp Neurol. Aug. 2005;64(8):706-15.
Anderson et al., Biomaterial microarrays: rapid, microscale screening of polymer-cell interaction. Biomaterials. Aug. 2005;26(23):4892-7.
Anderson et al., Crosslinking CD3 with CD2 using sepharose-immobilized antibodies enhances T lymphocyte proliferation. Cell Immunol. Sep. 1988;115(2):246-56.
Anderson et al., Nanoliter-scale synthesis of arrayed biomaterials and application to human embryonic stem cells. Nat Biotechnol. Jul. 2004;22(7):863-6.
Anderson, A role for nitric oxide in muscle repair: nitric oxide-mediated activation of muscle satellite cells. Mol Biol Cell. May 2000;11(5):1859-74.
Andersson et al., HSP70 promoter-driven activation of gene expression for immunotherapy using gold nanorods and near infrared light. Vaccines (Basel). Mar. 25, 2014;2(2):216-27.
Annabi et al., Controlling the porosity and microarchitecture of hydrogels for tissue engineering. Tissue Eng Part B Rev. Aug. 2010;16(4):371-83.
Annual Review. pp. 122-131, (2008).
Arany et al., At the edge of translation—materials to program cells for differentiation. Oral Dis. Apr. 2011;17(3):241-51.
Aschner et al., Metabolic memory for vascular disease in diabetes. Diabetes Technol Ther. Jun. 2012;14 Suppl 1:S68-74.
Atala et al., Endoscopic treatment of vesicoureteral reflux with a chondrocyte-alginate suspension. J Urol. Aug. 1994;152(2 Pt 2):641-3.
Aubin et al., Directed 3D cell alignment and elongation in microengineered hydrogels. Biomaterials. Sep. 2010;31(27):6941-6951.
Augst et al., Alginate hydrogels as biomaterials. Macromol Biosci. Aug. 7, 2006;6(8):623-33.
Babensee et al., Host response to tissue engineered devices. Advanced Drug Delivery Reviews. Aug. 3, 1998;33(1-2):111-139.
Bachelder et al., Acid-degradable polyurethane particles for protein-based vaccines: biological evaluation and in vitro analysis of particle degradation products. Mol Pharm. Sep.-Oct. 2008;5(5):876-84.
Bachem et al., Superior antigen cross-presentation and XCR1 expression define human CD11c+CD141+ cells as homologues of mouse CD8+ dendritic cells. J Exp Med. Jun. 7, 2010;207(6):1273-81.
Badovinac et al., Regulation of CD8+ T cells undergoing primary and secondary responses to infection in the same host. J Immunol. May 15, 2003;170(10):4933-42.
Bakri et al., Pharmacokinetics of intravitreal bevacizumab (Avastin). Ophthalmology. May 2007;114(5):855-9.
Balakrishna et al., Structural correlates of antibacterial and membrane-permeabilizing activities in acylpolyamines. Antimicrob Agents Chemother. Mar. 2006;50(3):852-61.
Banchereau et al., Dendritic cells and the control of immunity. Nature. Mar. 19, 1998;392(6673):245-52.
Bar-Cohen et al., Electroactive Polymer Actuators and Sensors. MRS Bullet. 2008;33(3):173-181.
Bar-Or et al., Induction of antigen-specific tolerance in multiple sclerosis after immunization with DNA encoding myelin basic

(56) References Cited

OTHER PUBLICATIONS protein in a randomized, placebo-controlled phase 1/2 trial. Arch Neurol. Oct. 2007;64(10):1407-15.
Barbero et al., Growth factor supplemented matrigel improves ectopic skeletal muscle formation—a cell therapy approach. J Cell Physiol. Feb. 2001;186(2):183-92.
Barbucci et al., Hyaluronic acid hydrogel in the treatment of osteoarthritis. Biomaterials. Dec. 2002;23(23):4503-13.
Baroja et al., The anti-T cell monoclonal antibody 9.3 (anti-CD28) provides a helper signal and bypasses the need for accessory cells in T cell activation with immobilized anti-CD3 and mitogens. Cell Immunol. Apr. 15, 1989;120(1):205-17.
Barrio et al., A two-dimensional numerical study of spatial pattern formation in interacting Turing systems. Bull Math Biol. May 1999;61(3):483-505.
Baskin et al., Copper-free click chemistry for dynamic in vivo imaging. Proc Natl Acad Sci U S A. Oct. 23, 2007;104(43):16793-7.
Bates, Improved muscle regeneration by combining VEGF with IGF1. Regen Med. Nov. 2010;5(6):853-4.
Beaucage et al., The Functionalization of Oligonucleotides Via Phosphoramidite Derivatives. Tetrahedron. Mar. 5, 1993;49(10)1925-1963.
Beauchamp et al., Dynamics of myoblast transplantation reveal a discrete minority of precursors with stem cell-like properties as the myogenic source. J Cell Biol. Mar. 22, 1999;144(6):1113-22.
Becker et al., Cytological demonstration of the clonal nature of spleen colonies derived from transplanted mouse marrow cells. Nature. Feb. 2, 1963;197:452-4.
Beduer et al., A compressible scaffold for minimally invasive delivery of large intact neuronal networks. Adv Healthc Mater. Jan. 28, 2015;4(2):301-12.
Beebe et al., Functional hydrogel structures for autonomous flow control inside microfluidic channels. Nature. Apr. 6, 2000;404(6778):588-90.
Bekiari et al., Study of poly(N,N-dimethylacrylamide)/CdS nanocomposite organic/inorganic gels. Langmuir. Sep. 14, 2004;20(19):7972-5.
Bell, Models for the specific adhesion of cells to cells. Science. May 12, 1978;200(4342):618- 27.
Bencherif et al., End-group effects on the properties of PEG-co-PGA hydrogels. Acta Biomater. Jul. 2009;5(6):1872-83.
Bencherif et al., Influence of cross-linker chemistry on release kinetics of PEG-co-PGA hydrogels. J Biomed Mater Res A. Jul. 2009;90(1):142-53.
Bencherif et al., Influence of the degree of methacrylation on hyaluronic acid hydrogels properties. Biomaterials. Apr. 2008;29(12):1739-49.
Bencherif et al., Injectable preformed scaffolds with shape-memory properties. Proc Natl Acad Sci U S A. Nov. 27, 2012;109(48):19590-5.
Bencherif et al., Nanostructured hybrid hydrogels prepared by a combination of atom transfer radical polymerization and free radical polymerization. Biomaterials. Oct. 2009;30(29):5270-8.
Bencherif et al., Synthesis by AGET ATRP of degradable nanogel precursors for in situ formation of nanostructured hyaluronic acid hydrogel. Biomacromolecules. Sep. 14, 2009;10(9):2499-507.
Benton et al., Photocrosslinking of gelatin macromers to synthesize porous hydrogels that promote valvular interstitial cell function. Tissue Eng Part A. Nov. 2009;15(11):3221-30.
Berg et al., Il-10 is a central regulator of cyclooxygenase-2 expression and prostaglandin production. J Immunol. Feb. 15, 2001;166(4):2674-80.
Bergstraesser et al., Stimulation and inhibition of human mammary epithelial cell duct morphogenesis in vitro. Proc Assoc Am Physicians. Mar. 1996;108(2):140-54.
Bhardwaj et al., TLR Agonists: Are They Good Adjuvants? Cancer J. 2010;16(4):382-391..
Bianco et al., The meaning, the sense and the significance: translating the science of mesenchymal stem cells into medicine. Nat Med. Jan. 2013;19(1):35-42.

Bierer et al., T cell receptors: adhesion and signaling. Adv Cancer Res. 1991;56:49-76.
Bilodeau et al., Regular Pyramid Punch Problem. J Appl Mech. 1992;59(3):519-523.
Bischoff, Proliferation of muscle satellite cells on intact myofibers in culture. Dev Biol. May 1986;115(1):129-39.
Bjork et al., Tuning the shape of mesoporous silica particles by alterations in parameter space: from rods to platelets. Langmuir. Nov. 5, 2013;29(44):13551-61.
Blumenthal et al., Polyurethane scaffolds seeded with genetically engineered skeletal myoblasts: a promising tool to regenerate myocardial function. Artif Organs. Feb. 2010;34(2):E46-54.
Boateng et al., Wound healing dressings and drug delivery systems: a review. J Pharm Sci. Aug. 2008;97(8):2892-923.
Boerckel et al., Mechanical regulation of vascular growth and tissue regeneration in vivo. Proc Natl Acad Sci U S A. Sep. 13, 2011;108(37):E674-80.
Bohl et al., Role of synthetic extracellular matrix in development of engineered dental pulp. J Biomater Sci Polym Ed. 1998;9(7):749-64.
Bojarova et al., Sugared biomaterial binding lectins: achievements and perspectives. Biomater Sci. Jul. 19, 2016;4(8):1142-60.
Bonauer et al., MicroRNA-92a controls angiogenesis and functional recovery of ischemic tissues in mice. Science. Jun. 26, 2009;324(5935):1710-3.
Boontheekul et al., Controlling alginate gel degradation utilizing partial oxidation and bimodal molecular weight distribution. Biomaterials. May 2005;26(15):2455-65.
Boontheekul et al., Regulating myoblast phenotype through controlled gel stiffness and degradation. Tissue Eng. Jul. 2007;13(7):1431-42.
Borselli et al., Functional muscle regeneration with combined delivery of angiogenesis and myogenesis factors. Proc Natl Acad Sci U S A. Feb. 23, 2010;107(8):3287-92.
Bouhadir et al., Degradation of partially oxidized alginate and its potential application for tissue engineering. Biotechnol Prog. Sep.-Oct. 17, 2001(5):945-50.
Bouhadir et al., Synthesis of Cross-Linked Poly(aldehyde guluronate) Hydrogels. Polymer. Jun. 1999;40(12):3575-3584.
Bowne et al., Injection of DNA encoding granulocyte-macrophage colony-stimulating factor recruits dendritic cells for immune adjuvant effects. Cytokines Cell Mol Ther. Dec. 1999;5(4):217-25.
Brignone et al., A phase I pharmacokinetic and biological correlative study of IMP321, a novel MHC class II agonist, in patients with advanced renal cell carcinoma. Clin Cancer Res. Oct. 1, 2009;15(19):6225-31.
Brinkman et al., Photo-cross-linking of type I collagen gels in the presence of smooth muscle cells: mechanical properties, cell viability, and function. Biomacromolecules. Jul.-Aug. 2003;4(4):890-5.
Brinkmann et al., Neutrophil extracellular traps kill bacteria. Science. Mar. 5, 2004;303(5663):1532-5.
Bristol-Myers Squibb, Investigational Anti-PD-1 Immunotherapy BMS-936558 Showed Clinical Activity in Phase 1 Trial of Patients with Previously-Treated non-Small-Cell Lung Cancer, Metastatic Melanoma adn Renal Cell Cancer. Financial Times. 3 pages, Jun. 2, 2012.
Brodie et al., In vivo migration and function of transferred HIV-1-specific cytotoxic T cells. Nat Med. Jan. 1999;5(1):34-41.
Brouwers et al., Can the growth factors PTHrP, Ihh and VEGF, together regulate the development of a long bone? J Biomech. 2006:39(15):2774-82.
Broxmeyer, Insights into the biology of cord blood stem/progenitor cells. Cell Prolif. Apr. 2011;44 Suppl 1:55-9.
Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;5(11):6278-86.
Bryant et al., Photo-patterning of porous hydrogels for tissue engineering. Biomaterials. Jul. 2007;28(19):2978-86.
Buckwalter et al., Form of Antigen Dictates Immunity: Irradiated Cell vs. Whole Cell Lysate Vaccination. J Immunol. Apr. 1, 2007;178(1 Suppl):S77.

(56) References Cited

OTHER PUBLICATIONS

Bullard et al., Fetal wound healing: current biology. World J Surg. Jan. 2003;27(1):54-61.
Buonaguro et al., Translating tumor antigens into cancer vaccines. Clin Vaccine Immunol. Jan. 2011;18(1):23-34.
Burdick et al., Controlled degradation and mechanical behavior of photopolymerized hyaluronic acid networks. Biomacromolecules. Jan.-Feb. 2005;6(1):386-91.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9.
Burger et al., Effect of VEGF and its receptor antagonist SU-5416, an inhibitor of angiogenesis, on processing of the beta-amyloid precursor protein in primary neuronal cells derived from brain tissue of Tg2576 mice. Int J Dev Neurosci. Nov. 2010;28(7):597-604.
Butler et al., Long-lived antitumor CD8+ lymphocytes for adoptive therapy generated using an artificial antigen-presenting cell. Clin Cancer Res. Mar. 15, 2007;13(6):1857-67.
Bégué et al., Vaccination against human papillomavirus. Implementation and efficacy against cervical cancer control. Bull Acad Natl Med. Dec. 2007;191(9):1805-16.
Callahan et al., At the bedside: CTLA-4- and PD-1-blocking antibodies in cancer immunotherapy. J Leukoc Biol. Jul. 2013;94(1):41-53.
Calvert, Electroactive Polymer Gels. Electroactive Polymer (EAP) Acutators as Artificial Muscle: Reality, Potential, and Challenges. Bar-Cohen, (Ed.), Spie Press, Bellingham, WA. 151-170. (2004).
Calvert, Gel Sensors and Actuators. MRS Bullet. 2008;33(3):207-212.
Cameron et al., The influence of substrate creep on mesenchymal stem cell behaviour and phenotype. Biomaterials. Sep. 2011;32(26):5979-93.
Cao et al., Promoting angiogenesis via manipulation of VEGF responsiveness with notch signaling. Biomaterials. Sep. 2009;30(25):4085-93.
care.diabetesjournals.org, Standards of Medical Care in Diabetes. Diabetes Care. Jan. 2013;36(Suppl 1):S1-S2.
Carlson et al., Notch signaling pathway and tissue engineering. Front Biosci. Sep. 1, 2007;12:5143-56.
Carmeliet et al., Angiogenesis in cancer and other diseases. Nature. Sep. 14, 2000;407(6801):249-57.
Carmeliet, Mechanisms of angiogenesis and arteriogenesis. Nat Med. Apr. 2000;6(4):389-95.
Casanova et al., Human Mannose-binding Lectin in Immunity: Friend, Foe, or Both ?. J Exp Med. 2004;199(10):1295-1299.
Caulfield et al., Regulation of major histocompatibility complex class II antigens on human alveolar macrophages by granulocyte-macrophage colony-stimulating factor in the presence of glucocorticoids. Immunology. Sep. 1999;98(1):104-10.
Ceriello et al., Clinical review 2: The "metabolic memory": is more than just tight glucose control necessary to prevent diabetic complications? J Clin Endocrinol Metab. Feb. 2009;94(2):410-5.
Ceriello et al., The emerging challenge in diabetes: the "metabolic memory". Vascul Pharmacol. Nov.-Dec. 2012;57(5-6):133-8.
Champion et al., Shape induced inhibition of phagocytosis of polymer particles. Pharm Res. Jan. 2009;26(1):244-9.
Chan et al., Antifibrotic effects of suramin in injured skeletal muscle after laceration. J Appl Physiol. Sep. 2003;95(2):771-80.
Chan et al., Helix induction in antimicrobial peptides by alginate in biofilms. J Biol Chem. Sep. 10, 2004;279(37):38749-54.
Chan et al., Traction dynamics of filopodia on compliant substrates. Science. Dec. 12, 2008;322(5908):1687-91.
Chang, Mouse models for studies of retinal degeneration and diseases. Methods Mol Biol. 2013;935:27-39.
Chao et al., Morphological control on SBA-15 mesoporous silicas via a slow self-assembling rate. J Mater Sci. 2009;44:6453-62.
Chapman, Endosomal proteases in antigen presentation. Curr Opin Immunol. Feb. 2006;18(1):78-84.
Che et al., Synthesis and characterization of chiral mesoporous silica. Nature. May 20, 2004;429(6989):281-4.
Chen et al., Adipogenic differentiation of adipose tissue-derived human mesenchymal stem cells: effect of gastric bypass surgery. Surg Endosc. Dec. 2012;26(12):3449-56.
Chen et al., Enhanced humoral and cell-mediated immune responses generated by cationic polymer-coated PLA microspheres with adsorbed HBsAg. Mol Pharm. Jun. 2, 2014;11(6):1772-84.
Chen et al., Functional Human Vascular Network Generated in Photocrosslinkable Gelatin Methacrylate Hydrogels. Adv Funct Mater. May 23, 2012;22(10):2027-2039.
Chen et al., Improved antigen cross-presentation by polyethyleneimine-based nanoparticles. Int J Nanomedicine. Jan. 6, 2011;6:77-84.
Chen et al., Integrated approach to designing growth factor delivery systems. FASEB J. Dec. 2007;21(14):3896-903.
Chen et al., Morphological control of mesoporous silica SBA-15 synthesized at low temperature without additives. J Porous Mater. 2011;18:211-6.
Chen et al., Polymeric growth factor delivery strategies for tissue engineering. Pharm Res. Aug. 2003;20(8):1103-12.
Chen et al., Quantitative proteomic profiling of pancreatic cancer juice. Proteomics. Jul. 2006;6(13):3871-9.
Chen et al., Skeletal muscle stem cells. Reprod Biol Endocrinol. Nov. 13, 2003;1:101. 7 pages.
Chen et al., Spatio-temporal VEGF and PDGF delivery patterns blood vessel formation and maturation. Pharm Res. Feb. 2007;24(2):258-64.
Cheung et al., Engineered Materials for Cancer Immunotherapy. Nano Today. Aug. 1, 2015;10(4):511-531.
Cheung et al., Scaffolds that mimic antigen-presenting cells enable ex vivo expansion of primary T cells. Nat Biotechnol. Feb. 2018;36(2):160-169.
Chiang et al., Whole tumor antigen vaccines. Semin Immunol. Jun. 2010;22(3):132-43.
Choi et al., Facile synthesis of high quality mesoporous SBA-15 with enhanced control of the porous network connectivity and wall thickness. Chem Commun (Camb). Jun. 21, 2003;(12):1340-1.
Choi et al., In vitro mineralization by preosteoblasts in poly(DL-lactide-co-glycolide) inverse opal scaffolds reinforced with hydroxyapatite nanoparticles. Langmuir. Jul. 20, 2010;26(14):12126-31.
Choi et al., Three-dimensional scaffolds for tissue engineering: the importance of uniformity in pore size and structure. Langmuir. Dec. 21, 2010;26(24):19001-6.
Choi, Replacement Organs, Hot Off the Press. New Scientist. 2003;177(2379):16.
Chou et al., Characterization of Photocross Linked Alginate Hydrogels for Nucleus Pulposus Cell Encapsulation. J Biomed Mater Res A. 2009;91A(1):187-194.
Chromiak et al., Bioreactor perfusion system for the long-term maintenance of tissue-engineered skeletal muscle organoids. In Vitro Cell Dev Biol Anim. Oct. 1998;34(9):694-703.
Clark et al., Myosin II and mechanotransduction: a balancing act. Trends Cell Biol. Apr. 2007;17(4):178-86.
Clauss et al., Interstitial transport of rabbit and sheep antibodies in normal and neoplastic tissues. Cancer Res. Jun. 15, 1990;50(12):3487-92.
ClinicalTrials.gov, NCT00729664, Multiple Ascending Dose (MDX1105-01) (Anti-PDL1). 4 pages, Sep. 3, 2015.
ClinicalTrials.gov, NCT00730639, A Phase 1 Study of Nivolumab (BMS-936558) in Subjects with Advanced or Recurrent Malignancies (MDX1106-03). 5 pages, Mar. 24, 2016.
ClinicalTrials.gov, NCT01352884, Study to Assess the Safety, and Pharmacokinetics of AMP-224 in Patients with Advanced Cancer. 3 pages, Sep. 2, 2016.
ClinicalTrials.gov, NCT01391143, Safety Study of MGA271 in Refractory Cancer. 4 pages, Sep. 28, 2016.
Cohen et al., Controlled delivery systems for proteins based on poly(lactic/glycolic acid) microspheres. Pharm Res. Jun. 1991;8(6):713-20.

(56) References Cited

OTHER PUBLICATIONS

Comisar et al., Engineering RGD nanopatterned hydrogels to control preosteoblast behavior: a combined computational and experimental approach. Biomaterials. Oct. 2007;28(30):4409-17.
Conboy et al., The regulation of Notch signaling controls satellite cell activation and cell fate determination in postnatal myogenesis. Dev Cell. Sep. 2002;3(3):397-409.
Conconi et al., In vitro and in vivo evaluation of acellular diaphragmatic matrices seeded with muscle precursors cells and coated with VEGF silica gels to repair muscle defect of the diaphragm. J Biomed Mater Res A. May 2009;89(2):304-16.
Conn et al., Purification of a glycoprotein vascular endothelial cell mitogen from a rat glioma-derived cell line. Proc Natl Acad Sci U S A. Feb. 1990;87(4):1323-7.
Cook et al., A sialomucopeptide liberated by trypsin from the human erythrocyte. Nature. Dec. 17, 1960;188:1011-2.
Cooper et al., Extended amplification in vitro and replicative senescence: key factors implicated in the success of human myoblast transplantation. Hum Gene Ther. Aug. 10, 2003;14(12):1169-79.
Cooper, A Genetic Pathogen Capture Technology for Sepsis Diagnosis. Submitted to the Department of Chemical Engineering in Partial Fulfillment of the Requirements for the Degree of Doctor of Philosophy in Medical and Engineering Physics at the Massachusetts Institute of Technology. 130 pages, May 1, 2013.
Cooper, Metabolic memory: implications for diabetic vascular complications. Pediatr Diabetes. Aug. 2009;10(5):343-6.
Corcione et al., CCL19 and CXCL12 trigger in vitro chemotaxis of human mantle cell lymphoma B cells. Clin Cancer Res. Feb. 1, 2004;10(3):964-71.
Cornelison et al., Single-cell analysis of regulatory gene expression in quiescent and activated mouse skeletal muscle satellite cells. Dev Biol. Nov. 15, 1997;191(2):270-83.
Cornelison et al., Syndecan-3 and syndecan-4 specifically mark skeletal muscle satellite cells and are implicated in satellite cell maintenance and muscle regeneration. Dev Biol. Nov. 1, 2001;239(1):79-94.
Coulson et al., Flow of Fluids through Granular Beds and Packed Columns Chemical Engineering, vol. 2. Third Edition. Pergamon Press. Chapter 4, pp. 125-171, (1978).
Crameri et al., Improved green fluorescent protein by molecular evolution using DNA shuffling. Nat Biotechnol. Mar. 1996;14(3):315-9.
Cuda et al., In vitro actin filament sliding velocities produced by mixtures of different types of myosin. Biophys J. Apr. 1997;72(4):1767-79.
Cukierman et al., Taking cell-matrix adhesions to the third dimension. Science. Nov. 23, 2001;294(5547):1708-12.
Cullen et al., Investigation of vascular endothelial growth factor effects on pulmonary endothelial monolayer permeability and neutrophil transmigration. Gen Pharmacol. Sep. 2000;35(3):149-57.
Curiel et al., Tumor immunotherapy: inching toward the finish line. J Clin Invest. Feb. 2002;109(3):311-2.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80.
D'Amico et al., The early progenitors of mouse dendritic cells and plasmacytoid predendritic cells are within the bone marrow hemopoietic precursors expressing Flt3. J Exp Med. Jul. 21, 2003;198(2):293-303.
Dainiak et al., Gelatin-fibrinogen cryogel dermal matrices for wound repair: preparation, optimisation and in vitro study. Biomaterials. Jan. 2010;31(1):67-76.
Damle et al., Stimulation via the CD3 and CD28 molecules induces responsiveness to IL-4 in CD4+CD29+CD45R-memory T lymphocytes. J Immunol. Sep. 15, 1989;143(6):1761-7.
Dar et al., Optimization of cardiac cell seeding and distribution in 3D porous alginate scaffolds. Biotechnol Bioeng. Nov. 5, 2002;80(3):305-12.
Daro et al., Polyethylene glycol-modified GM-CSF expands CD11b(high)CD11c(high) but not CD11b(low)CD11c(high) murine dendritic cells in vivo: a comparative analysis with Flt3 ligand. J Immunol. Jul. 1, 2000;165(1):49-58.
David et al., The in vitro Desensitization of Sensitive Cells by Trypsin. J Exp Med. Dec. 1, 1964;120:1189-200.
Davies et al., Antibody-antigen complexes. Annu Rev Biochem. 1990;59:439-73.
De Jong et al., Regulation of Notch signaling genes during BMP2-induced differentiation of osteoblast precursor cells. Biochem Biophys Res Commun. Jul. 16, 2004;320(1):100-7.
De Temmerman et al., Particulate vaccines: on the quest for optimal delivery and immune response. Drug Discov Today. Jul. 2011;16(13-14):569-82.
Del Chiaro et al., Early detection and prevention of pancreatic cancer: is it really possible today? World J Gastroenterol. Sep. 14, 2014;20(34):12118-31.
Dembo et al., Stresses at the cell-to-substrate interface during locomotion of fibroblasts. Biophys J. Apr. 1999;76(4):2307-16.
Den Haan et al., CD8(+) but not CD8(-) dendritic cells cross-prime cytotoxic T cells in vivo. J Exp Med. Dec. 18, 2000;192(12):1685-96.
Dengler et al., Mesoporous silica-supported lipid bilayers (protocells) for DNA cargo delivery to the spinal cord. J Control Release. Jun. 10, 2013;168(2):209-24.
Dennis et al., Excitability and contractility of skeletal muscle engineered from primary cultures and cell lines. Am J Physiol Cell Physiol. Feb. 2001;280(2):C288-95.
Dennis et al., Excitability and isometric contractile properties of mammalian constructs engineered in vitro. In Vitro Cell Dev Biol Anim. May 2000;36(5):327-35.
Deshmane et al., Monocyte chemoattractant protein-1 (MCP-1): an overview. J Interferon Cytokine Res. Jun. 2009;29(6):313-26.
Dexter et al., Conditions controlling the proliferation of haemopoietic stem cells in vitro. J Cell Physiol. Jun. 1977;91(3):335-44.
Diduch et al., Two cell lines from bone marrow that differ in terms of collagen synthesis, osteogenic characteristics, and matrix mineralization. J Bone Joint Surg Am. Jan. 1993;75(1):92-105.
Dieu et al., Selective recruitment of immature and mature dendritic cells by distinct chemokines expressed in different anatomic sites. J Exp Med. Jul. 20, 1998;188(2):373-86.
Diridollou et al., Skin ageing: changes of physical properties of human skin in vivo. Int J Cosmet Sci. Dec. 2001;23(6):353-62.
Discher et al., Tissue cells feel and respond to the stiffness of their substrate. Science. Nov. 18, 2005;310(5751):1139-43.
Disis et al., Granulocyte-macrophage colony-stimulating factor: an effective adjuvant for protein and peptide-based vaccines. Blood. Jul. 1, 1996;88(1):202-10.
Doan et al., Antigens and Receptors. Lippincott's Illustrated Reviews: Immunology. Wolters Kluwer/Lippincott Williams & Wilsons, Philadelphia. Chapter 12, pp. 11-23, (2008).
Doan et al., Subcellular localization of a sporulation membrane protein is achieved through a network of interactions along and across the septum. Mol Microbiol. Mar. 2005;55(6):1767-81.
Dolgin, Cancer vaccines: Material breach. Nature. Dec. 19, 2013;504(7480):S16-7.
Donati et al., New hypothesis on the role of alternating sequences in calcium-alginate gels. Biomacromolecules. Mar.-Apr. 2005;6(2):1031-40.
Dong et al., Antitumor effect of secreted Flt3-ligand can act at distant tumor sites in a murine model of head and neck cancer. Cancer Gene Ther. Feb. 2003;10(2):96-104.
Dor et al., Making vascular networks in the adult: branching morphogenesis without a roadmap. Trends Cell Biol. Mar. 2003;13(3):131-6.
Douay et al., Ex vivo production of human red blood cells from hematopoietic stem cells: what is the future in transfusion? Transfus Med Rev. Apr. 2007;21(2):91-100.
Drake et al., Koch Institute Symposium on Cancer Immunology and Immunotherapy. Cancer Immunology Researcy. 2013;1(4):217-22.

(56) References Cited

OTHER PUBLICATIONS

Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.

Dranoff, Cytokines in cancer pathogenesis and cancer therapy. Nat Rev Cancer. Jan. 2004;4(1):11-22.

Dranoff, GM-CSF-based cancer vaccines. Immunol Rev. Oct. 2002;188:147-54.

Drury et al., Hydrogels for tissue engineering: scaffold design variables and applications. Biomaterials. Nov. 2003;24(24):4337-51.

Dudley et al. Adoptive cell transfer therapy following non-myeloablative but lymphodepleting chemotherapy for the treatment of patients with refractory metastatic melanoma. J Clin Oncol. Apr. 1, 2005;23(10):2346-57.

Dudley et al., CD8+ enriched "young" tumor infiltrating lymphocytes can mediate regression of metastatic melanoma. Clin Cancer Res. Dec. 15, 2010;16(24):6122-31.

Dufort et al., Balancing forces: architectural control of mechanotransduction. Nat Rev Mol Cell Biol. May 2011;12(5):308-19.

Dupont et al., Role of YAP/TAZ in mechanotransduction. Nature. Jun. 8, 2011;474(7350):179-83.

Duraiswamy et al., Dual blockade of PD-1 and CTLA-4 combined with tumor vaccine effectively restores T-cell rejection function in tumors—response. Cancer Res. Jan. 15, 2014;74(2):633-4.

Duraiswamy et al., Dual blockade of PD-1 and CTLA-4 combined with tumor vaccine effectively restores T-cell rejection function in tumors. Cancer Res. Jun. 15, 2013;73(12):3591-603.

Edwards et al., Evaluation of biomechanical properties of human skin. Clin Dermatol. Jul.-Aug. 13, 1995(4):375-80.

Egea et al., Role of secreted glyceraldehyde-3-phosphate dehydrogenase in the infection mechanism of enterohemorrhagic and enteropathogenic *Escherichia coli*: interaction of the extracellular enzyme with human plasminogen and fibrinogen. Int J Biochem Cell Biol. 2007;39(6):1190-203.

Eggermont et al., Towards efficient cancer immunotherapy: advances in developing artificial antigen-presenting cells. Trends Biotechnol. Sep. 2014;32(9):456-65.

Egholm et al., Peptide Nucleic Acids (PNA). Oligonucleotide Analogues with an Achiral Peptide Backbone. J Am Chem Soc. 1992;114(5):1895-1897.

Egholm et al., PNA hybridizes to complementary oligonucleotides obeying the Watson-Crick hydrogen-bonding rules. Nature. Oct. 7, 1993;365(6446):566-8.

Ehrbar et al., Endothelial cell proliferation and progenitor maturation by fibrin-bound VEGF variants with differential susceptibilities to local cellular activity. J Control Release. Jan. 3, 2005;101(1-3):93-109.

Eiselt et al., Porous carriers for biomedical applications based on alginate hydrogels. Biomaterials. Oct. 2000;21(19):1921-7.

El-Backly et al., Regeneration of dentine/pulp-like tissue using a dental pulp stem cell/poly(lactic-co-glycolic) acid scaffold construct in New Zealand white rabbits. Aust Endod J. Aug. 2008;34(2):52-67.

El-Behi et al., The encephalitogenicity of T(H) 17 cells is dependent on IL-1- and IL-23-induced production of the cytokine GM-CSF. Nat Immunol. Jun. 2011;12(6):568-75.

Eldar et al., Elucidating mechanisms underlying robustness of morphogen gradients. Curr Opin Genet Dev. Aug. 2004; 14(4):435-9.

Eldar et al., Robustness of the BMP morphogen gradient in *Drosophila* embryonic patterning. Nature. Sep. 19, 2002;419(6904):304-8.

Eldar et al., Self-enhanced ligand degradation underlies robustness of morphogen gradients. Dev Cell. Oct. 2003;5(4):635-46.

Emens et al., The interplay of immunotherapy and chemotherapy: harnessing potential synergies. Cancer Immunol Res. May 2015;3(5):436-43.

Eming et al., Inflammation in wound repair: molecular and cellular mechanisms. J Invest Dermatol. Mar. 2007;127(3):514-25.

Engler et al., Matrix elasticity directs stem cell lineage specification. Cell. Aug. 25, 2006;126(4):677-89.

Engler et al., Microtissue elasticity: measurements by atomic force microscopy and its influence on cell differentiation. Methods Cell Biol. 2007;83:521-45.

Engler et al., Substrate compliance versus ligand density in cell on gel responses. Biophys J. Jan. 2004;86(1 Pt 1):617-28.

Ennett et al., Temporally regulated delivery of VEGF in vitro and in vivo. J Biomed Mater Res A. Oct. 2006;79(1):176-84.

Ennett, Temporal Delivery of Multiple Growth Factors from Polymer Scaffolds to Enhance Neovascularization. A dissertation submitted in partial fulfillment of the requirements for the degree of Doctor of Philosophy (Biomedical Engineering) in the University of Michigan. 186 pages, (2004).

Exposito et al., The fibrillar collagen family. Int J Mol Sci. Jan. 28, 2010;11(2):407-26.

Fadel et al., A carbon nanotube-polymer composite for T-cell therapy. Nat Nanotechnol. Aug. 2014;9(8):639-47.

Fadel et al., Enhanced cellular activation with single walled carbon nanotube bundles presenting antibody stimuli. Nano Lett. Jul. 2008;8(7):2070-6.

Faissner et al., Boundaries and inhibitory molecules in developing neural tissues. Glia. Apr. 1995;13(4):233-54.

Falanga, Wound healing and its impairment in the diabetic foot. Lancet. Nov. 12, 2005;366(9498):1736-43.

Falsey et al., Peptide and small molecule microarray for high throughput cell adhesion and functional assays. Bioconjug Chem. May-Jun. 2001;12(3):346-53.

Farrar et al., T helper subset development: roles of instruction, selection, and transcription. J Clin Invest. Feb. 2002;109(4):431-5.

Fauquemberque et al., HLA-A*0201-restricted CEA-derived peptide CAP1 is not a suitable target for T-cell-based immunotherapy. J Immunother. May 2010;33(4):402-13.

Ferrara et al., Angiogenesis as a therapeutic target. Nature. Dec. 15, 2005;438(7070):967-74.

Ferrara et al., Discovery and development of bevacizumab, an anti-VEGF antibody for treating cancer. Nat Rev Drug Discov. May 2004;3(5):391-400.

Fesnak et al., Engineered T cells: the promise and challenges of cancer immunotherapy. Nat Rev Cancer. Aug. 23, 2016;16(9):566-81.

Fischbach et al., Polymeric Systems for Bioinspired Delivery of Angiogenic Molecules. Adv Polym Sci. 2006;203:191-221.

Fischer et al., A brilliant monomeric red fluorescent protein to visualize cytoskeleton dynamics in Dictyostelium. FEBS Lett. Nov. 5, 2004;577(1-2):227-32.

Fischer et al., Visualizing cytoskeleton dynamics in mammalian cells using a humanized variant of monomeric red fluorescent protein. FEBS Lett. May 1, 2006;580(10):2495-502.

Fisher et al., The study of protein mechanics with the atomic force microscope. Trends Biochem Sci. Oct. 1999;24(10):379-84.

Folkman, Angiogenesis. Annu Rev Med. 2006;57:1-18.

Fonseca et al., Capitalizing on the immunogenicity of dying tumor cells. Clin Cancer Res. Mar. 15, 2008;14(6):1603-8.

Fontaine et al., Surgical treatment of peripheral circulation disorders. Helv Chir Acta. Dec. 1954;21(5-6):499-533.

Fox, Management of worsening multiple sclerosis with mitoxantrone: a review. Clin Ther. Apr. 2006;28(4):461-74.

Fransen et al., Local immunomodulation for cancer therapy: Providing treatment where needed. Oncoimmunology. Nov. 1, 2013;2(11):e26493.

Friedenstein et al., Fibroblast precursors in normal and irradiated mouse hematopoietic organs. Exp Hematol. Sep. 1976;4(5):267-74.

Friedrich et al., Promoter traps in embryonic stem cells: a genetic screen to identify and mutate developmental genes in mice. Genes Dev. Sep. 1991;5(9):1513-23.

Fukushima et al., The use of an antifibrosis agent to improve muscle recovery after laceration. Am J Sports Med. Jul.-Aug. 2001;29(4):394-402.

Furdui et al., Immunomagnetic T cell capture from blood for PCR analysis using microfluidic systems. Lab Chip. Dec. 2004;4(6):614-8.

(56) References Cited

OTHER PUBLICATIONS

Furqan et al., STAT inhibitors for cancer therapy. J Hematol Oncol. Dec. 5, 2013;6:90. 11 pages.
Gamvrellis et al., Vaccines that facilitate antigen entry into dendritic cells. Immunol Cell Biol. Oct. 2004;82(5):506-16.
Gao et al., Immune cell recruitment and cell-based system for cancer therapy. Pharm Res. Apr. 2008;25(4):752-68.
Gardel et al., Traction stress in focal adhesions correlates biphasically with actin retrograde flow speed. J Cell Biol. Dec. 15, 2008;183(6):999-1005.
Garlie et al., T cells coactivated with immobilized anti-CD3 and anti-CD28 as potential immunotherapy for cancer. J Immunother. Jul. 1999;22(4):336-45.
Gasic et al., Removal and regeneration of the cell coating in tumour cells. Nature. Oct. 13, 1962;196:170.
Gauthier et al., Temporary increase in plasma membrane tension coordinates the activation of exocytosis and contraction during cell spreading. Proc Natl Acad Sci U S A. Aug. 30, 2011;108(35):14467-72.
Geerligs et al., Linear viscoelastic behavior of subcutaneous adipose tissue. Biorheology. 2008;45(6):677-88.
GenBank Accession No. 000082.2, May 10, 2014.
GenBank Accession No. 000091.4, May 10, 2014.
GenBank Accession No. 000230.2, Dec. 17, 2012.
GenBank Accession No. 000514.3, Aug. 19, 2012.
GenBank Accession No. 000572.2, May 18, 2014.
GenBank Accession No. 000601.4, Nov. 25, 2012.
GenBank Accession No. 000614.3, Sep. 9, 2012.
GenBank Accession No. 000629.3, May 4, 2014.
GenBank Accession No. 000638.3, May 4, 2014.
GenBank Accession No. 000660.4, Dec. 9, 2012.
GenBank Accession No. 000749.2, May 4, 2014.
GenBank Accession No. 000758.3, May 4, 2014.
GenBank Accession No. 000800.3, Mar. 4, 2012.
GenBank Accession No. 000876.3, Apr. 13, 2014.
GenBank Accession No. 000885.4, Apr. 13, 2014.
GenBank Accession No. 000954.1, Jun. 13, 2014.
GenBank Accession No. 000963.3, Jun. 13, 2014.
GenBank Accession No. 001001522.1, May 18, 2014.
GenBank Accession No. 001096124.1, Dec. 16, 2012.
GenBank Accession No. 001102654.1, Dec. 16, 2012.
GenBank Accession No. 001111283.1, Dec. 9, 2012.
GenBank Accession No. 001171630.1, Dec. 9, 2012.
GenBank Accession No. 001202.3, Nov. 18, 2012.
GenBank Accession No. 001836.2, May 3, 2014.
GenBank Accession No. 001845.4, May 3, 2014.
GenBank Accession No. 001892.1, May 18, 2014.
GenBank Accession No. 001901.2, May 18, 2014.
GenBank Accession No. 002010.2, Dec. 9, 2012.
GenBank Accession No. 002421.3. May 11, 2014.
GenBank Accession No. 002506.2, Dec. 9, 2012.
GenBank Accession No. 002632.4, May 4, 2011.
GenBank Accession No. 002973.1, May 3, 2014.
GenBank Accession No. 002982.3, May 3, 2014.
GenBank Accession No. 003236.2, Aug. 21, 2011.
GenBank Accession No. 003239.2, Feb. 18, 2014.
GenBank Accession No. 003254.2, Jan. 5, 2013.
GenBank Accession No. 003255.2, Jan. 6, 2013.
GenBank Accession No. 003259.2, Nov. 25, 2012.
GenBank Accession No. 003263.3, Jan. 5, 2013.
GenBank Accession No. 003264.3, Jan. 6, 2013.
GenBank Accession No. 003268.5, Nov. 25, 2012.
GenBank Accession No. 003368.1, May 5, 2014.
GenBank Accession No. 003377.4, May 5, 2014.
GenBank Accession No. 003383.2, May 5, 2014.
GenBank Accession No. 003392.4, May 5, 2014.
GenBank Accession No. 004460.1, May 25, 2014.
GenBank Accession No. 004469.4, May 25, 2014.
GenBank Accession No. 005420.1, May 11, 2014.
GenBank Accession No. 005429.3, Mar. 31, 2014.
GenBank Accession No. 006059.2, Oct. 28, 2012.
GenBank Accession No. 006068.4, Oct. 28, 2012.
GenBank Accession No. 015719.3, Feb. 26, 2014.
GenBank Accession No. 016562.3, Jan. 6, 2013.
GenBank Accession No. 030956.3, Oct. 28, 2012.
GenBank Accession No. 033023.4, Nov. 18, 2012.
GenBank Accession No. 056534.2, Feb. 26, 2014.
GenBank Accession No. 057646.1, Jan. 6, 2013.
GenBank Accession No. 112218.2, Oct. 28, 2012.
GenBank Accession No. 138554.4, Dec. 29, 2012.
GenBank Accession No. 138636.4, Dec. 23, 2012.
GenBank Accession No. 170731.4, Dec. 9, 2012.
GenBank Accession No. 205819.3, Dec. 6, 2012.
GenBank Accession No. 205820.1, Jan. 5, 2013.
GenBank Accession No. 205823.2, Jan. 6, 2013.
GenBank Accession No. 570912.2, Nov. 18, 2012.
GenBank Accession No. 612564.1, Dec. 29, 2012.
GenBank Accession No. 619542.1, Dec. 23, 2012.
GenBank Accession No. 991388.2, Dec. 6, 2012.
GenBank Accession No. 991389.1, Jan. 5, 2013.
GenBank Accession No. 991392.1, Jan. 6, 2013.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. U76381.2, Jul. 12, 1999.
Genes et al., Effect of substrate mechanics on chondrocyte adhesion to modified alginate surfaces. Arch Biochem Biophys. Feb. 15, 2004;422(2):161-7.
Gerhardt et al., VEGF guides angiogenic sprouting utilizing endothelial tip cell filopodia. J Cell Biol. Jun. 23, 2003;161(6):1163-77.
Gilboa, DC-based cancer vaccines. J Clin Invest. May 2007;117(5):1195-203.
Gimmi et al., B-cell surface antigen B7 provides a costimulatory signal that induces T cells to proliferate and secrete interleukin 2. Proc Natl Acad Sci U S A. Aug. 1, 1991;88(15):6575-9.

(56) References Cited

OTHER PUBLICATIONS

Glasbey et al., Image Analysis and Three-Dimensional Modelling of Pores in Soil Aggregates. Eur J Soil Sci. Sep. 1991;42(3):479-486.
Gnjatic et al., Toll-like receptor agonists: are they good adjuvants? Cancer J. Jul.-Aug. 2010;16(4):382-91.
Godbey et al. Tracking the intracellular path of poly(ethylenimine)/DNA complexes for gene delivery. Proc Natl Acad Sci U S A. Apr. 27, 1999;96(9):5177-81.
Goddard et al., Polymer surface modification for the attachment of bioactive compounds. Progress in Polymer Science. Jul. 2007;32(7):698-725.
Gospodarowicz et al., Effect of fibroblast growth factor on the division and fusion of bovine myoblasts. J Cell Biol. Aug. 1976;70(2 pt 1):395-405.
Grabowska et al., Systemic in vivo delivery of siRNA to tumours using combination of polyethyleneimine and transferrin-polyethyleneimine conjugates. Biomater Sci. Nov. 2015;3(11):1439-48.
Graessley, Entangled Linear, Branched and Network Polymer Systems—Molecular Theories. Adv Poly Sci. 1982;47:67-117.
Griffith et al., Tissue engineering—current challenges and expanding opportunities. Science. Feb. 8, 2002;295(5557):1009-14.
Grimmer et al., Tracheal reconstruction using tissue-engineered cartilage. Arch Otolaryngol Head Neck Surg. Oct. 2004;130(10):1191-6.
Gros et al., A common somitic origin for embryonic muscle progenitors and satellite cells. Nature. Jun. 16, 2005;435(7044):954-8.
Guillaume et al., Two abundant proteasome subtypes that uniquely process some antigens presented by HLA class I molecules. Proc Natl Acad Sci U S A. Oct. 26, 2010;107(43):18599-604.
Gullberg et al., Extracellular matrix and its receptors during development. Int J Dev Biol. Oct. 1995;39(5):845-54.
Guo et al., Droplet microfluidics for high-throughput biological assays. Lab Chip. Jun. 21, 2012;12(12):2146-55.
Gupta et al., Magnetically controlled targeted micro-carrier systems. Life Sci. 1989;44(3):175-86.
Gurkan et al., The mechanical environment of bone marrow: a review. Ann Biomed Eng. Dec. 2008;36(12):1978-91.
Gussoni et al., Dystrophin expression in the mdx mouse restored by stem cell transplantation. Nature. Sep. 23, 1999;401(6751):390-4.
Halim et al., Biologic and synthetic skin substitutes: An overview. Indian J Plast Surg. Sep. 2010;43(Suppl):S23-8.
Hamby et al., Small molecule inhibitors of tumor-promoted angiogenesis, including protein tyrosine kinase inhibitors. Pharmacol Ther. May-Jun. 1999;82(2-3):169-93.
Hamdy et al., Targeting dendritic cells with nano-particulate PLGA cancer vaccine formulations. Adv Drug Deliv Rev. Sep. 10, 2011;63(10-11):943-55.
Hamilton et al., GM-CSF Biology. Growth Factors. Dec. 2004;22(4):225-31.
Hamilton, GM-CSF in inflammation and autoimmunity. Trends Immunol. Aug. 2002;23(8):403-8.
Han et al., Synthesis of rod-like mesoporous silica using mixed surfactants of cetyltrimethylammonium bromide and cetyltrimethylammonium chloride as templates. Materials Letters. 2003;57:4520-4.
Hanada, Efficacy of rehabilitative therapy in regional musculoskeletal conditions. Best Pract Res Clin Rheumatol. Feb. 2003;17(1):151-66.
Hansen et al., Comparison of clinical grade type 1 polarized and standard matured dendritic cells for cancer immunotherapy. Vaccine. Jan. 11, 2013;31(4):639-46.
Hansen et al., Integrin binding and cell spreading on extracellular matrix act at different points in the cell cycle to promote hepatocyte growth. Mol Biol Cell. Sep. 1994;5(9):967-75.
Harding et al., CD28-mediated signalling co-stimulates murine T cells and prevents induction of anergy in T-cell clones. Nature. Apr. 16, 1992;356(6370):607-9.
Harris et al., Open pore biodegradable matrices formed with gas foaming. J Biomed Mater Res. Dec. 5, 1998;42(3):396-402.

Harrison, What is the status of reaction-diffusion theory thirty-four years after turing? J Theor Biol. Apr. 21, 1987;125(4):369-84.
Hartgerink et al., Peptide-amphiphile nanofibers: a versatile scaffold for the preparation of self-assembling materials. Proc Natl Acad Sci U S A. Apr. 16, 2002;99(8):5133-8.
Hartmann et al., CpG DNA: a potent signal for growth, activation, and maturation of human dendritic cells. Proc Natl Acad Sci U S A. Aug. 3, 1999;96(16):9305-10.
Hasan et al., Artificial Antigen Presenting Cells: An Off the Shelf Approach for Generation of Desirable T-Cell Populations for Broad Application of Adoptive Immunotherapy. Advancements in Genetic Engineering. 2015;4(3):1-10.
Hashimoto et al., Development of alginate wound dressings linked with hybrid peptides derived from laminin and elastin. Biomaterials. Mar.-Apr. 2004;25(7-8):1407-14.
Haso et al., Anti-CD22-chimeric antigen receptors targeting B-cell precursor acute lymphoblastic leukemia. Blood. Feb. 14, 2013;121(7):1165-74.
Hawke et al., Myogenic satellite cells: physiology to molecular biology. J Appl Physiol (1985). Aug. 2001;91(2):534-51.
Heath, Cells for tissue engineering. Trends Biotechnol. Jan. 2000;18(1):17-9.
Helm et al., Synergy between interstitial flow and VEGF directs capillary morphogenesis in vitro through a gradient amplification mechanism. Proc Natl Acad Sci U S A. Nov. 1, 2005;102(44):15779-84.
Henry et al., VIVA Investigators. The VIVA trial: Vascular endothelial growth factor in Ischemia for Vascular Angiogenesis. Circulation. Mar. 18, 2003;107(10):1359-65.
Hermanson, Bioconjugate Techniques. Academic Press, New York. pp. 152-186, (1996).
Heslop et al., Transplanted primary neonatal myoblasts can give rise to functional satellite cells as identified using the Myf5nlacZI+ mouse. Gene Ther. May 2001;8(10):778-83.
Hildner et al., Batf3 deficiency reveals a critical role for CD8alpha+ dendritic cells in cytotoxic T cell immunity. Science. Nov. 14, 2008;322(5904):1097-100.
Hill et al., Designing scaffolds to enhance transplanted myoblast survival and migration. Tissue Eng. May 2006;12(5):1295-304.
Hill et al., Muscle satellite (stem) cell activation during local tissue injury and repair. J Anat. Jul. 2003;203(1):89-99.
Hill, Macroporous Scaffold Architecture, Peptide, HGF/FGF and Myoblast Incorporation Enhance Myogenesis. IADR/AADR/CADR 83rd General Session. Mar. 9-12, 2005. Poster #2829.
Hirano et al., Peptide and Protein Presenting Materials for Tissue Engineering. Adv Mat. Jan. 16, 2004;16(1):17-25.
Hodge-Dufour et al., Inhibition of interferon gamma induced interleukin 12 production: a potential mechanism for the anti-inflammatory activities of tumor necrosis factor. Proc Natl Acad Sci U S A. Nov. 10, 1998;95(23):13806-11.
Hodi et al., Immunologic and clinical effects of antibody blockade of cytotoxic T lymphocyte-associated antigen 4 in previously vaccinated cancer patients. Proc Natl Acad Sci U S A. Feb. 26, 2008;105(8):3005-10.
Hodi et al., Improved survival with ipilimumab in patients with metastatic melanoma. N Engl J Med. Aug. 19, 2010;363(8):711-23.
Holland et al., Dual growth factor delivery from degradable oligo(poly(ethylene glycol) fumarate) hydrogel scaffolds for cartilage tissue engineering. Journal of Controlled Release. 2005;101:111-125.
Holland et al., Transforming growth factor-beta 1 release from oligo(poly(ethylene glycol)fumarate) hydrogels in conditions that model the cartilage wound healing environment. J Control Release. Jan. 8, 2004;94(1):101-14.
Hollyman et al., Manufacturing validation of biologically functional T cells targeted to CD19 antigen for autologous adoptive cell therapy. J Immunother. Feb.-Mar. 2009;32(2):169-80.
Horsley et al., IL-4 acts as a myoblast recruitment factor during mammalian muscle growth. Cell. May 16, 2003;113(4):483-94.
Hsiong et al., Differentiation stage alters matrix control of stem cells. J Biomed Mater Res A. Apr. 2008;85A(1):145-56.

(56) References Cited

OTHER PUBLICATIONS

Huang et al., Fabrication and in vitro Testing of Polymeric Delivery Systems for Condensed DNA. J Biomed Mater Res. 2003;67:1384-1392.
Huang et al., Long-Term In Vivo Gene Expression via Delivery of PEI-DNA Condensates From Porous Polymer Scaffolds. Hum Gene Ther. 2005;16(5):609-617.
Hubbell et al., Materials Engineering for Immunomodulation. Nature. 2009;462:449-460.
Hubbell, Biomaterials in tissue engineering. Biotechnology (N Y). Jun. 1995;13(6):565-76.
Huebsch et al., Harnessing traction-mediated manipulation of the cell/matrix interface to control stem-cell fate. Nat Mater. Jun. 2010;9(6):518-26.
Humphries et al., Integrin ligands at a glance. J Cell Sci. Oct. 1, 2006;119(Pt 19):3901-3.
Huppa et al., T-cell-antigen recognition and the immunological synapse. Nat Rev Immunol. Dec. 2003;3(12):973-83.
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Hutson et al., Synthesis and characterization of tunable poly(ethylene glycol): gelatin methacrylate composite hydrogels. Tissue Eng Part A. Jul. 2011;17(13-14):1713-23.
Hwang et al., Fabrication of three-dimensional porous cell-laden hydrogel for tissue engineering. Biofabrication. Sep. 2010;2(3):035003. 12 pages.
Ichida et al., A small-molecule inhibitor of tgf-Beta signaling replaces sox2 in reprogramming by inducing nanog. Cell Stem Cell. Nov. 6, 2009;5(5):491-503.
Iellem et al., Unique chemotactic response profile and specific expression of chemokine receptors CCR4 and CCR8 by CD4(+)CD25(+) regulatory T cells. J Exp Med. Sep. 17, 2001;194(6):847-53.
Ihnat et al., Hypothesis: the 'metabolic memory', the new challenge of diabetes. Diabet Med. Jun. 2007;24(6):582-6.
Il et al., A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. Apr. 2006;69(4):1288-95.
Irintchev et al., Formation of Skeletal Muscle After Subcutaneous Implantation of Cultured Myoblasts. Bio/Technology. p. 366, Abstract 153.06, Jun. 1995.
Irvine et al., Engineering synthetic vaccines using cues from natural immunity. Nat Mater. Nov. 2013;12(11):978-90.
Isern et al., Self-renewing human bone marrow mesenspheres promote hematopoietic stem cell expansion. Cell Rep. May 30, 2013;3(5):1714-24.
Ishihara et al., Roles of bradykinin in vascular permeability and angiogenesis in solid tumor. Int Immunopharmacol. Mar. 2002;2(4):499-509.
Iwamoto et al., Preparation of an Ionic Polymer Gel Microactuator and Measurement of its Periodic Motions. Nippon Kagaku Kaishi. 1997;9:609-614.
Jain et al., Macroporous interpenetrating cryogel network of poly(acrylonitrile) and gelatin for biomedical applications. J Mater Sci Mater Med. Dec. 2009;20 Suppl 1:S173-9.
Jain, Molecular Regeneration of Vessel Maturation. Nat Med. Jun. 1, 2003;9:685-693.
Jain, The manufacturing techniques of various drug loaded biodegradable poly(lactide-co-glycolide) (PLGA) devices. Biomaterials. Dec. 2000;21(23):2475-90.
Jankovic et al., In the absence of IL-12, CD4(+) T cell responses to intracellular pathogens fail to default to a Th2 pattern and are host protective in an IL-10(-/-) setting. Immunity. Mar. 2002;16(3):429-39.
Janmey et al., From tissue mechanics to transcription factors. Differentiation. Oct. 2013;86(3):112-20.
Jego et al., Plasmacytoid dendritic cells induce plasma cell differentiation through type I interferon and interleukin 6. Immunity. Aug. 2003;19(2):225-34.
Jiang et al., Two-piconewton slip bond between fibronectin and the cytoskeleton depends on talin. Nature. Jul. 17, 2003;424(6946):334-7.
Jiang et al., Click hydrogels, microgels and nanogels: emerging platforms for drug delivery and tissue engineering. Biomaterials. Jun. 2014;35(18):4969-85.
Jiang et al., Self-organization of periodic patterns by dissociated feather mesenchymal cells and the regulation of size, number and spacing of primordia. Development. Nov. 1999;126(22):4997-5009.
Jiang, Application of polymers in nucleic acid delivery. Thesis in partial fulfillment of the requirements for the Doctor of Philosophy degree in Pharmacy in the Graduate College of The University of Iowa. 138 pages, Dec. 2011.
Jinushi et al., Enhancing the clinical activity of granulocyte-macrophage colony-stimulating factor-secreting tumor cell vaccines. Immunol Rev. Apr. 2008;222:287-98.
Jinushi et al., MFG-E8-mediated uptake of apoptotic cells by APCs links the pro- and antiinflammatory activities of GM-CSF. J Clin Invest. Jul. 2007;117(7):1902-13.
Johansson, Controlling the Pore Size and Morphology of Mesoporous Silica. Linkoping Studies in Science and Technology Licentiate Thesis No. 1451, 53 pages, (2010).
John et al., Passive and active mechanisms trap activated CD8+ T cells in the liver. J Immunol. May 1, 2004;172(9):5222-9.
Johnson et al., Activation of skeletal muscle satellite cells and the role of fibroblast growth factor receptors. Exp Cell Res. Aug. 1995;219(2):449-53.
Jokinen et al., Integrin-mediated cell adhesion to type I collagen fibrils. J Biol Chem. Jul. 23, 2004;279(30):31956-63.
Jugdutt et al., Aging and defective healing, adverse remodeling, and blunted post-conditioning in the reperfused wounded heart. J Am Coll Cardiol. Apr. 8, 2008;51(14):1399-403.
June et al., Adoptive cellular therapy: a race to the finish line. Sci Transl Med. Mar. 25, 2015;7(280):280ps7.
June et al., The B7 and CD28 receptor families. Immunol Today. Jul. 1994;15(7):321-31.
Juntanon et al., Electrically controlled release of sulfosalicylic acid from crosslinked poly(vinyl alcohol) hydrogel. Int J Pharm. May 22, 2008;356(1-2):1-11.
Kang et al., Effect of Porous Structure on the Degradation of Freeze-Dried Gelatin Hydrogels. J Bioact Compat Poly. Jul. 1, 1999;14(4):331-343.
Kanzler et al., Therapeutic targeting of innate immunity with Toll-like receptor agonists and antagonists. Nat Med. May 2007;13(5):552-9.
Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005;54(1):78-84.
Katayama et al., Integrated analysis of the genome and the transcriptome by FANTOM. Brief Bioinform. Sep. 2004;5(3):249-58.
Kathuria et al., Synthesis and characterization of elastic and macroporous chitosan-gelatin cryogels for tissue engineering. Acta Biomater. Jan. 2009;5(1):406-18.
Kawai et al., Innate immune recognition of viral infection. Nat Immunol. Feb. 2006;7(2):131-7.
Kawashima et al., Pulmonary delivery of insulin with nebulized DL-lactide/glycolide copolymer (PLGA) nanospheres to prolong hypoglycemic effect. J Control Release. Nov. 1, 1999;62(1-2):279-87.
Kearney et al., Macroscale delivery systems for molecular and cellular payloads. Nat Mater. Nov. 2013;12(11):1004-17.
Kennedy et al., Rapid and extensive collapse from electrically responsive macroporous hydrogels. Adv Healthc Mater. Apr. 2014;3(4):500-7.
Khetan et al., Degradation-mediated cellular traction directs stem cell fate in covalently crosslinked three-dimensional hydrogels. Nat Mater. May 2013;12(5):458-65.

(56) References Cited

OTHER PUBLICATIONS

Khownium et al., Novel endotoxin-sequestering compounds with terephthalaldehyde-bis-guanylhydrazone scaffolds. Bioorg Med Chem Lett. Mar. 1, 2006;16(5):1305-8.

Kim et al., An overview of cartilage tissue engineering. Yonsei Med J. Dec. 2000;41(6):766-73.

Kim et al., Galectin-3 binding protein promotes cell motility in colon cancer by stimulating the shedding of protein tyrosine phosphatase kappa by proprotein convertase 5. Biochem Biophys Res Commun. Jan. 7, 2011;404(1):96-102.

Kim et al., Injectable, spontaneously assembling, inorganic scaffolds modulate immune cells in vivo and increase vaccine efficacy. Nat Biotechnol. Jan. 2015;33(1):64-72.

Kim et al., Multifunctional capsule-in-capsules for immunoprotection and trimodal imaging. Angew Chem Int Ed Engl. Mar. 1, 2011;50(10):2317-21.

Kim et al., The effect of VEGF on the myogenic differentiation of adipose tissue derived stem cells within thermosensitive hydrogel matrices. Biomaterials. Feb. 2010;31(6):1213-8.

Kinoshita et al., Successive injections in mdx mice of myoblasts grown with bFGF. Neuromuscul Disord. May 1996;6(3):187-93.

Kisak et al. The vesosome—a multicompartment drug delivery vehicle. Curr Med Chem. Jan. 2004;11(2):199-219.

Klebanoff et al., CD8+ T-cell memory in tumor immunology and immunotherapy. Immunol Rev. Jun. 2006;211:214-24.

Klein et al., Cell-Cycle Control by Physiological Matrix Elasticity and In Viivo Tissue Stiffening. Curr Biol. Sep. 29, 2009;19:1511-1518.

Klinman. Immunotherapeutic uses of CpG oligodeoxynucleotides. Nat Rev Immunol. Apr. 2004;4(4):249-58.

Kohane, Microparticles and nanoparticles for drug delivery. Biotechnol Bioeng. Feb. 1, 2007;96(2):203-9.

Kohrt et al., Donor immunization with WT1 peptide augments antileukemic activity after MHC-matched bone marrow transplantation. Blood. Nov. 10, 2011;118(19):5319-29.

Kondo et al., A reaction-diffusion wave on the skin of the marine angelfish *Pomacanthus*. Nature. Aug. 31, 1995;376(6543):765-8.

Kong et al., Controlling Degradation of Hydrogels via the Size of Cross-Linked Junctions. Adv Mater. Nov. 30, 2004;16(21):1917-1921.

Kong et al., Controlling rigidity and degradation of alginate hydrogels via molecular weight districution. Biomacromolecules. 2004;5:1720-7.

Kong et al., Decoupling the Dependence of Rheological/Mechanical Properties of Hydrogels from Solids Concentration. Polymer. 2002;43(23):6239-6246.

Kong et al., Design of biodegradable hydrogel for the local and sustained delivery of angiogenic plasmid DNA. Pharm Res. May 2008;25(5):1230-8.

Kong et al., Designing alginate hydrogels to maintain viability of immobilized cells. Biomaterials. Oct. 2003;24(22):4023-9.

Kong et al., FRET measurements of cell-traction forces and nanoscale clustering of adhesion ligands varied by substrate stiffness. Proc Natl Acad Sci U S A. Mar. 22, 2005;102(12):4300-5.

Kong et al., Non-viral gene delivery regulated by stiffness of cell adhesion substrates. Nat Mater. Jun. 2005;4(6):460-4.

Koo et al., Bioorthogonal copper-free click chemistry in vivo for tumor-targeted delivery of nanoparticles. Angew Chem Int Ed Engl. Nov. 19, 2012;51(47):11836-40.

Kosuge et al., Morphological Control of Rod- and Fiberlike SBA-15 Type Mesoporous Silica Using Water-Soluble Sodium Silicate. Chem Mater. 2004;16:899-905.

Kratky et al., Direct activation of antigen-presenting cells is required for CD8+ T-cell priming and tumor vaccination. Proc Natl Acad Sci U S A. Oct. 18, 2011;108(42):17414-9.

Kratz, Albumin as a drug carrier: design of prodrugs, drug conjugates and nanoparticles. J Control Release. Dec. 18, 2008;132(3):171-83.

Krieg, Development of TLR9 agonists for cancer therapy. J Clin Invest. May 2007;117(5):1184-94.

Krishnamachari et al., PLGA Microparticles that Co-deliver Antigen and Toll Like Receptor Ligand Adjuvants for Applications in Cancer Immunotherapy. AAPS Annual Meeting and Exposition. Nov. 9, 2009. 1 page.

Kumamoto et al., Induction of tumor-specific protective immunity by in situ Langerhans cell vaccine. Nat Biotechnol. Jan. 2002;20(1):64-9.

Kumar et al., Toll-like receptors and innate immunity. Biochem Biophys Res Commun. Oct. 30, 2009;388(4):621-5.

Kupferschmidt et al., Mesoporous silica particles potentiate antigen-specific T-cell responses. Nanomedicine (Lond). 2014;9(12):1835-46.

Kuwahara et al., Cell delivery using an injectable and adhesive transglutaminase-gelatin gel. Tissue Eng Part C Methods. Aug. 2010;16(4):609-18.

Kwon et al., Electrically erodible polymer gel for controlled release of drugs. Nature. Nov. 28, 1991;354(6351):291-3.

Kwon et al., In vivo targeting of dendritic cells for activation of cellular immunity using vaccine carriers based on pH-responsive microparticles. Proc Natl Acad Sci U S A. Dec. 20, 2005;102(51):18264-8.

Kyi et al., Checkpoint blocking antibodies in cancer immunotherapy. FEBS Lett. Jan. 21, 2014;588(2):368-76.

Lacy et al., Cytokine release from innate immune cells: association with diverse membrane trafficking pathways. Blood. 2011;118(1):9-18.

Langenkamp et al., Kinetics of dendritic cell activation: impact on priming of TH1, TH2 and nonpolarized T cells. Nat Immunol. Oct. 2000;1(4):311-6.

Langer et al., Tissue engineering. Science. May 14, 1993;260(5110):920-6.

Lanzavecchia et al., Regulation of T cell immunity by dendritic cells. Cell. Aug. 10, 2001;106(3):263-6.

Lao et al., Magnetic and hydrogel composite materials for hyperthermia applications. J Mater Sci Mater Med. Oct. 2004;15(10):1061-4.

Latorre et al., Applications of magnetic nanoparticles in medicine: magnetic fluid hyperthermia. P R Health Sci J. Sep. 2009;28(3):227-38.

Latz et al., TLR9 signals after translocating from the ER to CpG DNA in the lysosome. Nat Immunol. Feb. 2004;5(2):190-8.

Lauterbach et al., Mouse CD8alpha+ DCs and human BDCA3+ DCs are major producers of IFN-lambda in response to poly IC. J Exp Med. Nov. 22, 2010;207(12):2703-17.

Lauw et al., Proinflammatory effects of IL-10 during human endotoxemia. J Immunol. Sep. 1, 2000;165(5):2783-9.

Leach et al., Coating of VEGF-releasing scaffolds with bioactive glass for angiogenesis and bone regeneration. Biomaterials. Jun. 2006;27(17):3249-55.

Lee et al., Chemical tumor-targeting of nanoparticles based on metabolic glycoengineering and click chemistry. ACS Nano. Mar. 25, 2014;8(3):2048-63.

Lee et al., Controlling Mechanical and Swelling Properties of Alginate Hydrogels Independently by Cross-Linker Type and Cross-Linking Density. Macromolecules. Apr. 2000;33(11):4291-4294.

Lee et al., Effect of dual treatment with SDF-1 and BMP-2 on ectopic and orthotopic bone formation. PLoS One. Mar. 17, 2015;10(3):e0120051, 15 pages.

Lee et al., Engineering liver tissue spheroids with inverted colloidal crystal scaffolds. Biomaterials. Sep. 2009;30(27):4687-94.

Lee et al., Hydrogel Formation via Vell Crosslinking. Advanced Materials. Nov. 2003;15(21):1828-1832.

Lee et al., Hydrogels for tissue engineering. Chem Rev. Jul. 2001;101(7):1869-79.

Lee et al., Intravenous hMSCs improve myocardial infarction in mice because cells embolized in lung are activated to secrete the anti-inflammatory protein TSG-6. Cell Stem Cell. Jul. 2, 2009;5(1):54-63.

Lee et al., The immunological synapse balances T cell receptor signaling and degradation. Science. Nov. 14, 2003;302(5648):1218-22.

(56) References Cited

OTHER PUBLICATIONS

Lefaucheur et al., The cellular events of injured muscle regeneration depend on the nature of the injury. Neuromuscul Disord. Nov. 1995;5(6):501-9.
Lele et al., Investigating complexity of protein-protein interactions in focal adhesions. Biochem Biophys Res Commun. May 9, 2008;369(3):929-34.
Lensch et al., Scientific and clinical opportunities for modeling blood disorders with embryonic stem cells. Blood. Apr. 1, 2006;107(7):2605-12.
Leor et al., Cells, scaffolds, and molecules for myocardial tissue engineering. Pharmacol Ther. Feb. 2005;105(2):151-63.
Leshem et al., Hepatocyte growth factor (HGF) inhibits skeletal muscle cell differentiation: a role for the bHLH protein twist and the cdk inhibitor p27. J Cell Physiol. Jul. 2000;184(1):101-9.
Letsinger et al., Phosphoramidate analogs of oligonucleotides. J Org Chem. Nov. 1970;35(11):3800-3.
Levental et al., Soft biological materials and their impact on cell function. Soft Matter. 2007;3:299-306.
Levine et al., Effects of CD28 costimulation on long-term proliferation of CD4+ T cells in the absence of exogenous feeder cells. J Immunol. Dec. 15, 1997;159(12):5921-30.
Li et al., Effect of growth factors and extracellular matrix materials on the proliferation and differentiation of microencapsulated myoblasts. J Biomater Sci Polym Ed. 2003;14(6):533-49.
Li et al., Effects of Three-Dimensional Scaffolds on Cell Organization and Tissue Development. Biotechnology and Bioprocess Engineering. Oct. 2001;6(5):311-325.
Li et al., Mesoporous silica nanoparticles in biomedical applications. Chem Soc Rev. Apr. 7, 2012;41(7):2590-605.
Li et al., pH sensitive Laponite/alginate hybrid hydrogels: swelling behaviour and release mechanism. Soft Matter. 2011;7:6231-6238.
Li et al., Purified hybrid cells from dendritic cell and tumor cell fusions are superior activators of antitumor immunity. Cancer Immunol Immunother. Nov. 2001;50(9):456-62.
Li et al., Recent advances of biomaterials in biotherapy. Regen Biomater. Jun. 2016;3(2):99-105.
Li et al., The effect of surface modification of mesoporous silica micro-rod scaffold on immune cell activation and infiltration. Biomaterials. Mar. 2016;83:249-56.
Li, TNF-alpha is a mitogen in skeletal muscle. Am J Physiol Cell Physiol. Aug. 2003;285(2):C370-6.
Liao et al., Synthesis of mesoporous silica nanoparticle-encapsulated alginate microparticles for sustained release and targeting therapy. J Biomed Mater Res B Appl Biomater. Feb. 2014;102(2):293-302.
Liederer et al., Enzymes involved in the bioconversion of ester-based prodrugs. J Pharm Sci. Jun. 2006;95(6):1177-95.
Lin et al., Transdermal regulation of vascular network bioengineering using a photopolymerizable methacrylated gelatin hydrogel. Biomaterials. Sep. 2013;34(28):6785-96.
Lindstein et al., Regulation of lymphokine messenger RNA stability by a surface-mediated T cell activation pathway. Science. Apr. 21, 1989;244(4902):339-43.
Linsley et al., The role of the CD28 receptor during T cell responses to antigen. Annu Rev Immunol. 1993;11:191-212.
Lipson et al., Ipilimumab: an anti-CTLA-4 antibody for metastatic melanoma. Clin Cancer Res. Nov. 15, 2011;17(22):6958-62.
Lipton et al., Developmental fate of skeletal muscle satellite cells. Science. Sep. 21, 1979;205(4412):1292-4.
Liu et al., Heterobifunctional poly(ethylene glycol)-tethered bone morphogenetic protein-2-stimulated bone marrow mesenchymal stromal cell differentiation and osteogenesis. Tissue Eng. May 2007;13(5):1113-24.
Liu et al., Immunostimulatory CpG oligodeoxynucleotides enhance the immune response to vaccine strategies involving granulocyte-macrophage colony-stimulating factor. Blood. Nov. 15, 1998;92(10):3730-6.
Liu et al., Nanostructured materials designed for cell binding and transduction. Biomacromolecules. 2001 Summer;2(2):362-8.
Liu et al., On the viscoelastic character of liver tissue: experiments and modelling of the linear behaviour. Biorheology. 2000;37(3):191-201.
Liu et al., Porous nanoparticle supported lipid bilayers (protocells) as delivery vehicles. J Am Chem Soc. Feb. 4, 2009;131(4):1354-5.
Liu et al., Preparation of uniform calcium alginate gel beads by membrane emulsification coupled with internal gelation. Journal of Applied Polymer Science. Nov. 22, 2002;87(5):848-852.
Liu, Dendritic cell subsets and lineages, and their functions in innate and adaptive immunity. Cell. Aug. 10, 2001;106(3):259-62.
Lo et al., Cell movement is guided by the rigidity of the substrate. Biophys J. Jul. 2000;79(1):144-52.
Lodish et al., Collagen: The Fibrous Proteins of the Matrix. Molecular Cell Biology. W.H. Freeman, New York. 2000;Section 22.3:979-985.
Lopez et al., Magnetic Applications of Polymer Gels. Macromol Symp. 2001;166(1):173-178.
Lozinsky et al., Polymeric cryogels as promising materials of biotechnological interest. Trends Biotechnol. Oct. 2003;21(10):445-51.
Lu et al., Muscle-derived stem cells seeded into acellular scaffolds develop calcium-dependent contractile activity that is modulated by nicotinic receptors. Urology. Jun. 2003;61(6):1285-91.
Lubeck, The costs of musculoskeletal disease: health needs assessment and health economics. Best Pract Res Clin Rheumatol. Jun. 2003;17(3):529-39.
Ludewig et al., Immunotherapy with dendritic cells directed against tumor antigens shared with normal host cells results in severe autoimmune disease. J Exp Med. Mar. 6, 2000;191(5):795-804.
Lumelsky et al., Differentiation of embryonic stem cells to insulin-secreting structures similar to pancreatic islets. Science. May 18, 2001;292(5520):1389-94.
Lungu et al., Linear and Branched PEIs (Polyethylenimines) and Their Property Space. Int J Mol Sci. Apr. 13, 2016;17(4):555.
Lutolf et al., Repair of bone defects using synthetic mimetics of collagenous extracellular matrices. Nat Biotechnol. May 2003;21(5):513-8.
Lutterotti et al., Antigen-specific tolerance by autologous myelin peptide-coupled cells: a phase 1 trial in multiple sclerosis. Sci Transl Med. Jun. 5, 2013;5(188):188ra75.
Mach et al., Differences in dendritic cells stimulated in vivo by tumors engineered to secrete granulocyte-macrophage colony-stimulating factor or Flt3-ligand. Cancer Res. Jun. 15, 2000;60(12):3239-46.
Magram et al., IL-12-deficient mice are defective but not devoid of type 1 cytokine responses. Ann N Y Acad Sci. Oct. 31, 1996;795:60-70.
Mahony et al., Mesoporous silica nanoparticles act as a self-adjuvant for ovalbumin model antigen in mice. Small. Sep. 23, 2013;9(18):3138-46.
Mailander et al., Complete remission in a patient with recurrent acute myeloid leukemia induced by vaccination with WT1 peptide in the absence of hematological or renal toxicity. Leukemia. Jan. 2004;18(1):165-6.
Maini, Spatial and spatio-temporal patterns in a cell-haptotaxis model. J Math Biol. 1989;27(5):507-22.
Majeti et al., Identification of a hierarchy of multipotent hematopoietic progenitors in human cord blood. Cell Stem Cell. Dec. 13, 2007;1(6):635-45.
Maldonado et al., How tolerogenic dendritic cells induce regulatory T cells. Adv Immunol. 2010;108:111-65.
Maley et al., Extracellular matrix, growth factors,genetics: their influence on cell proliferation and myotube formation in primary cultures of adult mouse skeletal muscle. Exp Cell Res. Jul. 1995;219(1):169-79.
Malhotra et al., Use of an oncolytic virus secreting GM-CSF as combined oncolytic and immunotherapy for treatment of colorectal and hepatic adenocarcinomas. Surgery. Apr. 2007;141(4):520-9.
Malmqvist, Biospecific interaction analysis using biosensor technology. Nature. Jan. 14, 1993;361(6408):186-7.
Mammoto et al., Mechanical control of tissue and organ development. Development. May 2010;137(9):1407-20.

(56) References Cited

OTHER PUBLICATIONS

Manavski et al., Vascular niche controls organ regeneration. Circ Res. Mar. 28, 2014;114(7):1077-9.
Mandal et al., Polymer-based synthetic dendritic cells for tailoring robust and multifunctional T cell responses. ACS Chem Biol. Feb. 20, 2015;10(2):485-92.
Mangsbo et al., Enhanced tumor eradication by combining CTLA-4 or PD-1 blockade with CpG therapy. J Immunother. Apr. 2010;33(3):225-35.
Mansoor et al., Engineering T cells for cancer therapy. Br J Cancer. Nov. 14, 2005;93(10):1085-91.
Manzari-Tavakoli et al., The Cross-Talks Among Bone Morphogenetic Protein (BMP) Signaling and Other Prominent Pathways Involved in Neural Differentiation. Front Mol Neurosci. Mar. 15, 2022;15:827275, 15 pages.
Martinsen et al., Alginate as immobilization material: I. Correlation between chemical and physical properties of alginate gel beads. Biotechnol Bioeng. Jan. 5, 1989;33(1):79-89.
Marui et al., Simultaneous application of basic fibroblast growth factor and hepatocyte growth factor to enhance the blood vessels formation. J Vasc Surg. Jan. 2005;41(1):82-90.
Masedunskas et al., Role for the actomyosin complex in regulated exocytosis revealed by intravital microscopy. Proc Natl Acad Sci U S A. Aug. 16, 2011;108(33):13552-7.
Massia et al., An RGD spacing of 440 nm is sufficient for integrin alpha V beta 3-mediated fibroblast spreading and 140 nm for focal contact and stress fiber formation. J Cell Biol. Sep. 1991;114(5):1089-100.
Matthew et al., Subperiosteal behaviour of alginate and cellulose wound dressing materials. Biomaterials. Mar. 1995;16(4):275-8.
Maus et al., Ex vivo expansion of polyclonal and antigen-specific cytotoxic T lymphocytes by artificial APCs expressing ligands for the T-cell receptor, CD28 and 4-1BB. Nat Biotechnol. Feb. 2002;20(2):143-8.
McColl, Chemokines and dendritic cells: a crucial alliance. Immunol Cell Biol. Oct. 2002;80(5):489-96.
McConnell et al., Vaccination with outer membrane complexes elicits rapid protective immunity to multidrug-resistant Acinetobacter baumannii. Infect Immun. Jan. 2011;79(1):518-26.
McDonald et al., Early fracture callus displays smooth muscle-like viscoelastic properties ex vivo: implications for fracture healing. J Orthop Res. Nov. 2009;27(11):1508-13.
McKay et al., Click chemistry in complex mixtures: bioorthogonal bioconjugation. Chem Biol. Sep. 18, 2014;21(9):1075-101.
McKinney-Freeman et al., Muscle-derived hematopoietic stem cells are hematopoietic in origin. Proc Natl Acad Sci U S A. Feb. 5, 2002;99(3):1341-6.
McKinnon et al., Biophysically defined and cytocompatible covalently adaptable networks as viscoelastic 3D cell culture systems. Adv Mater. Feb. 12, 2014;26(6):865-72.
McPherron et al., Regulation of skeletal muscle mass in mice by a new TGF-beta superfamily member. Nature. May 1, 1997;387(6628):83-90.
McQualter et al., Granulocyte macrophage colony-stimulating factor: a new putative therapeutic target in multiple sclerosis. J Exp Med. Oct. 1, 2001;194(7):873-82.
McWhorter et al., Modulation of macrophage phenotype by cell shape. Proc Natl Acad Sci USA. Oct. 22, 2013;110(43):17253-8.
Mehta et al., Engineering New Approaches to Cancer Vaccines. Cancer Immunol Res. Aug. 2015;3(8):836-43.
Meier et al., Peptide Nucleic Acids(PNAs)-Unusual Properties of Noionic Oligonucleotide Analogues. Angewandte Chemie, Int'l Edition. Aug. 1992;31(8):1008-1010.
Melero-Martin et al., Engineering robust and functional vascular networks in vivo with human adult and cord blood-derived progenitor cells. Circ Res. Jul. 18, 2008;103(2):194-202. Includes supplementary materials.
Melief et al., Immunotherapy of established (pre)malignant disease by synthetic long peptide vaccines. Nat Rev Cancer. May 2008;8(5):351-60.
Melief et al., T-cell immunotherapy of tumors by adoptive transfer of cytotoxic T lymphocytes and by vaccination with minimal essential epitopes. Immunol Rev. Jun. 1995;145:167-77.
Mellman et al., Dendritic cells: specialized and regulated antigen processing machines. Cell. Aug. 10, 2001;106(3):255-8.
Menetry et al., Suturing Versus Immobilization of a Muscle Laceration: A Morphological and Functional Study in a Mouse Model. Am J Sports Med. 1999;27(2):222-229.
Meng et al., Use of a lipid-coated mesoporous silica nanoparticle platform for synergistic gemcitabine and paclitaxel delivery to human pancreatic cancer in mice. ACS Nano. 2015;9(4):3540-57.
Meraz et al., Mesoporous Silicon Particles for the Presentation of Tumor Antigens and Adjuvant for Anti-Cancer Immunity. Cancer Res. 2011;71(S24):159s-160s, Abstract #P1-01-12.
Merck, Merck Announces Presentation of Interim Data from Phase 1B Study of MK-3475, Investigational anti-PD-1 Immunotherapy, in Previously-Treated Patients with Non-Small Cell Lung Cancer (NSCLC) at 15th World Conference on Lung Cancer. Merck Newsroom Home. 3 pages, Oct. 29, 2013.
Merkel et al., Using mechanobiological mimicry of red blood cells to extend circulation times of hydrogel microparticles. Proc Natl Acad Sci U S A. Jan. 11, 2011;108(2):586-91.
Merriam-Webster, Transient. Merriam-Webster Dictionary. Web. Jul. 18, 2014. www.merriam-webster.com/dictionary/transient. 3 pages.
MeSH, Nivolumab. Retrieved online at: https://www.ncbi.nlm.nih.gov/mesh/?term=nivolumab. 2 pages, (2010).
Metters et al., Fundamental studies of biodegradable hydrogels asmaterials. Biomed Sci Instrum. 1999;35:33-8.
Meyer et al., Biodegradable nanoellipsoidal artificial antigen presenting cells for antigen specific T-cell activation. Small. Apr. 2015;11(13):1519-25.
Meyer et al., Clinical investigations of Toll-like receptor agonists. Expert Opin Investig Drugs. Jul. 17, 2008(7):1051-65.
Meylan et al., Intracellular pattern recognition receptors in the host response. Nature. Jul. 6, 2006;442(7098):39-44.
MGI, Mouse Facts. Retrieved online at: http://www.informatics.jax.org/mgihome/other/mouse_facts1.shtml. 2 pages. Jul. 31, 2018.
Miljkovic et al., Chondrogenesis, bone morphogenetic protein-4 and mesenchymal stem cells. Osteoarthritis Cartilage. Oct. 2008;16(10):1121-30.
Millar et al., Prediction of local recurrence, distant metastases, and death after breast-conserving therapy in early-stage invasive breast cancer using a five-biomarker panel. J Clin Oncol. Oct. 1, 2009;27(28):4701-8.
Miller et al., Hepatocyte growth factor affects satellite cell activation and differentiation in regenerating skeletal muscle. Am J Physiol Cell Physiol. Jan. 2000;278(1):C174-81.
Miller et al., Lipopolysaccharide sequestrants: structural correlates of activity and toxicity in novel acylhomospermines. J Med Chem. Apr. 7, 2005;48(7):2589-99.
Miller et al., Melanoma. N Engl J Med. Jul. 6, 2006;355(1):51-65.
Milone et al., Powered and controlled T-cell production. Nat Biomed Eng. Mar. 2018;2(3):148-150.
Miralles et al., Actin dynamics control SRF activity by regulation of its coactivator MAL. Cell. May 2, 2003;113(3):329-42.
Mitchell et al., The exogenous administration of basic fibroblast growth factor to regenerating skeletal muscle in mice does not enhance the process of regeneration. Growth Factors. 1996;13(1-2):37-55.
Miyata et al., Biomolecule-sensitive hydrogels. Adv Drug Deliv Rev. Jan. 17, 2002;54(1):79-98.
Mohan et al., Novel Porous, Polysaccharide Scaffolds for Tissue Engineering Applications. Trends Biomater Artif Organs. 2005;18(2):219-224.
Moioli et al., Matrices and scaffolds for drug delivery in dental, oral and craniofacial tissue engineering. Adv Drug Deliv Rev. May 30, 2007;59(4-5):308-24.
Molinari et al., Modification of surface membrane antigens by trypsin. Proc Soc Exp Biol Med. Apr. 1975;148(4):991-4.
Molloy et al., Movement and force produced by a single myosin head. Nature. Nov. 9, 1995;378(6553):209-12.

(56) References Cited

OTHER PUBLICATIONS

Mooney et al., Cytoskeletal filament assembly and the control of cell spreading and function by extracellular matrix. J Cell Sci. Jun. 1995; 108 (Pt 6):2311-20.
Mooney et al., Switching from differentiation to growth in hepatocytes: control by extracellular matrix. J Cell Physiol. Jun. 1992;151(3):497-505.
Moser et al., Dendritic cell regulation of TH1-TH2 development. Nat Immunol. Sep. 2000;1(3):199-205.
Mu et al., Identification and characterization of a mannose-binding lectin from Nile tilapia (Oreochromis niloticus). Fish Shellfish Immunol. 2017;67:244-253.
Mulder et al., Wound Management: Past, Present, and Future. Clinicians' Pocket Guide to Chronic Wound Repair. Springhouse Corporation, Springhouse, Pennsylvania. 1998:85-90.
Muralidharan-Chari et al., ARF6-regulated shedding of tumor cell-derived plasma membrane microvesicles. Curr Biol. Dec. 1, 2009;19(22):1875-85.
Murdan, Electro-responsive drug delivery from hydrogels. J Control Release. Sep. 19, 2003;92(1-2):1-17.
Murray et al., Discussion: Turing's Theory of Morphogenesis—Its Influence on Modelling Biological Pattern and Form. Bull Math Biol. 1990;52(1-2):119-152.
Nagai et al., A variant of yellow fluorescent protein with fast and efficient maturation for cell-biological applications. Nat Biotechnol. Jan. 2002;20(1):87-90.
Naik et al., Development of plasmacytoid and conventional dendritic cell subtypes from single precursor cells derived in vitro and in vivo. Nat Immunol. Nov. 2007;8(11):1217-26.
NCBI Accession No. 000749.2, Apr. 1, 2012.
NCBI Accession No. 001020537, Jan. 30, 2011.
NCBI Accession No. 001020538, Jan. 30, 2011.
NCBI Accession No. 001020539, Jan. 30, 2011.
NCBI Accession No. 001020540, Jan. 30, 2011.
NCBI Accession No. 001028928, Jan. 30, 2011.
NCBI Accession No. 001193, May 3, 2014.
NCBI Accession No. 001552.2, Mar. 16, 2014.
NCBI Accession No. 001561.5, Mar. 16, 2014.
NCBI Accession No. 003237.2, May 25, 2014.
NCBI Accession No. 003265, Dec. 30, 2012.
NCBI Accession No. 003318.1, May 4, 2014.
NCBI Accession No. 003327.3, May 4, 2014.
NCBI Accession No. 003367, Jan. 30, 2011.
NCBI Accession No. 004119, Apr. 14, 2013.
NCBI Accession No. 004448.3, Apr. 23, 2014.
NCBI Accession No. 005009.2, Apr. 27, 2014.
NCBI Accession No. 005018.2, Apr. 27, 2014.
NCBI Accession No. 006274.2, Mar. 31, 2013.
NCBI Accession No. 017442, Apr. 14, 2012.
NCBI Accession No. 059138, Apr. 14, 2012.
NCBI Accession No. 181780.3, Jan. 27, 2014.
NCBI Accession No. 861445.3, Jan. 27, 2014.
NCBI, MeSH. Nivolumab. Retrieved online at: https://www.ncbi.nlm.nih/gov/mesh/?term=nivolumab. 3 pages, (2010).
Nehls et al., A novel, microcarrier-based in vitro assay for rapid and reliable quantification of three-dimensional cell migration and angiogenesis. Microvasc Res. Nov. 1995;50(3):311-22.
Nestle et al., Vaccination of melanoma patients with peptide- or tumorlysate-pulsed dendritic cells. Nature Medicine. Mar. 1, 1998;4(3):328-32.
Niamlang et al., Electrically controlled release of salicylic acid from poly(p-phenylene vinylene)/polyacrylamide hydrogels. Int J Pharm. Apr. 17, 2009;371(1-2):126-33.
Nichol et al., Cell-laden microengineered gelatin methacrylate hydrogels. Biomaterials. Jul. 2010;31(21):5536-44.
Nicodemus et al., Cell encapsulation in biodegradable hydrogels for tissue engineering applications. Tissue Eng Part B Rev. Jun. 2008;14(2):149-65.
Niessen et al., The alpha 6 beta 4 integrin is a receptor for both laminin and kalinin. Exp Cell Res. Apr. 1994;211(2):360-7.

NIH—National Cancer Institute, AMP-224, anti-PD-1 fusion protein AMP-224. Retrieved online at: https://www.cancer/gov/publications/dictionaries/cancer-drug/def/anti-pd-1-fusion-protein-amp-224. 1 page, (2019).
Noguera-Troise et al., Blockade of Dll4 inhibits tumour growth by promoting non-productive angiogenesis. Nature. Dec. 21, 2006;444(7122):1032-7.
Nuttelman et al., Dexamethasone-functionalized gels induce osteogenic differentiation of encapsulated hMSCs. J Biomed Mater Res A. Jan. 2006;76(1):183-95.
Ní Annaidh et al., Characterization of the anisotropic mechanical properties of excised human skin. J Mech Behav Biomed Mater. Jan. 2012;5(1):139-48.
O'Garra et al., Are dendritic cells afraid of commitment? Nat Immunol. Dec. 2004;5(12):1206-8.
O'Shea et al., Type 1 IFNs and regulation of TH1 responses: enigmas both resolved and emerge. Nat Immunol. Jul. 2000;1(1):17-9.
Ohashi et al., Surgical excision combined with autologous whole tumor cell vaccination is an effective therapy for murine neuroblastoma. J Pediatr Surg. Aug. 2006;41(8):1361-8.
Ohlstein et al., The stem cell niche: theme and variations. Curr Opin Cell Biol. Dec. 2004;16(6):693-9.
Oldenburg et al., TLR13 recognizes bacterial 23S rRNA devoid of erythromycin resistance-forming modification. Science. Aug. 31, 2012;337(6098):1111-5.
Oldenhove et al., Decrease of Foxp3+ Treg cell number and acquisition of effector cell phenotype during lethal infection. Immunity. Nov. 20, 2009;31(5):772-86.
Oneto et al., Implantable biomaterial based on click chemistry for targeting small molecules. Acta Biomaterialia. 2014;10:5099-5105.
Orner et al., Arrays for the combinatorial exploration of cell adhesion. J Am Chem Soc. Sep. 8, 2004;126(35):10808-9.
Osunkoya et al., Synthesis and fate of immunological surface receptors on cultured Burkitt lymphoma cells. Int J Cancer. Mar. 15, 1969;4(2):159-65.
Ota et al., Percutaneous subxiphoid access to the epicardium using a miniature crawling robotic device. Innovations (Phila). 2006 Fall;1(5):227-31.
Overwijk et al., Tumor regression and autoimmunity after reversal of a functionally tolerant state of self-reactive CD8+ T cells. J Exp Med. Aug. 18, 2003;198(4):569-80.
Ozawa et al., Microenvironmental VEGF concentration, not total dose, determines a threshold between normal and aberrant angiogenesis. J Clin Invest. Feb. 2004;113(4):516-27.
Padilla et al., Insufficient TLR activation contributes to the slow development of CD8+ T cell responses in Trypanosoma cruzi infection. J Immunol. Jul. 15, 2009;183(2):1245-52.
Page-McCaw et al., Matrix metalloproteinases and the regulation of tissue remodelling. Nat Rev Mol Cell Biol. Mar. 2007;8(3):221-33.
Pailler-Mattei et al., In vivo measurements of the elastic mechanical properties of human skin by indentation tests. Med Eng Phys. Jun. 2008;30(5):599-606.
Pajonk et al., From sol-gel to aerogels and cryogels. J Non Cryst Solids. May 1990;(1-3):66-67.
Palacio et al., Interleukin 10 and tumor necrosis factor alpha gene expression in respiratory and peripheral muscles. Relation to sarcolemmal damage. Arch Bronconeumol. Jul. 2002;38(7):311-6.
Paradee et al., Effects of crosslinking ratio, model drugs, and electric field strength on electrically controlled release for alginate-based hydrogel. J Mater Sci Mater Med. Apr. 2012;23(4):999-1010.
Pardoll, The blockade of immune checkpoints in cancer immunotherapy. Mar. 22, 2012;12(4):252-64.
Parekh et al., Modulus-driven differentiation of marrow stromal cells in 3D scaffolds that is independent of myosin-based cytoskeletal tension. Biomaterials. Mar. 2011;32(9):2256-64.
Parekkadan et al., Mesenchymal stem cell-derived molecules reverse fulminant hepatic failure. PLoS One. Sep. 26, 2007;2(9):e941.
Park et al., Photopolymerized hyaluronic acid-based hydrogels andnetworks. Biomaterials. Mar. 2003;24(6):893-900.
Parker et al., Effect of mitoxantrone on outcome of children with first relapse of acute lymphoblastic leukaemia (ALL R3): an open-label randomised trial. Lancet. Dec. 11, 2010;376(9757):2009-17.

(56) References Cited

OTHER PUBLICATIONS

Partridge et al., Conversion of mdx myofibres from dystrophin-negative to -positive by injection of normal myoblasts. Nature. Jan. 12, 1989;337(6203):176-9.
Patterson et al., Differential binding of chemokines to macrophageshuman inflamed synovium. Arthritis Res. 2002;4(3):209-14.
Pawlaczyk et al., Age-dependent biomechanical properties of the skin. Postepy Dermatol Alergol. Oct. 2013;30(5):302-6.
Pedersen et al., Induction of regulatory dendritic cells by dexamethasone and 1alpha,25-Dihydroxyvitamin D(3). Immunol Lett. Jan. 30, 2004;91(1):63-9.
Pek et al., The effect of matrix stiffness on mesenchymal stem cellthixotropic gel. Biomaterials. Jan. 2010;31(3):385-91.
Pelinkovic et al., Tissue engineering and gene therapy of the musculoskeletal system with muscle cells. Z Orthop Ihre Grenzgeb. Sep.-Oct. 2000;138(5):402-6.
Pena et al., Effects of TGF-beta and TGF-beta neutralizing antibodies on fibroblast-induced collagen gel contraction: implications for proliferative vitreoretinopathy. Invest Ophthalmol Vis Sci. May 1994;35(6):2804-8.
Perica et al., Enrichment and Expansion with Nanoscale Artificial Antigen Presenting Cells for Adoptive Immunotherapy. ACS Nano. Jul. 28, 2015;9(7):6861-71.
Peters et al., Engineering vascular networks in porous polymer matrices.Res. Jun. 15, 2002;60(4):668-78.
Peyton et al., The use of poly(ethylene glycol) hydrogels to investigate the impact of ECM chemistry and mechanics on smooth muscle cells. Biomaterials. Oct. 2006;27(28):4881-93.
Phillippi, Patterning of Multiple Cell Lineages from a Single Stem Cell Population. Annual Meeting of the American Society for Cell Biology. Dec. 10, 2006.
Pinho et al., PDGFRa and CD51 mark human nestin+ sphere-forming mesenchymal stem cells capable of hematopoietic progenitor cell expansion. J Exp Med. Jul. 1, 2013;210(7):1351-67.
Platten et al., Cancer Immunotherapy by Targeting IDO1/TDO and Their Downstream Effectors. Front Immunol. Jan. 12, 2015;5:673. 7 pages.
Pluen et al., Role of tumor-host interactions in interstitial diffusion of macromolecules: cranial vs. subcutaneous tumors. Proc Natl Acad Sci U S A. Apr. 10, 2001;98(8):4628-33.
Pooyan et al., Conjugates bearing multiple formyl-methionyl peptides display enhanced binding to but not activation of phagocytic cells. Bioconjug Chem. Mar.-Apr. 2002;13(2):216-23.
Pope et al., Organ-specific regulation of the CD8 T cell response to Listeria monocytogenes infection. J Immunol. Mar. 1, 2001;166(5):3402-9.
Porter et al., Separation of Natural Populations of Coliform Bacteria from Freshwater and Sewage by Magnetic-Bead Cell Sorting. J Microbiol Meth. 1998;33(3):221-226.
Pouzet et al., Factors affecting functional outcome after autologous skeletal myoblast transplantation. Ann Thorac Surg. Mar. 2001;71(3):844-50; discussion 850-1.
PRNewswire, GlaxoSmithKline and Amplimmune Form Global Strategic Collaboration. Alliance to Focus on AMP-224 for Cancer and Other Diseases. 3 pages, Aug. 4, 2010.
Pulendran et al., Flt3-ligand and granulocyte colony-stimulating factor mobilize distinct human dendritic cell subsets in vivo. J Immunol. Jul. 1, 2000;165(1):566-72.
Qi et al., Patterned differentiation of individual embryoid bodies in spatially organized 3D hybrid microgels. Adv Mater. Dec. 7, 2010;22(46):5276-81.
Qiao et al., Synthesis and Bio-adsorptive Properties of Large-Pore Periodic Mesoporous Organosilica Rods. Chem Mater. 2005;17:6172-6.
Qin et al., CD22-Targeted Chimeric Antigen Receptor (CAR) T Cells Containing The 4-1BB Costimulatory Domain Demonstrate Enhanced Persistence and Superior Efficacy Against B-Cell Precursor Acute Lymphoblastic Leukemia (ALL) Compared To Those Containing CD28. Blood. 2013;122:1431.
Qin et al., Soft lithography for micro- and nanoscale patterning. Nat Protoc. Mar. 2010;5(3):491-502.
Qiu et al., Environment-sensitive hydrogels for drug delivery. Adv Drug Deliv Rev. Dec. 31, 2001;53(3):321-39.
Qu et al., Development of approaches to improve cell survival in myoblast transfer therapy. J Cell Biol. Sep. 7, 1998;142(5):1257-67.
Qu-Petersen et al., Identification of a novel population of muscle stem cells in mice: potential for muscle regeneration. J Cell Biol. May 27, 2002;157(5):851-64.
Quezada et al., CTLA4 blockade and GM-CSF combination immunotherapy alters the intratumor balance of effector and regulatory T cells. J Clin Invest. Jul. 2006;116(7):1935-45.
Quintana et al., Autoantibody patterns in diabetes-prone NOD mice and in standard C57BL/6 mice. J Autoimmun. Nov. 2001;17(3):191-7.
Raeber et al., Molecularly engineered PEG hydrogels: a novel model system for proteolytically mediated cell migration. Biophys J. Aug. 2005;89(2):1374-88.
Rajagopalan et al., Regional angiogenesis with vascular endothelial growth factor in peripheral arterial disease: a phase II randomized, double-blind, controlled study of adenoviral delivery of vascular endothelial growth factor 121 in patients with disabling intermittent claudication. Circulation. Oct. 21, 2003;108(16):1933-8.
Ramón-Azcón et al., Gelatin methacrylate as a promising hydrogel for 3D microscale organization and proliferation of dielectrophoretically patterned cells. Lab on a Chip. Aug. 21, 2012;12(16):2959-69.
Randolph et al., Migration of dendritic cell subsets and their precursors. Annu Rev Immunol. 2008;26:293-316.
Ranganath et al., Harnessing the mesenchymal stem cell secretome for the treatment of cardiovascular disease. Cell Stem Cell. Mar. 2, 2012;10(3):244-58.
Raposo et al., Extracellular vesicles: exosomes, microvesicles, and friends. J Cell Biol. Feb. 18, 2013;200(4):373-83.
Rappolee et al., Macrophage-derived growth factors. Curr Top Microbiol Immunol. 1992;181:87-140.
Rapraeger, Syndecan-regulated receptor signaling. J Cell Biol. May 29, 2000;149(5):995-8.
Reddy et al., Exploiting lymphatic transport and complement activation in nanoparticle vaccines. Nat Biotechnol. Oct. 2007;25(10):1159-64.
Reimann et al., Satellite Cells in Normal and Regenerated Soleus Muscles of mdx and Control Mice. Eur J Neurosci. 1998;10:366, Abstract No. 153.07.
Reis E Sousa., Activation of dendritic cells: translating innate into adaptive immunity. Curr Opin Immunol. Feb. 2004;16(1):21-5.
Rhoads et al., Satellite cell-mediated angiogenesis in vitro coincides with a functional hypoxia-inducible factor pathway. Am J Physiol Cell Physiol. Jun. 2009;296(6):C1321-8.
Ribas et al., Phase III randomized clinical trial comparing tremelimumab with standard-of-care chemotherapy in patients with advanced melanoma. J Clin Oncol. Feb. 10, 2013;31(5):616-22.
Richards Grayson et al., Multi-pulse drug delivery from a resorbable polymeric microchip device. Nat Mater. Nov. 2003;2(11):767-72.
Richardson et al., Polymeric system for dual growth factor delivery. Nat Biotechnol. Nov. 2001;19(11):1029-34.
Riddell et al., Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington. Human Gene Therapy. Jun. 1992;3(3):319-338.
Riddell et al., Principles for adoptive T cell therapy of human viral diseases. Annu Rev Immunol. 1995;13:545-86.
Riddell et al., Restoration of viral immunity in immunodeficient humans by the adoptive transfer of T cell clones. Science. Jul. 10, 1992;257(5067):238-41.
Riddell et al., The use of anti-CD3 and anti-CD28 monoclonal antibodies to clone and expand human antigen-specific T cells. J Immunol Methods. Apr. 17, 1990;128(2):189-201.
Riddle et al., Role of poly(lactide-co-glycolide) particle size on gas-foamed scaffolds. J Biomater Sci Polym Ed. 2004;15(12):1561-70.

(56) References Cited

OTHER PUBLICATIONS

Ridgway et al., Inhibition of Dll4 signalling inhibits tumour growth by deregulating angiogenesis. Nature. Dec. 21, 2006;444(7122):1083-7.
Rinderknecht et al., The amino acid sequence of human insulin-like growth factor I and its structural homology with proinsulin. J Biol Chem. Apr. 25, 1978;253(8):2769-76.
Rizzo et al., An improved cyan fluorescent protein variant useful for FRET. Nat Biotechnol. Apr. 2004;22(4):445-9.
Roccaro et al., BM mesenchymal stromal cell-derived exosomes facilitate multiple myeloma progression. J Clin Invest. Apr. 2013;123(4):1542-55.
Rodriguez et al., Minimal "Self" peptides that inhibit phagocytic clearance and enhance delivery of nanoparticles. Science. Feb. 22, 2013;339(6122):971-5.
Rosenberg et al., Adoptive cell transfer as personalized immunotherapy for human cancer. Science. Apr. 3, 2015;348(6230):62-8.
Rosenberg et al., Cancer immunotherapy: moving beyond current vaccines. Nat Med. Sep. 2004;10(9):909-15.
Rosenberg et al., Durable complete responses in heavily pretreated patients with metastatic melanoma using T-cell transfer immunotherapy. Clin Cancer Res. Jul. 1, 2011;17(13):4550-7.
Roth et al., SC68896, a novel small molecule proteasome inhibitor, exerts antiglioma activity in vitro and in vivo. Clin Cancer Res. Nov. 1, 2009;15(21):6609-18.
Rowlands et al., Directing osteogenic and myogenic differentiation of MSCs: interplay of stiffness and adhesive ligand presentation. Am J Physiol Cell Physiol. Oct. 2008;295(4):C1037-44.
Rowley et al., Alginate hydrogels as synthetic extracellular matrix materials. Biomaterials. Jan. 1999;20(1):45-53.
Rowley et al., Alginate type and RGD density control myoblast phenotype. J Biomed Mater Res. May 2002;60(2):217-23.
Rowley et al., Biomaterials to Spatially Regulate Cell Fate. Adv Mater. Jun. 2002;14(12):886-889.
Rubbi et al., Evidence of surface antigen detachment during incubation of cells with immunomagnetic beads. J Immunol Methods. Dec. 3, 1993;166(2):233-41.
Rubin et al., Dissociation of heparan sulfate and receptor binding domains of hepatocyte growth factor reveals that heparan sulfate-c-met interaction facilitates signaling. J Biol Chem. Aug. 31, 2001;276(35):32977-83.
Ryten et al., ATP regulates the differentiation of mammalian skeletal muscle by activation of a P2X5 receptor on satellite cells. J Cell Biol. Jul. 22, 2002;158(2):345-55.
Ryu et al., The construction of three-dimensional micro-fluidic scaffolds of biodegradable polymers by solvent vapor based bonding of micro-molded layers. Biomaterials. Feb. 2007;28(6):1174-84.
Sacchetti et al., Self-renewing osteoprogenitors in bone marrow sinusoids can organize a hematopoietic microenvironment. Cell. Oct. 19, 2007;131(2):324-36.
Sahdev et al., Biomaterials for nanoparticle vaccine delivery systems. Pharm Res. Oct. 2014;31(10):2563-82.
Sakai et al., An injectable, in situ enzymatically gellable, gelatin derivative for drug delivery and tissue engineering. Biomaterials. Jul. 2009;30(20):3371-7.
Salem et al., Defining the antigen-specific T-cell response to vaccination and poly(I:C)/TLR3 signaling: evidence of enhanced primary and memory CD8 T-cell responses and antitumor immunity. J Immunother. May-Jun. 28, 2005(3):220-8.
Salvador et al., Combination of immune stimulating adjuvants with poly(lactide-co-glycolide) microspheres enhances the immune response of vaccines. Vaccine. Jan. 11, 2012;30(3):589-96.
Salvay et al., Inductive tissue engineering with protein and DNA-releasing scaffolds. Mol Biosyst. Jan. 2006;2(1):36-48.
Sano et al., Swift development of protective effector functions in naive CD8(+) T cells against malaria liver stages. J Exp Med. Jul. 16, 2001;194(2):173-9.
Sansonetti, The innate signaling of dangers and the dangers of innate signaling. Nat Immunol. Dec. 2006;7(12):1237-42.

Sarkar et al., Condensation of oligonucleotides assembled into nicked and gapped duplexes: potential structures for oligonucleotide delivery. Nucleic Acids Res. Jan. 7, 2005;33(1):143-51.
Sato, Human dendritic cells. Biotherapy. Nov. 2004;18(6):467-77.
Saxena et al., Skeletal muscle tissue engineering using isolated myoblasts on synthetic biodegradable polymers: preliminary studies. Tissue Eng. Dec. 1999;5(6):525-32.
Schaefer et al., Innate immunity in the human female reproductive tract: antiviral response of uterine epithelial cells to the TLR3 agonist poly(I:C). J Immunol. Jan. 15, 2005;174(2):992-1002.
Scheel et al., Toll-like receptor-dependent activation of several human blood cell types by protamine-condensed mRNA. Eur J Immunol. May 2005;35(5):1557-66.
Schijns et al., Mice lacking IL-12 develop polarized Th1 cells during viral infection. J Immunol. Apr. 15, 1998;160(8):3958-64.
Schnorrer et al., The dominant role of CD8+ dendritic cells in cross-presentation is not dictated by antigen capture. Proc Natl Acad Sci U S A. Jul. 11, 2006;103(28):10729-34.
Schofield, The relationship between the spleen colony-forming cell and stem cell. Blood Cells. 1978;4(1-2):7-25.
Schuler et al., The use of dendritic cells in cancer immunotherapy. Curr Opin Immunol. Apr. 15, 2003(2):138-47.
Schwartz, A cell culture model for T lymphocyte clonal anergy. Science. Jun. 15, 1990;248(4961):1349-56.
Schwartz, Integrins and extracellular matrix in mechanotransduction. Perspect Biol. Dec. 2010;2(12):a005066.
Seale et al., Pax7 is required for the specification of myogenic satellite cells. Cell. Sep. 15, 2000;102(6):777-86.
Sensi et al., Unique tumor antigens: evidence for immune control of genome integrity and immunogenic targets for T cell-mediated patient-specific immunotherapy. Clin Cancer Res. Sep. 1, 2006;12(17):5023-32.
Shah et al., An injectable bone marrow-like scaffold enhances T cell immunity after hematopoietic stem cell transplantation. Nat Biotechnol. Mar. 2019;37(3):293-302, with correction Nat Biotechnol. Nov. 2021;39:1466.
Shakweh et al., Design and characterisation of poly(lactide-co-glycolide) small particulate systems for the delivery of immunostimulant CpG oligonucleotide. J Nanosci Nanotechnol. Sep.-Oct. 2006;6(9-10):2811-20.
Shaner et al., Improved monomeric red, orange and yellow fluorescent proteins derived from *Discosoma* sp. red fluorescent protein. Nat Biotechnol. Dec. 2004;22(12):1567-72.
Shansky et al., A simplified method for tissue engineering skeletal muscle organoids in vitro. In Vitro Cell Dev Biol Anim. Oct. 1997;33(9):659-61.
Shapiro et al., Sizing it up: cellular MRI using micron-sized iron oxide particles. Magn Reson Med. Feb. 2005;53(2):329-38.
Sheehan et al., Skeletal muscle satellite cell proliferation in response to members of the fibroblast growth factor family and hepatocyte growth factor. J Cell Physiol. Dec. 1999;181(3):499-506.
Sheppard et al., Polyethyleneimine is a potent systemic adjuvant for glycoprotein antigens. Int Immunol. Oct. 2014;26(10):531-8.
Sheridan et al., Bioabsorbable polymer scaffolds for tissue engineering capable of sustained growth factor delivery. J Control Release. Feb. 14, 2000;64(1-3):91-102.
Shi et al., A novel Toll-like receptor that recognizes vesicular stomatitis virus. J Biol Chem. Feb. 11, 2011;286(6):4517-24.
Shi et al., Granulocyte-macrophage colony-stimulating factor (GM-CSF) and T-cell responses: what we do and don't know. Cell Res. Feb. 2006;16(2):126-33.
Shibuya et al., Anti-CD3/anti-CD28 bead stimulation overcomes CD3 unresponsiveness in patients with head and neck squamous cell carcinoma. Arch Otolaryngol Head Neck Surg. Apr. 2000;126(4):473-9.
Shin et al., Contractile forces sustain and polarize hematopoiesis from stem and progenitor cells. Cell Stem Cell. Jan. 2, 2014;14(1):81-93.
Shin et al., Lamins regulate cell trafficking and lineage maturation of adult hematopoietic cells. Proc Natl Acad Sci U S A. Nov. 19, 2013;110(47):18892-7.

(56) References Cited

OTHER PUBLICATIONS

Shin et al., Myosin-II inhibition and soft 2D matrix maximize multinucleation and cellular projections typical of platelet-producing megakaryocytes. Proc Natl Acad Sci U S A. Jul. 12, 2011;108(28):11458-63.
Shoichet et al., Stability of hydrogels used in cell encapsulation: An in vitro comparison of alginate and agarose. Biotechnol Bioeng. May 20, 1996;50(4):374-81.
Shortman et al., Steady-state and inflammatory dendritic-cell development. Nat Rev Immunol. Jan. 2007;7(1):19-30.
Shukla, Controlled Generation of Progenitor T-cells from Hematopoietic Stem Cells and Pluripotent Stem Cells. A thesis submitted in conformity with the requirements for the degree of Doctorate of Philosophy, Institute of Biomaterials and Biomedical Engineering, University of Toronto. 214 pages, (2017).
Sick et al., WNT and DKK determine hair follicle spacing through a reaction-diffusion mechanism. Science. Dec. 1, 2006;314(5804):1447-50.
Siegwart et al., Synthesis, characterization, and in vitro cell culture viability of degradable poly(N-isopropylacrylamide-co-5,6-benzo-2-methylene-1,3-dioxepane)-based polymers and crosslinked gels. J Biomed Mater Res A. Nov. 2008;87(2):345-58.
Silva et al., Effects of VEGF temporal and spatial presentation on angiogenesis. Biomaterials. Feb. 2010;31(6):1235-41.
Silva et al., Material-based deployment enhances efficacy of endothelial progenitor cells. Proc Natl Acad Sci U S A. Sep. 23, 2008;105(38):14347-52.
Silva et al., Spatiotemporal control of vascular endothelial growth factor delivery from injectable hydrogels enhances angiogenesis. J Thromb Haemost. Mar. 2007;5(3):590-8.
Simmons et al., GM-CSF as a systemic adjuvant in a phase II prostate cancer vaccine trial. Prostate. Jun. 1, 1999;39(4):291-7.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-710.
Singer et al., Cutaneous wound healing. N Engl J Med. Sep. 2, 1999;341(10):738-46.
Singh et al., Hydrogels and scaffolds for immunomodulation. Adv Mater. Oct. 2014;26(38):6530-41.
Skokos et al., CD8-DCs induce IL-12-independent Th1 differentiation through Delta 4 Notch-like ligand in response to bacterial LPS. J Exp Med. Jul. 9, 2007;204(7):1525-31.
Skuk et al., Efficacy of myoblast transplantation in nonhuman primates following simple intramuscular cell injections: toward defining strategies applicable to humans. Exp Neurol. May 2002;175(1):112-26.
Skuk et al., Myoblast transplantation: the current status of a potential therapeutic tool for myopathies. J Muscle Res Cell Motil. 2003;24(4-6):285-300.
Sletten et al., A hydrophilic azacyclooctyne for Cu-free click chemistry. Org Lett. Jul. 17, 2008;10(14):3097-9.
SmidsrØd et al., Alginate as immobilization matrix for cells. Trends Biotechnol. Mar. 1990;8(3):71-8.
Sobral et al., Antigen-free cancer vaccine to treat poorly immunogenic tumors. Cancer Immunol Res. 2019;7(2 Suppl):Abstract B045.
Sohier et al., Critical factors in the design of growth factor releasing scaffolds for cartilage tissue engineering. Expert Opin Drug Deliv. May 2008;5(5):543-66.
Solon et al., Fibroblast adaptation and stiffness matching to soft elastic substrates. Biophys J. Dec. 15, 2007;93(12):4453-61.
Sonawane et al., Chloride accumulation and swelling in endosomes enhances DNA transfer by polyamine-DNA polyplexes. J Biol Chem. Nov. 7, 2003;278(45):44826-31.
Springer et al., The lymphocyte function-associated LFA-1, CD2, and LFA-3 molecules: cell adhesion receptors of the immune system. Annu Rev Immunol. 1987;5:223-52.
Stachowiak et al., Inverse opal hydrogel-collagen composite scaffolds as a supportive microenvironment for immune cell migration. J Biomed Mater Res A. Jun. 1, 2008;85(3):815-28.

Stanley et al., Transjugular intrahepatic portosystemic shunt as a treatment for protein-losing enteropathy caused by portal hypertension. Gastroenterology. Dec. 1996;111(6):1679-82.
Steenblock et al., A comprehensive platform for ex vivo T-cell expansion based on biodegradable polymeric artificial antigen-presenting cells. Mol Ther. Apr. 2008;16(4):765-72.
Steenblock et al., An artificial antigen-presenting cell with paracrine delivery of IL-2 impacts the magnitude and direction of the T cell response. J Biol Chem. Oct. 7, 2011;286(40):34883-92.
Steinman et al., Taking dendritic cells into medicine. Nature. Sep. 27, 2007;449(7161):419-26.
Stephen et al., Biopolymer implants enhance the efficacy of adoptive T-cell therapy. Nat Biotechnol. Jan. 2015;33(1):97-101.
Stockmann et al., Exploring isonitrile-based click chemistry for ligation with biomolecules. Organic & Biomolecular Chemistry. 2011;9:7300-7302.
Storrie et al., Sustained delivery of plasmid DNA from polymeric scaffolds for tissue engineering. Adv Drug Deliv Rev. Jul. 7, 2006;58(4):500-14.
Straub et al., Animal models for muscular dystrophy show different patterns of sarcolemmal disruption. J Cell Biol. Oct. 20, 1997;139(2):375-85.
Sun et al., Biomimetic interpenetrating polymer network hydrogels based on methacrylated alginate and collagen for 3D pre-osteoblast spreading and osteogenic differentiation. Soft Matter. Jan. 12, 2012;8:2398-2404.
Sun et al., Highly stretchable and tough hydrogels. Nature. Sep. 6, 2012;489(7414):133-6.
Sun et al., Sustained vascular endothelial growth factor delivery enhances angiogenesis and perfusion in ischemic hind limb. Pharm Res. Jul. 2005;22(7):1110-6.
Sunshine et al., Nanoengineering approaches to the design of artificial antigen-presenting cells. Nanomedicine. 2013;8(7):1173-89.
Sunshine et al., Particle shape dependence of CD8+ T cell activation by artificial antigen presenting cells. Biomaterials. Jan. 2014;35(1):269-277.
Super et al., Biomaterial vaccines capturing pathogen-associated molecular patterns protect against bacterial infections and septic shock. Nat Biomed Eng. Jan. 2022;6(1):8-18.
Suri et al., Photopatterned collagen-hyaluronic acid interpenetrating polymer network hydrogels. Acta Biomater. Sep. 2009;5(7):2385-97.
Suzuki et al., A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007;67(5):2351-9.
Swift et al., Nuclear lamin-A scales with tissue stiffness and enhances matrix-directed differentiation. Science. Aug. 30, 2013;341(6149):1240104. 17 pages.
Syed et al., Stem cell therapy market. Nat Rev Drug Discov. Mar. 2013;12(3):185-6.
Tabata et al., Enhanced Vascularization and Tissue Granulation by Basic Fibroblast Growth Factor Impregnated in Gelatin Hydrogels. Journal of Controlled Release. Sep. 1994;31(2):189-199.
Takahashi et al., Induction of pluripotent stem cells from adult human fibroblasts by defined factors. Cell. Nov. 30, 2007;131(5):861-72.
Takamura et al., Regulatory role of lymphoid chemokine CCL19 and CCL21 in the control of allergic rhinitis. J Immunol. 2007;179(9):5897-5906.
Takeshita et al., Therapeutic angiogenesis. A single intraarterial bolus of vascular endothelial growth factor augments revascularization in a rabbit ischemic hind limb model. J Clin Invest. Feb. 1994;93(2):662-70.
Tamura et al., Immunotherapy of tumors with autologous tumor-derived heat shock protein preparations. Science. Oct. 3, 1997;278(5335):117-20.
Tanaka et al., Collapse of gels in an electric field. Science. Oct. 29, 1982;218(4571):467-9.
Tang et al., Combining radiation and immunotherapy: a new systemic therapy for solid tumors? Cancer Immunol Res. Sep. 2014;2(9):831-8.

(56) References Cited

OTHER PUBLICATIONS

Tannous, Gaussia luciferase reporter assay for monitoring biological processes in culture and in vivo. Nat Protoc. 2009;4(4):582-91.
Tatsumi et al., HGF/SF is present in normal adult skeletal muscle and is capable of activating satellite cells. Dev Biol. Feb. 1, 1998;194(1):114-28.
Ten Dijke et al., Growth Factors for Wound Healing. Nat Biotechnol. 1989;7:793-798.
Thelin et al., In Vivo Enrichment of Diabetogenic T Cells. Diabetes. Aug. 2017;66(8):2220-2229.
Thielemann et al., Pore structure and surface area of silica SBA-15: influence of washing and scale-up. Beilstein J Nanotechnol. 2011;2:110-8.
Thomas et al., Intravenous infusion of bone marrow in patients receiving radiation and chemotherapy. N Engl J Med. Sep. 12, 1957;257(11):491-6.
Thornton et al., Shape retaining injectable hydrogels for minimally invasive bulking. J Urol. Aug. 2004;172(2):763-8.
Thurner et al., Vaccination with mage-3A1 peptide-pulsed mature, monocyte-derived dendritic cells expands specific cytotoxic T cells and induces regression of some metastases in advanced stage IV melanoma. J Exp Med. Dec. 6, 1999;190(11):1669-78.
Thurston et al., The Delta paradox: DLL4 blockade leads to more tumour vessels but less tumour growth. Nat Rev Cancer. May 2007;7(5):327-31.
Tidball, Inflammatory cell response to acute muscle injury. Med Sci Sports Exerc. Jul. 1995;27(7):1022-32.
Titan et al., Growth Factor Delivery to a Bovine Defect Using Leukocyte-Rich Platelet-Rich Concentrates on a Hyaluronic Acid Scaffold. Arthroscopy: The Journal of Arthroscopic and Related Surgery. Pre-publication edition, 33 pages, Dec. 2019.
Tomer et al., Electrically Controlled Release of Macromolecules from Cross-Linked Hyaluronic Acid Hydrogels. Journal of Controlled Release. Mar. 1995:33(3):405-413.
Tong et al., Engineering interpenetrating network hydrogels as biomimetic cell niche with independently tunable biochemical and mechanical properties. Biomaterials. Feb. 2014;35(6):1807-15.
Tourniaire et al., Polymer microarrays for cellular adhesion. Chem Commun (Camb). May 28, 2006;(20):2118-20.
Trappmann et al., Extracellular-matrix tethering regulates stem-cell fate. Nat Mater. May 27, 2012;11(7):642-9.
Trappmann et al., How cells sense extracellular matrix stiffness: a material's perspective. Curr Opin Biotechnol. Oct. 2013;24(5):948-53.
Tripathi et al., Elastic and macroporous agarose-gelatin cryogels with isotropic and anisotropic porosity for tissue engineering. J Biomed Mater Res A. Sep. 1, 2009;90(3):680-94.
Tsien, The green fluorescent protein. Annu Rev Biochem. 1998;67:509-44.
Turing, The Chemical Basis of Morphogenesis. Philosophical Transactions of the Royal Society of London. Series B. 1952;237(641):37-72.
Turtle et al., Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. Blood. 2015;126:184.
Turtle et al., CD19 Car-T cells of defined CD4+:CD8+ composition in adult B cell ALL patients. J Clin Invest. Jun. 1, 2016;126(6):2123-38.
Uchida et al., Immunization by particle bombardment of antigen-loaded poly-(DL-lactide-co-glycolide) microspheres in mice. Vaccine. Mar. 15, 2006;24(12):2120-30.
Ugarte et al., Notch signaling enhances osteogenic differentiation while inhibiting adipogenesis in primary human bone marrow stromal cells. Exp Hematol. Jul. 2009;37(7):867-875.e1.
Uhlenbruck, Action of proteolytic enzymes on the human erythrocyte surface. Nature. Apr. 8, 1961;190:181.
Ulrich et al., Probing cellular mechanobiology in three-dimensional culture with collagen-agarose matrices. Biomaterials. Mar. 2010;31(7):1875-84.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al., Stem cell niches in the adult mouse heart. Proc Natl Acad Sci U S A. Jun. 13, 2006;103(24):9226-31.
Van Berkel et al., Metal-free triazole formation as a tool for bioconjugation. Chembiochem. Sep. 3, 2007;8(13):1504-8.
Van De Walle et al., Jagged2 acts as a Delta-like Notch ligand during early hematopoietic cell fate decisions. Blood. Apr. 28, 2011;117(17):4449-59.
Van Der Bruggen et al., Peptide Database: T cell-defined tumor antigens. Cancer Immunity. Retrieved online at: http://www.cancerimmunity.org/peptide/ 59 pages. (2013).
Van Duin et al., Triggering TLR signaling in vaccination. Trends Immunol. Jan. 2006;27(1):49-55.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Van Elsas et al., Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. Aug. 20, 2001;194(4):481-9.
Van Tendeloo et al., Induction of complete and molecular remissions in acute myeloid leukemia by Wilms' tumor 1 antigen-targeted dendritic cell vaccination. Proc Natl Acad Sci U S A. Aug. 3, 2010;107(31):13824-9.
Vandenburgh et al., Tissue-engineered skeletal muscle organoids for reversible gene therapy. Hum Gene Ther. Nov. 10, 1996;7(17):2195-200.
Veldhoen et al., TGFbeta1, a "Jack of all trades": the link with pro-inflammatory IL-17-producing T cells. Trends Immunol. Aug. 2006;27(8):358-61.
Venturoni et al., Investigations into the polymorphism of rat tail tendon fibrils using atomic force microscopy. Biochem Biophys Res Commun. Apr. 4, 2003;303(2):508-13.
Vieira et al., Polysaccharide-based hydrogels: preparation, characterization, and drug interaction behaviour. Biomacromolecules. Apr. 2008;9(4):1195-9.
Vieira et al., The bulk of endogenously produced IgG2a is eliminated from the serum of adult C57BL/6 mice with a half-life of 6-8 days. Eur J Immunol. Jul. 1986;16(7):871-4.
Vieira et al., The half-lives of serum immunoglobulins in adult mice. Eur J Immunol. Feb. 1988;18(2):313-6.
Villadangos et al., Intrinsic and cooperative antigen-presenting functions of dendritic-cell subsets in vivo. Nat Rev Immunol. Jul. 2007;7(7):543-55.

(56) References Cited

OTHER PUBLICATIONS

Villadangos, Presentation of antigens by MHC class II molecules: getting the most out of them. Mol Immunol. Sep. 2001;38(5):329-46.
Vincent et al., Stem cell differentiation: Post-degradation forces kick in. Nat Mater. May 2013;12(5):384-6.
Vogel et al., Local force and geometry sensing regulate cell functions. Nat Rev Mol Cell Biol. Apr. 2006;7(4):265-75.
Von Dassow et al., The segment polarity network is a robust developmental module. Nature. Jul. 13, 2000;406(6792):188-92.
W.H.O., World Health Organization, Global Burden of Musculoskeletal Disease Revealed in new WHO Report. Bull World Health Organ. 2003;81(11):853-854.
W.H.O., World Health Organization, The World Health Report 2004: Changing History. The World Health Report. 2004:1-169.
Wakim et al., Dendritic cell-induced memory T cell activation in nonlymphoid tissues. Science. Jan. 11, 2008;319(5860):198-202.
Wan et al., Peritoneal macrophage uptake, pharmacokinetics and biodistribution of macrophage-targeted PEG-fMLF (N-formyl-methionyl-leucyl-phenylalanine) nanocarriers for improving HIV drug delivery. Pharm Res. Nov. 2007;24(11):2110-9.
Wang et al., Biological activity of bevacizumab, a humanized anti-VEGF antibody in vitro. Angiogenesis. 2004;7(4):335-45.
Wang et al., Biomaterial-based scaffold for in situ chemo-immunotherapy to treat poorly immunogenic tumors. Nat Commun. Nov. 10, 2020;11(1):5696, 41 pages with supplementary materials.
Wang et al., Bone Morphogenetic Protein (BMP) signaling in development and human diseases. Genes Dis. Sep. 2014;1(1):87-105.
Wang et al., Evolution of new nonantibody proteins via iterative somatic hypermutation. Proc Natl Acad Sci U S A. Nov. 30, 2004;101(48):16745-9.
Wang et al., Mechanotransduction at a distance: mechanically coupling the extracellular matrix with the nucleus. Nat Rev Mol Cell Biol. Jan. 2009;10(1):75-82.
Wang et al., Mouse CD229 Ligation Co-stimulates T Cell Activation. The Journal of Immunology. May 2012;188(suppl 1):176.7.
Wang et al., Photothermal effects of supramolecularly assembled gold nanoparticles for the targeted treatment of cancer cells. Angew Chem Int Ed Engl. May 17, 2010;49(22):3777-81.
Wang-Gillam et al., A phase I study of IMP321 and gemcitabine as the front-line therapy in patients with advanced pancreatic adenocarcinoma. Invest New Drugs. Jun. 2013;31(3):707-13.
Warner et al., Cyclooxygenases: new forms, new inhibitors, and lessons from the clinic. FASEB J. May 2004;18(7):790-804.
Weeks et al., The effects of chemokine, adhesion and extracellular matrix molecules on binding of mesenchymal stromal cells to poly(I-lactic acid). Cytotherapy. Oct. 2012;14(9):1080-8.
Wegman et al., Combination of bone morphogenetic protein-2 plasmid DNA with chemokine CXCL12 creates an additive effect on bone formation onset and vol. Eur Cell Mater. Jul. 27, 2015;30:1-11.
Wegmann et al., Polyethyleneimine is a potent mucosal adjuvant for viral glycoprotein antigens. Nat Biotechnol. Sep. 2012;30(9):883-8.
Wei et al., Global mapping of H3K4me3 and H3K27me3 reveals specificity and plasticity in lineage fate determination of differentiating CD4+ T cells. Immunity. Jan. 16, 2009;30(1):155-67.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Weiner, Induction and mechanism of action of transforming growth factor-beta-secreting Th3 regulatory cells. Immunol Rev. Aug. 2001;182:207-14.
Weisenberger et al., Comprehensive DNA Methylation Analysis on the Illumina® Infinium® Assay Platform. Illumina, Inc., 4 pages, Mar. 25, 2008.
Weiss et al., The demonstration of rupture of cell surfaces by an immunological technique. Exp Cell Res. Apr. 1963;30:331-8.
Wen et al., Mechanically Robust Gelatin-Alginate IPN Hydrogels by a Combination of Enzymatic and Ionic Crosslinking Approaches. Macromol Mater Eng. Apr. 2014;299(4):504-513.
Wernig et al., Function of skeletal muscle tissue formed after myoblast transplantation into irradiated mouse muscles. J Physiol. Jan. 15, 2000;522 Pt 2:333-45.
White et al., Leukemia inhibitory factor enhances regeneration in skeletal muscles after myoblast transplantation. Muscle Nerve. May 2001;24(5):695-7.
Wieland et al., Engineering molecular circuits using synthetic biology in mammalian cells. Annu Rev Chem Biomol Eng. 2012;3:209-34.
Wikipedia, Matrigel. Retrieved online at: https://en.wikipedia.org/wiki/Matrigel. 4 pages, Oct. 10, 2018.
Wipff et al., Myofibroblast contraction activates latent TGF-beta1 from the extracellular matrix. J Cell Biol. Dec. 17, 2007;179(6):1311-23.
Wolchok et al., Nivolumab plus ipilimumab in advanced melanoma. N Engl J Med. Jul. 11, 2013;369(2):122-33.
Wong et al., Focal adhesion kinase links mechanical force to skin fibrosis via inflammatory signaling. Nat Med. Dec. 11, 2011;18(1):148-52.
Wong et al., Mechanical force prolongs acute inflammation via T-cell-dependent pathways during scar formation. FASEB J. Dec. 2011;25(12):4498-510.
Wong et al., Pushing back: wound mechanotransduction in repair and regeneration. J Invest Dermatol. Nov. 2011;131(11):2186-96.
Wozniak et al., Mechanotransduction in development: a growing role for contractility. Nat Rev Mol Cell Biol. Jan. 2009;10(1):34-43.
Wright et al., Muscle-based gene therapy and tissue engineering for the musculoskeletal system. Drug Discov Today. Jul. 1, 2001;6(14):728-733.
Wu et al., Intraperitoneal administration of poly(I:C) with polyethylenimine leads to significant antitumor immunity against murine ovarian tumors. Cancer Immunol Immunother. Aug. 2011;60(8):1085-96.
Xia et al., Polyethyleneimine coating enhances the cellular uptake of mesoporous silica nanoparticles and allows safe delivery of siRNA and DNA constructs. ACS Nano. Oct. 27, 2009;3(10):3273-86.
Xie et al., Preparation and Application of Surface-Coated Superparamagnetic Nanobeads in the Isolation of Genomic DNA. J Magn Magnetic Mater. Jun. 2004;277(1-2):16-23.
Xiong et al., Transcription Factor STAT3 as a Novel Molecular Target for Cancer Prevention. Cancers (Basel). Apr. 16, 2014;6(2):926-57.
Xue et al., Efficient cancer cell capturing SiNWAs prepared via surface-initiated SET-LRP and click chemistry. Polymer Chemistry. 2015;6:3708-15. Pre-publication edition.
Yamazaki et al., CD8+ CD205+ splenic dendritic cells are specialized to induce Foxp3+ regulatory T cells. J Immunol. Nov. 15, 2008;181(10):6923-33.
Yancopoulos et al., Vascular-specific growth factors and blood vessel formation. Nature. Sep. 14, 2000;407(6801):242-8.
Yang et al., The effect of incorporating RGD adhesive peptide in polyethylene glycol diacrylate hydrogel on osteogenesis of bone marrow stromal cells. Biomaterials. Oct. 2005;26(30):5991-8.
Yee et al., Melanocyte destruction after antigen-specific immunotherapy of melanoma: direct evidence of t cell-mediated vitiligo. J Exp Med. Dec. 4, 2000;192(11):1637-44.
Yeung et al., Effects of substrate stiffness on cell morphology, cytoskeletal structure, and adhesion. Cell Motil Cytoskeleton. Jan. 2005;60(1):24-34.
Yoo et al., Bio-inspired, bioengineered and biomimetic drug delivery carriers. Nat Rev Drug Discov. Jul. 1, 2011;10(7):521-35.
Yoon, Hidden Markov Models and their Applications in Biological Sequence Analysis. Curr Genomics. Sep. 2009;10(6):402-15.
Young et al., Gelatin as a delivery vehicle for the controlled release of bioactive molecules. J Control Release. Dec. 5, 2005;109(1-3):256-74.
Yu et al., Induced pluripotent stem cell lines derived from human somatic cells. Science. Dec. 21, 2007;318(5858):1917-20.

(56) References Cited

OTHER PUBLICATIONS

Yu et al., Specific bone cells produce DLL4 to generate thymus-seeding progenitors from bone marrow. J Exp Med. May 4, 2015;212(5):759-74.

Yu, Designed synthesis of mono-dispersed silica-based nanostructures and their applications in drug/gene delivery. A thesis submitted for the degree of Doctor of Philosophy at The University of Queensland in 2014, 196 pages.

Yuen et al., Mimicking nature by codelivery of stimulant and inhibitor to create temporally stable and spatially restricted angiogenic zones. Proc Natl Acad Sci U S A. Oct. 19, 2010;107(42):17933-8.

Yuk et al., Electric current-sensitive drug delivery systems using sodium alginate/polyacrylic acid composites. Pharm Res. Jul. 1992;9(7):955-7.

Zammit et al., Kinetics of myoblast proliferation show that resident satellite cells are competent to fully regenerate skeletal muscle fibers. Exp Cell Res. Nov. 15, 2002;281(1):39-49.

Zammit et al., Muscle satellite cells adopt divergent fates: a mechanism for self-renewal? J Cell Biol. Aug. 2, 2004;166(3):347-57.

Zappasodi et al., The effect of artificial antigen-presenting cells with preclustered anti-CD28/-CD3/-LFA-1 monoclonal antibodies on the induction of ex vivo expansion of functional human antitumor T cells. Haematologica. Oct. 2008;93(10):1523-34.

Zeltinger et al., Effect of pore size and void fraction on cellular adhesion, proliferation, and matrix deposition. Tissue Eng. Oct. 2001;7(5):557-72.

Zemel et al., Optimal matrix rigidity for stress fiber polarization in stem cells. Nat Phys. Jun. 1, 2010;6(6):468-473.

Zhang et al., A comparative study of the antigen-specific immune response induced by co-delivery of CpG ODN and antigen using fusion molecules or biodegradable microparticles. J Pharm Sci. Dec. 2007;96(12):3283-92.

Zhang et al., A tension-induced mechanotransduction pathway promotes epithelial morphogenesis. Nature. Mar. 3, 2011;471(7336):99-103.

Zhang et al., Generation of a syngeneic mouse model to study the effects of vascular endothelial growth factor in ovarian carcinoma. Am J Pathol. Dec. 2002;161(6):2295-309.

Zhang et al., Talin depletion reveals independence of initial cell spreading from integrin activation and traction. Nat Cell Biol. Sep. 2008;10(9):1062-8.

Zhao et al., A cell-permeable Stat3 SH2 domain mimetic inhibits Stat3 activation and induces antitumor cell effects in vitro. J Biol Chem. Nov. 12, 2010;285(46):35855-65.

Zhao et al., Active scaffolds for on-demand drug and cell delivery. Proc Natl Acad Sci U S A. Jan. 4, 2011;108(1):67-72.

Zhao et al., Directed cell migration via chemoattractants released from degradable microspheres. Biomaterials. Aug. 2005;26(24):5048-63.

Zhao et al., Stress-relaxation behavior in gels with ionic and covalent crosslinks. J Appl Phys. Mar. 15, 2010;107(6):63509.

Zhou et al., Instability of the transcription factor Foxp3 leads to the generation of pathogenic memory T cells in vivo. Nat Immunol. Sep. 2009;10(9):1000-7.

Zhou et al., Microstructure and Mechanical Properties of Poly(L-lactide) Scaffolds Fabricated by Gelatin Particle Leaching Method. J Appl Polymer Sci. Nov. 5, 2005;98(3):1373-1379.

Zizzari et al., The Macrophage Galactose-Type C-Type Lectin (MGL) Modulates Regulatory T Cell Functions. PLoS One. Jul. 6, 2015;10(7):e0132617. 12 pages.

Japanese Office Action for Application No. 2016-565339, dated Jan. 8, 2019. 9 pages.

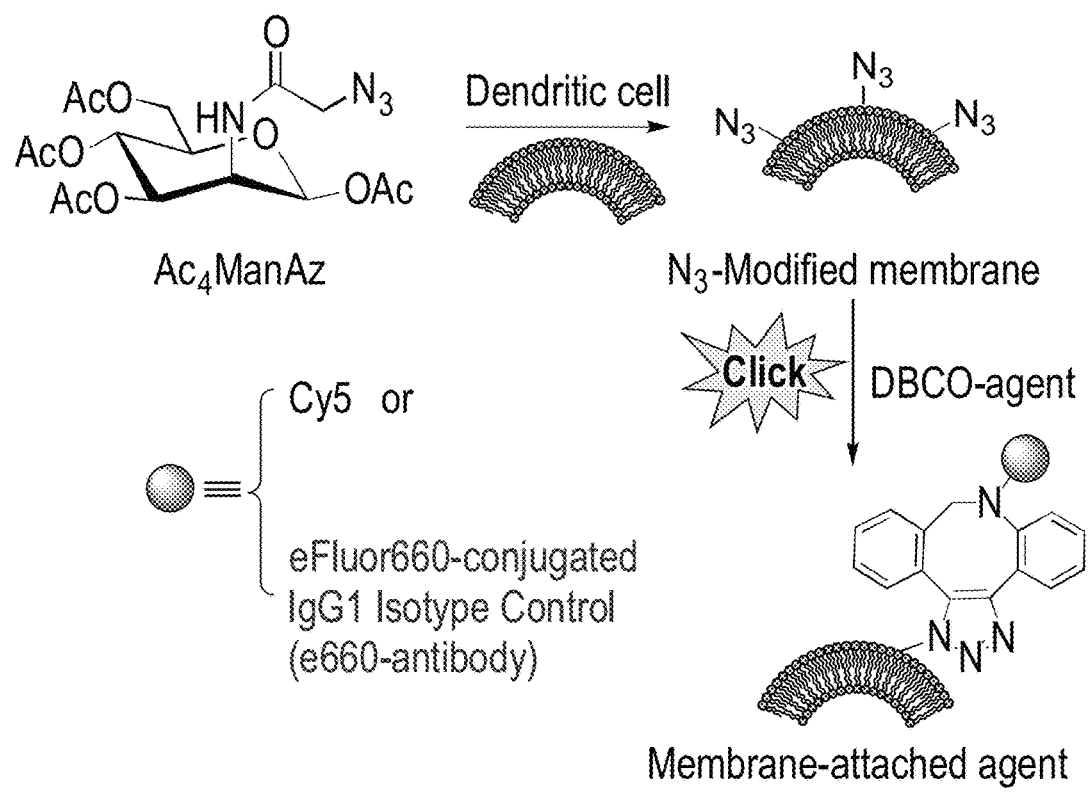
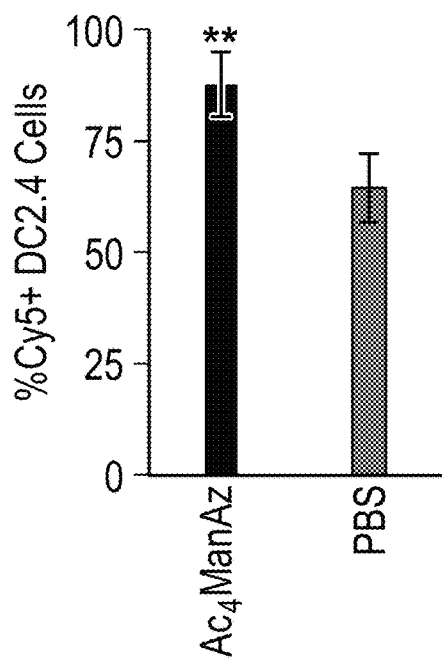
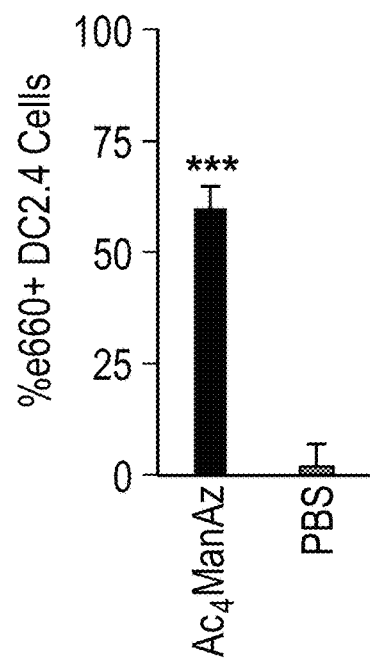
FIG. 2A
FIG. 2B
FIG. 2C

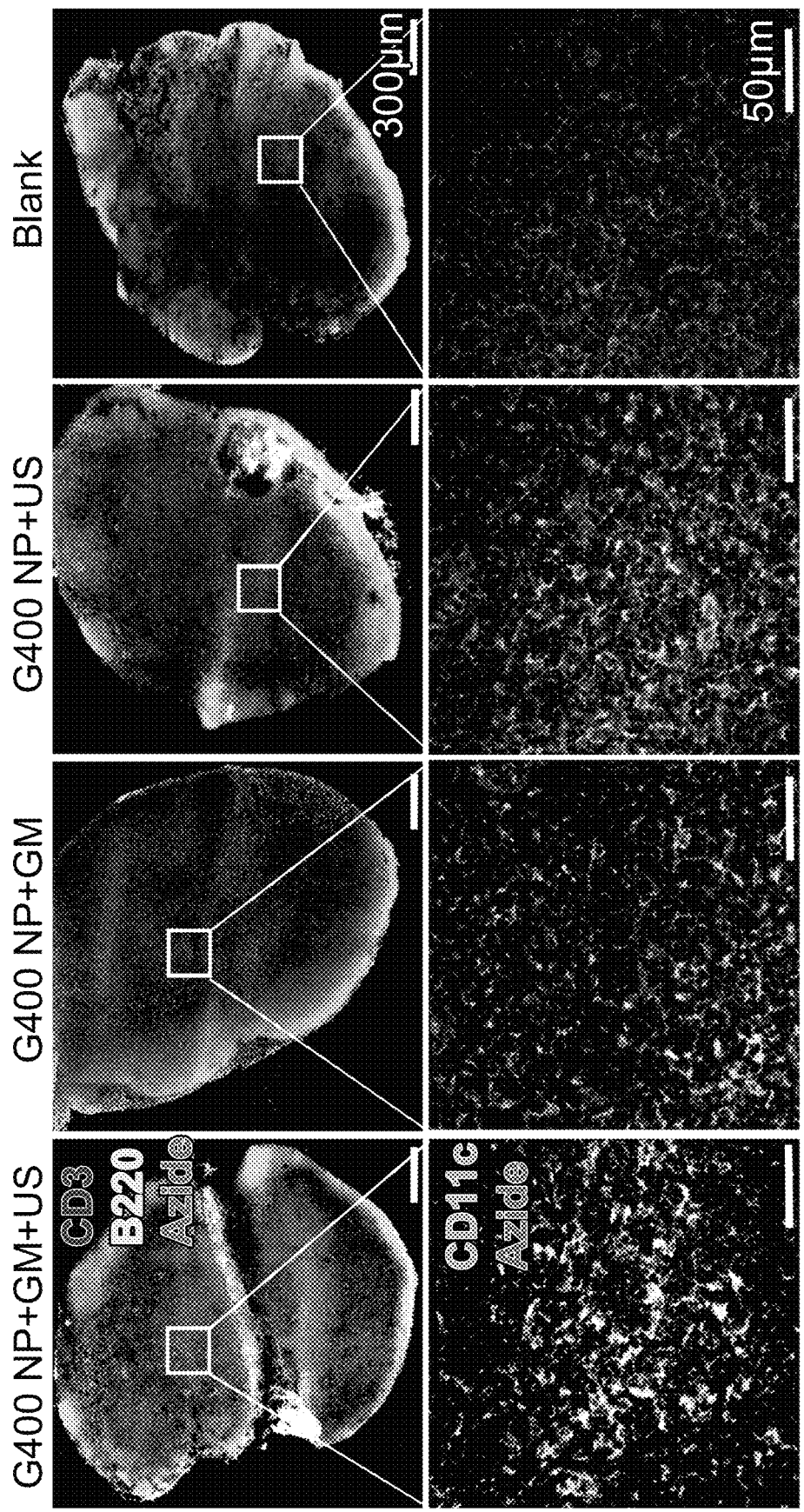

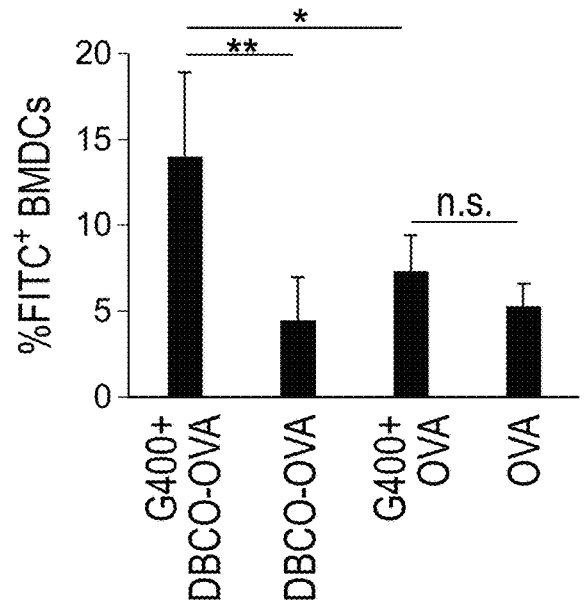
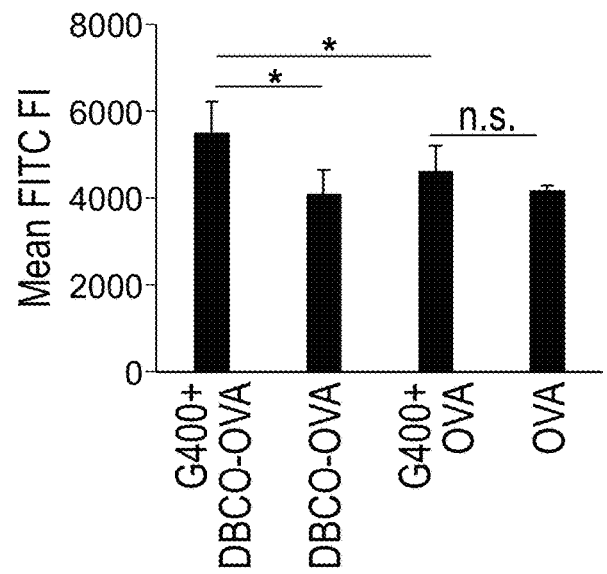
FIG. 5A
FIG. 5B
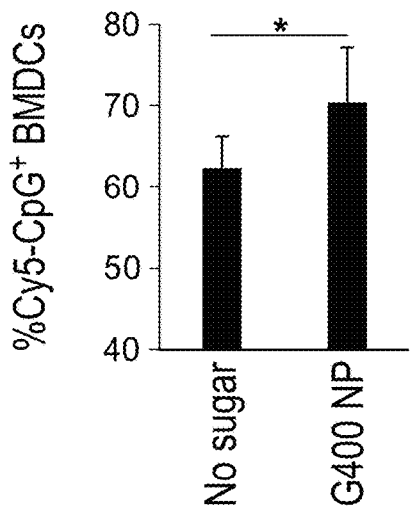
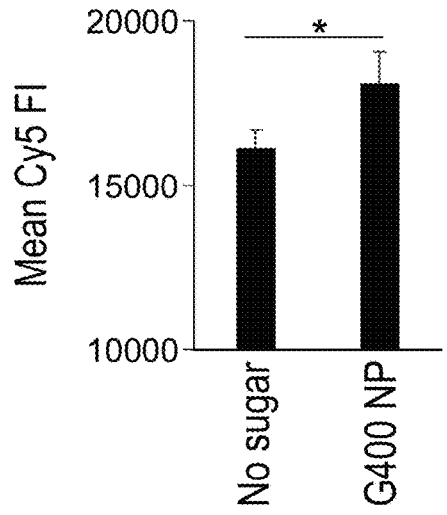
FIG. 5C
FIG. 5D

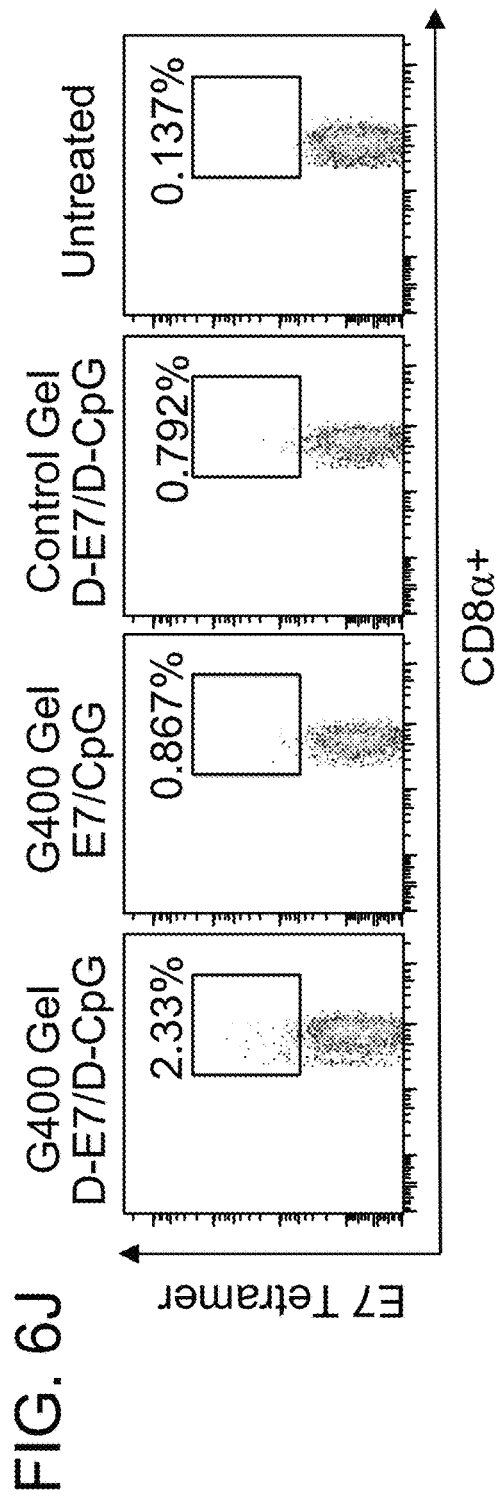
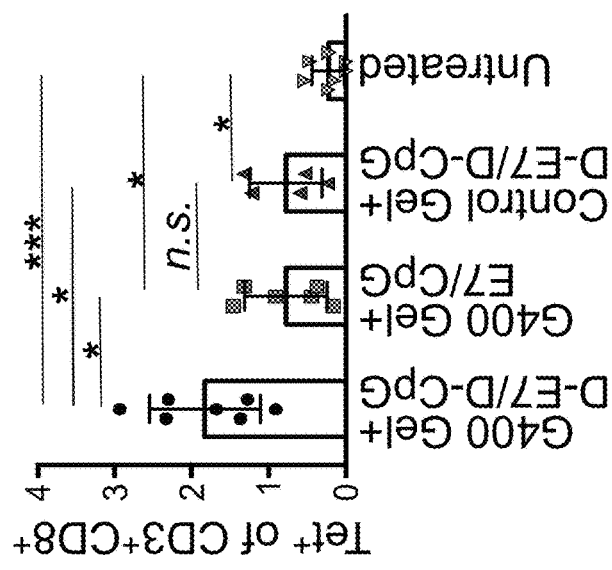
FIG. 6J
FIG. 6K

FIG. 7C

```
AGATCT GCCGCCACCATGGTACCGGCGACGCTGCTCCTGCTGTTGGCGGCCCTGGCT   BglII
       M  V  P  A  T  L  L  L  L  A  A  L  A                  Signal peptide CCGACTCAGACCCGCGCGGAAATGTGTACCTGTCCACTCCCGTATCCCGTATTGAGCAT   Cysteine for CLICK
P  T  Q  T  R  A  K  L  G  T  C  P  P  P  V  S  E  H          Linker GCTGACATCCGGGTCAAGAATTACAGTGTGAACTCTGTGAACATCCACCCTCCCAGCTCT
A  D  I  V  K  N  Y  S  V  N  S  R  E  Y  V  C  N  S          IL-15R GGCTTTAAGCGGAAAGCTGGAACATCCCTCATCGAGTGTGTCATCAACAAGAACACA
G  F  K  R  K  A  G  T  S  L  I  E  C  V  I  N  K  N  T AATGTTGCCCACTGGACAACTCCCAGCCTCAAGTGCATCAGAGACCCCTCCTAGCTTCT
N  V  A  H  W  T  T  P  S  L  K  C  I  R  D  P  S  L  A  S GGAGGCGGAGGCTCTGGTGGAGGCGGTTCTGGAGGAGGATCTGGTGGTGGTGGTAAC     Linker
G  G  G  G  S  G  G  G  G  S  G  G  G  G  S  G  G  G  G  N TGGATAGATGTAAGATATGACCTGGAGAAATTGAAAGCCTTATTCATCTATTCATATT
W  I  D  V  R  Y  D  L  E  K  I  E  S  L  I  Q  S  I  H      IL-15

GACACCACTTTATACACTGACAGTGACTTTCATCCCAGTTGCAAAGTAACTGCAATGAAC
D  T  T  L  Y  T  D  S  D  F  H  P  S  C  K  V  T  A  M  N

TGCTTTCTCCTGGAATTGCAAGTGATCTTACCTTGCAAACAGCACTCTGTCTTCACAAGAATGTTAGCA
C  F  L  L  E  L  Q  V  I  L  H  E  Y  S  N  M  T  L  N

ACAGTAAGAAACGTGCTCTACCTTGCAAACAGCACTCTGTCTTCTAACAAGAATGTAGCA
T  V  R  N  V  L  A  N  S  T  L  S  S  N  K  N  V  A

GAATCTGGCTGCAAGGAATGTGAGGAGGAGAGAAACCTTCACGAGTTTTTGCAA
E  S  G  C  K  E  C  E  E  L  E  E  K  T  F  T  E  F  L  Q

AGCTTTATACGCATTGTCCAAATGTTCATCAACAACGTCCGGATCCGTTACCCTACGAC   EcoRI
S  F  I  R  I  V  Q  M  F  I  N  T  S  G  Y  P  Y  D          HA tag

GTGCCCGACTACGCCCTGA GAATTC
V  P  D  Y  A       *
```

DTT: + − + −

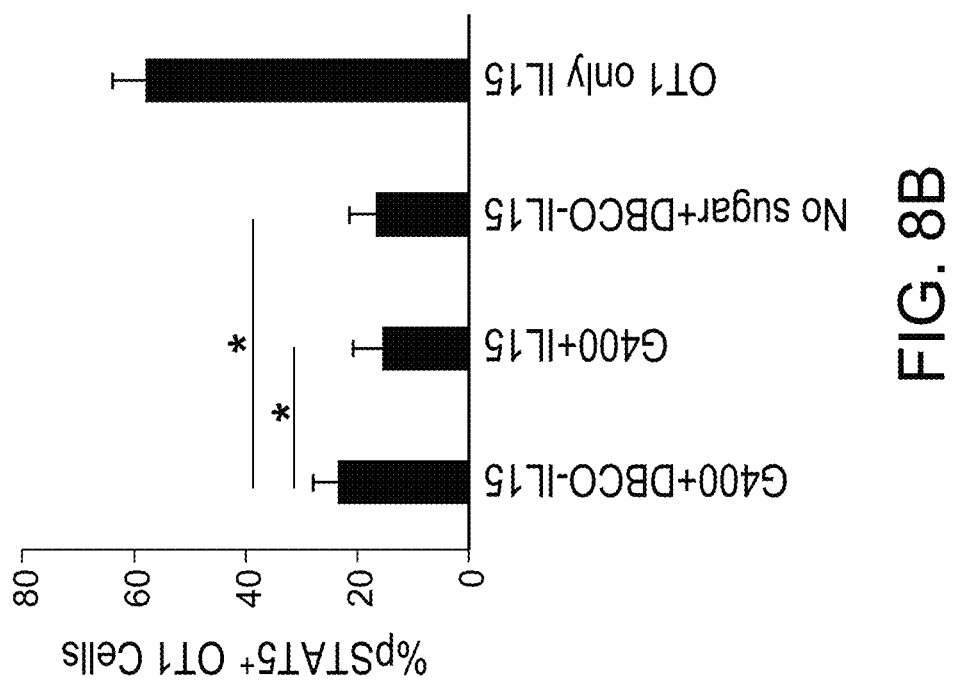
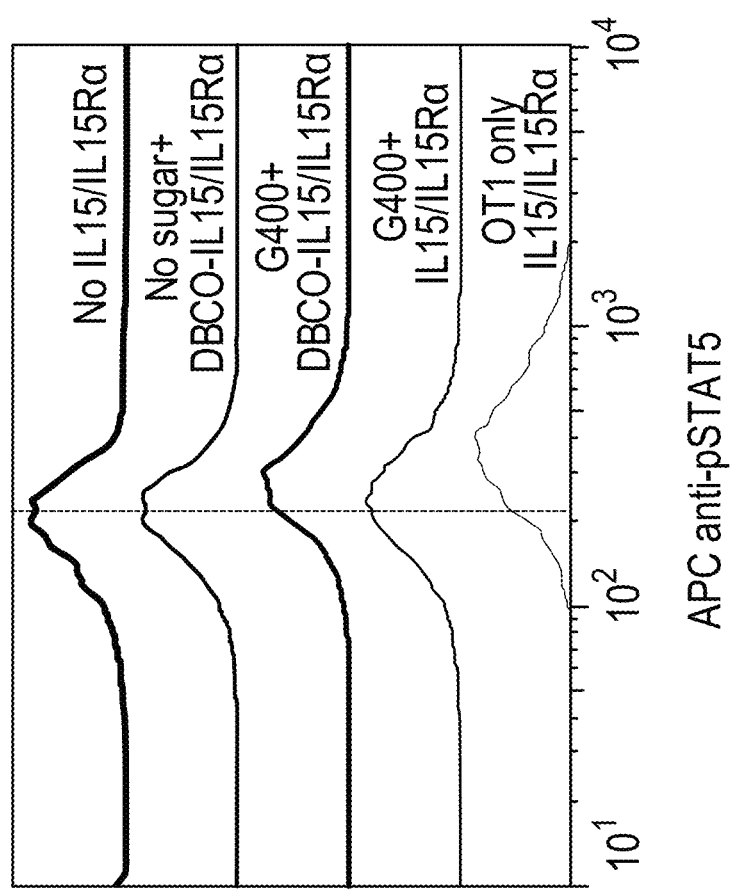
FIG. 8B
FIG. 8A

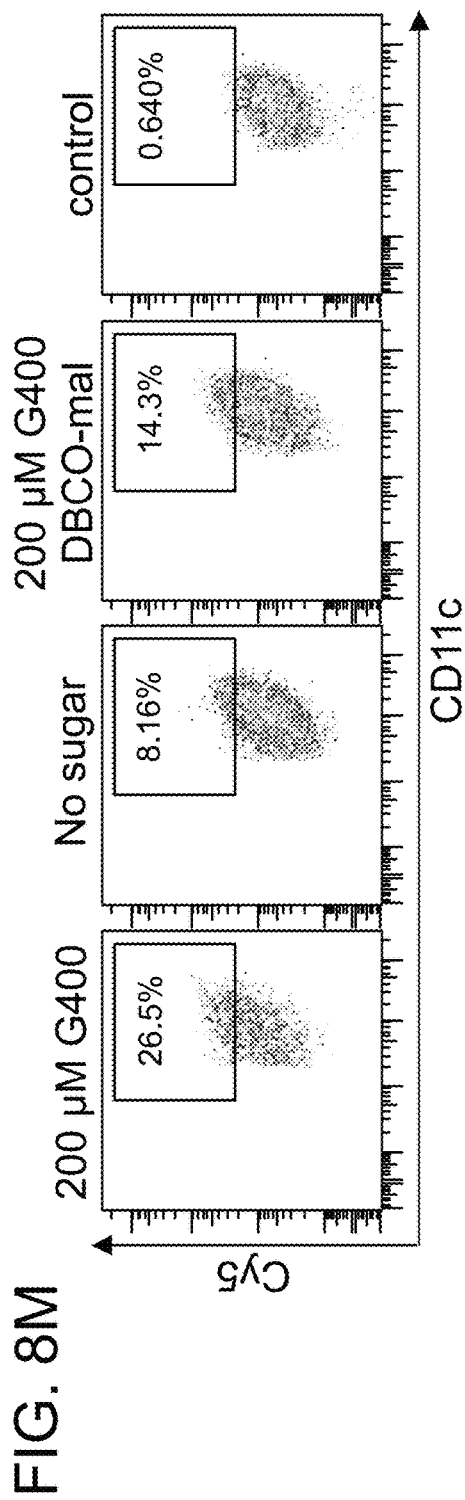
FIG. 8M
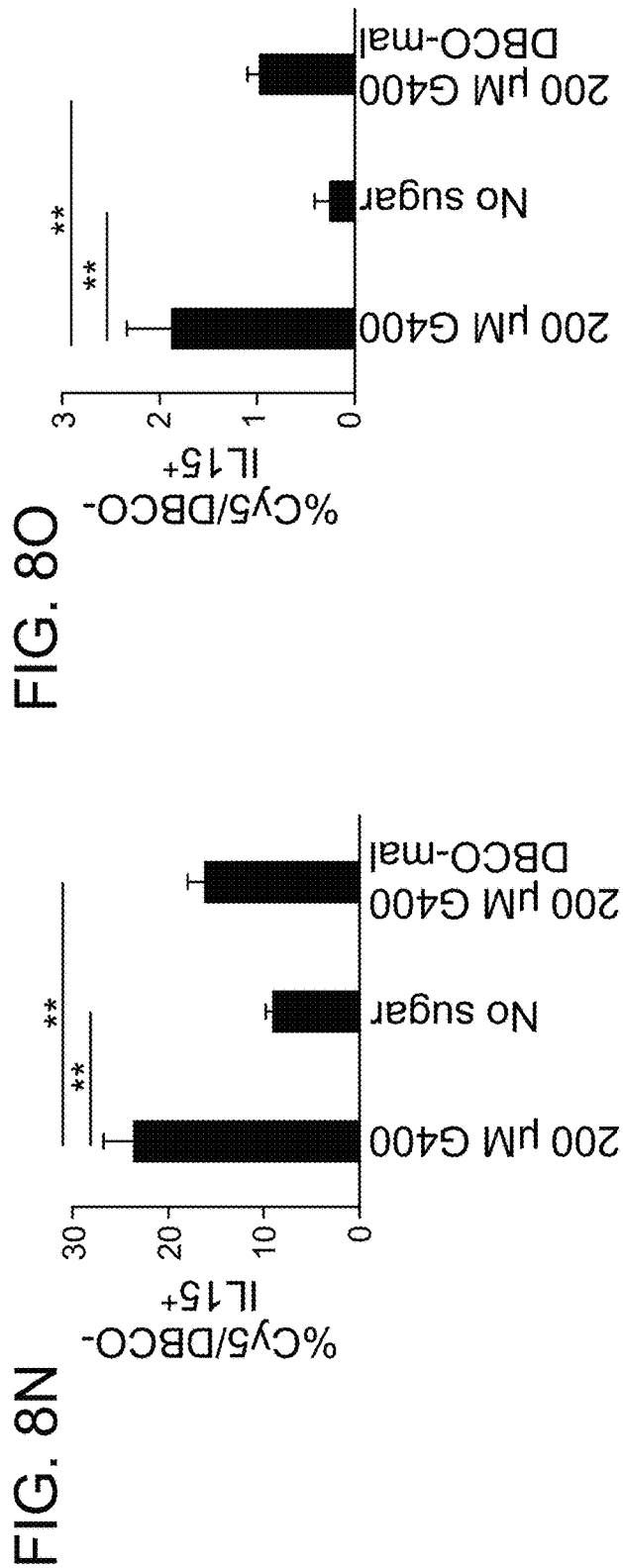
FIG. 8O
FIG. 8N

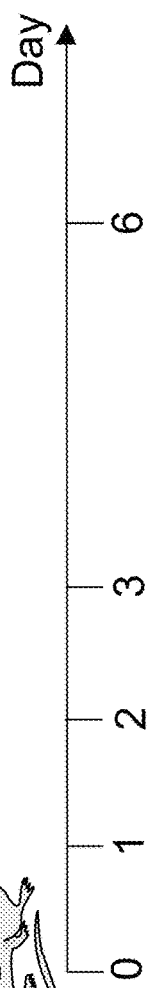
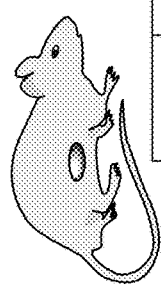
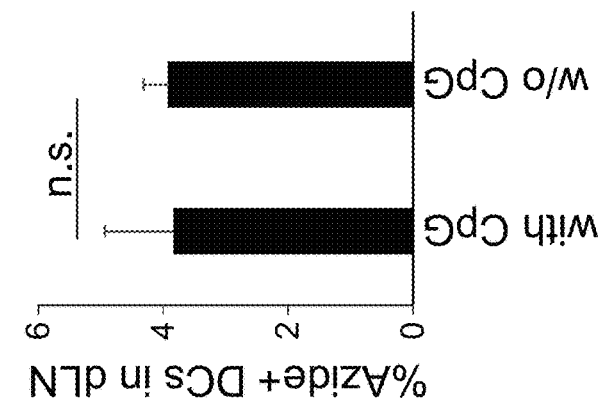
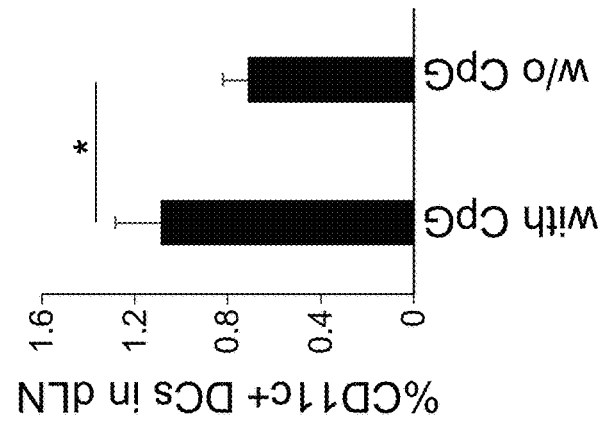
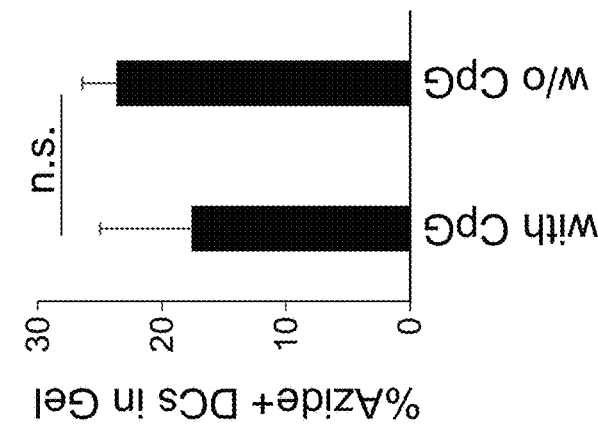

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ile Ile Asn Phe Glu Lys Leu
1               5

<210> SEQ ID NO 2
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (16)..(735)

<400> SEQUENCE: 2
```

```
agatctgccg ccacc atg gta ccg gcg acg ctg ctc ctg ctg ttg gcg gcc          51
                 Met Val Pro Ala Thr Leu Leu Leu Leu Ala Ala
                 1               5                   10 gcc ctg gct ccg act cag acc cgc gcg aaa tgt ggt acc acg tgt cca           99
Ala Leu Ala Pro Thr Gln Thr Arg Ala Lys Cys Gly Thr Thr Cys Pro
            15                  20                  25 cct ccc gta tct att gag cat gct gac atc cgg gtc aag aat tac agt          147
Pro Pro Val Ser Ile Glu His Ala Asp Ile Arg Val Lys Asn Tyr Ser
30                  35                  40 gtg aac tcc agg gag agg tat gtc tgt aac tct ggc ttt aag cgg aaa          195
Val Asn Ser Arg Glu Arg Tyr Val Cys Asn Ser Gly Phe Lys Arg Lys
45                  50                  55                  60 gct gga aca tcc acc ctg att gag tgt gtg atc aac aag aac aca aat          243
Ala Gly Thr Ser Thr Leu Ile Glu Cys Val Ile Asn Lys Asn Thr Asn
                65                  70                  75 gtt gcc cac tgg aca act ccc agc ctc aag tgc atc aga gac ccc tcc          291
Val Ala His Trp Thr Thr Pro Ser Leu Lys Cys Ile Arg Asp Pro Ser
            80                  85                  90 cta gct tct gga ggc gga ggc tct ggt gga ggc ggt tct gga gga gga          339
Leu Ala Ser Gly Gly Gly Gly Ser Gly Gly Gly Gly Ser Gly Gly Gly
            95                  100                 105 gga tct ggt ggt ggt ggt aac tgg ata gat gta aga tat gac ctg gag          387
Gly Ser Gly Gly Gly Gly Asn Trp Ile Asp Val Arg Tyr Asp Leu Glu
110                 115                 120 aaa att gaa agc ctt att caa tct att cat att gac acc act tta tac          435
Lys Ile Glu Ser Leu Ile Gln Ser Ile His Ile Asp Thr Thr Leu Tyr
125                 130                 135                 140 act gac agt gac ttt cat ccc agt tgc aaa gtt act gca atg aac tgc          483
Thr Asp Ser Asp Phe His Pro Ser Cys Lys Val Thr Ala Met Asn Cys
                145                 150                 155 ttt ctc ctg gaa ttg cag gtt att tta cat gag tac agt aac atg act          531
Phe Leu Leu Glu Leu Gln Val Ile Leu His Glu Tyr Ser Asn Met Thr
            160                 165                 170 ctt aat gaa aca gta aga aac gtg ctc tac ctt gca aac agc act ctg          579
Leu Asn Glu Thr Val Arg Asn Val Leu Tyr Leu Ala Asn Ser Thr Leu
        175                 180                 185 tct tct aac aag aat gta gca gaa tct ggc tgc aag gaa tgt gag gag          627
Ser Ser Asn Lys Asn Val Ala Glu Ser Gly Cys Lys Glu Cys Glu Glu
190                 195                 200 ctg gag gag aaa acc ttc aca gag ttt ttg caa agc ttt ata cgc att          675
Leu Glu Glu Lys Thr Phe Thr Glu Phe Leu Gln Ser Phe Ile Arg Ile
205                 210                 215                 220 gtc caa atg ttc atc aac acg tcc gga tct ggt tac ccc tac gac gtg          723
Val Gln Met Phe Ile Asn Thr Ser Gly Ser Gly Tyr Pro Tyr Asp Val
                225                 230                 235 ccc gac tac gcc tgagaattc                                                744
Pro Asp Tyr Ala
            240

<210> SEQ ID NO 3
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Val Pro Ala Thr Leu Leu Leu Leu Ala Ala Ala Leu Ala Pro
1               5                   10                  15
```

```
Thr Gln Thr Arg Ala Lys Cys Gly Thr Cys Pro Pro Pro Val Ser
            20                  25                  30

Ile Glu His Ala Asp Ile Arg Val Lys Asn Tyr Ser Val Asn Ser Arg
            35                  40                  45

Glu Arg Tyr Val Cys Asn Ser Gly Phe Lys Arg Lys Ala Gly Thr Ser
 50                      55                  60

Thr Leu Ile Glu Cys Val Ile Asn Lys Asn Thr Asn Val Ala His Trp
 65                  70                  75                  80

Thr Thr Pro Ser Leu Lys Cys Ile Arg Asp Pro Ser Leu Ala Ser Gly
                 85                  90                      95

Gly Gly Gly Ser Gly Gly Gly Ser Gly Gly Gly Ser Gly Gly
            100                 105                 110

Gly Gly Asn Trp Ile Asp Val Arg Tyr Asp Leu Glu Lys Ile Glu Ser
            115                 120                 125

Leu Ile Gln Ser Ile His Ile Asp Thr Thr Leu Tyr Thr Asp Ser Asp
    130                 135                 140

Phe His Pro Ser Cys Lys Val Thr Ala Met Asn Cys Phe Leu Leu Glu
145                 150                 155                 160

Leu Gln Val Ile Leu His Glu Tyr Ser Asn Met Thr Leu Asn Glu Thr
                165                 170                 175

Val Arg Asn Val Leu Tyr Leu Ala Asn Ser Thr Leu Ser Ser Asn Lys
            180                 185                 190

Asn Val Ala Glu Ser Gly Cys Lys Glu Cys Glu Glu Leu Glu Glu Lys
            195                 200                 205

Thr Phe Thr Glu Phe Leu Gln Ser Phe Ile Arg Ile Val Gln Met Phe
    210                 215                 220

Ile Asn Thr Ser Gly Ser Gly Tyr Pro Tyr Asp Val Pro Asp Tyr Ala
225                 230                 235                 240

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tccatgacgt tcctgacgtt                                                    20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttagggttag ggttagggtt aggg                                               24
```

COMPOSITIONS AND METHODS FOR LABELING AND MODULATION OF CELLS IN VITRO AND IN VIVO

CROSS-REFERENCE TO RELATED APPLICATIONS

This Application is a continuation of International Patent Application No.: PCT/US2019/051621, filed on Sep. 18, 2019, which claims the benefit of U.S. Provisional Application 62/733,378, filed on Sep. 19, 2018. The entire contents of each of these applications are incorporated herein by reference in their entirety.

GOVERNMENT SUPPORT

This invention was made with Government support under CA214369, and CA223255 awarded by the National Institutes of Health. The Government has certain rights in the invention.

BACKGROUND OF THE INVENTION

There are many challenges inherent in identifying and/or modulating specific cell types in vivo. Antibodies are commonly used for cell-specific targeting in vivo, however, this strategy requires identification of cell-specific antigens, and accessibility of antibodies to the target cells, and can be limited by internalization of the antibody and its cognate antigen from the cell surface. In the context of cancer immunotherapy, cancer vaccines that activate dendritic cells (DCs) against tumor-specific antigens show great promise, but this approach is limited by the inability to specifically target and temporally control DCs in vivo.

SUMMARY OF THE INVENTION

Disclosed herein are compositions and methods for metabolically labeling cells using click chemistry reagents. The compositions and methods disclosed herein provide a specific and efficient means of localizing desired agents to a variety of cell types in vivo and in vitro.

Disclosed herein are compositions and methods for labeling cells using click chemistry reagents. The compositions and methods disclosed herein provide a specific and efficient means of localizing desired agents to a variety of cell types in vivo and in vitro.

Accordingly, in one aspect, the present invention provides a click functionalized polysaccharide polymer which is a product of radical-catalyzed polymerization. The radical-catalyzed polymerization involves a reaction between one or more saccharide monomers and each saccharide monomer includes a saccharide molecule, a click reagent attached to the saccharide molecule, and a moiety including a functional group amenable to radical polymerization attached to the saccharide molecule.

In another aspect, the present invention provides a click-functionalized amphiphilic polymer which is a product of radical-catalyzed polymerization. The radical catalyzed polymerization involves a reaction between a reagent including a hydrophilic portion and one or more saccharide monomers and each saccharide monomer includes a saccharide molecule, a click reagent attached to the saccharide molecule, and a moiety including a functional group amenable to radical polymerization attached to the saccharide molecule.

In various embodiments of the above aspects or any other aspect of the invention delineated herein, the saccharide molecule is selected from the group consisting of mannose, galactose, fucose and sialic acid. In another embodiment, the saccharide molecule is mannose.

In various embodiments of the above aspects or any other aspect of the invention delineated herein, the click reagent is attached to the saccharide molecule at the C2 position. In another embodiment, the click reagent is selected from the group consisting of azide, dibenzocyclooctyne (DBCO), transcyclooctene, tetrazine and norbornene and variants thereof. In another embodiment, the click reagent is azide.

In various embodiments of the above aspects or any other aspect of the invention delineated herein, the moiety including a functional group amenable to radical polymerization is attached to the saccharide molecule at the C1 position, the C3 position, the C4 position or the C5 position. In another embodiment, the moiety including a functional group amenable to radical polymerization is attached to the saccharide molecule at the C1 position.

In various embodiments of the above aspects or any other aspect of the invention delineated herein, the moiety including a functional group amenable to radical polymerization includes a double bond. In another embodiment, the moiety including a functional group amenable to radical polymerization includes an acrylate or methacrylate.

In various embodiments of the above aspects or any other aspect of the invention delineated herein, the saccharide molecule further includes one or more hydrolysable substituents at the C1 position, the C3 position, the C4 position or C5 position. In another embodiment, the hydrolysable substituent is represented by formula (1):

wherein R is alkyl. In another embodiment, R is methyl.

In various embodiments of the above aspects or any other aspect of the invention delineated herein, the radical-catalyzed polymerization is reversible addition-fragmentation chain transfer (RAFT) polymerization involving the use of a RAFT agent. In another embodiment, the RAFT agent includes a thiocarbonate moiety, a dithiocarbamate moiety or a dithiobenzoate moiety. In another embodiment, the RAFT agent includes a thiocarbonate moiety. In still another embodiment, the RAFT agent includes 2-(dodecylthiocarbonothioylthio)-2-methylpropionate. In yet another embodiment, the RAFT agent includes poly(ethylene glycol) methyl ether 2-(dodecylthiocarbonothioylthio)-2-methylpropionate.

In one aspect, the present invention provides a click functionalized polymer including repeating saccharide units, wherein each saccharide unit is attached to a click reagent. In one embodiment, the polymer further includes a hydrophilic portion.

In various embodiments of the above aspects or any other aspect of the invention delineated herein, the saccharide unit includes a saccharide selected from the group consisting of mannose, galactose, fucose and sialic acid. In another embodiment, the saccharide unit includes mannose.

In various embodiments of the above aspects or any other aspect of the invention delineated herein, the click reagent is attached to the saccharide unit at the C2 position of the saccharide. In another embodiment, the click reagent is selected from the group consisting of azide, dibenzocyclooctyne (DBCO), transcyclooctene, tetrazine and norbomene and variants thereof. In still another embodiment, the click reagent is azide.

In various embodiments of the above aspects or any other aspect of the invention delineated herein, the saccharide unit further includes one or more hydrolysable substituents at the C1 position, the C3 position, the C4 position or C5 position of the saccharide. In another embodiment, the hydrolysable substituent is represented by formula (1):

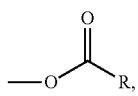

(1)

wherein R is alkyl. In still another embodiment, R is methyl.

In various embodiments of the above aspects or any other aspect of the invention delineated herein, the polymer includes 10 to 1000 saccharide units. In another embodiment, the polymer includes 20 to 500, 100 to 500 or 200 to 600 saccharide units.

In various embodiments of the above aspects or any other aspect of the invention delineated herein, the polymer includes the structure of formula (2):

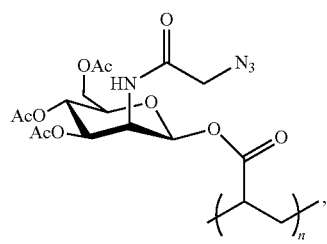

(2)

wherein n is a number between 10 and 1000.

In various embodiments of the above aspects or any other aspect of the invention delineated herein, the hydrophilic portion includes a hydrophilic polymer. In another embodiment, the hydrophilic polymer is polyethylene oxide (PEG). In still another embodiment, the PEG includes between 20 and 450 PEG units. In yet another embodiment, the polymer includes the structure of formula (3):

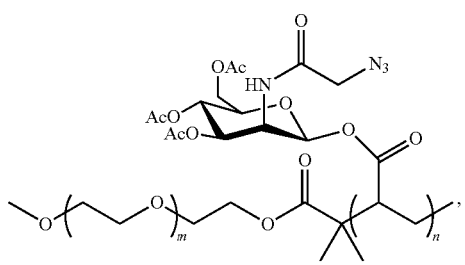

(3)

wherein n is a number between 10 and 1000; and m is a number between 45 and 200.

In another embodiment, the polymer includes the structure of formula (4)

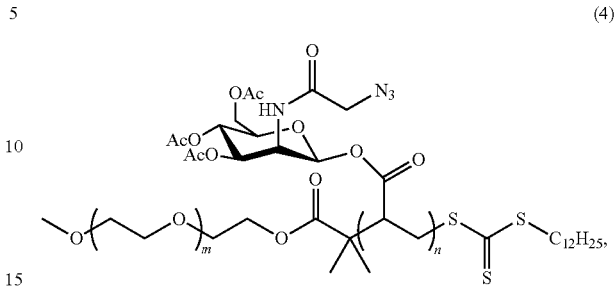

(4)

wherein n is a number between 10 and 1000; and m is a number between 45 and 200.

In one aspect, the present invention provides a nanoparticle for labeling cells with a click reagent including the polymer in various embodiments of the above aspects or any other aspect of the invention delineated herein. In one embodiment, the nanoparticle is self-assembling.

In another aspect, the present invention provides a nanoparticle including a saccharide molecule and a click reagent attached to the saccharide molecule. In one embodiment, the saccharide molecule is selected from the group consisting of mannose, galactose, fucose and sialic acid. In another embodiment, the saccharide molecule is mannose.

In various embodiments of the above aspects or any other aspect of the invention delineated herein, the click reagent is attached to the saccharide molecule at the C2 position. In another embodiment, the click reagent is selected from the group consisting of azide, dibenzocyclooctyne (DBCO), transcyclooctene, tetrazine and norbornene and variants thereof.

In yet another embodiment, the click reagent is azide.

In various embodiments of the above aspects or any other aspect of the invention delineated herein, the saccharide molecule further includes one or more hydrolysable substituents at the C1 position, the C3 position, the C4 position or C5 position of the saccharide. In another embodiment, the hydrolysable substituent is represented by formula

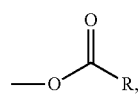

(1)

wherein R is alkyl. In still another embodiment, R is methyl.

In various embodiments of the above aspects or any other aspect of the invention delineated herein, the nanoparticle is selected from the group consisting of a carbon-based nanoparticle, a ceramic nanoparticle, a metal nanoparticle, a semiconductor nanoparticle, a polymeric nanoparticle and a lipid-based nanoparticle. In another embodiment, the nanoparticle is a lipid-based nanoparticle. In still another embodiment, the lipid-based nanoparticle is a liposome or a micelle. In yet another embodiment, the nanoparticle is a semiconductor nanoparticle. In yet another embodiment, the semiconductor nanoparticle is a silica nanoparticle.

The present invention provides a device including (a) a polymer scaffold; (b) a click reagent; and (c) a chemoattractant for immune cells. In one embodiment, the click reagent includes the polymer in various embodiments of the above aspects or any other aspect of the invention delineated herein, or the nanoparticle in various embodiments of the above aspects or any other aspect of the invention delineated herein. In another embodiment, the click reagent includes a polymer including the structure of formula (4):

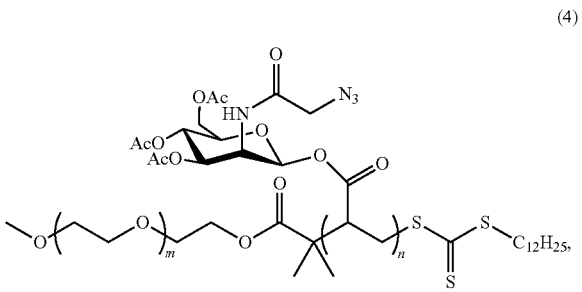

(4)

wherein n is a number between 10 and 1000; and m is a number between 45 and 200. In still another embodiment, the click reagent is provided as a nanoparticle.

In various embodiments of the above aspects or any other aspect of the invention delineated herein, the device includes silica rods.

In various embodiments of the above aspects or any other aspect of the invention delineated herein, the polymer scaffold includes a polymer or co-polymer of polylactic acid, polyglycolic acid, PLGA, alginate or an alginate derivative, gelatin, collagen, agarose, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride) or poly(vinylpyrrolidone).

In various embodiments of the above aspects or any other aspect of the invention delineated herein, the polymer scaffold is a cryogel.

In various embodiments of the above aspects or any other aspect of the invention delineated herein, the polymer scaffold is a hydrogel. In another embodiment, the hydrogel includes a polymer or co-polymer of alginate, or an alginate derivative.

In various embodiments of the above aspects or any other aspect of the invention delineated herein, the polymer scaffold includes macropores.

In various embodiments of the above aspects or any other aspect of the invention delineated herein, the polymer scaffold includes porogen hydrogel microbeads, wherein the porogen hydrogel microbeads degrade at least 10% faster than the polymer scaffold following implantation in the body of a subject. In another embodiment, the porogen hydrogel microbeads comprise oxidized alginate.

In various embodiments of the above aspects or any other aspect of the invention delineated herein, the chemoattractant for immune cells includes GM-CSF, Flt3L, CCL-19, CCL-20, CCL-21, N-formyl peptide, fractalkine, monocyte chemotactic protein-1, and MIP-3u.

In various embodiments of the above aspects or any other aspect of the invention delineated herein, the chemoattractant for immune cells is conjugated to gold nanoparticles.

In various embodiments of the above aspects or any other aspect of the invention delineated herein, the polymer scaffold further includes an adjuvant. In another embodiment, the adjuvant is a toll-like receptor (TLR) ligand. In still another embodiment, the TLR ligand includes a cytosine-guanosine oligonucleotide (CpG-ODN) or polyinosinic:polycytidylic acid (poly(I:C))

In various embodiments of the above aspects or any other aspect of the invention delineated herein, the device includes an antigen. In another embodiment, the antigen is a cancer antigen. In still another embodiment, the antigen is selected from the group consisting of central nervous system (CNS) cancer antigen, CNS germ cell tumor antigen, lung cancer antigen, leukemia antigen, acute myeloid leukemia antigen, multiple myeloma antigen, renal cancer antigen, malignant glioma antigen, medulloblastoma antigen, breast cancer antigen, prostate cancer antigen, Kaposi's sarcoma antigen, ovarian cancer antigen, adenocarcinoma antigen, or melanoma antigen. In yet another embodiments, the cancer antigen is selected from a group consisting of MAGE series of antigens (MAGE-1 is an example), MART-1/melana, tyrosinase, ganglioside, gp100, GD-2, O-acetylated GD-3, GM-2, MUC-1, Sos1, Protein kinase C-binding protein, Reverse transcriptase protein, AKAP protein, VRK1, KIAA1735, T7-1, T11-3, T11-9, *Homo Sapiens* telomerase ferment (hTRT), Cytokeratin-19 (CYFRA21-1), SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3), CTCL tumor antigen sel-1, CTCL tumor antigen sel4-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B1 ANTIGEN (MAGE-XP ANTIGEN) (DAM10), MAGE-B2 ANTIGEN (DAM6), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A; parathyroid secretory protein 1, DUPAN-2, CA 19-9, CA 72-4, CA 195, Carcinoembryonic antigen (CEA), Trp2, ovalbumin, M27, and M30. In another embodiment, the cancer antigen comprises a cancer cell lysate or a live attenuated cancer cell. In still another embodiment, the cancer antigen comprises a melanoma antigen.

In various embodiments of the above aspects or any other aspect of the invention delineated herein, the device includes a cytokine.

In one aspect, the present invention provides a device including an alginate hydrogel, wherein the alginate hydrogel includes nanoparticles including a polymer including the structure of formula (4):

(4)

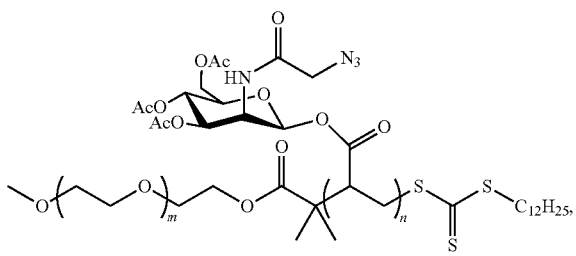

wherein n is a number between 10 and 1000; and m is a number between 45 and 200; (b) GM-CSF; and (c) porogen hydrogel microbeads including oxidized alginate, wherein the porogen hydrogel microbeads degrade at least 10% faster than the alginate hydrogel following implantation in the body of a subject. In one embodiment, GM-CSF is conjugated to gold nanoparticles.

In various embodiments of the above aspects or any other aspect of the invention delineated herein, the alginate hydrogel further includes a cancer antigen. In another embodiment, the cancer antigen is a melanoma antigen.

In various embodiments of the above aspects or any other aspect of the invention delineated herein, the alginate hydrogel further includes an adjuvant. In another embodiment, the adjuvant includes a toll-like receptor (TLR) ligand. In still another embodiment, the TLR ligand includes a cytosine-guanosine oligonucleotide (CpG-ODN) or polyinosinic: polycytidylic acid (poly(I:C)).

In various embodiments of the above aspects or any other aspect of the invention delineated herein, the device further includes a cytokine.

The present invention provides an in vitro method of labeling a cell with a click chemistry reagent, including contacting the cell with the polymer in various embodiments of the above aspects or any other aspect of the invention delineated herein.

The present invention provides an in vitro method of labeling a cell with a click chemistry reagent, including contacting the cell with the nanoparticle in various embodiments of the above aspects or any other aspect of the invention delineated herein.

The present invention provides an in vitro method of labeling a cell with a click chemistry reagent, including contacting the cell with the device in various embodiments of the above aspects or any other aspect of the invention delineated herein.

In various embodiments of the above aspects or any other aspect of the invention delineated herein, the cell is selected from the group consisting of an epithelial cell, a fibroblast cell, a neuronal cell, an endothelial cell, or an immune cell. In another embodiment, the cell is an immune cell. In still another embodiment, the immune cell is a dendritic cell, a T cell, a macrophage, a B cell, or a neutrophil. In yet another embodiment, the immune cell is a CAR-T cell or Sipuleucel-T.

In various embodiments of the above aspects or any other aspect of the invention delineated herein, the method further includes contacting the cell with a second click chemistry reagent coupled to an agent targeted to the labeled cell, wherein the second click chemistry reagent can selectively react with the click reagent present on the labeled cell.

In various embodiments of the above aspects or any other aspect of the invention delineated herein, the method further includes administering the labeled cell to a subject. In another embodiment, the method further includes administering to the subject a second click chemistry reagent coupled to an agent targeted to the labeled cell, wherein the second click chemistry reagent can selectively react with the click reagent present on the labeled cell.

In another aspect, the present invention provides an in vivo method of labeling an immune cell in a subject with a click chemistry reagent, including: (a) administering to the subject the device in various embodiments of the above aspects or any other aspect of the invention delineated herein, and (b) maintaining the device in the subject for a period of time sufficient for recruitment of immune cells to the device. In one embodiment, the period of time sufficient for recruitment of immune cells is 3 days or more.

In various embodiments of the above aspects or any other aspect of the invention delineated herein, the method further includes (c) applying ultrasound to the device in the subject, following step (b).

In various embodiments of the above aspects or any other aspect of the invention delineated herein, the method further includes administering to the subject a second click chemistry reagent coupled to an agent targeted to the immune cell, wherein the second click chemistry reagent can selectively react with the click reagent present in the device. In another embodiment, the agent targeted to the immune cell is a protein, a peptide, a nucleic acid, or a small molecule. In still another embodiment, the agent targeted to the immune cell is a protein or a peptide.

In various embodiments of the above aspects or any other aspect of the invention delineated herein, the agent targeted to the immune cell is a detectable label. In another embodiment, the detectable label is a fluorescent label or a radio-label.

In various embodiments of the above aspects or any other aspect of the invention delineated herein, the agent targeted to the immune cell is a cancer antigen. In one embodiment, the cancer antigen is selected from the group consisting of a central nervous system (CNS) cancer antigen, CNS germ cell tumor antigen, lung cancer antigen, leukemia antigen, acute myeloid leukemia antigen, multiple myeloma antigen, renal cancer antigen, malignant glioma antigen, medulloblastoma antigen, breast cancer antigen, prostate cancer antigen, Kaposi's sarcoma antigen, ovarian cancer antigen, adenocarcinoma antigen, or melanoma antigen. In still another embodiment, the cancer antigen is selected from a group consisting of MAGE series of antigens (MAGE-1 is an example), MART-1/melana, tyrosinase, ganglioside, gp100, GD-2, O-acetylated GD-3, GM-2, MUC-1, Sos1, Protein kinase C-binding protein, Reverse transcriptase protein, AKAP protein, VRK1, KIAA1735, T7-1, T11-3, T11-9, *Homo Sapiens* telomerase ferment (hTRT), Cytokeratin-19 (CYFRA21-1), SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3), CTCL tumor antigen sel-1, CTCL tumor antigen sel4-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B1 ANTIGEN (MAGE-XP ANTIGEN) (DAM10), MAGE-B2 ANTIGEN (DAM6), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A; parathyroid secretory protein 1, DUPAN-2, CA 19-9, CA 72-4, CA 195, Carcinoembryonic antigen (CEA), Trp2, ovalbumin, M27, and M30. In yet another embodiment, the cancer antigen is a melanoma antigen.

In various embodiments of the above aspects or any other aspect of the invention delineated herein, the agent targeted to the immune cell is an adjuvant. In another embodiment, the adjuvant is a cytokine and/or a cytokine receptor. In still another embodiment, the adjuvant includes IL-15, IL-15Rα, IL-1β, IL-2, IL-12, IL-15, IL-18, TNFα, IFNγ, or a combination thereof. In another embodiment, the adjuvant includes an IL-15/IL-15Rα fusion protein.

In various embodiments of the above aspects or any other aspect of the invention delineated herein, the click reagent present in the device includes an azide, and wherein the second click chemistry reagent includes dibenzocyclooctyne (DBCO).

In various embodiments of the above aspects or any other aspect of the invention delineated herein, the click reagent present in the device includes tetrazine, and wherein the second click chemistry reagent includes trans-cyclooctene (TCO) or norbornene.

In another aspect, the present invention provides a method of promoting an immune response to an antigen in a subject, including: (a) administering to the subject the device in various embodiments of the above aspects or any other aspect of the invention delineated herein; (b) maintaining the device in the subject for a period of time sufficient for recruitment of immune cells; (c) applying ultrasound to the device in the subject; and (d) administering to the subject a second click chemistry reagent coupled to the antigen, wherein the second click chemistry reagent can selectively react with the click reagent present in the device; thereby promoting an immune response to the antigen in the subject. In one embodiment, the antigen is a cancer antigen. In another embodiment, the immune response includes increasing the number of antigen specific dendritic cells; increasing the number of antigen specific CD8+ T cells; improving the activation and proliferation of CD8+ T cells; or improving neoantigen-specific CD8+ T cell response.

In still another aspect, the present invention provides a method of promoting an immune response to an antigen in a subject, including: (a) administering to the subject the device In various embodiments of the above aspects or any other aspect of the invention delineated herein; (b) maintaining the device in the subject for a period of time sufficient for recruitment of immune cells; (c) applying ultrasound to the device in the subject; and (d) administering to the subject a second click chemistry reagent coupled to an adjuvant, wherein the second click chemistry reagent can selectively react with the click chemistry reagent present in the device; thereby promoting an immune response to the antigen in the subject. In one embodiment, the polymer scaffold includes the antigen. In one embodiment, the antigen is a cancer antigen.

In various embodiments of the above aspects or any other aspect of the invention delineated herein, the adjuvant includes IL-15, IL-15Rα, IL-1β, IL-2, IL-12, IL-15, IL-18, TNFα, IFNγ, or a combination thereof.

In various embodiments of the above aspects or any other aspect of the invention delineated herein the adjuvant includes an IL-15/IL-15Rα fusion protein. In certain embodiments, the second click chemistry reagent coupled to the adjuvant is administered to the subject a plurality of times. In still another embodiment, the immune response includes increasing the number of antigen specific dendritic cells; increasing the number of antigen specific CD8+ T cells; improving the activation and proliferation of CD8+ T cells; or improving neoantigen-specific CD8+ T cell response.

In one aspect, the present invention provides a method promoting an immune response to an antigen in a subject, including: (a) administering to the subject a device including an alginate hydrogel, wherein the alginate hydrogel includes (i) nanoparticles including a polymer including the structure of formula (4):

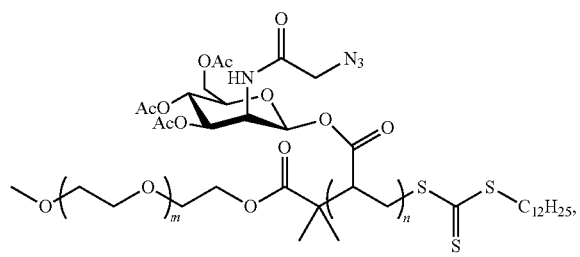

(4)

wherein n is a number between 10 and 1000; and m is a number between 45 and 200; (ii) GM-CSF; (iii) porogen hydrogel microbeads including oxidized alginate, wherein the porogen hydrogel microbeads degrade at least 10% faster than the alginate hydrogel following implantation in the body of a subject; and (iv) the antigen; (b) maintaining the device in the subject for a period of time sufficient for recruitment of immune cells; (c) applying ultrasound to the device in the subject; and (d) administering to the subject an IL-15/IL-15Rα fusion protein coupled to DBCO; thereby promoting an immune response to the antigen in the subject. In one embodiment, the device further includes CpG-ODN. In another embodiment, the IL-15/IL-15Rα fusion protein coupled to DBCO is administered to the subject a plurality of times. In still another embodiment, the immune response includes increasing the number of antigen specific dendritic cells; increasing the number of antigen specific CD8+ T cells; improving the activation and proliferation of CD8+ T cells; or improving neoantigen-specific CD8+ T cell response.

In one aspect, the present invention provides a method of preventing or treating a disease in a subject, including: (a)

administering to the subject the device of any of the foregoing aspects or any other aspect of the invention delineated herein; (b) maintaining the device in the subject for a period of time sufficient for recruitment of immune cells; (c) applying ultrasound to the device in the subject; and (d) administering to the subject a second click chemistry reagent coupled to the antigen, wherein the second click chemistry reagent can selectively react with the click reagent present in the device; thereby preventing or treating the disease in the subject. In one embodiment, the antigen is a cancer antigen. In another embodiment, the disease is a cancer.

In another aspect, the present invention provides a method of preventing or treating a disease in a subject, including: (a) administering to the subject the device of any of the foregoing aspects or any other aspect of the invention delineated herein; (b) maintaining the device in the subject for a period of time sufficient for recruitment of immune cells; (c) applying ultrasound to the device in the subject; and (d) administering to the subject a second click chemistry reagent coupled to an adjuvant, wherein the second click chemistry reagent can selectively react with the click chemistry reagent present in the device; thereby promoting an immune response to the antigen in the subject. In one embodiment, the polymer scaffold includes the antigen. In one embodiment, the antigen is a cancer antigen. In another embodiment, the adjuvant includes IL-15, IL-15Rα, IL-1β, IL-2, IL-12, IL-15, IL-18, TNFα, IFNγ, or a combination thereof. In still another embodiment, the adjuvant includes an IL-15/IL-15Rα fusion protein. In certain embodiments, the second click chemistry reagent coupled to the adjuvant is administered to the subject a plurality of times. In yet another embodiment, the disease is a cancer.

In still another aspect, the present invention provides a method of preventing or treating a disease in a subject, including: (a) administering to the subject a device including an alginate hydrogel, wherein the alginate hydrogel includes (i) nanoparticles including a polymer including the structure of formula (4):

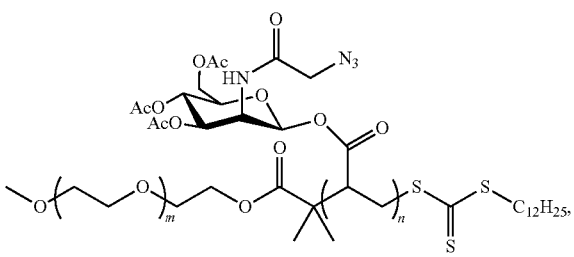

(4)

wherein n is a number between 10 and 1000; and m is a number between 45 and 200; (ii) GM-CSF; (iii) porogen hydrogel microbeads including oxidized alginate, wherein the porogen hydrogel microbeads degrade at least 10% faster than the alginate hydrogel following implantation in the body of a subject; and (iv) the antigen; (b) maintaining the device in the subject for a period of time sufficient for recruitment of immune cells; (c) applying ultrasound to the device in the subject; and (d) administering to the subject an IL-15/IL-15Rα fusion protein coupled to DBCO; thereby preventing or treating the disease. In one embodiment, the device further includes CpG-ODN. Alternatively or in combination, the IL-15/IL-15Rα fusion protein coupled to DBCO is administered to the subject a plurality of times. In still another embodiment, the disease is a cancer. In yet another embodiment, the IL-15/IL-15Rα fusion protein coupled to DBCO is administered to the subject a plurality of times.

In one aspect, the present invention provide a kit including: (a) the device in various embodiments of the above aspects or any other aspect of the invention delineated herein; and (b) a second click chemistry reagent coupled to an agent targeting immune cells, wherein the second click chemistry reagent can selectively react with the click reagent present in the device.

In another aspect, the present invention provides the polymer in various embodiments of the above aspects or any other aspect of the invention delineated herein for use in an in vivo method of labeling a cell in a subject with a click chemistry reagent.

In another aspect, the present invention provides the nanoparticle in various embodiments of the above aspects or any other aspect of the invention delineated herein for use in an in vivo method of labeling a cell in a subject with a click chemistry reagent.

In another aspect, the present invention provides the device in various embodiments of the above aspects or any other aspect of the invention delineated herein for use in an in vivo method of labeling a cell in a subject with a click chemistry reagent.

In one aspect, the present invention provides the polymer, nanoparticle, or device in various embodiments of the above aspects or any other aspect of the invention delineated herein, wherein the cell is an immune cell.

In one aspect, the present invention provides the polymer in various embodiments of the above aspects or any other aspect of the invention delineated herein for use in promoting an immune response to an antigen in a subject.

In another aspect, the present invention provides the polymer in various embodiments of the above aspects or any other aspect of the invention delineated herein for use in treating a cancer or reducing tumor burden in a subject.

In one aspect, the present invention provides the nanoparticle in various embodiments of the above aspects or any other aspect of the invention delineated herein for use in promoting an immune response to an antigen in a subject.

In another aspect, the present invention provides the nanoparticle in various embodiments of the above aspects or any other aspect of the invention delineated herein for use in treating a cancer or reducing tumor burden in a subject.

In one aspect, the present invention provides the device in various embodiments of the above aspects or any other aspect of the invention delineated herein for use in promoting an immune response to an antigen in a subject.

In another aspect, the present invention provides the device in various embodiments of the above aspects or any other aspect of the invention delineated herein for use in treating a cancer or reducing tumor burden in a subject.

In one aspect, the present invention provides an immune cell including a cell surface glycoprotein including a carbohydrate covalently linked to a click reagent. In one embodiment, the click reagent includes azide, dibenzocyclooctyne (DBCO), transcyclooctene, tetrazine and/or norbornene, or variants thereof.

In various embodiments of the above aspects or any other aspect of the invention delineated herein, the carbohydrate is covalently coupled to an agent by a linkage formed through reaction of the click reagent linked to the carbohydrate with a counterpart click reagent linked to the agent. In another embodiment, the agent is an antigen. In still another embodiment, the antigen is a cancer antigen. In yet another embodiment, the agent is an adjuvant. In another embodiment, the agent is an IL-15/IL-15Rα fusion protein.

BRIEF DESCRIPTION OF THE DRAWINGS

FIG. 1A illustrates in situ recruitment and metabolic labeling of immune cells, such as dendritic cells (DCs) in pore forming gels, such as alginate gels. In the exemplary embodiment, the porogens in alginate gels form macropores via hydrolysis over time, enabling the homing of recruited immune cells, such as DCs. A labeling agent, such as azido-sugar materials, in the bulk phase of the alginate gels are then burst released using ultrasound, endocytosed and metabolized by the immune cells, such as DCs, resulting in azido-labeled glycoproteins on cell membranes. FIG. 1B illustrates the migration of labelled immune cells, such as azido-labeled DCs from the gel scaffold to other parts of the body, such as lymph nodes and subsequent targeting of immunomodulatory agents via certain coupling mechanism, such as Click chemistry.

FIGS. 2A-2R illustrate that G400 NP can metabolically label DCs and shows on-demand ultrasound-triggered release from pore-forming alginate gels in vitro and in vivo.

FIGS. 2A-2C illustrate azido-labeled DCs can be well detected by DBCO/e660-antibody via Click chemistry. FIG. 2A is a schematic illustration of metabolic labeling of DC2.4 cells and subsequent detection of cell-surface azides using DBCO-agents.

FIGS. 2B and 2C are graphs showing the percentage of $Cy5^+$ cells (FIG. 2B) and $e660^+$ cells (FIG. 2C) after incubating DC2.4 cells with $Ac_4ManAz$ (50 µM) for three days and detecting with DBCO-Cy5 and DBCO/e660-antibody, respectively for 30 min. All the numerical data are presented as mean±SD ($0.01<*P≤0.05$; $P≤0.01$; $*P≤0.001$).

FIGS. 2D, 2I-2K, and 2O illustrate that G25 and G400 NP can enter and metabolically label DCs with azido groups.

FIG. 2I provides confocal images of BMDCs after incubating with Cy5-labeled G25 NP for 0.5 and 2 hours, respectively. Endosomes/lysosomes were stained with Lysotracker green (green). Cell membrane and nuclei were stained with Alexa fluor 594-wheat germ agglutinin (grey) and DAPI (blue), respectively. Scale bar: 10 µm.

FIGS. 2J and 2K are graph showing uptake of Cy5-labeled G25 NP by BMDCs over time. FL: fluorescence intensity.

FIG. 2N is a graph showing percentage of $azide^+$ BMDCs after 3-d incubation with $Ac_4ManAz$, G25 NP, and G400 NP, respectively (n=6).

FIG. 2O is graph showing mean e660 fluorescence intensity of BMDCs after incubating with sugar materials for three days and detecting with DBCO/e660-antibody for 30 minutes.

FIG. 2R is a graph showing in vivo release profiles of G400 NP, as quantified from FIG. 2Q (n=4).

FIG. 3A is a schematic illustration of time frame of the in vivo study. Pore-forming alginate gels containing GM-CSF and G400 NP were subcutaneously injected into C57BL/6 mice on day 0, followed by ultrasound treatment on day 3 and analyses on day 6 (n=6).

FIG. 3N provides representative confocal images of dLN sections which were stained with DBCO/efluor660-antibody, pacific blue-conjugated anti-CD3, FITC-conjugated anti-CD11c, and PE-conjugated anti-B220.

FIG. 3O is a graph showing percentage of azide+ DCs in the gel scaffold over time. FIG. 3P is a graph showing percentage of azide+ DCs in dLNs over time. FIG. 3Q is a graph showing percentage of azide+ F4/80+ macrophagocytes over time.

FIG. 3S is a graph showing total number of DCs in dLNs.

FIGS. 3D, 3E, 3G, 3I, 3L, 3M, 3R and 3S illustrate that pore-forming alginate gels containing G400 NP and GM-CSF recruit and metabolically label DCs with azido groups in vivo.

FIGS. 4A-4J and FIGS. 5A-5L illustrate that azido-labeled DCs mediate targeted delivery of DBCO-agents via Click chemistry. FIG. 4A is a schematic illustration showing time frame of the study. Pore-forming alginate gels loaded with GM-CSF and G400 NP were subcutaneously injected into C57BL/6 mice on day 0, followed by ultrasound treatment on day 3 and intravenous injection of DBCO-Cy5 on day 8 (n=4) or as otherwise indicated. Mice treated with gels without G400 NP (control gel) or mice treated with G400 NP solution (G400 SQ) were used as controls.

For FIGS. 4B-4D, DBCO-Cy5 was injected on day 8 (n=4). FIG. 4B is a graph showing quantification of Cy5 fluorescence in LNs at 24 hours post DBCO-Cy5 injection.

FIG. 4C is a graph showing Cy5 fluorescence intensity ratio of dLN to NdLN.

FIG. 4D provides IVIS imaging of dLNs and NdLNs at 24 hours post DBCO-Cy-5 injection.

For the analyses illustrated in FIGS. 4E-4H, after injection of gels on day 0 and ultrasound treatment on day 3, DBCO-Cy5 was intravenously injected on day 15 (n=4-5).

Figure 4A:
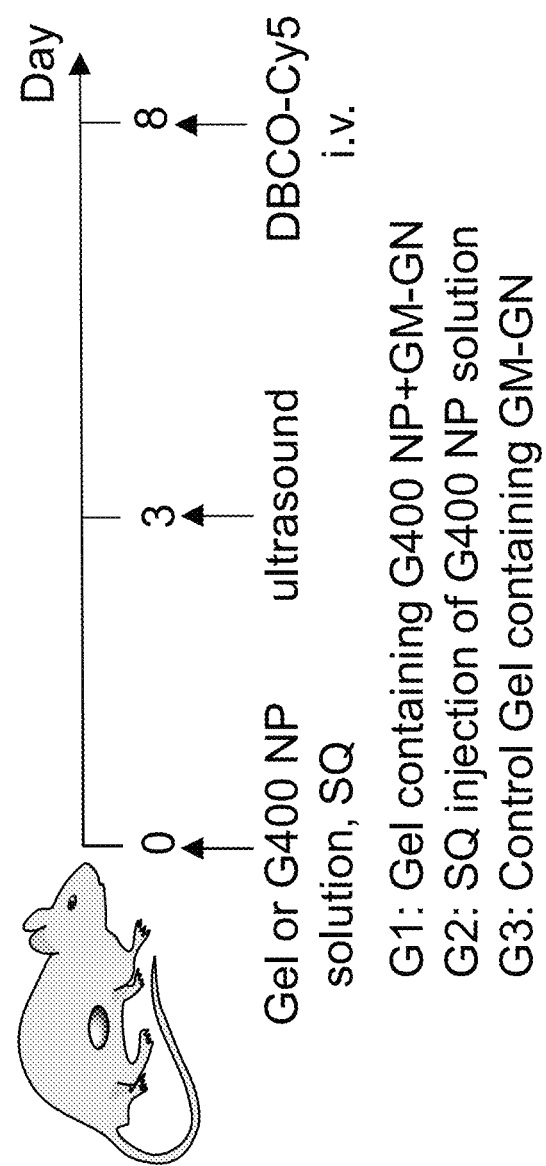
Figure 4B:
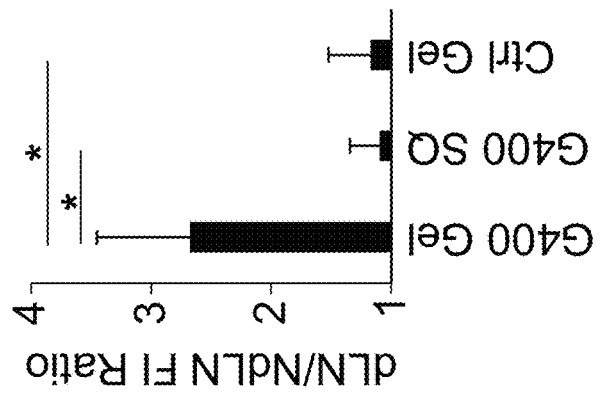
Figure 4C:
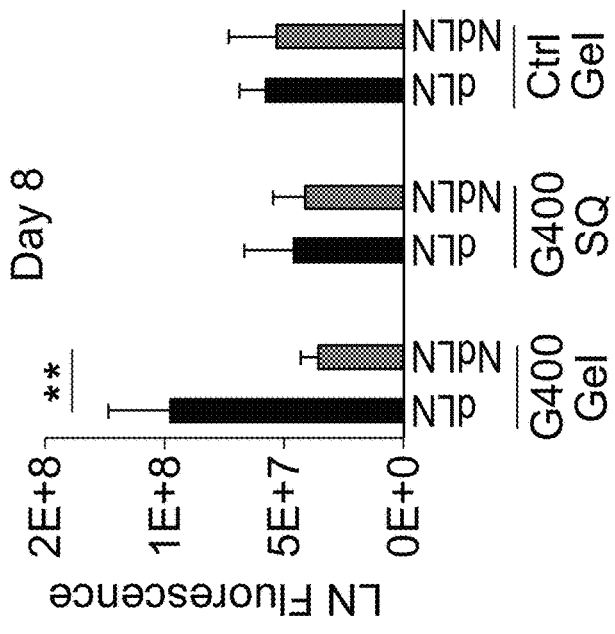
Figure 4D:
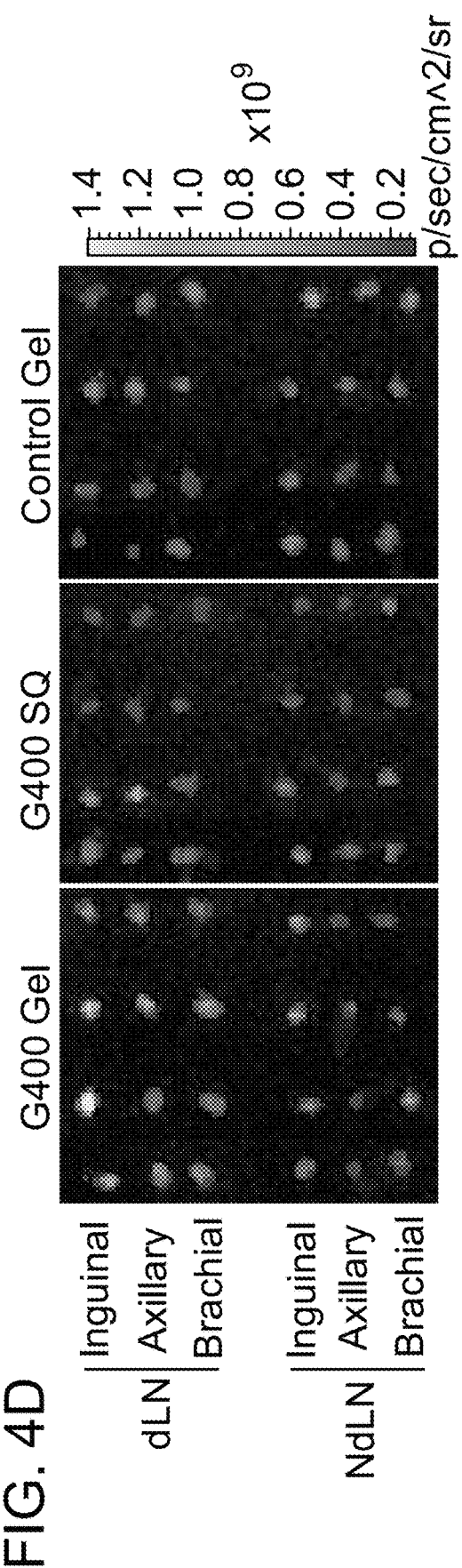
Figure 4E:
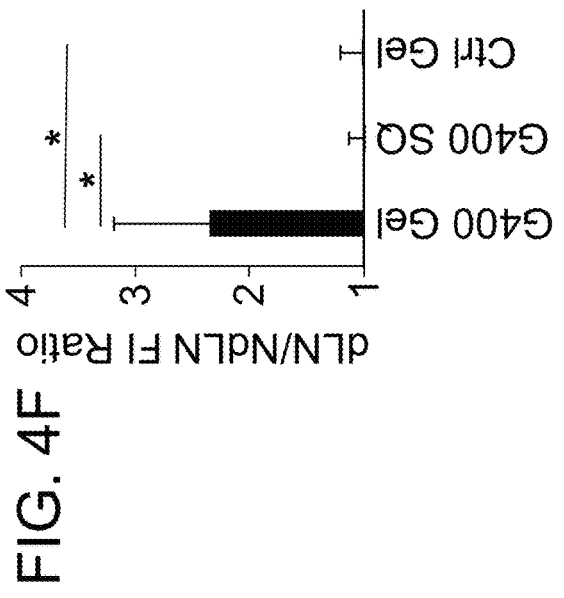

FIG. 4E is a graph showing quantification of Cy5 fluorescence in LNs at 24 hours post DBCO-Cy5 injection.

Figure 4F:
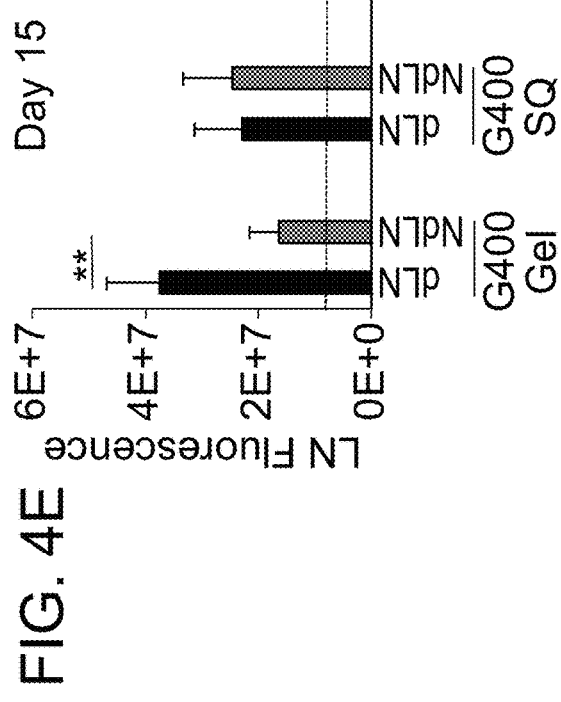

FIG. 4F is a graph showing Cy5 fluorescence intensity ratio of dLN to NdLN.

Figure 4G:
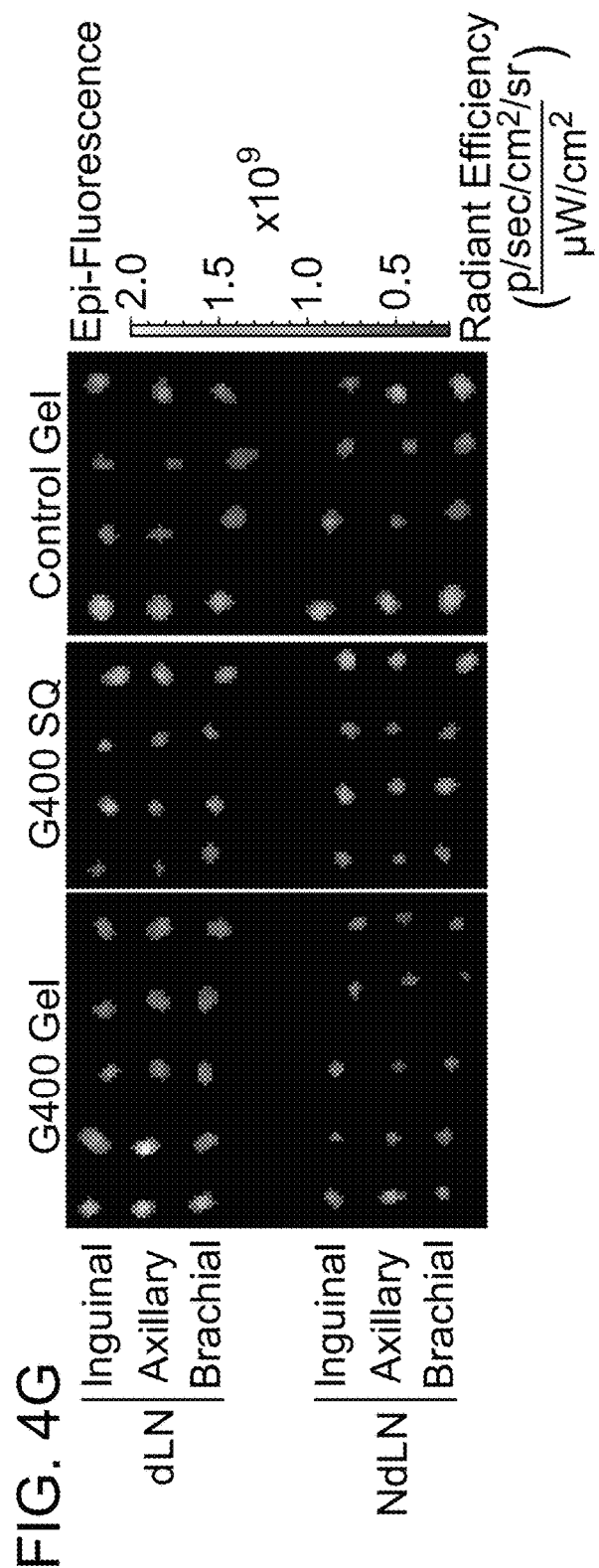

FIG. 4G provides IVIS imaging of dLNs and NdLNs at 24 hours post DBCO-Cy5 injection.

Figure 4H:
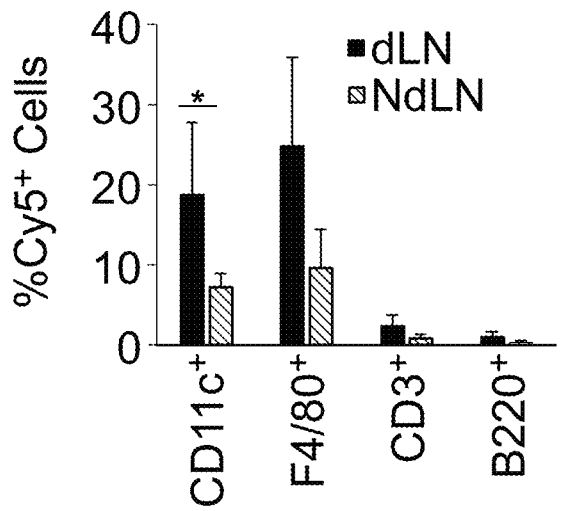

FIG. 4H is a graph showing percentage of Cy5+ cells among CD11c+, F4/80+, CD3+, B220+ cells, respectively.

Figure 4I:
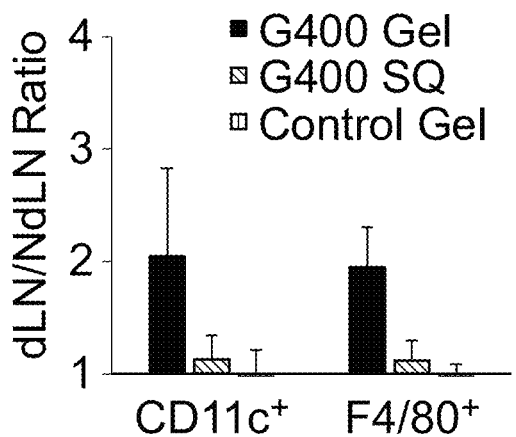

FIG. 4I is a graph showing dLN/NdLN Cy5 fluorescence intensity ratio.

Figure 4J:
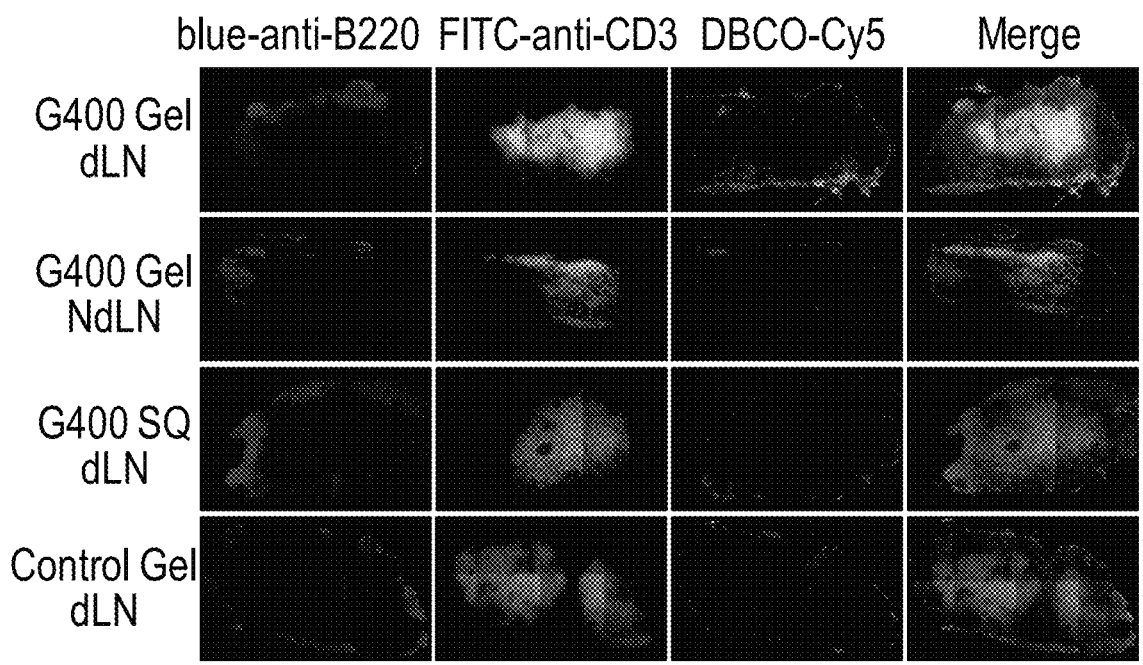

FIG. 4J provides representative confocal images of LN sections which were stained with pacific blue-conjugated anti-B220 and FITC-conjugated anti-CD11c. Scale bar represents 200 μm.

FIGS. 4D, 4G, and 4H-4J illustrate that azido-labeled DCs mediate targeted delivery of DBCO-Cy5 to dLNs via Click chemistry.

FIGS. 5A-5D illustrate that azido-labeled DCs in LNs mediate targeted delivery of DBCO-OVA and DBCO-CpG In vitro via Click chemistry.

FIGS. 5A and 5B are graphs showing percentage of FITC+ BMDCs (FIG. 5A) and mean FITC fluorescence intensity of BMDCs (FIG. 5A) after incubation with DBCO/FITC-OVA and FITC-OVA (1 μg/mL in OVA equivalent), respectively for 30 min. BMDCs were pretreated with G400 NP (200 μM) or PBS for three days.

FIGS. 5C and 5D are graphs showing percentage of Cy5+ BMDCs (FIG. 5C) and mean Cy5 fluorescence intensity of BMDCs (FIG. 5D) after incubation with DBCO/Cy5-CpG (50 ng/mL) for 30 min. BMDCs were pretreated with G400 NP (200 μM) and PBS, respectively for three days.

Figure 5E:
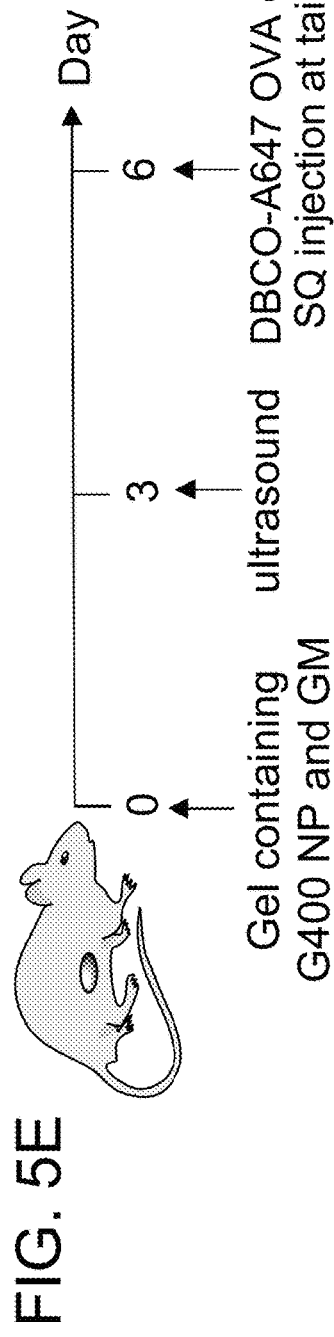

FIG. 5E is a schematic illustration of time frame of LN targeted delivery of DBCO-OVA. After injection of gels on day 0 and ultrasound treatment on day 3, Alexa fluor647 (A647)-conjugated DBCO-OVA or OVA was subcutaneously injected at tail base.

Figure 5G:
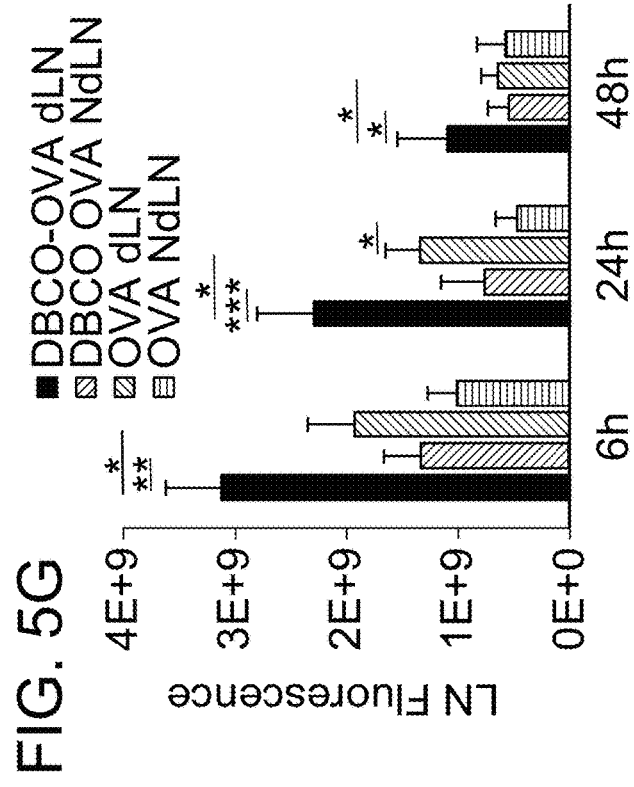
Figure 5F:
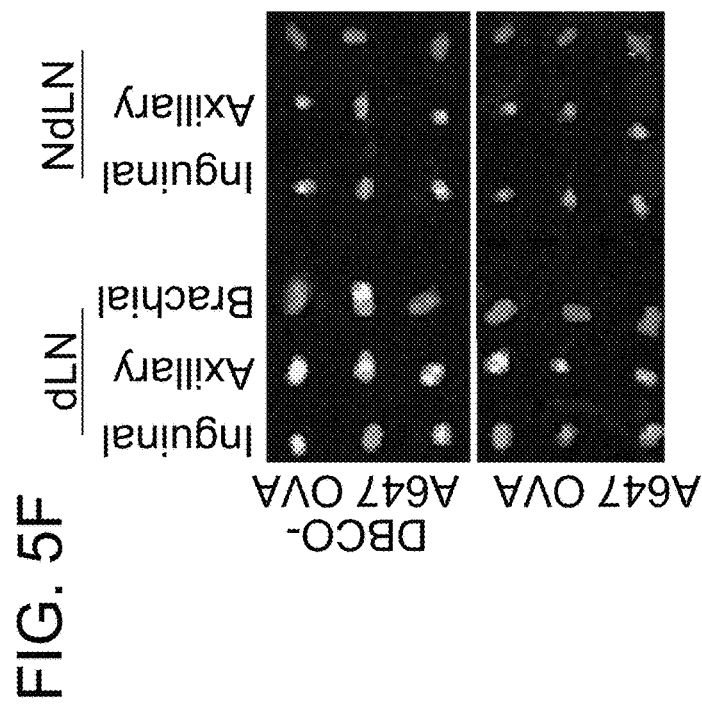

FIG. 5F provides IVIS imaging of dLNs and NdLNs at 6 hours post injection of A647-conjugated DBCO-OVA or OVA.

FIG. 5G is a graph showing quantification of A647 fluorescence in LNs at 6, 24, and 48 hours post injection of A647-conjugated DBCO-OVA or OVA, respectively.

Figure 5H:
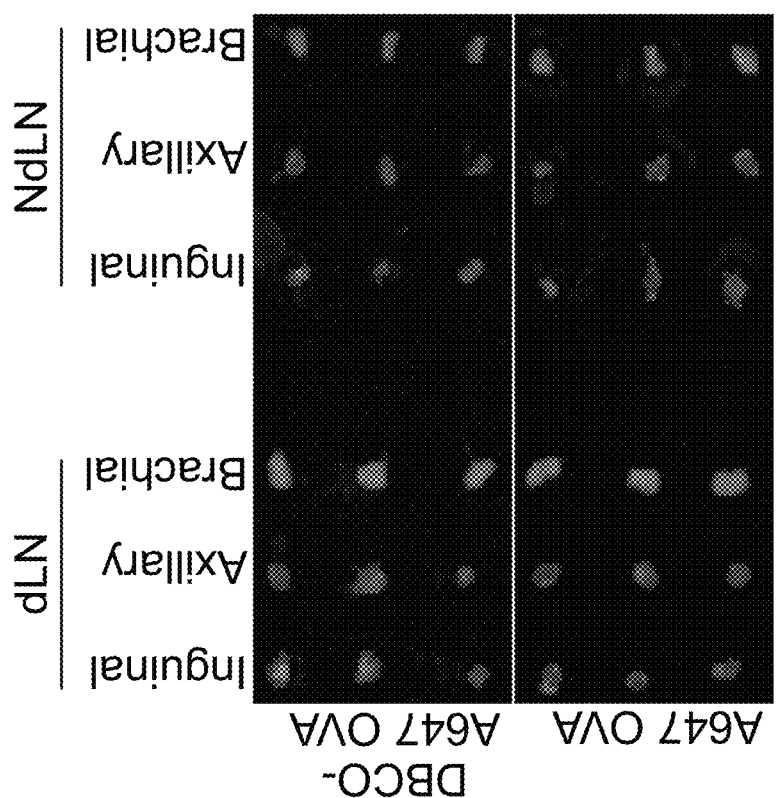
Figure 5H:
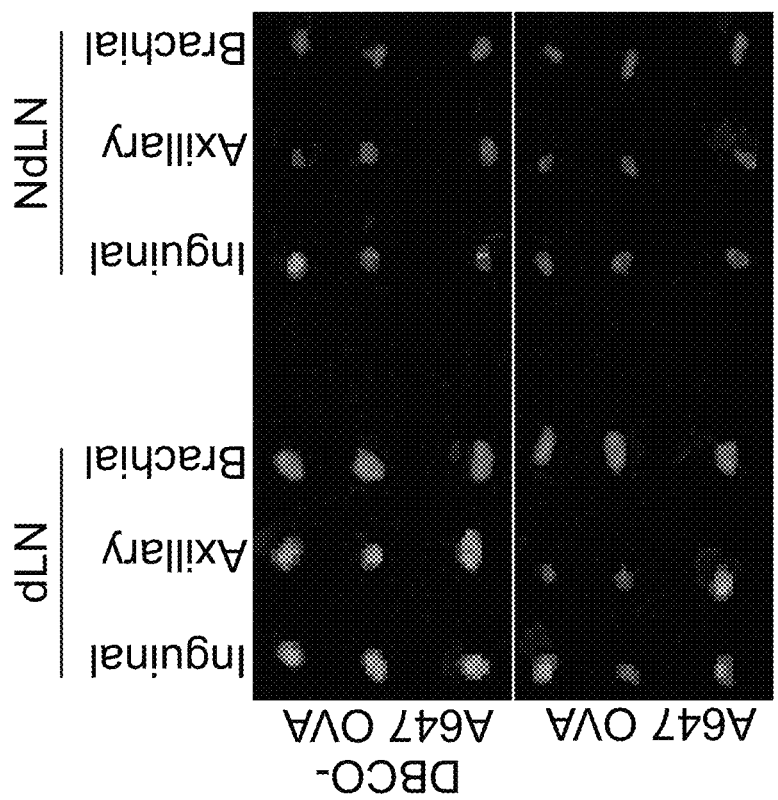

FIG. 5H provides IVIS imaging of dLNs and NdLNs at 24 hours (left panel) and 48 hours (right panel) post injection of A647-conjugated DBCO-OVA or OVA.

Figure 5I:
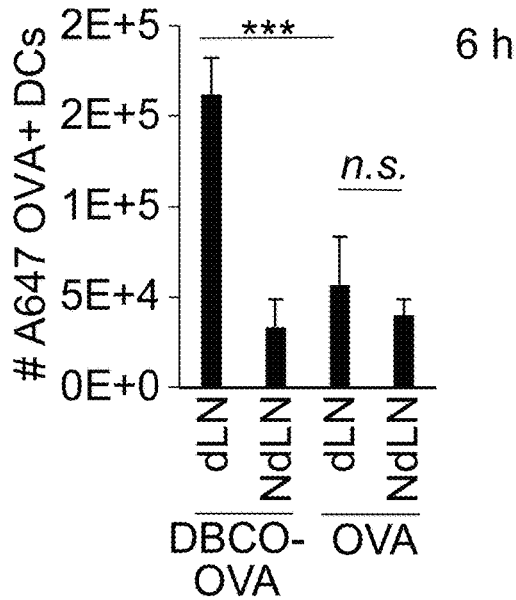

FIG. 5I is a graph showing total number of A647 OVA+ DCs in LNs at 6 hours post injection of A647-conjugated DBCO-OVA or OVA, respectively.

Figure 5J:
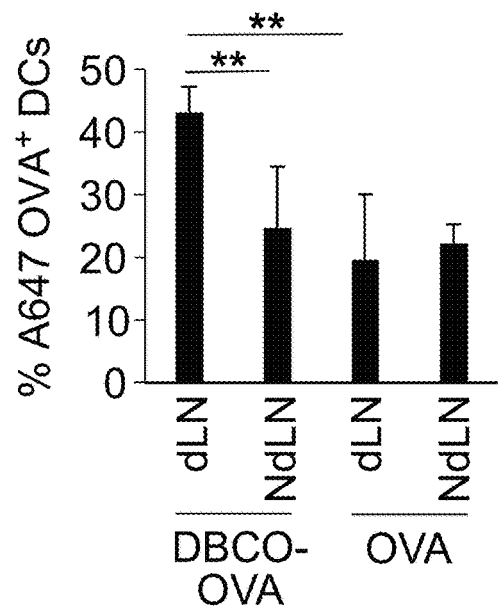

FIG. 5J is a graph showing percentage of A647 OVA+ DCs in LNs at 6 hours post injection of A647-conjugated DBCO-OVA or OVA.

Figure 5K:
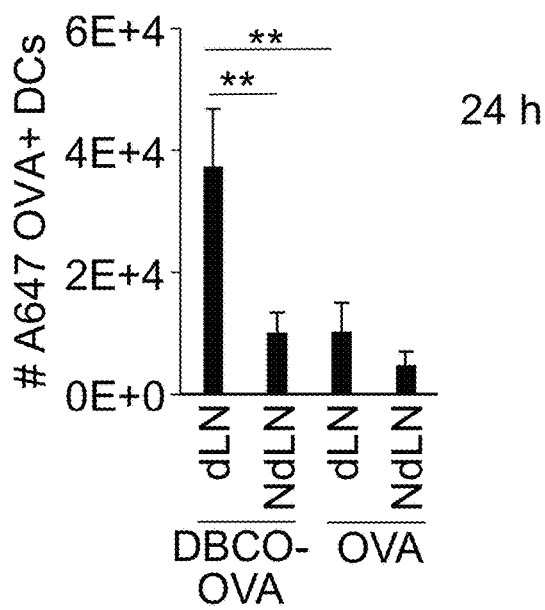

FIG. 5K is a graph showing total number of A647 OVA+ DCs in LNs at 24 hours post injection of A647-conjugated DBCO-OVA or OVA, respectively.

Figure 5L:
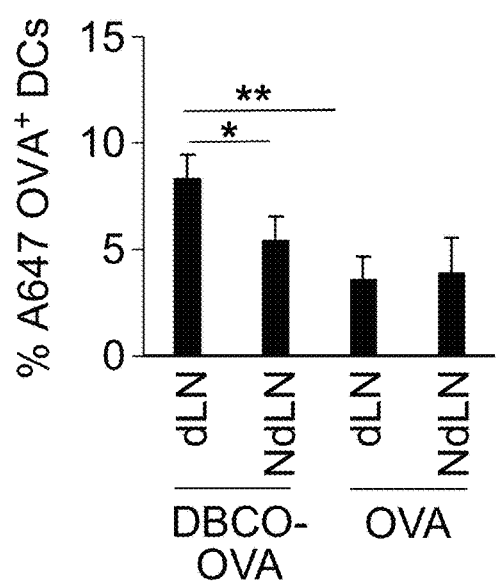

FIG. 5L is a graph showing percentage of A647 OVA+ DCs in LNs at 24 hours post injection of A647-conjugated DBCO-OVA or OVA.

FIGS. 5H, 5J, and 5L illustrate that azido-labeled DCs in LNs mediate targeted delivery of DBCO-OVA and DBCO-CpG via Click chemistry.

Figure 6A:
Figure 6B:
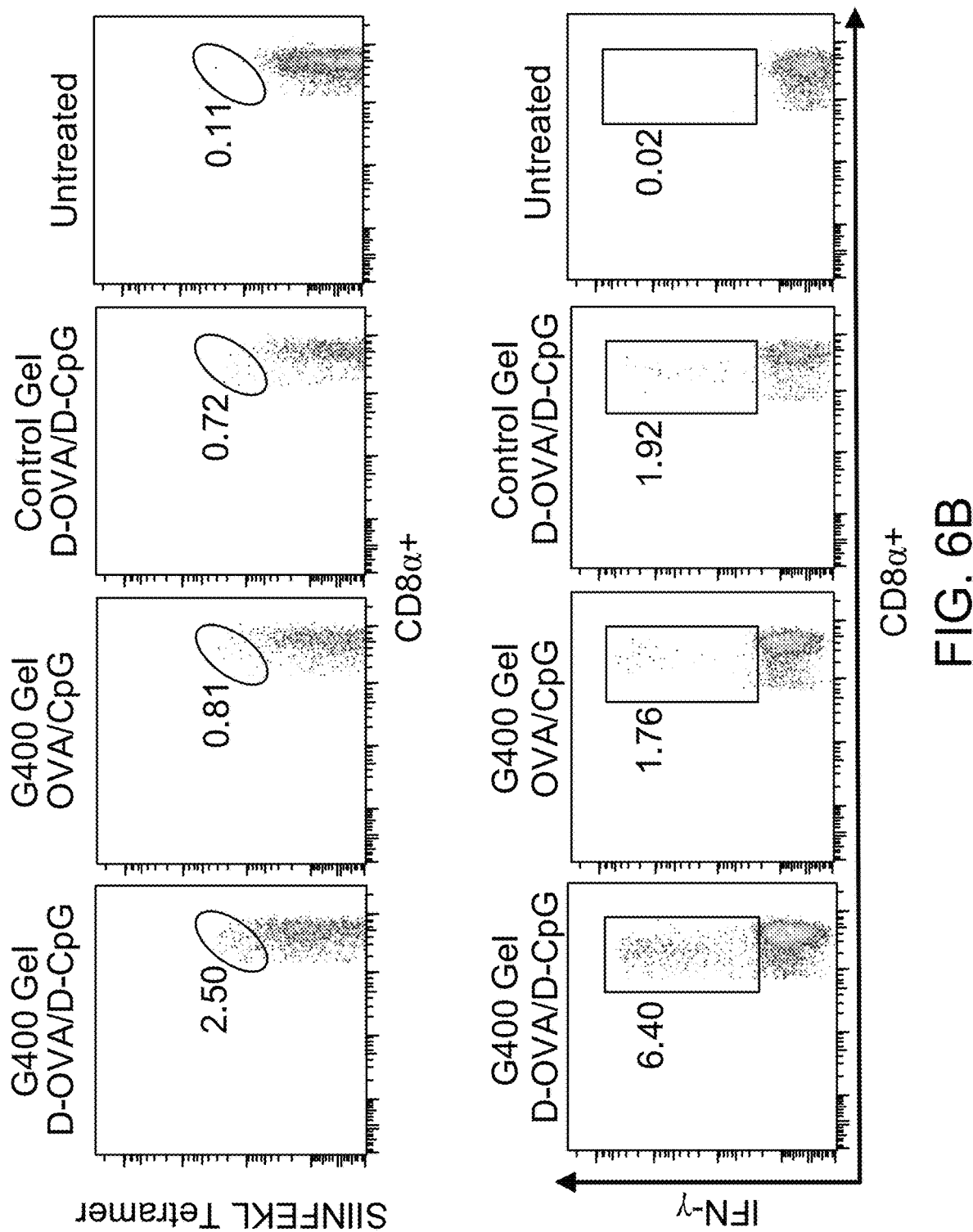
Figure 6C:
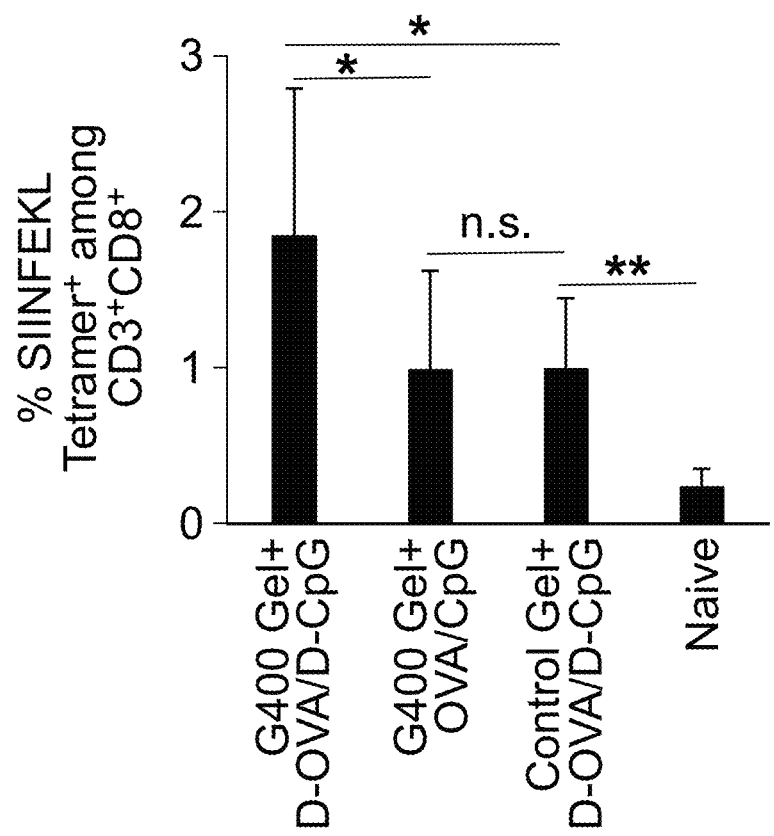
Figure 6D:
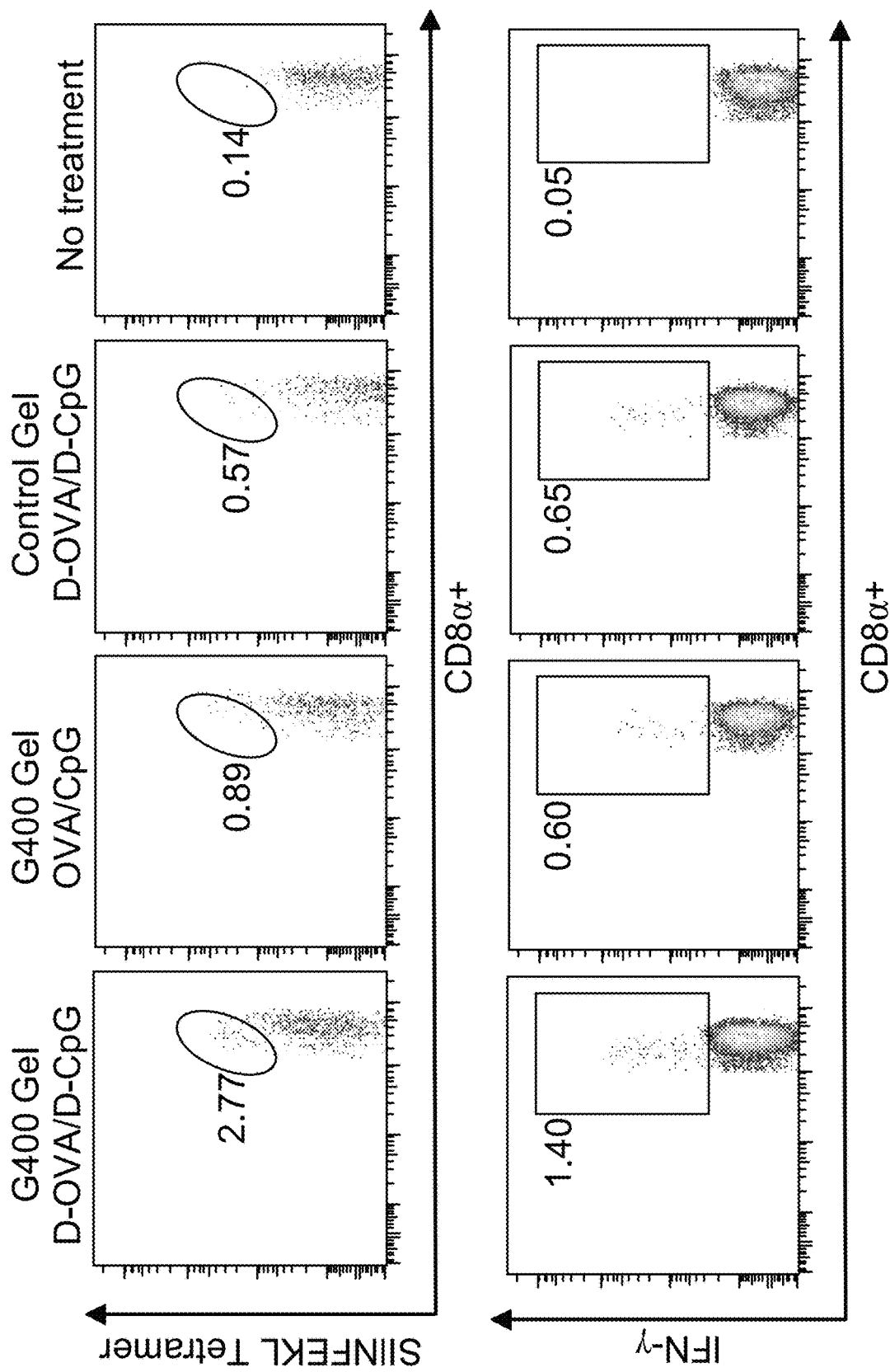
Figure 6E:
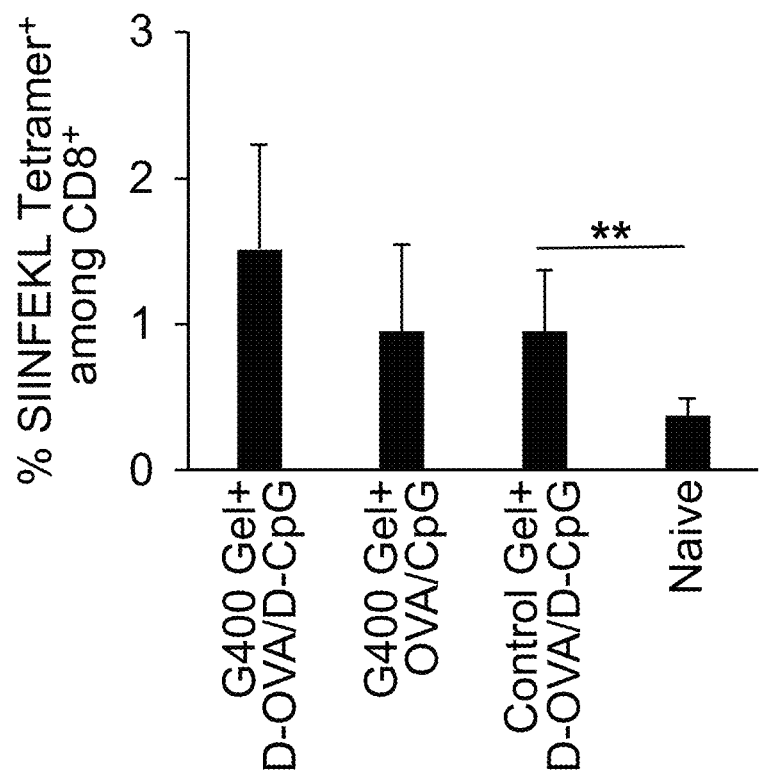
Figure 6G:
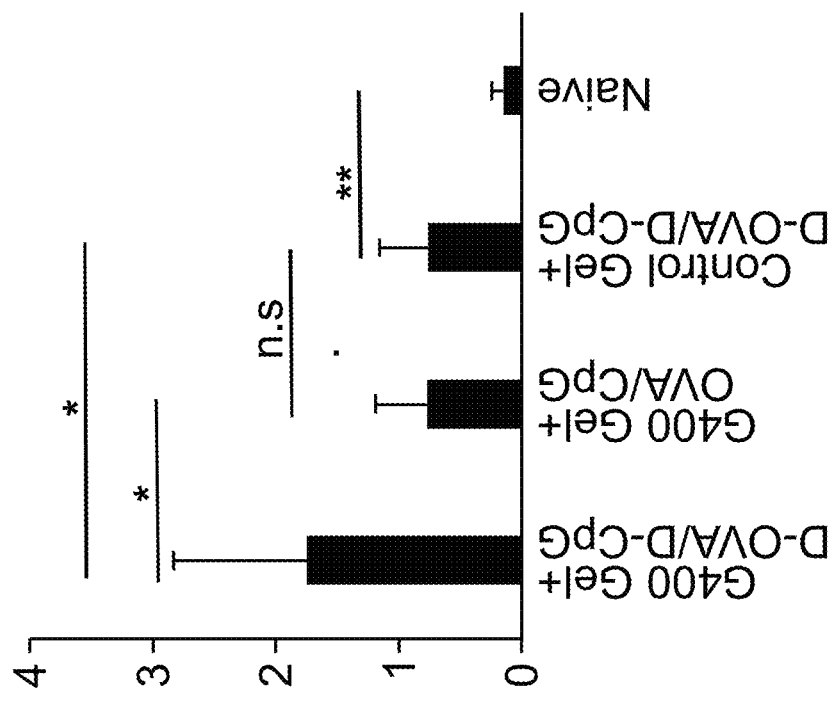
Figure 6F:
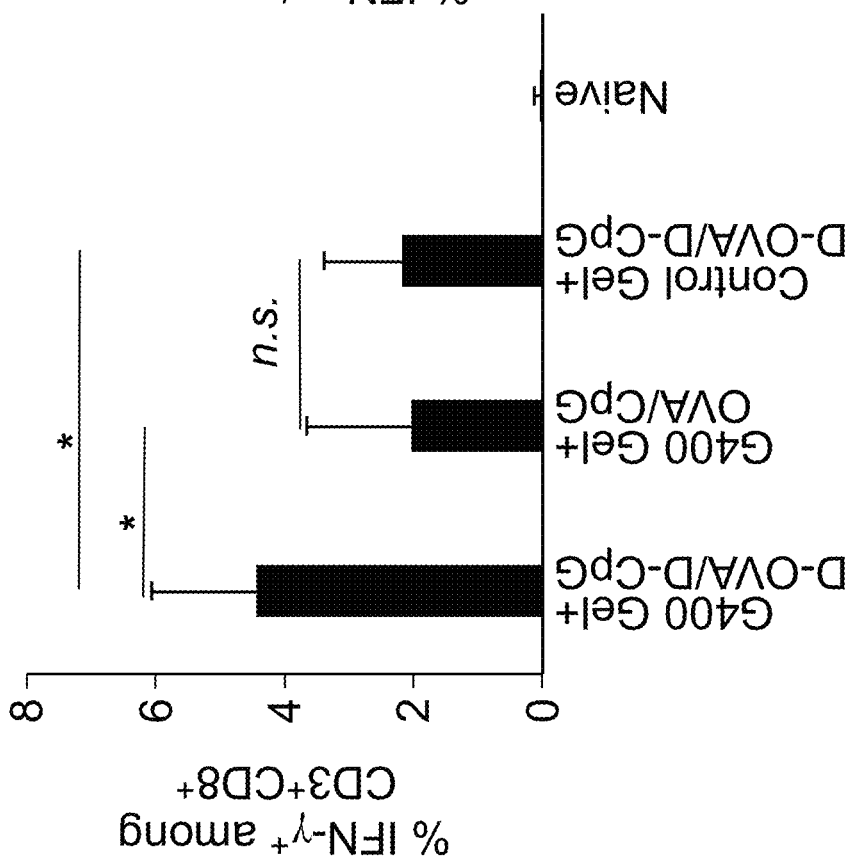
Figures 6H, 6I:
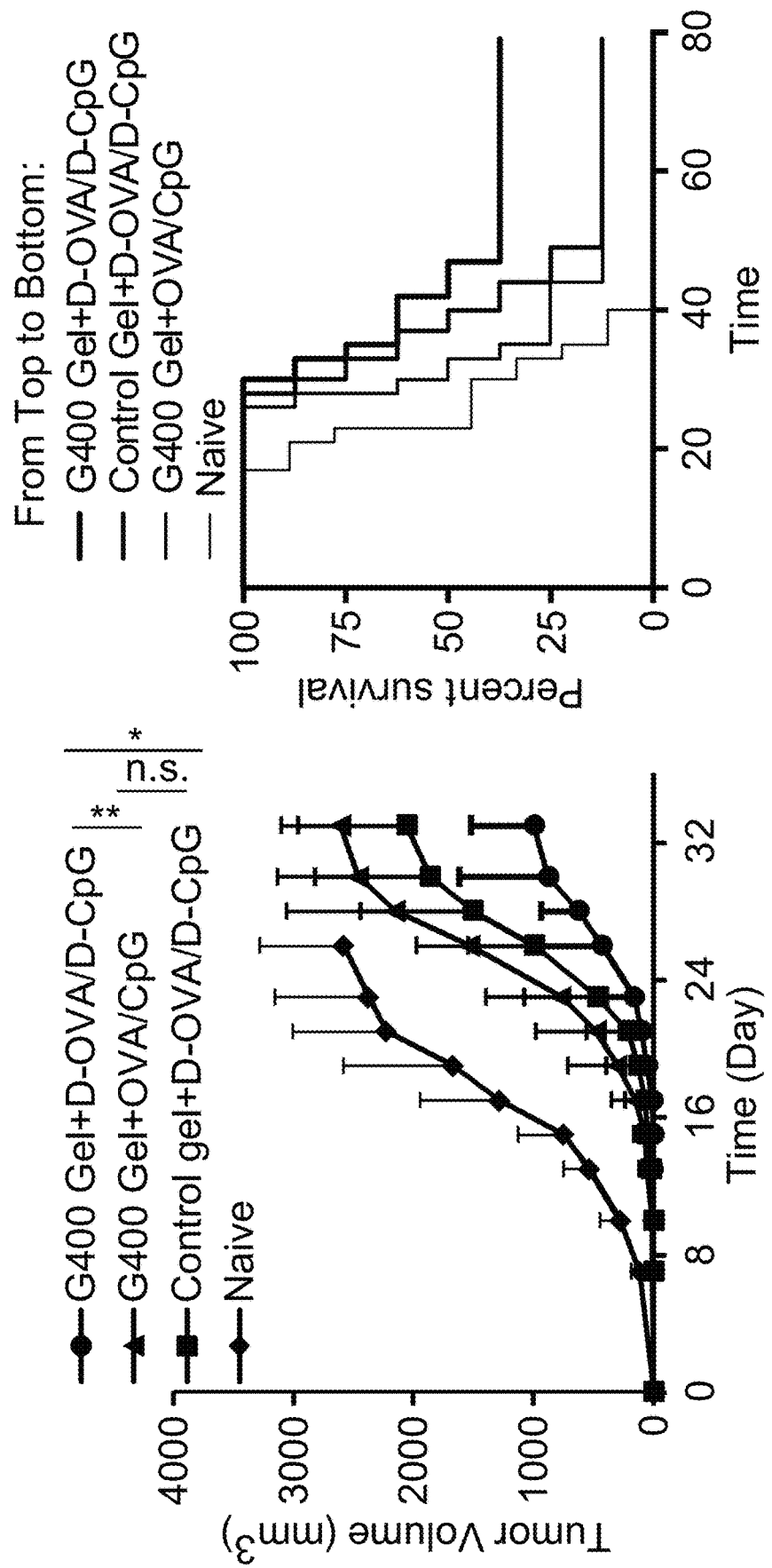
Figure 6L:
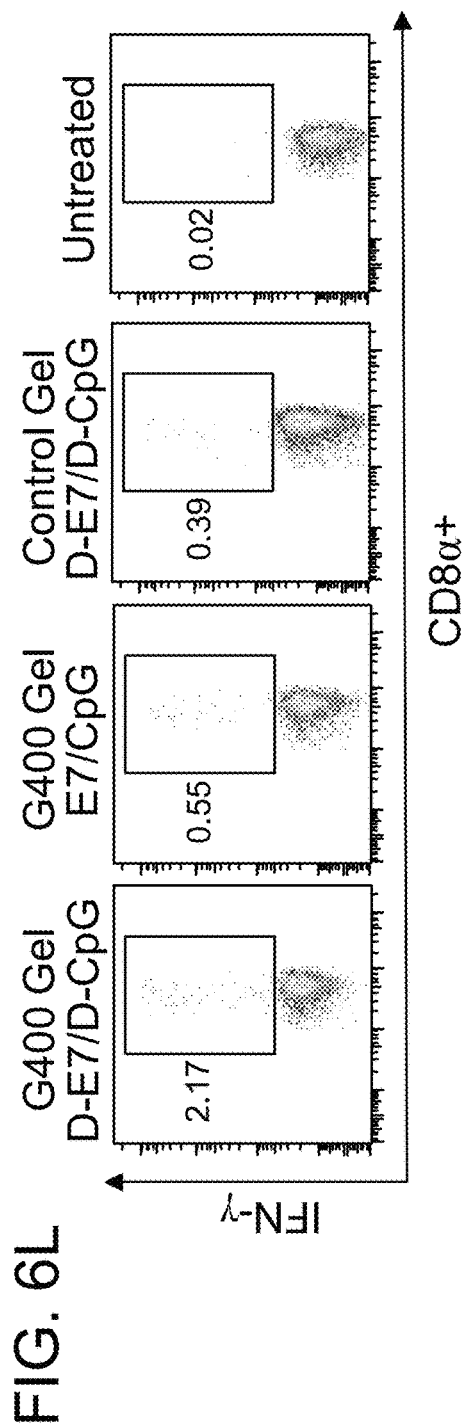
Figure 6M:
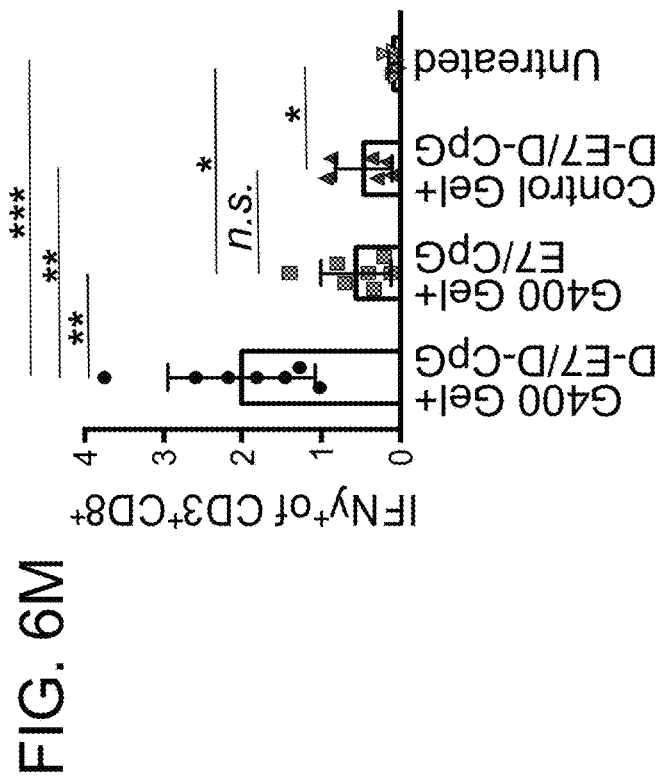
Figure 6N:
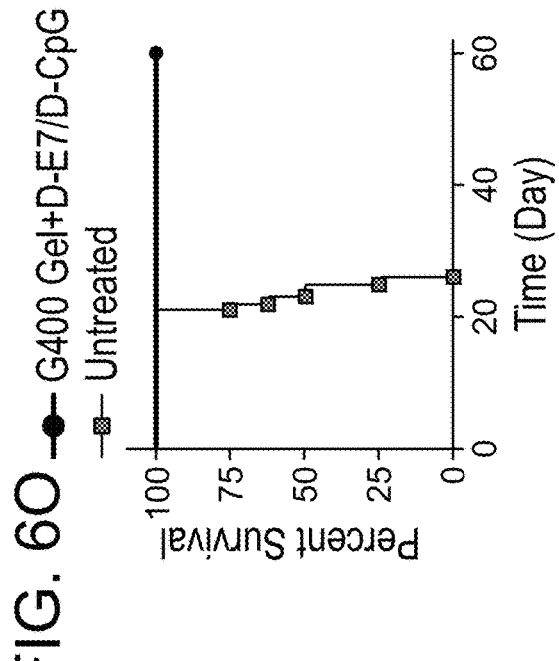
Figure 6O:
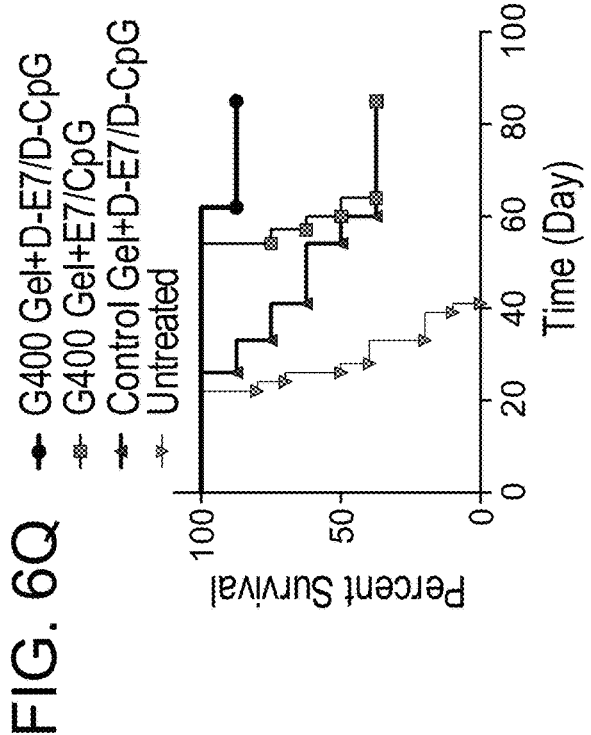
Figure 6P:
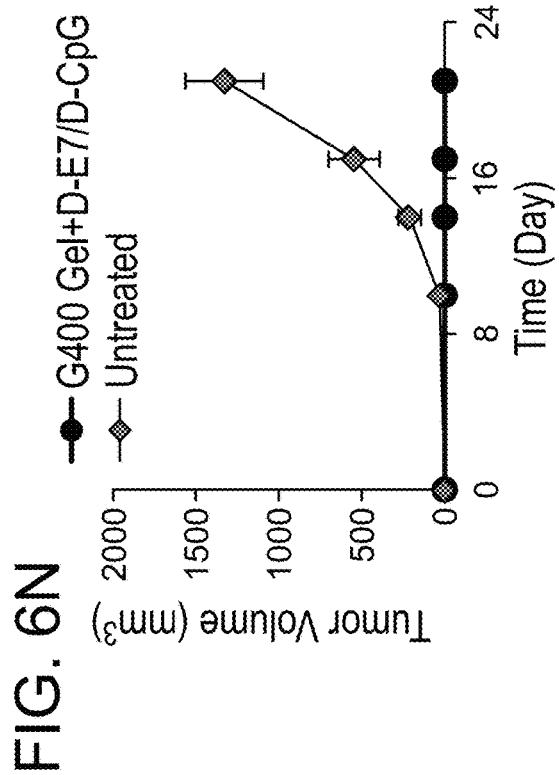
Figure 6Q:
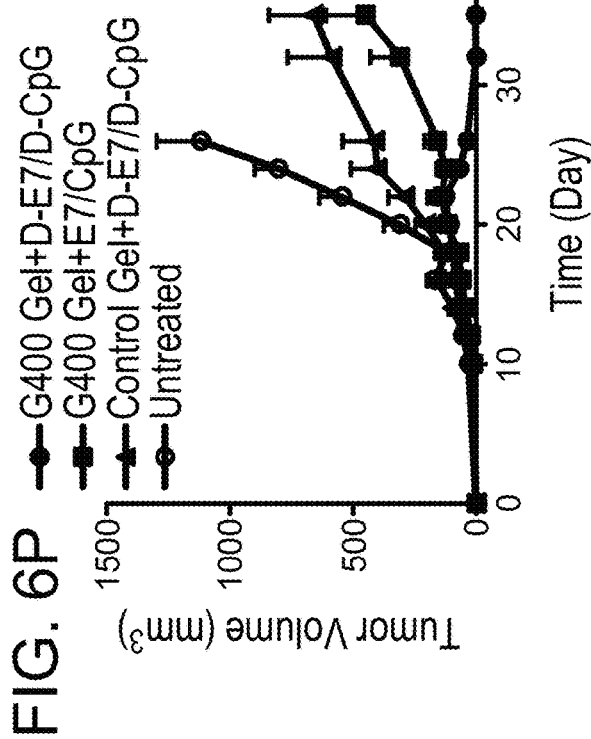

FIGS. 6A-6Q illustrate azido labeling of DCs coupled with DBCO-OVA and DBCO-CpG generates potent cellular immune responses.

FIG. 6A is a schematic illustration showing the analysis process. Pore-forming gels loaded with G400 NP and GM-CSF (G400 gel) were subcutaneously injected on day 0, followed by ultrasound treatment on day 3, and tail base subcutaneous injection of DBCO-OVA and DBCO-CpG on day 6 (n=8). Mice treated with G400 gel and OVA/CpG or control gel containing GM-CSF alone and DBCO-OVA/DBCO-CpG were used as controls.

FIG. 6B provides representative FACS plots of tetramer+ CD8+ (upper row) and IFN-γ*CD8+ (lower row) T cells in PBMCs on day 14. PBMCs were re-stimulated with OVA CD4 and CD8 epitopes ex vivo.

FIG. 6C is a graph showing percentage of SIINFEKL tetramer+ cells among CD8+ T cells in PBMCs on day 14.

FIG. 6D provides representative FACS plots of SIINFEKL tetramer+ (upper row) CD8+ and IFN-γ+CD8+ (lower row) T cells in PBMCs on day 20.

FIG. 6E is a graph showing percentage of SIINFEKL tetramer+ cells among CD8+ T cells in PBMCs on day 20.

FIG. 6F is a graph showing percentage of IFN-γ+ cells among CD8+ T cells in PBMCs.

FIG. 6G is a graph showing percentage of IFN-γ+ cells among CD8+ T cells in PBMCs on day 20, in response to in vitro SIINFEKL re-stimulation.

FIGS. 6D, 6E and 6G illustrate azido-labeled DCs coupled with DBCO-OVA and DBCO-CpG generate potent cellular immune responses against OVA.

For FIGS. 6H and 6I, following subcutaneous injection of gels loaded with G400 NP and GM-CSF on day 0, ultrasound treatment on day 3, and tail base subcutaneous injection of DBCO-OVA and DBCO-CpG on day 6, mice were inoculated with E.G7-OVA tumor cells on day 25 (n=8).

FIG. 6H is a graph showing average E.G7-OVA tumor volume of each group over the course of the prophylactic tumor study (n=8).

FIG. 6I is a graph showing Kaplan-Meier plots for all groups (n=8).

FIGS. 6J-6M show following subcutaneous injection of gels loaded with G400 NP and GM-CSF on day 0, ultrasound treatment on day 3, and subcutaneous injection of DBCO-E7 and DBCO-CpG on days 6, 8, and 10.

FIGS. 6J and 6K show (FIG. 6J) representative FACS plots and (FIG. 6K) percentage of E7 tetramer+ cells among CD8+ T cells in PBMCs on day 16.

FIGS. 6L and 6M show (FIG. 6L) representative FACS plots and (FIG. 6M) percentage of IFN-γ+ cells among CD8+ T cells in PBMCs on day 16.

FIG. 6N shows average TC-1 tumor volume of each group over the course of the prophylactic tumor study (n=7-9).

FIG. 6O shows Kaplan-Meier plots for all groups (n=7-9).

In FIGS. 6P and 6Q, TC-1 tumors were inoculated on day 0, followed by subcutaneous injection of gels loaded with G400 NP and GM-CSF on day 4, ultrasound treatment on day 7, and subcutaneous injection of DBCO-E7 and DBCO-CpG on day 10, 12, and 14.

FIG. 6P shows that average TC-1 tumor volume of each group over the course of the study (n=8-10).

FIG. 6Q shows Kaplan-Meier plots for all groups (n=8-10).

All the numerical data in FIGS. 6A-6O are presented as mean±SD ($0.01<*P≤0.05$; $P≤0.01$; $*P≤0.001$).

Figure 7A:
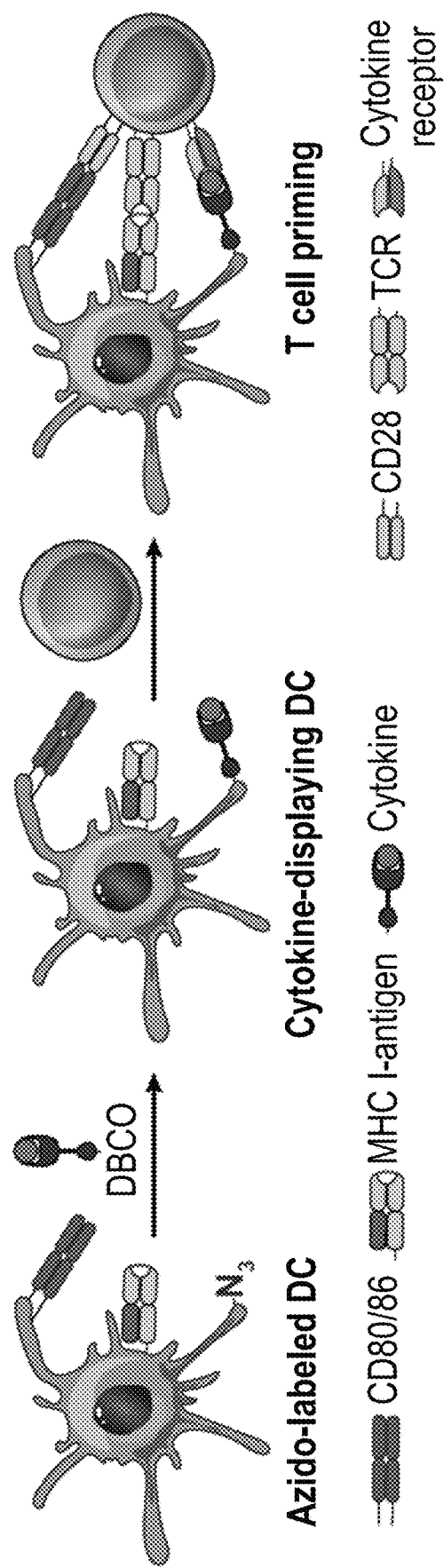

FIGS. 7A-7R, 8A-8L, 9A-9I, and 10A-10N illustrate azido labeled DCs enable surface display of IL-15/IL-15Rα for improved CD8+ T cell priming. FIG. 7A is a schematic illustration of conjugation of DBCO-IL-15/IL-15Rα to azido-labeled DCs and subsequent T cell priming.

Figure 7B:
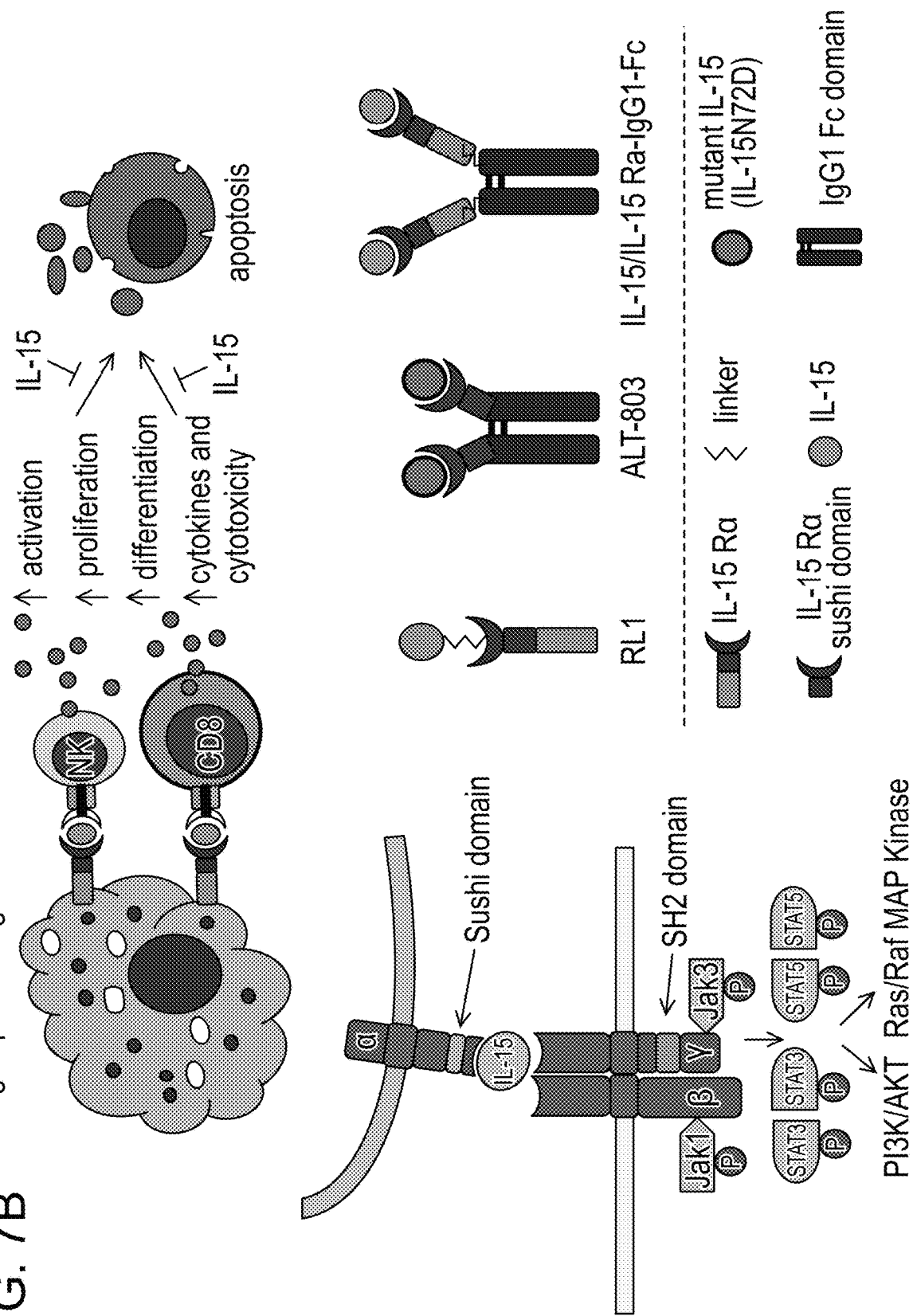

FIG. 7B is a schematic illustration of IL-15 function and IL-15/IL-15Rα fusion proteins. IL-15 binds to IL-15 receptor a (IL-15Rα) on the surface of antigen presenting cells to induce the proliferation of CD8+ T cells and natural killer cells. (Top panel). IL-15Rα contains a Sushi domain that is important for binding IL-15. The cell surface IL-15/IL-15Rα complex binds to JAK3 kinase and activates JAK-STAT signal pathway to activate CD8+ T cells and/or other immune effector cells. (Bottom left panel). Several fusion proteins, including IL-15/IL-15Rα fusion protein, have been utilized to improve T cells or other immune effector cells function. (Bottom right panel).

Figure 7D:
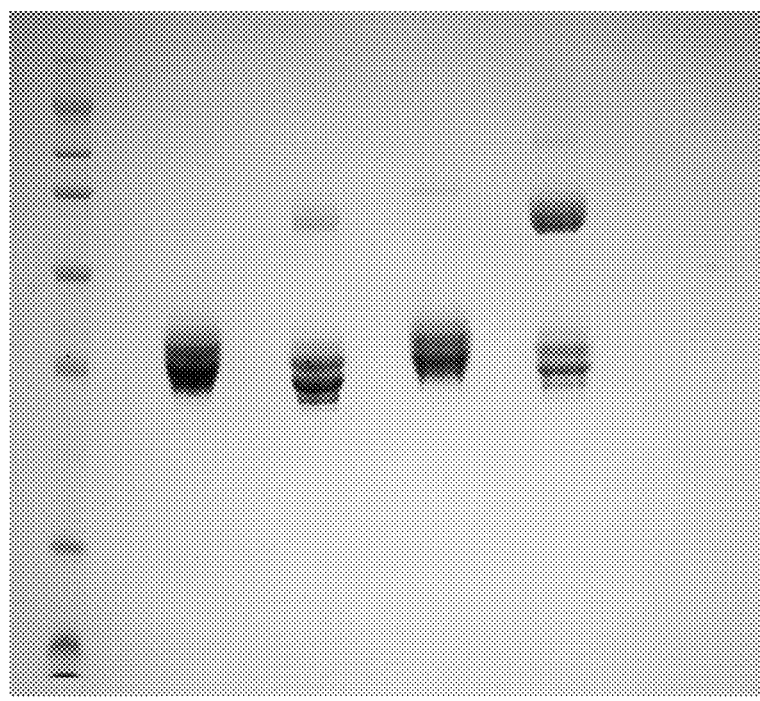
Figure 7E:
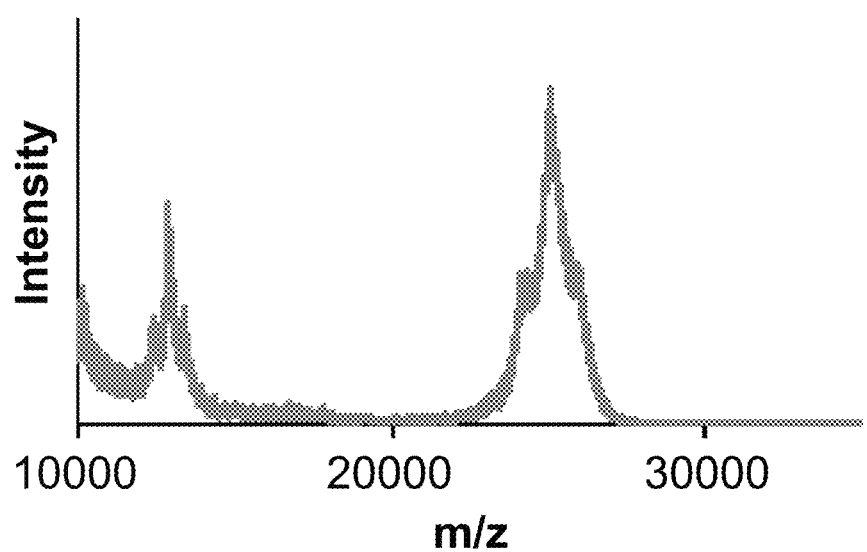

FIGS. 7C-7E illustrate synthesis and characterization of IL-15/IL-15Rα. FIG. 7C is a schematic illustration of amino acid sequence and structure of IL-15/IL-15Rα. FIG. 7D provides an electrophoresis image showing protein bands of monomer and dimer IL-15/IL-15Rα following purification through HA, Superose 6 columns. FIG. 7E is a graph showing MALDI spectrum of IL-15/IL-15Rα.

FIGS. 7F-7I illustrate synthesis and characterization of DBCO-IL-15/IL-15Rα.

Figure 7F:
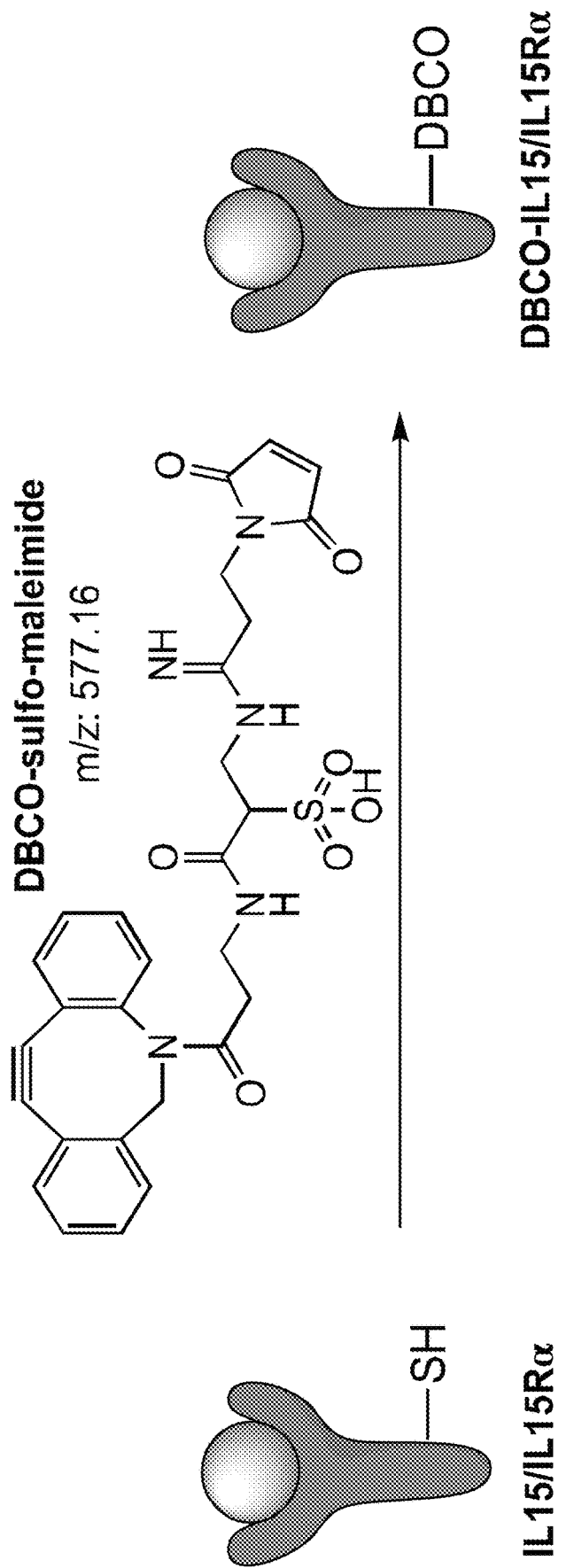
Figure 7G:
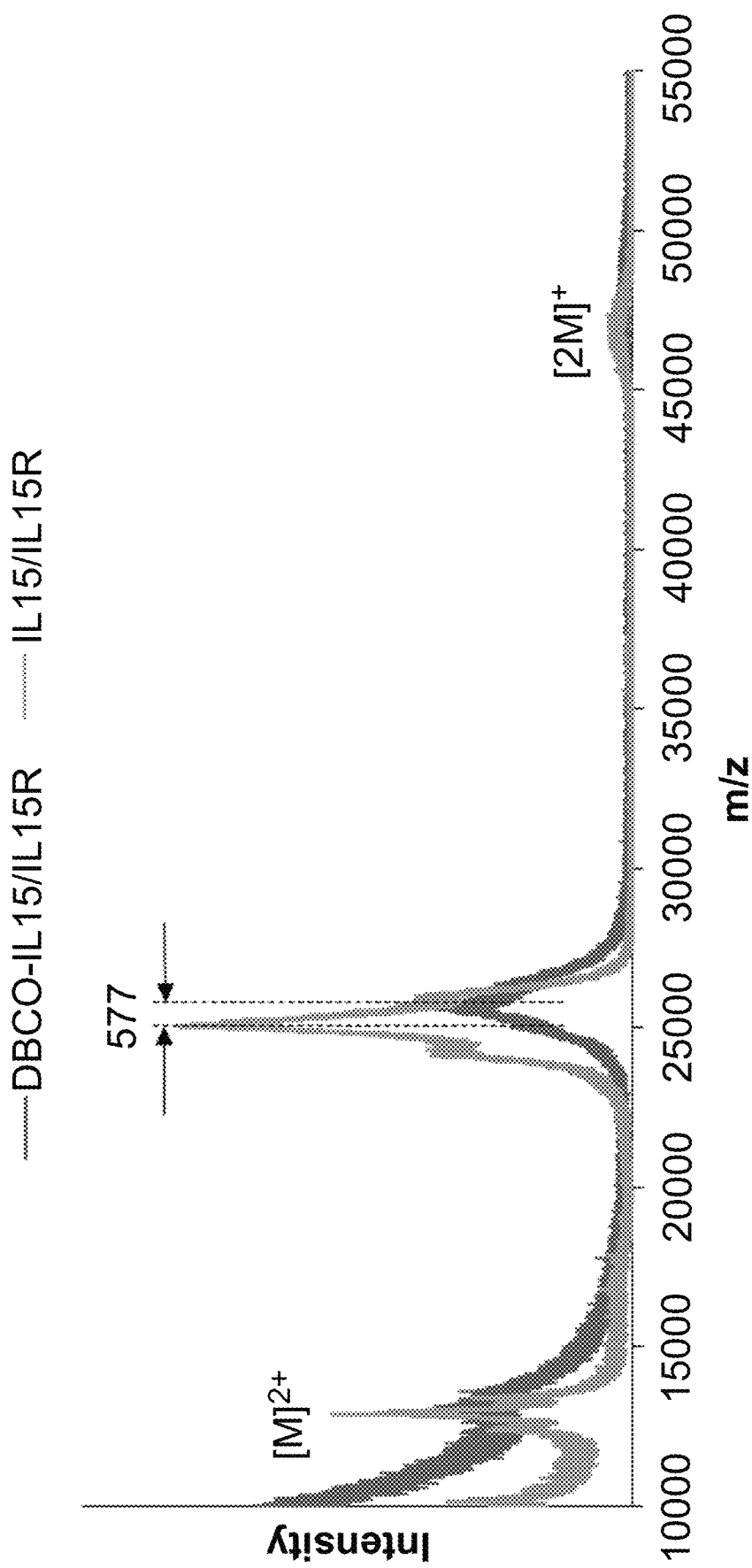
Figure 7H:
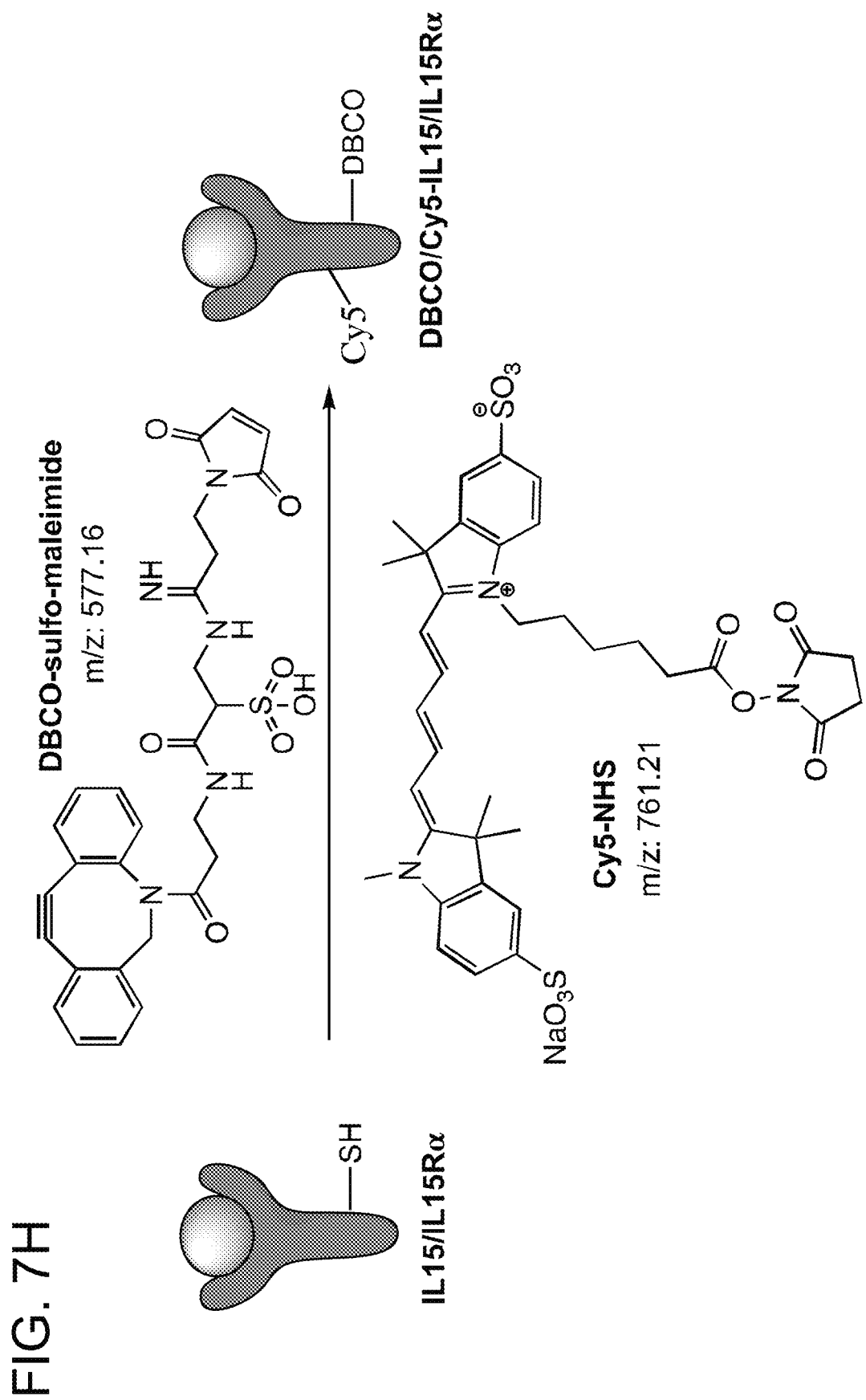
Figure 7I:
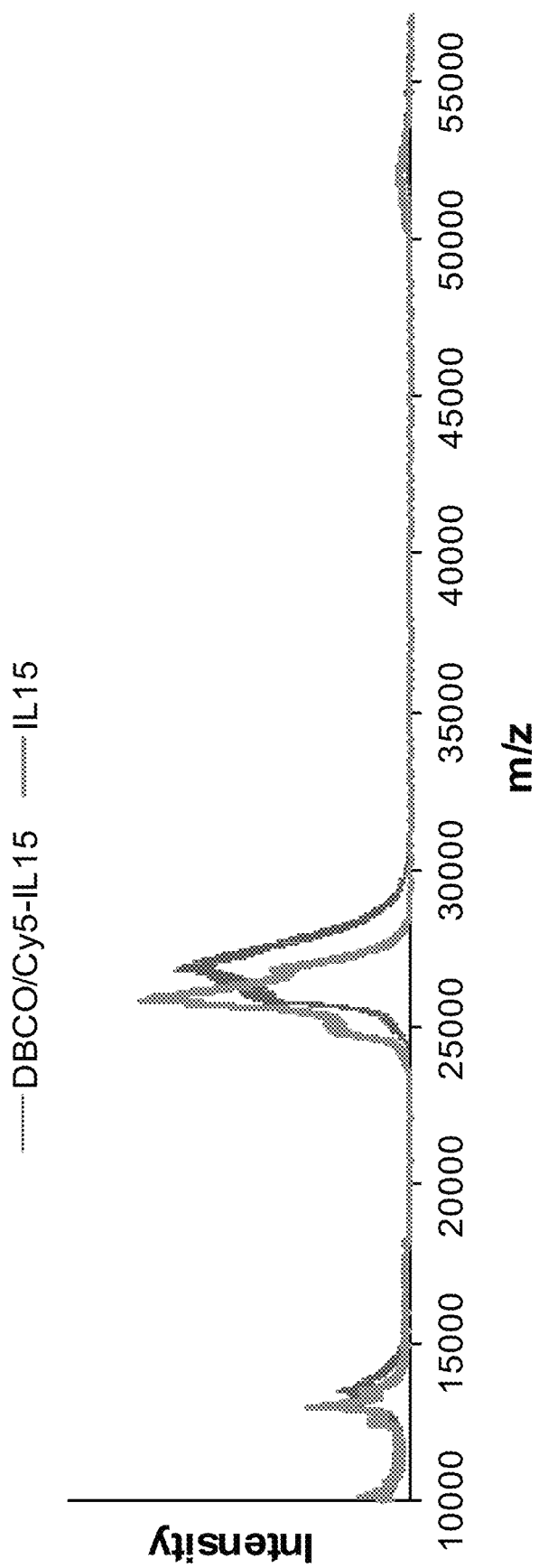

FIG. 7F is a schematic illustration of synthetic route of DBCO-IL-15/IL-15Rα. FIG. 7G is MALDI spectra of IL-15/IL-15Rα and DBCO-IL-15/IL-15Rα. FIG. 7H is a schematic illustration of synthetic route of DBCO/Cy5-IL-15/IL-15Rα. FIG. 7I is MALDI spectra of IL-15/IL-15Rα and DBCO/Cy5-IL-15/IL-15Rα.

Figure 7J:
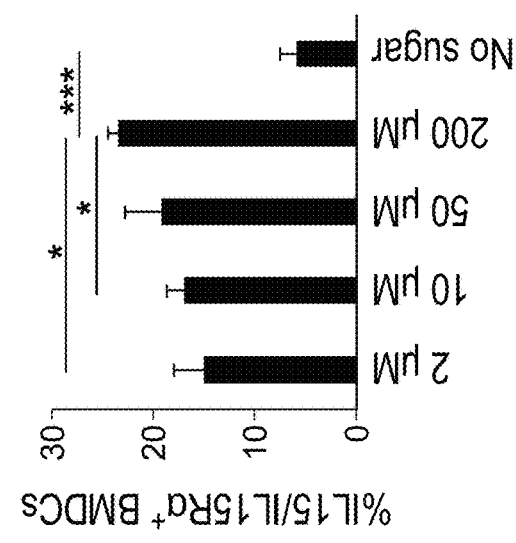

FIG. 7J is a graph showing percentage of IL15/IL15Rα-displaying BMDCs after 30-min incubation with Cy5-IL-15/IL-15Rα (200 ng/mL). BMDCs were pretreated with G400 NP or PBS for three days.

Figure 7K:
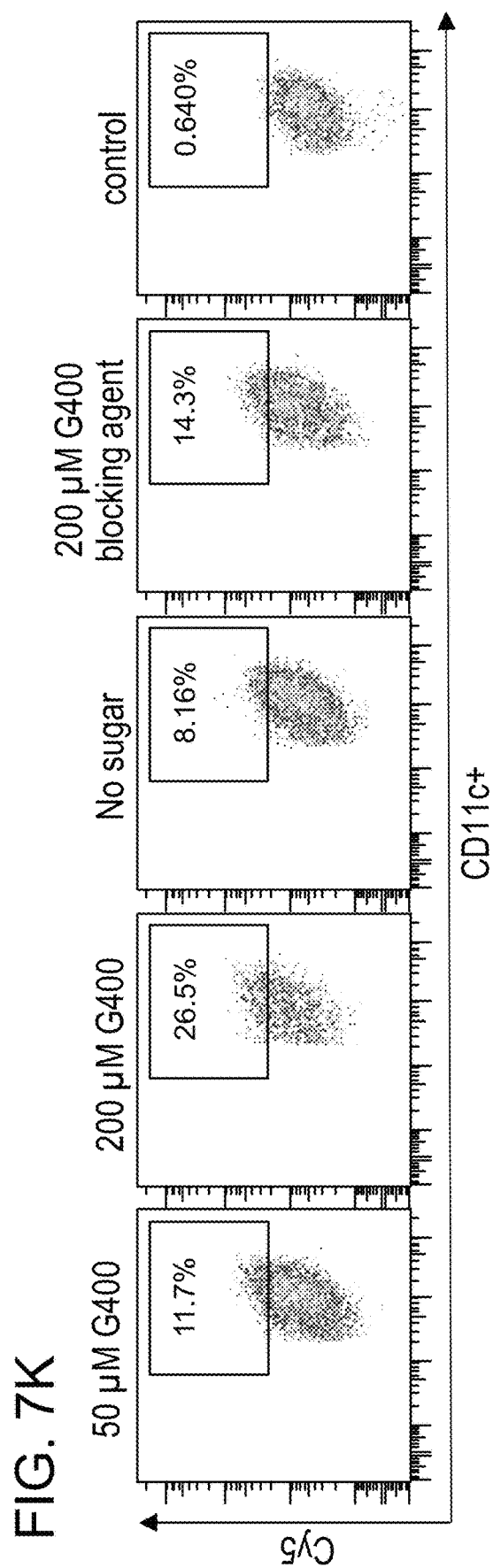
Figure 7L:
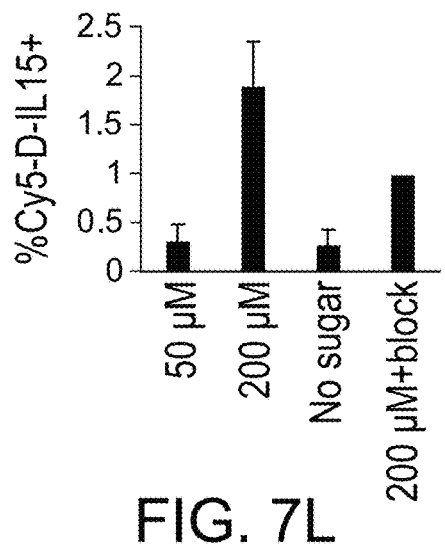
Figure 7M:
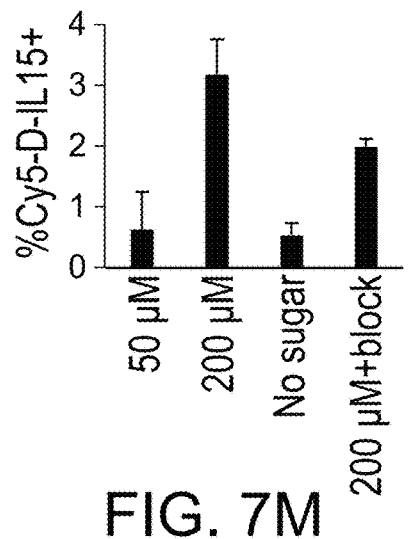
Figure 7N:
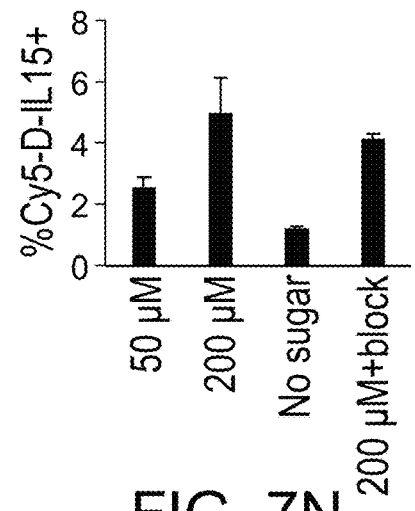
Figure 7O:
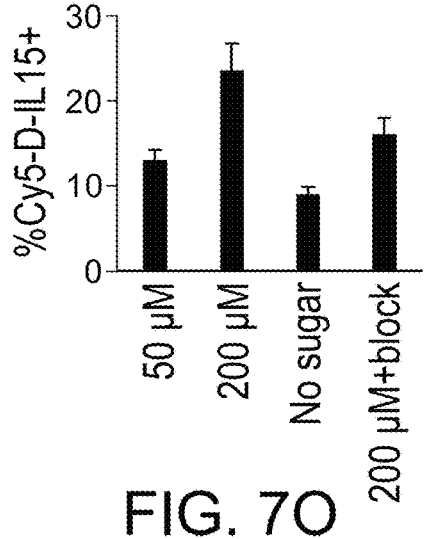
Figure 7P:
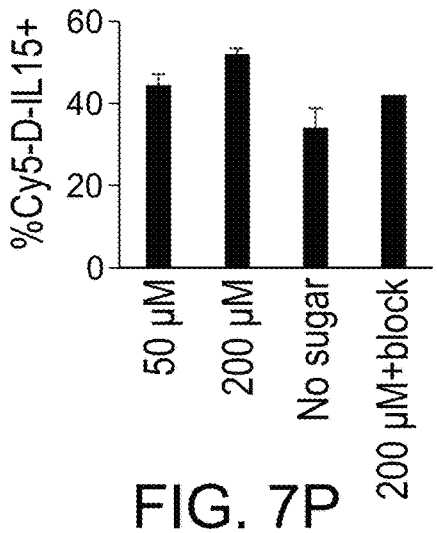

FIGS. 7K-7P illustrate that azido-labeled DCs can covalently capture Cy5/DBCO-IL-15/IL-15Rα in vivo. FIG. 7K provides representative FACS plots of Cy5+ CD11c+ BMDCs after 3-d incubation with G400 NP and 30-min incubation with Cy5/DBCO-modified IL-15/IL-15Rα (100 ng/mL). For the blocking group, cells were simultaneously treated with Cy5/DBCO-modified IL-15/IL-15Rα and DBCO-sulfo-maleimide. FIGS. 7L-7P show percentage of Cy5+ DCs at 1 ng/mL (FIG. 7L), 5 ng/mL (FIG. 7M), 20 ng/mL (FIG. 7N), 100 ng/mL (FIG. 7O), and 500 ng/mL (FIG. 7P) Cy5/DBCO-IL-15/IL-15Rα, respectively.

Figures 7Q, 7R:
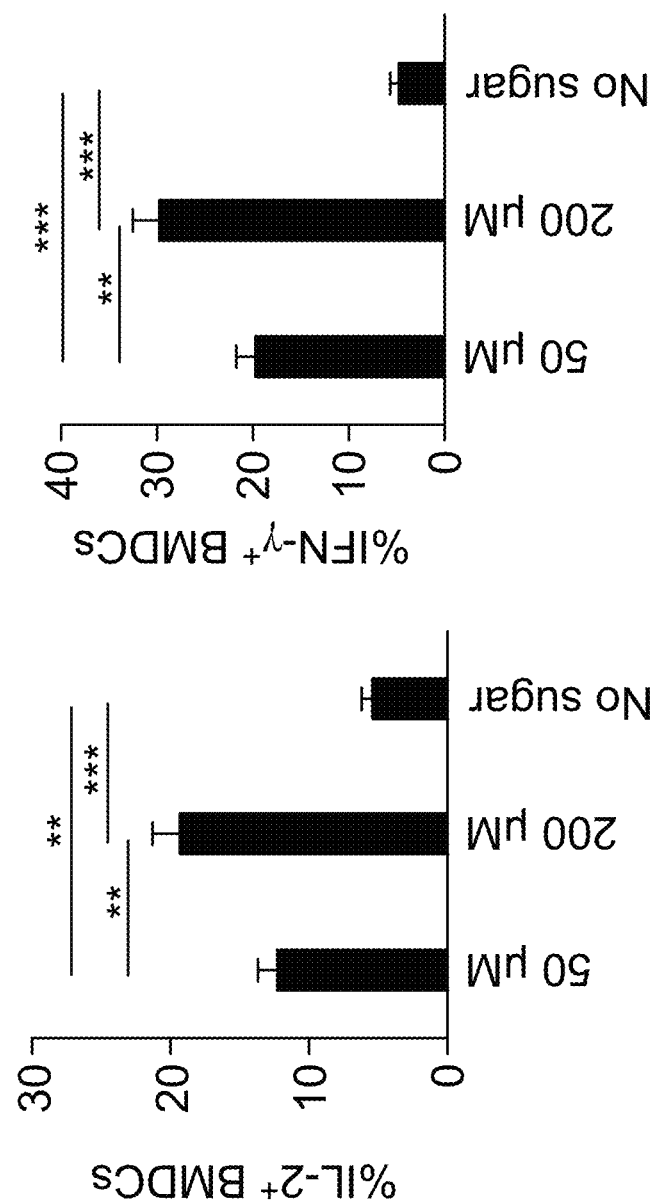

FIGS. 7Q and 7R are graphs showing percentage of IL-2 (FIG. 7Q) and IFN-γ (FIG. 7R) BMDCs after 30-min incubation with Cy5-IL-15/IL-15Rα (200 ng/mL). BMDCs were pretreated with G400 NP or PBS for three days.

FIGS. 8A-8E and 8M-8O illustrate that Azido-labeled DCs can covalently capture Cy5/DBCO-IL15/IL15Rα, which induces the pSTAT5 expression of OT1 cells in vitro. BMDCs were treated with G400 NP (200 μM) or PBS for three days, incubated with different concentrations of DBCO-IL-15/IL-15Rα or IL-15/IL-15Rα for 30 min, and then co-cultured with OT1 cells for 1.5 hours. OT1 cells treated with soluble IL-15/IL-15Rα for 1 hour were used as controls.

Figure 8D:
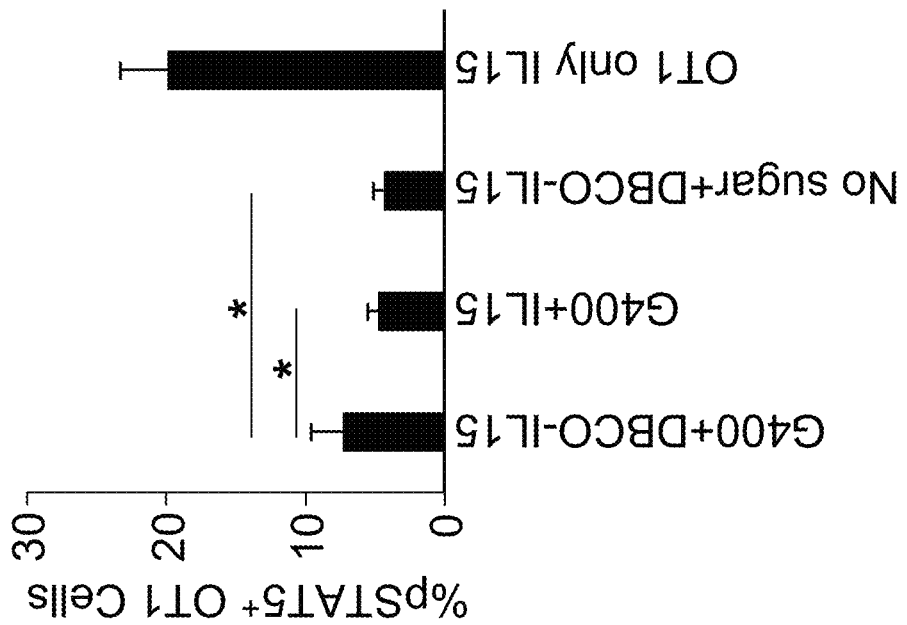
Figure 8C:
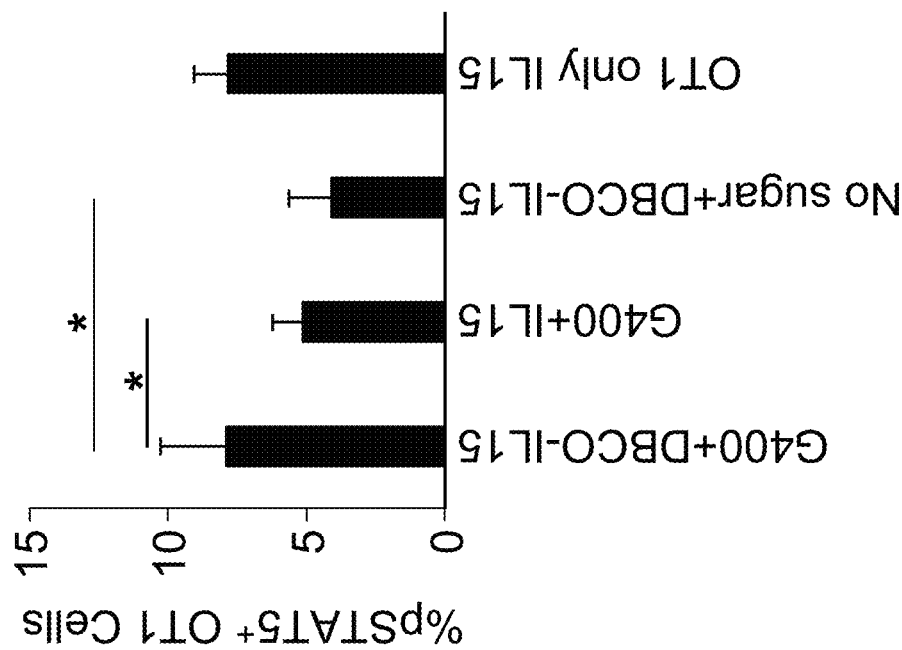
Figure 8E:
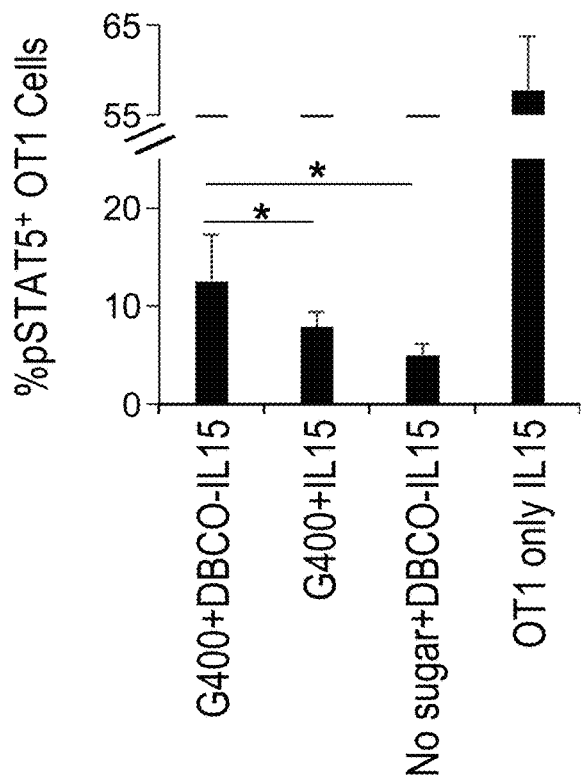

FIG. 8A provides representative pSTAT5 histograms of OT1 cells. FIG. 8B is a graph showing percentage of pSTAT5+ OT1 cells at 20 ng/mL DBCO-IL-15/IL-15Rα or IL-15/IL-15Rα. OT1 cells treated with 5 ng/mL IL-15/IL-15Rα for 1 hour were used as controls. FIGS. 8C-8E are graphs showing the percentage of pSTAT5+ OT1 cells at a DBCO-IL-15/IL-15Rα (or IL-15/IL-15Rα) concentration of 0.2 ng/mL (FIG. 8C), 1 ng/mL (FIG. 8D), and 5 ng/mL (FIG. 8E), respectively.

Figure 8F:
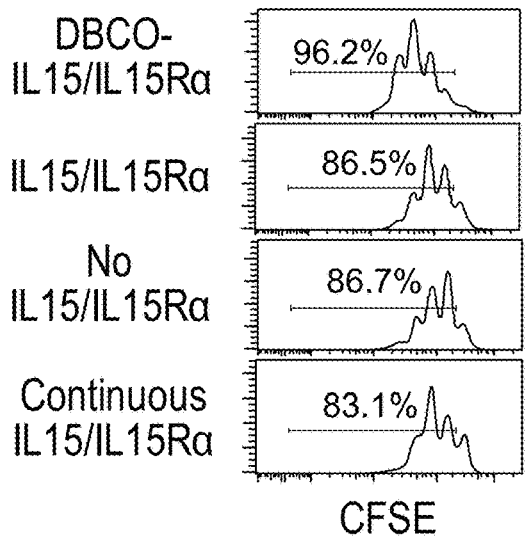
Figure 8G:
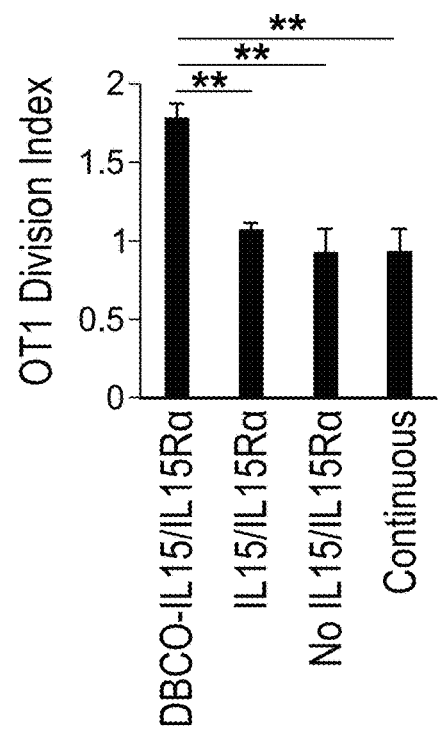

FIGS. 8F and 8G provide representative FACS plots (FIG. 8F) and a graph (FIG. 8G) showing division index of CFSE-stained OT1 cells after 3-day incubation with BMDCs pretreated with G400 NP (n=4). For FIGS. 8F, 8G and and 8J, BMDCs were incubated with G400 NP (200 μM) or PBS for three days, further incubated with DBCO-IL-15/IL-15Rα or IL-15/IL-15Rα (20 ng/mL) for 30 min, and co-cultured with CFSE-stained OT1 cells in the presence of 5 nM SIINFEKL peptide. DC-OT1 co-cultures in the absence of IL-15/IL-15Rα or in the continuous presence of IL-15/IL-15Rα were used as the control.

Figure 8H:
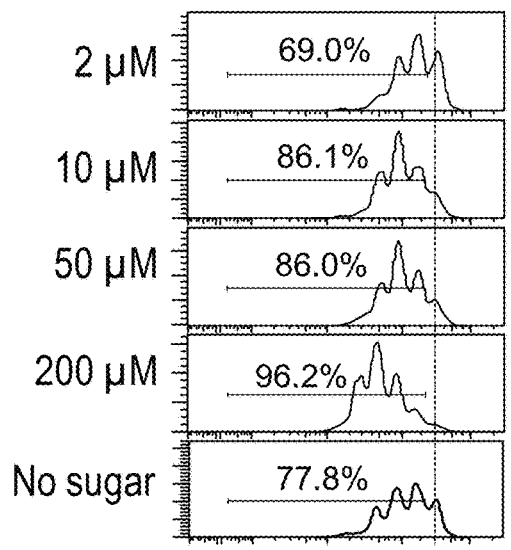
Figure 8I:
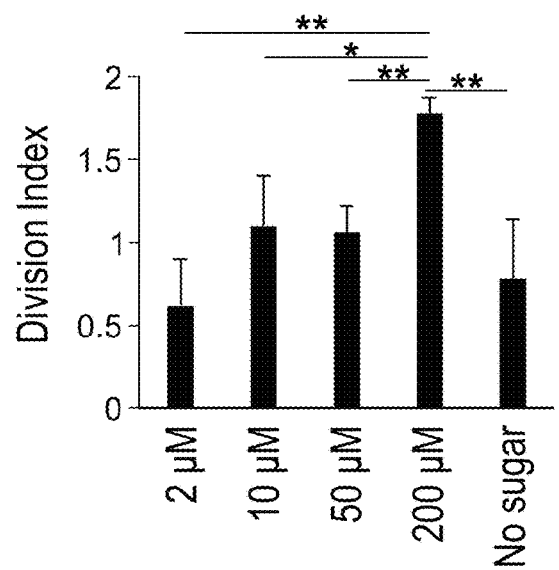
Figure 8J:
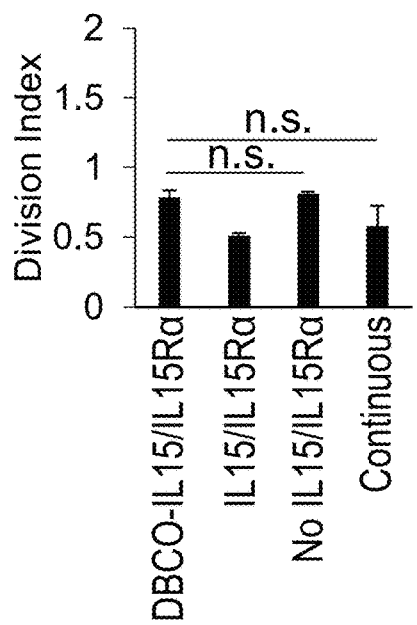

For FIGS. 8H and 8I, BMDCs were pretreated with G400 NP or PBS for 3 days, incubated with DBCO-IL-15/IL-15Rα or IL-15/IL-15Rα (20 ng/mL) for 30 min, and then cultured with CFSE-stained OT1 cells for 3 days in the presence of SIINFEKL (5 nM). FIGS. 8H and 8I provide representative FACS plots (FIG. 8H) and a graph (FIG. 8I) showing division index of CFSE-stained OT1 cells after 3-day incubation with IL-15/IL-15Rα-conjugated BMDCs or control BMDCs for 3 days FIG. 8J is a graph showing division index of CFSE-stained OT1 cells after 3-day incubation with BMDCs without G400 NP treatment.

Figure 8K:
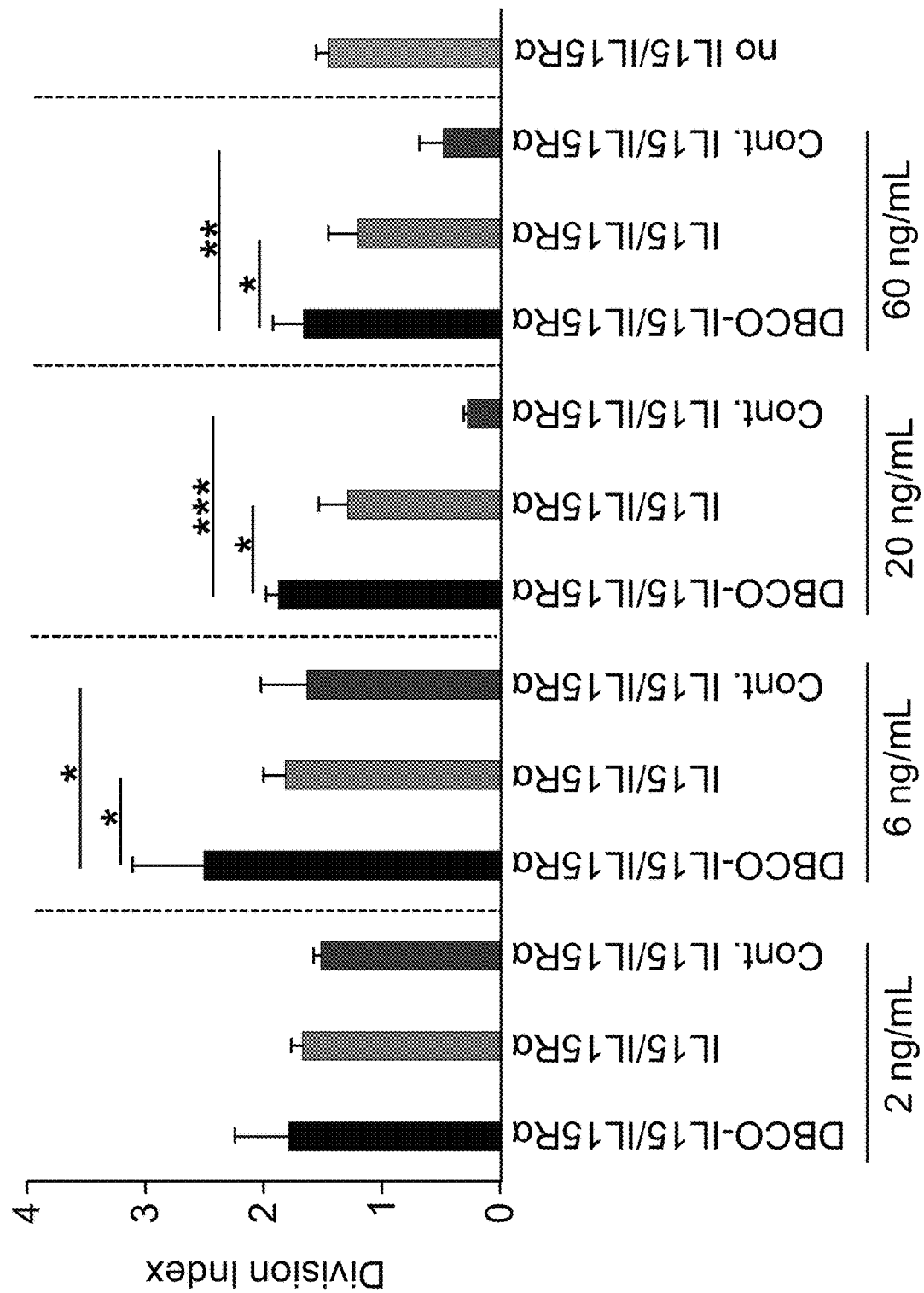
Figure 8L:
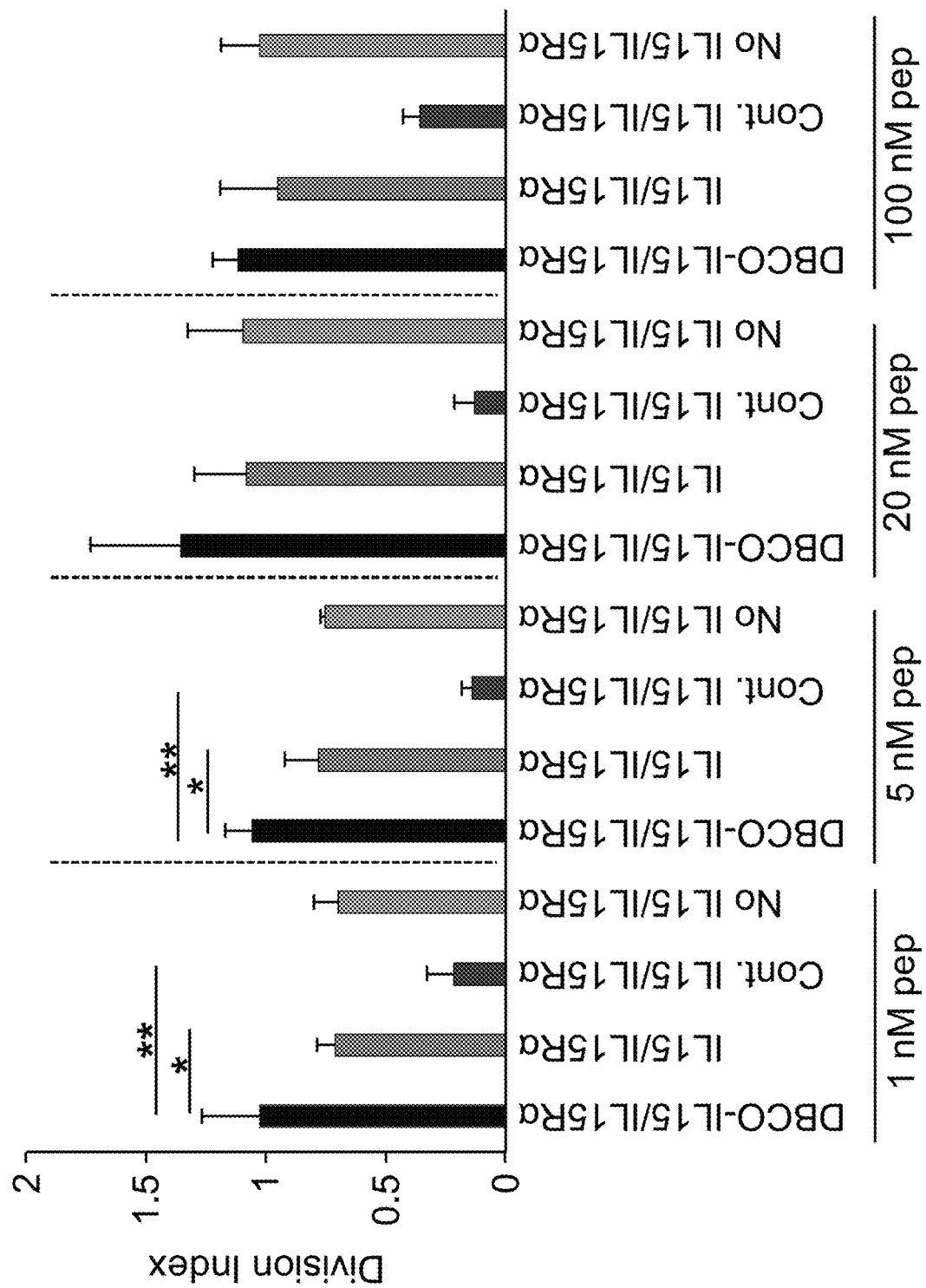

For FIGS. 8K and 8L, BMDCs were pretreated with G400 NP (200 μM) for three days, pulsed with SIINFEKL and CpG (1 nM) for 24 hours, and incubated with DBCO-IL-15/IL-15Rα or IL-15/IL-15Rα for 30 min. DC-T co-cultures in the continuous presence of IL-15/IL-15Rα were used as controls.

FIG. 8K is a graph showing division index of OT1 cells after 3-day incubation with BMDCs that were treated with different concentrations of DBCO-IL-15/IL-15Rα or IL-15/IL-15Rα. The concentration of SIINFEKL was kept at 5 nM.

FIG. 8L is a graph showing division index of OT1 cells after 3-day incubation with BMDCs that were pulsed with different concentrations of SIINFEKL (1, 5, 20, and 100 nM, respectively). The concentration of DBCO-IL-15/IL-15Rα was kept at 20 ng/mL.

FIG. 8M shows representative FACS plots of $Cy5^+$ $CD11c^+$ BMDCs after 3-d incubation with G400 NP and 30-min incubation with Cy5/DBCO-modified IL15/IL15Rα (100 ng/mL). For the blocking group, cells were simultaneously treated with Cy5/DBCO-modified IL15/IL15Rα and DBCO-maleimide.

FIGS. 8N and 8O show percentage of $Cy5^+$ DCs at (FIG. 8N) 100 ng/mL and (FIG. 8O) 5 ng/mL Cy5/DBCO-IL15/IL15Rα, respectively. All the numerical data in FIGS. 8A-8C and 8M-8O are presented as mean±SD ($0.01<*P\leq0.05$; $P\leq0.01$; $*P\leq0.001$).

FIGS. 8H, 8I, 8K, and 8L illustrate that IL-15/IL-15Rα conjugated on the surface of BMDCs via Click chemistry promotes the proliferation of OT1 cells in the presence of SIINFEKL.

FIGS. 9A-9D illustrate pore-forming gel vaccine loaded with M27, M30, G400 NP, GM-CSF, and CpG can label recruited DCs with azido groups. FIG. 9A is a schematic illustration of time frame of the labeling study. FIG. 9B is a graph showing percentage of $azide^+$ DCs in the gel scaffold. FIG. 9C is a graph showing percentage of $CD11c^+$ DCs among all recruited cells in dLN. FIG. 9D is a graph showing percentage of $azide^+$ DCs in dLN.

Figure 9E:
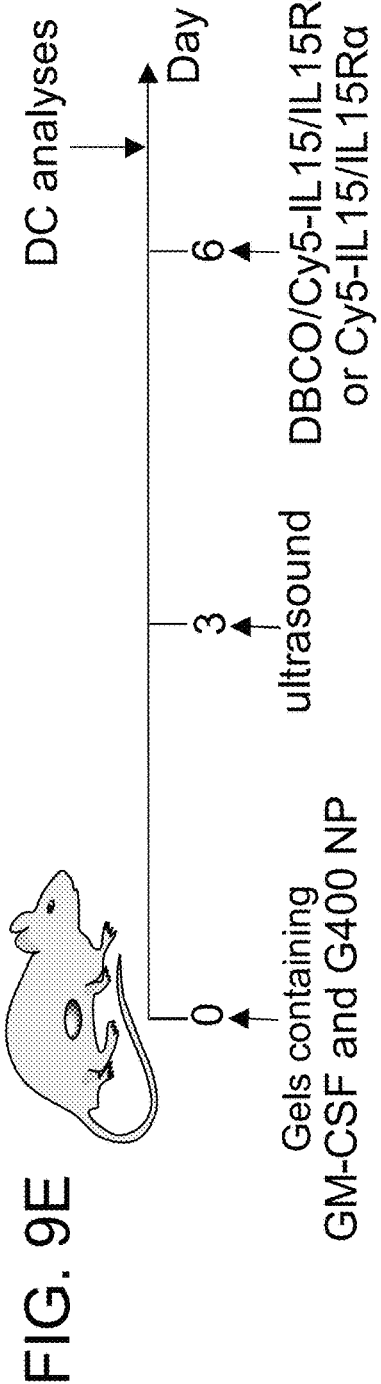
Figure 9G:
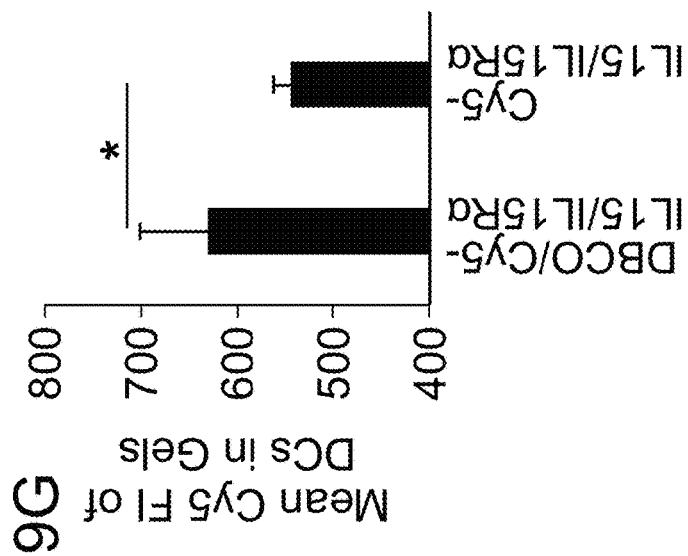
Figure 9F:
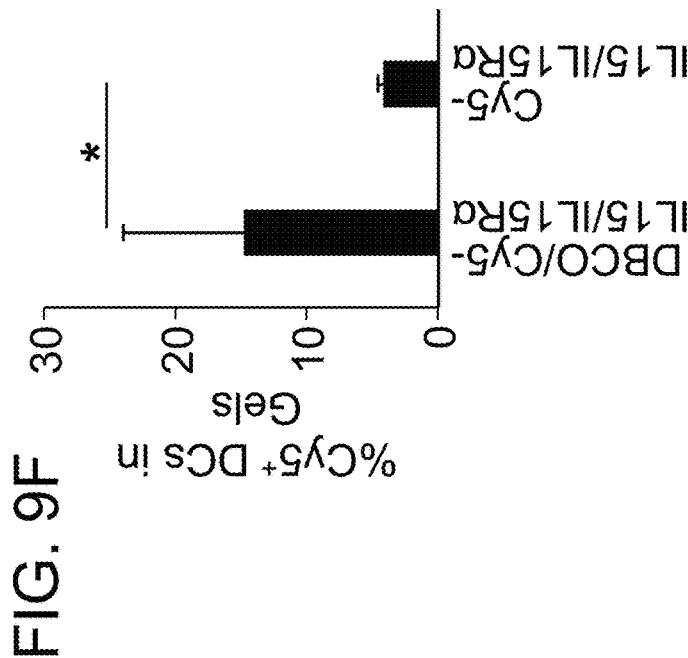
Figure 9H:
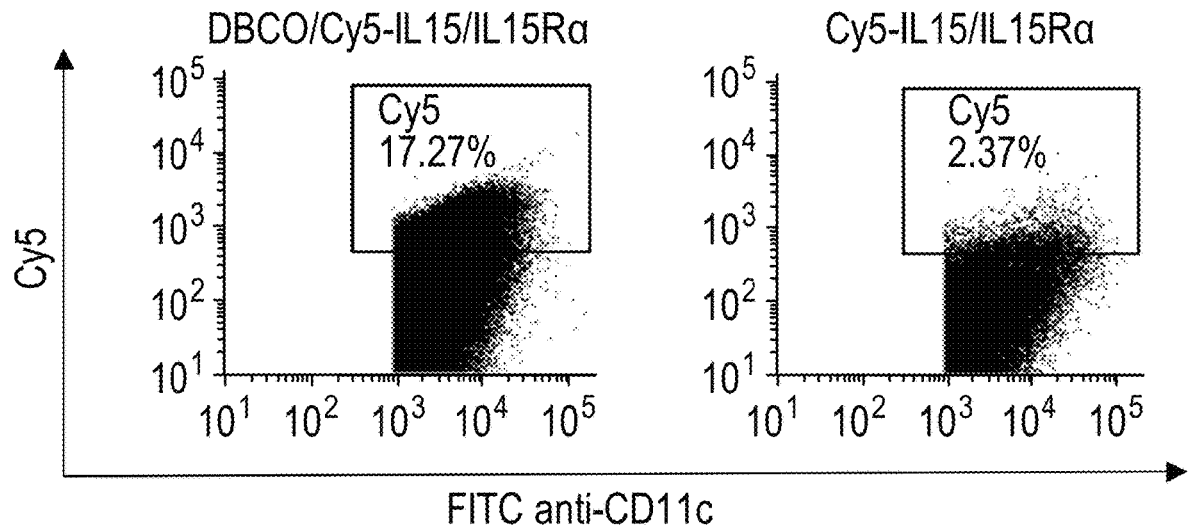
Figure 9I:
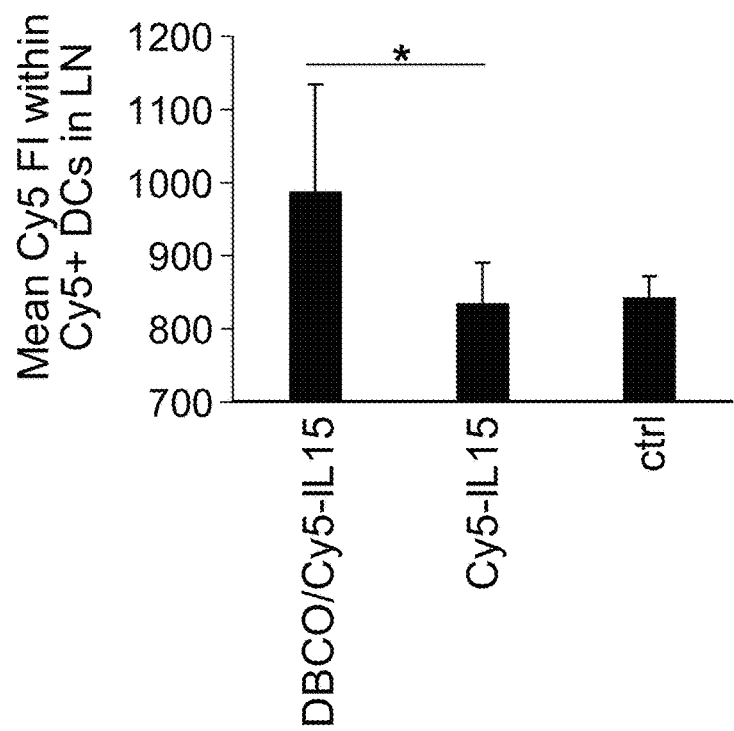

FIGS. 9E-9I illustrate azido-labeled DCs enable conjugation of DBCO/Cy5-IL-15/IL-15Rα in vivo via Click chemistry. FIG. 9E is a schematic illustration of time frame of the study. Pore-forming gels containing GM-CSF and G400 NP were subcutaneously injected on day 0, followed by ultrasound treatment on day 3 and tail base subcutaneous injection of DBCO/Cy5-IL-15/IL-15Rα or Cy5-IL-15/IL-15Rα (200 ng) on day 6. Gel scaffolds were excised for analyses 16 hours later (n=5). FIG. 9F is a graph showing percentage of $Cy5^+$ DCs ($CD11b^+CD11c^+$) in gel scaffolds. FIG. 9G is a graph showing mean Cy5 fluorescence intensity of DCs in gel scaffolds. FIG. 9H provides representative FACS plots of $Cy5^+CD11c^+$ DCs in gel scaffolds. FIG. 9I is a graph showing mean Cy5 fluorescence intensity of $Cy5^+$ DCs in LNs. FIGS. 9E, 9H, and 9I illustrate that azido-labeled DCs enable conjugation of DBCO/Cy5-IL15/IL15Rα in vivo via Click chemistry.

FIGS. 10A-10F illustrate that pore forming gel vaccine loaded with M27, M30, G400 NP, GM-CSF, and CpG generates neoantigen-specific $CD8^+$ and $CD4^+$ T cell responses.

Figure 10A:
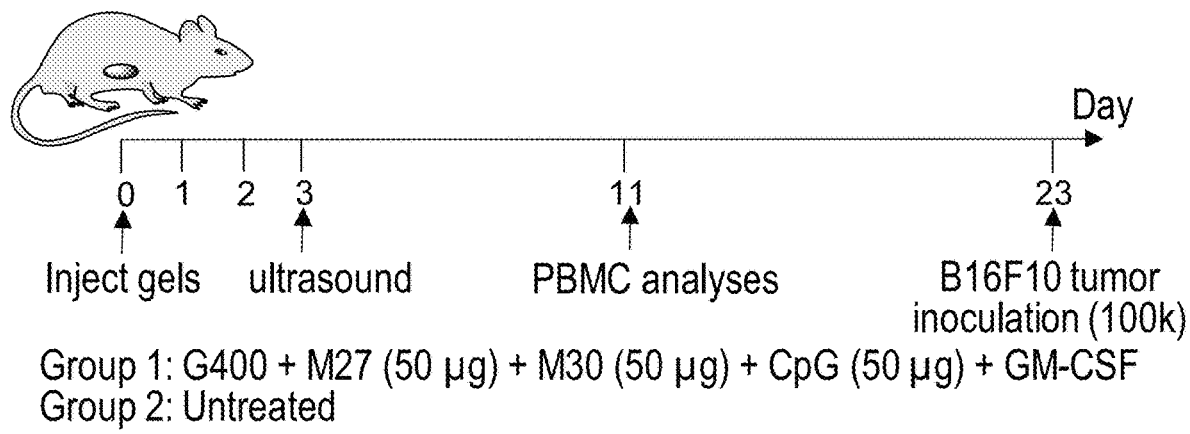

FIG. 10A is a schematic illustration of the time frame of vaccination study.

Figure 10B:
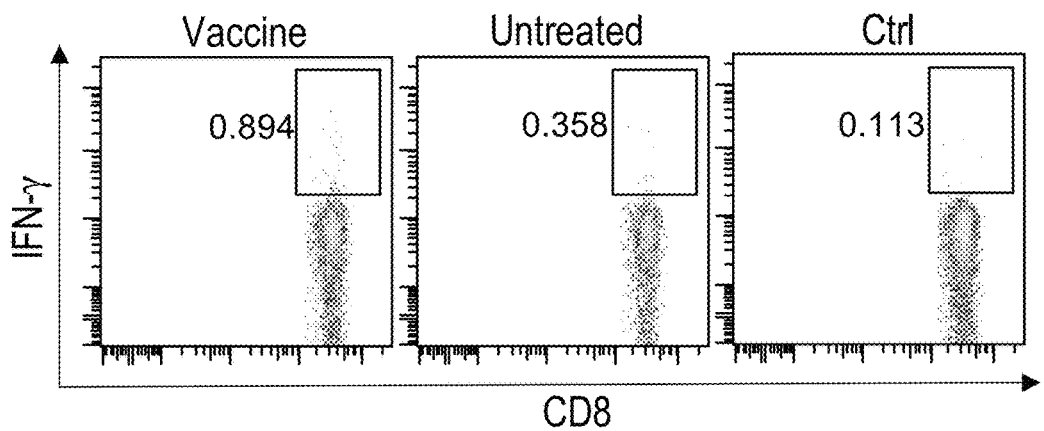
Figure 10C:
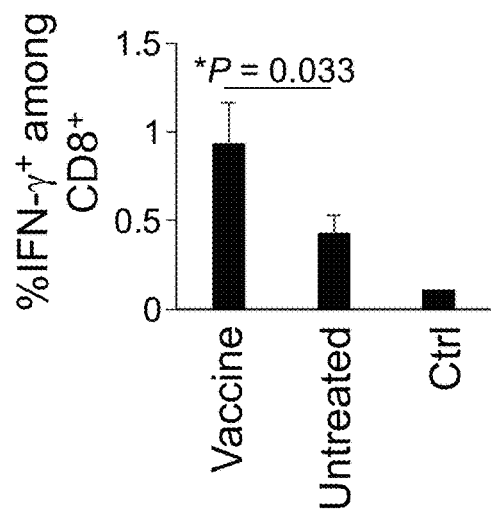

FIGS. 10B and 10C provides representative FACS plots (FIG. 10B) and a graph (FIG. 10C) showing percentage of IFN-$\gamma^+$ $CD8^+$ T cells in PBMCs on day 11 (n=4).

Figure 10D:
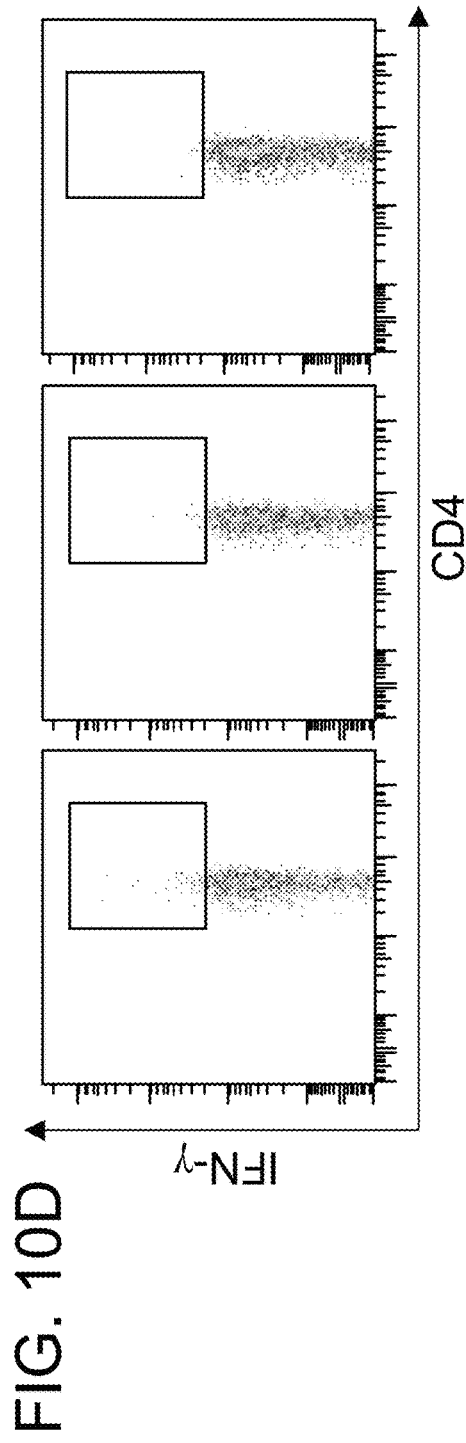
Figure 10F:
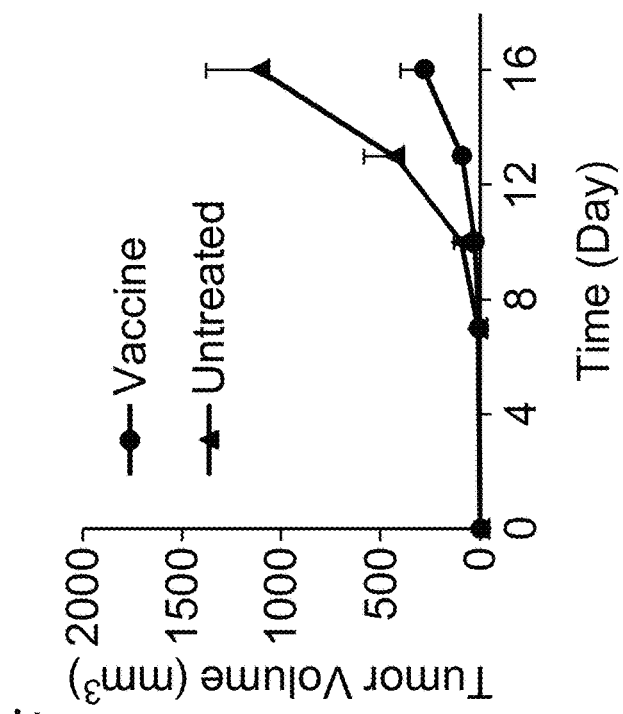
Figure 10E:
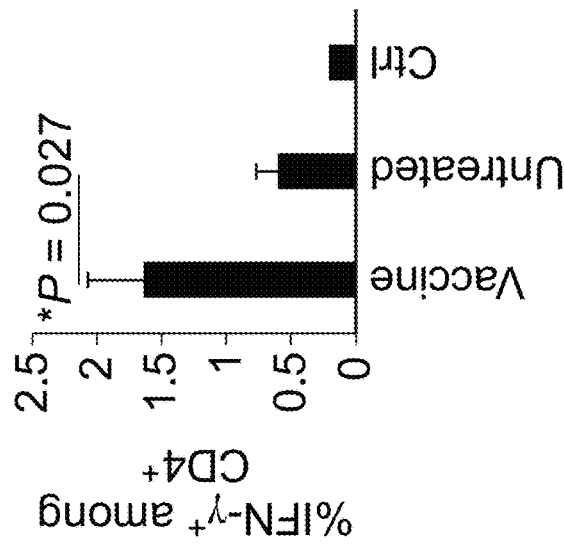

FIGS. 10D and 10E provides representative FACS plots (FIG. 10D) and a graph (FIG. 10E) showing percentage of IFN-$\gamma^+$ $CD4^+$ T cells in PBMCs on day 11 (n=4). PBMCs were restimulated with M27 and M30 ex vivo prior to IFN-γ staining. PBMCs without peptide restimulation were used as controls.

FIG. 10F is a graph showing average tumor volume of each group over the course of prophylactic study (n=4).

Figure 10G:
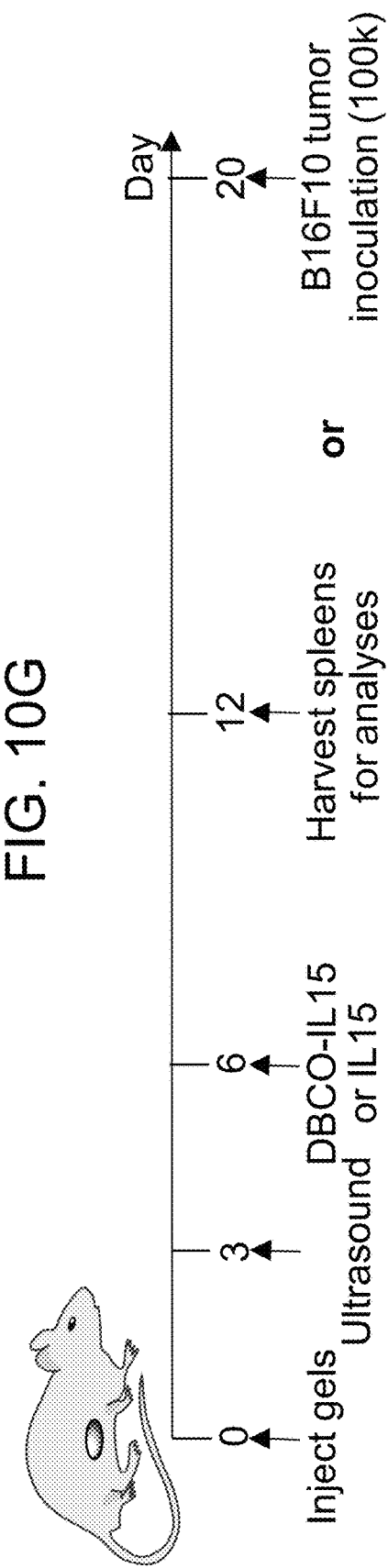

FIG. 10G is a schematic illustration showing time frame of vaccination study. Pore forming gels containing GM-CSF, CpG, M27, M30, and G400 NP were subcutaneously injected on day 0, followed by ultrasound treatment on day 3 and tail base subcutaneous injection of DBCO-IL-15/IL-15Rα or IL-15/IL-15Rα on day 6.

Figure 10H:
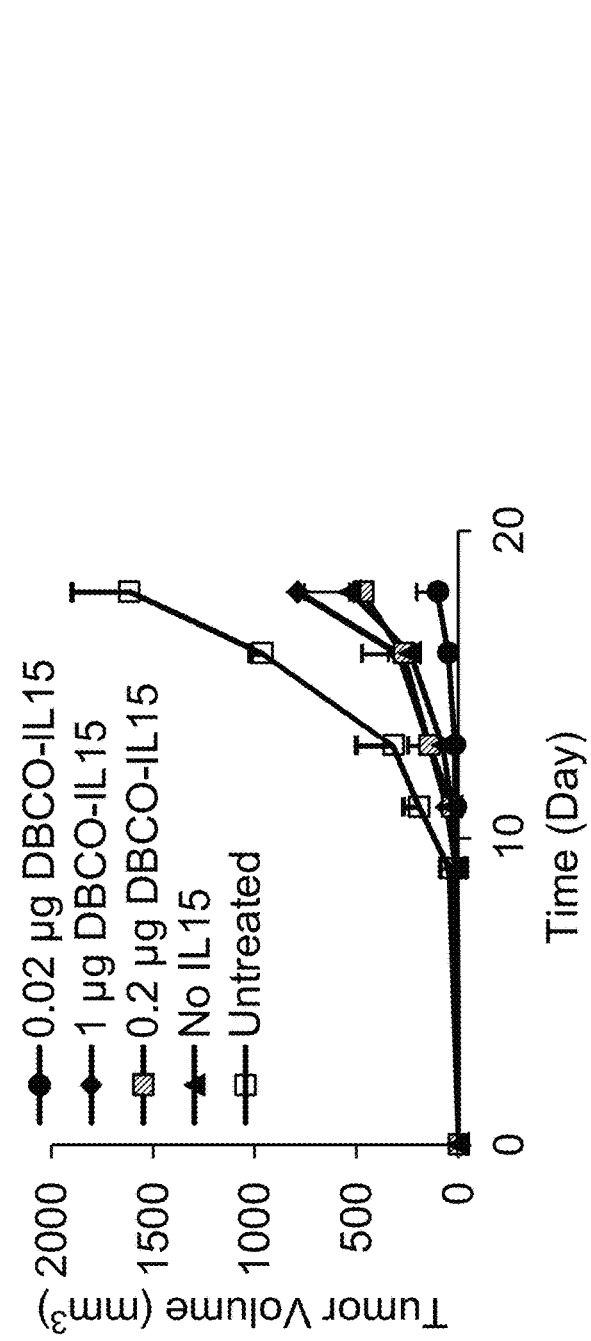

FIG. 10H is a graph showing average tumor volume of each group over the course of prophylactic study (n=6). B16F10 tumor cells ($1\times10^5$) were subcutaneously injected on day 20.

Figure 10J:
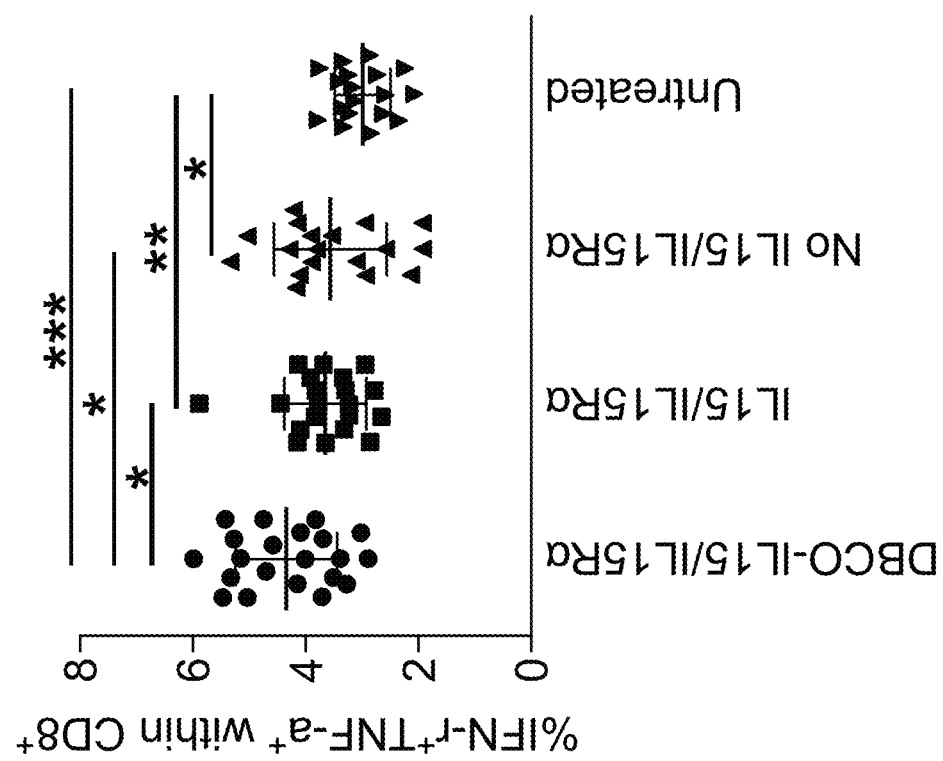
Figure 10I:
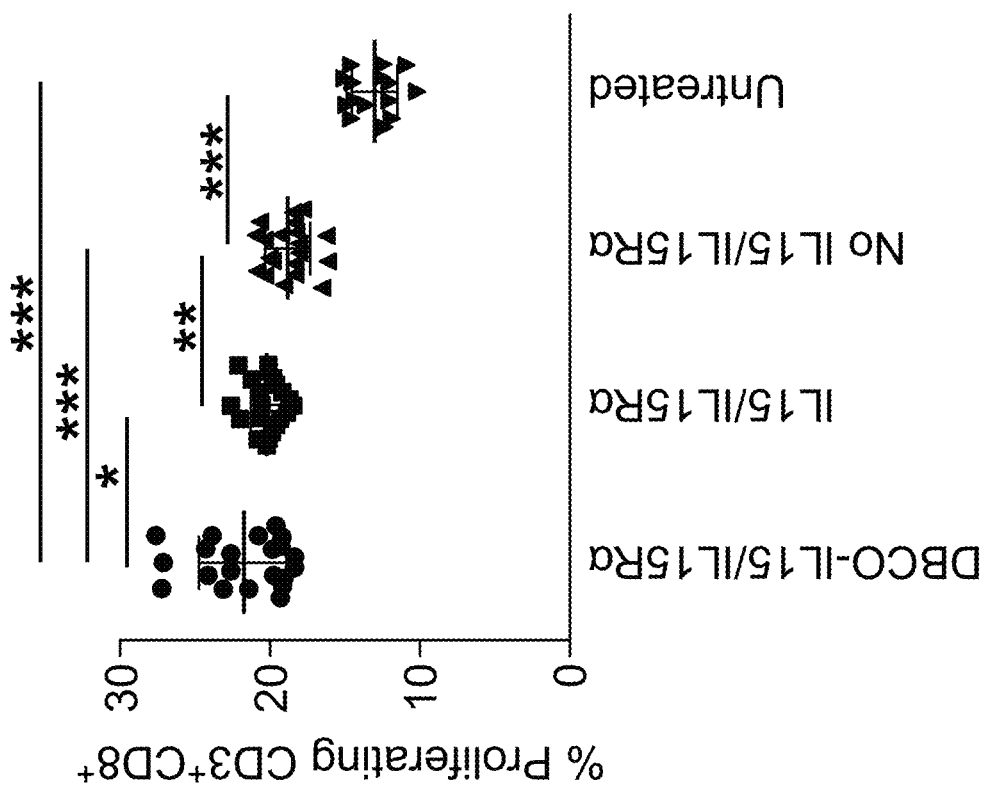

FIGS. 10I and 10J are graphs showing percentage of proliferating $CD8^+$ T cells (FIG. 10I) and IFN-$\gamma^+$TNFα$^+$ $CD8^+$ T cells (FIG. 10J) after culturing CFSE-stained splenic $CD8^+$ T cells with $CD11c^+$ DCs in the presence of M27 for 3 days. Spleens were harvested on day 12.

Figure 10L:
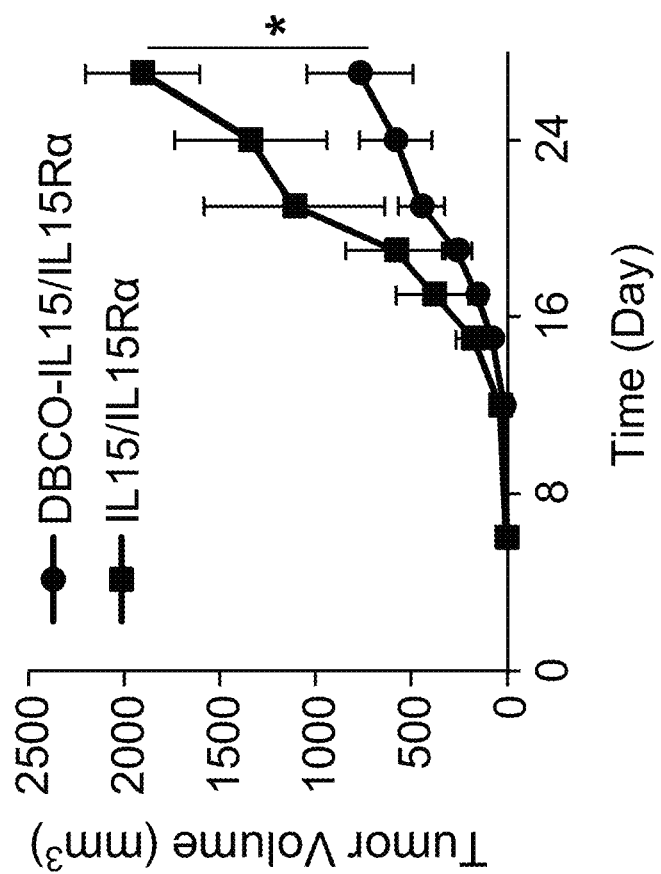
Figure 10K:
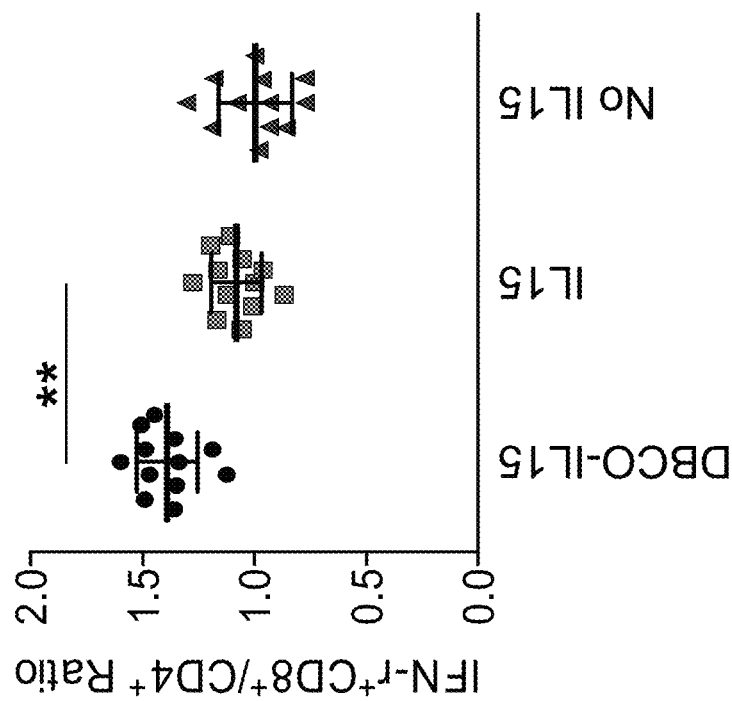

FIG. 10K is a dot graph showing number ratio of IFN-γ$^+$ $CD8^+$ to IFN-γ$^+$ $CD4^+$ T cells in splenocytes on day 12. DBCO-IL-15/IL-15Rα (20 ng) or IL-15/IL-15Rα (20 ng) were injected in this study.

FIG. 10L is a graph showing average tumor volume of each group over the course of prophylactic study (n=6). 100k B16F10 tumor cells were subcutaneously injected on day 20. The numerical data in FIG. 9L are presented as mean±SEM.

FIGS. 10G, 10H, and 10K illustrate that conjugation of DBCO-IL-15/IL-15Rα to azido-labeled DCs improves neoantigen-specific $CD8^+$ T cell responses.

Figure 10N:
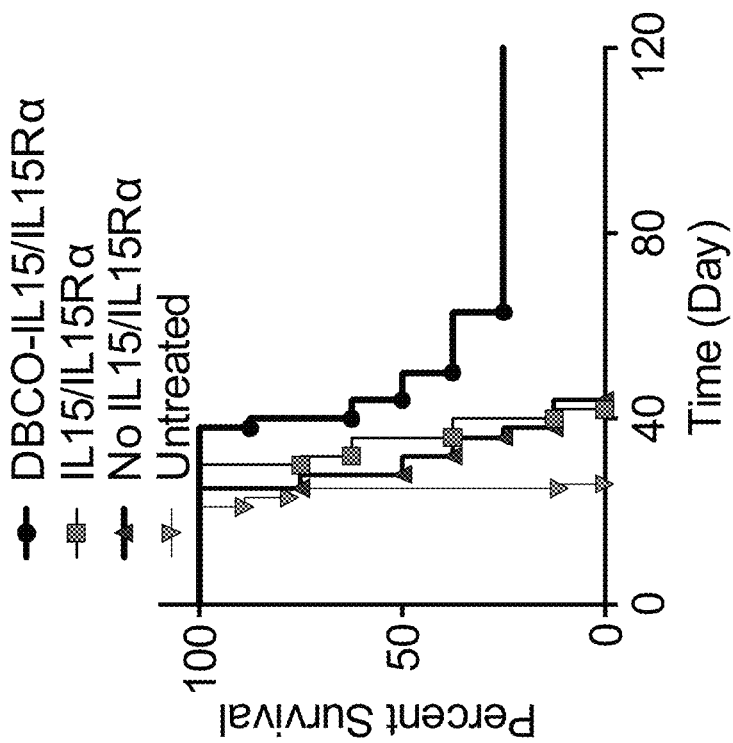
Figure 10M:
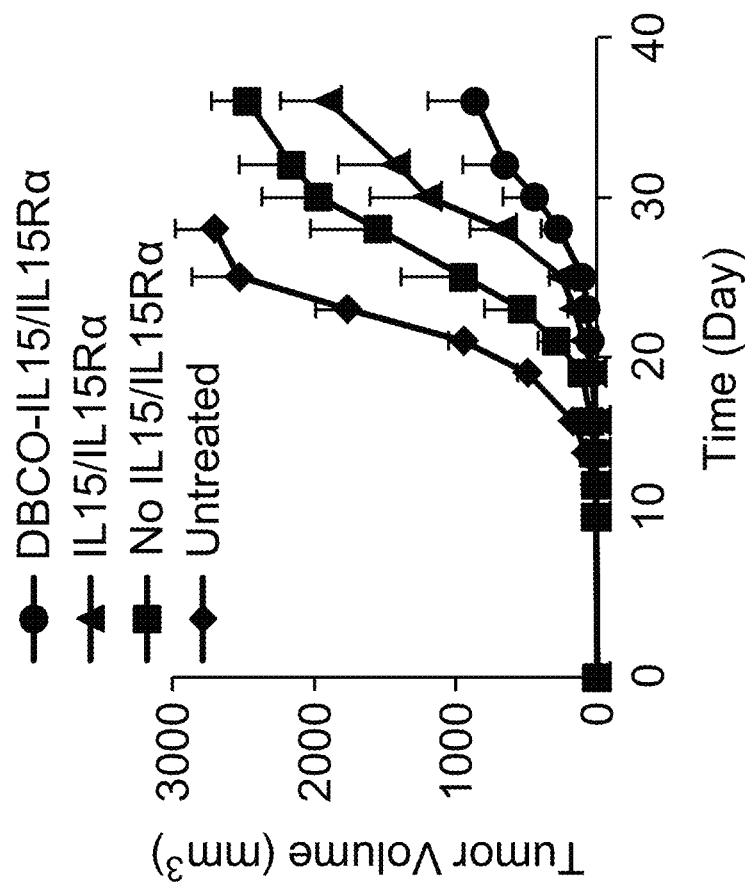

For FIGS. 10M and 10N, B16F10 tumors were inoculated on day 0 and gels containing GM-CSF, CpG, M27, M30, gpi 00, TRP2 and G400 NP were subcutaneously injected on day 5, followed by ultrasound treatment on day 8 and DBCO-IL15/IL15Rα or IL15/1L15Rα (20 ng) administration on day 11, 13, and 15.

FIG. 10M shows average B16F10 tumor volume of each group over the course of the therapeutic study (n=8).

FIG. 10N shows Kaplan-Meier plots for all groups (n=:8). All the numerical data are presented as mean±SD, with the exceptions in FIG. 10M, which are expressed as mean SEM ($0.01<P\leq0.05$; $P\leq0.01$; $*P\leq0.001$) FIGS. 11A-11C illustrate that pore forming gel vaccine loaded with M27, M30, G400 NP, GM-CSF, and CpG has therapeutic effect again tumor.

Figure 11A:
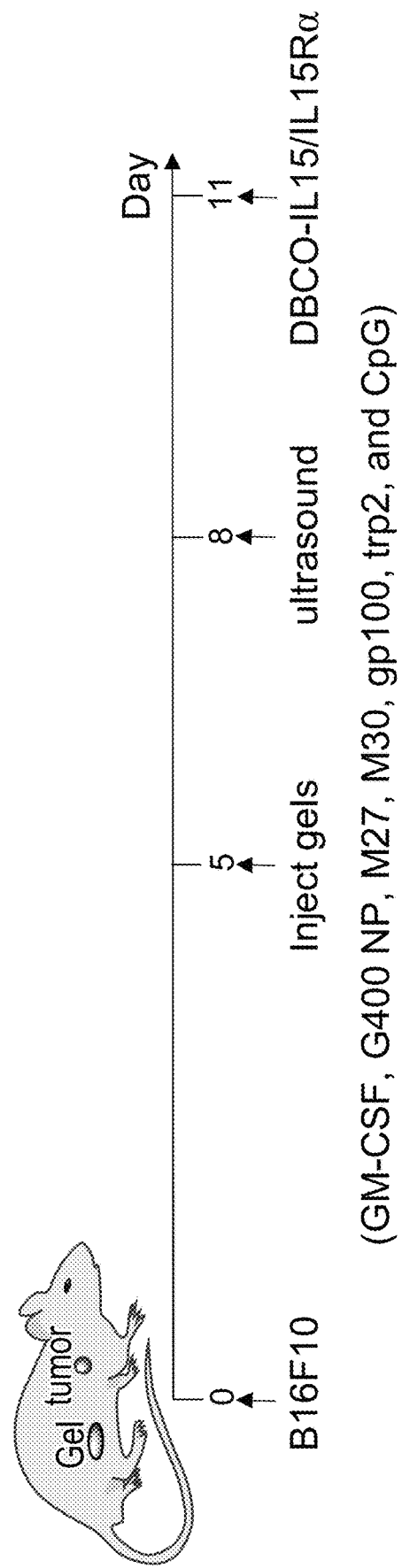

FIG. 11A is a schematic illustration of time frame of the study. Mice were inoculated with E.G7-OVA tumor cells on day 0. Pore forming gels containing GM-CSF, CpG, M27, M30, and G400 NP were subcutaneously injected on day 5, followed by ultrasound treatment on day 8 and tail base subcutaneous injection of DBCO-IL-15/IL-15Rα on day 11. Three control groups are (1) tail base subcutaneous injection of IL-15 at day 11; (2) no IL-15 injection; and (3) no treatment.

Figure 11B:
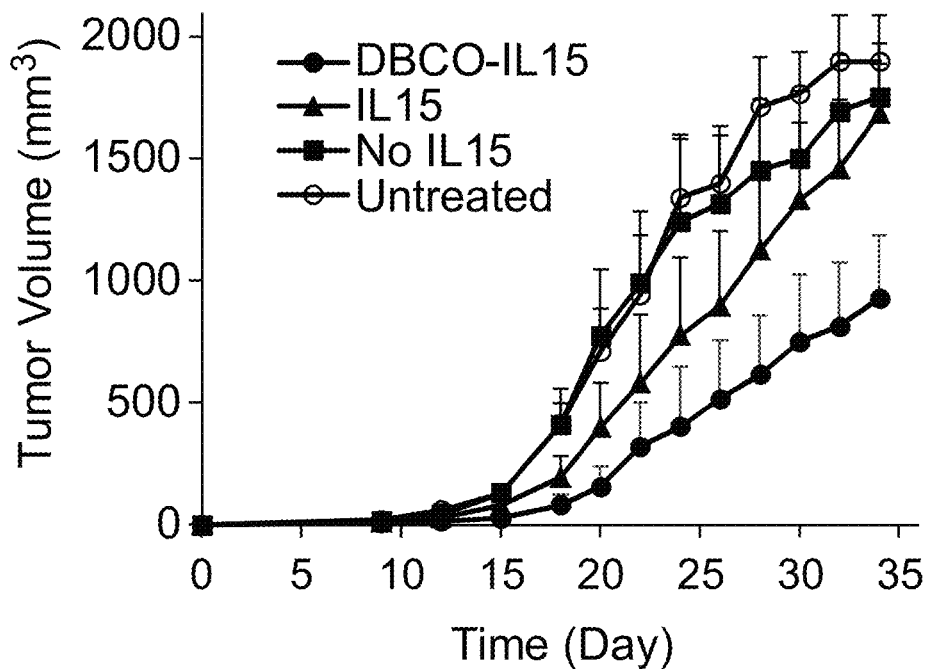

FIG. 11B is a graph showing average E.G7-OVA tumor volume of each group over the course of the therapeutic tumor study.

Figure 11C:
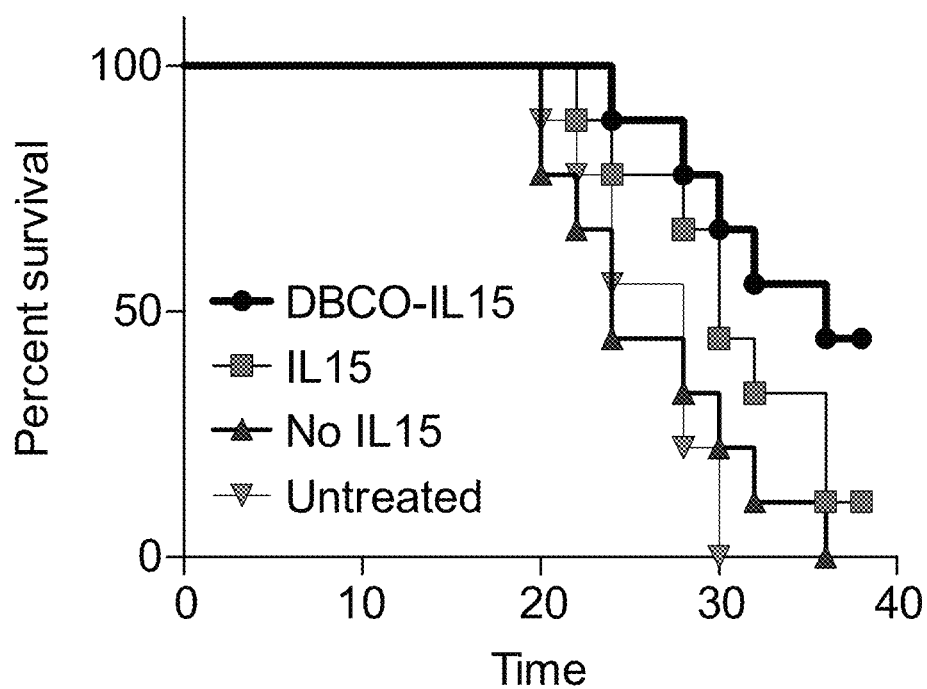

FIG. 11C is a graph showing Kaplan-Meier plots for all groups.

All the numerical data shown in the Figures are presented as mean±SD unless otherwise indicated.

DETAILED DESCRIPTION OF THE INVENTION

Disclosed herein are compositions and methods for labeling cells using click chemistry reagents. The compositions and methods disclosed herein provide a specific and efficient means of localizing desired agents to a variety of cell types in vivo and in vitro.

I. Definitions

In order that the present invention may be more readily understood, certain terms are first defined.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

The use of the terms "a" and "an" and "the" and similar referents in the context of describing the invention (especially in the context of the following claims) are to be construed to cover both the singular and the plural (i.e., one or more), unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited.

The term "about" or "approximately" usually means within 5%, or more preferably within 1%, of a given value or range.

The term "biocompatible" as used herein refers to a substance or other material that is non-toxic and/or non-immunogenic. For example, a biocompatible material does not induce a significant immune response or deleterious tissue reaction, e.g., toxic reaction or significant irritation, over time when implanted into or placed adjacent to the biological tissue of a subject.

As used herein, the term "subject" includes any subject who may benefit from being administered a hydrogel or an implantable drug delivery device of the invention. The term "subject" includes animals, e.g., vertebrates, amphibians, fish, mammals, non-human animals, including humans and primates, such as chimpanzees, monkeys and the like. In one embodiment of the invention, the subject is a human. The term "subject" also includes agriculturally productive livestock, for example, cattle, sheep, goats, horses, pigs, donkeys, camels, buffalo, rabbits, chickens, turkeys, ducks, geese and bees; and domestic pets, for example, dogs, cats, caged birds and aquarium fish, and also so-called test animals, for example, hamsters, guinea pigs, rats and mice.

Generally, the term "treatment" or "treating" is defined as the application or administration of a therapeutic agent to a patient, or application or administration of a therapeutic agent to an isolated tissue or cell line from a patient, said patient having a disease, a symptom of disease or a predisposition toward a disease, with the purpose to cure, heal, alleviate, relieve, alter, remedy, ameliorate, improve or affect the disease, the symptoms of disease or the predisposition toward disease. Thus, treating can include suppressing, inhibiting, preventing, treating, or a combination thereof. Treating refers, inter alia, to increasing time to disease progression, expediting remission, inducing remission, augmenting remission, speeding recovery, increasing efficacy of or decreasing resistance to alternative therapeutics, or a combination thereof. "Suppressing" or "inhibiting", refers, inter alia, to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. In one embodiment the symptoms are primary, while in another embodiment, symptoms are secondary. "Primary" refers to a symptom that is a direct result of a disorder, e.g., diabetes, while, secondary refers to a symptom that is derived from or consequent to a primary cause. Symptoms may be any manifestation of a disease or pathological condition.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%. Accordingly, as used herein, the term "treatment" or "treating" includes any administration of a compound described herein and includes: (i) preventing the disease from occurring in a subject which may be predisposed to the disease but does not yet experience or display the pathology or symptomatology of the disease; (ii) inhibiting the disease in an subject that is experiencing or displaying the pathology or symptomatology of the diseased (i.e., arresting further development of the pathology and/or symptomatology); or (iii) ameliorating the disease in a subject that is experiencing or displaying the pathology or symptomatology of the diseased (i.e., reversing the pathology and/or symptomatology).

Efficacy of treatment is determined in association with any known method for diagnosing the disorder. Alleviation of one or more symptoms of the disorder indicates that the compound confers a clinical benefit. Any of the therapeutic methods described to above can be applied to any suitable subject including, for example, mammals such as dogs, cats, cows, horses, rabbits, monkeys, and most preferably, humans.

II. Click Chemistry Reagents

In one embodiment, the invention features compositions and reagents for labeling cells, e.g., immune cells, using click chemistry reagents. Metabolic glycoengineering of unnatural sugars, azido-sugars for example, provides a facile yet powerful way to introduce chemical groups onto the cell surface in the form of glycoproteins. For specifically labeling cells in an in vivo environment, these agents can be incorporated into scaffold devices, as described herein. For example, the click chemistry reagents disclosed herein can be incorporated into a device comprising a hydrogel scaffold, that specifically recruits immune cells, for example, dendritic cells (DCs). Click-labeled cells can be targeted in vitro or in vivo with agents of interest coupled to a counterpart click moiety. In this manner, virtually any agent can be targeted to cells, and covalently coupled to cell surface glycoproteins, using click chemistry.

Click Functionalized Polymers

In some examples, the present invention provides a click functionalized polysaccharide polymer which is a product of radical-catalyzed polymerization involving a reaction between one or more saccharide monomers. In this radical-catalyzed polymerization, saccharide monomers are polymerized together to form a polysaccharide polymer. Each saccharide monomer involved in the radical-catalyzed polymerization comprises a saccharide molecule; a click reagent that is attached to the saccharide molecule; and a moiety comprising a functional group amenable to radical polymerization that is attached to the saccharide molecule. The product of the radical-catalyzed polymerization is a click functionalized polysaccharide polymer that comprises repeating saccharide units, in which each saccharide unit is attached, e.g., covalently attached, to a click reagent.

In other examples, the present invention also provides a click-functionalized amphiphilic polymer which is a product of radical-catalyzed polymerization involving a reaction between a reagent comprising a hydrophilic portion and one or more saccharide monomers. In this radical-catalyzed polymerization, saccharide monomers are polymerized together to form a polysaccharide polymer, and the hydrophilic portion becomes attached to the polysaccharide polymer. Each saccharide monomer involved in the radical-catalyzed polymerization comprises a saccharide molecule; a click reagent that is attached to the saccharide molecule; and a moiety comprising a functional group amenable to radical polymerization attached to the saccharide molecule. Thus, in some examples, the product of this radical-catalyzed polymerization is a click functionalized polysaccharide polymer that comprises a hydrophilic portion and repeating saccharide units, and in which each saccharide unit is attached, e.g., covalently attached, to a click reagent.

Figure 1A:
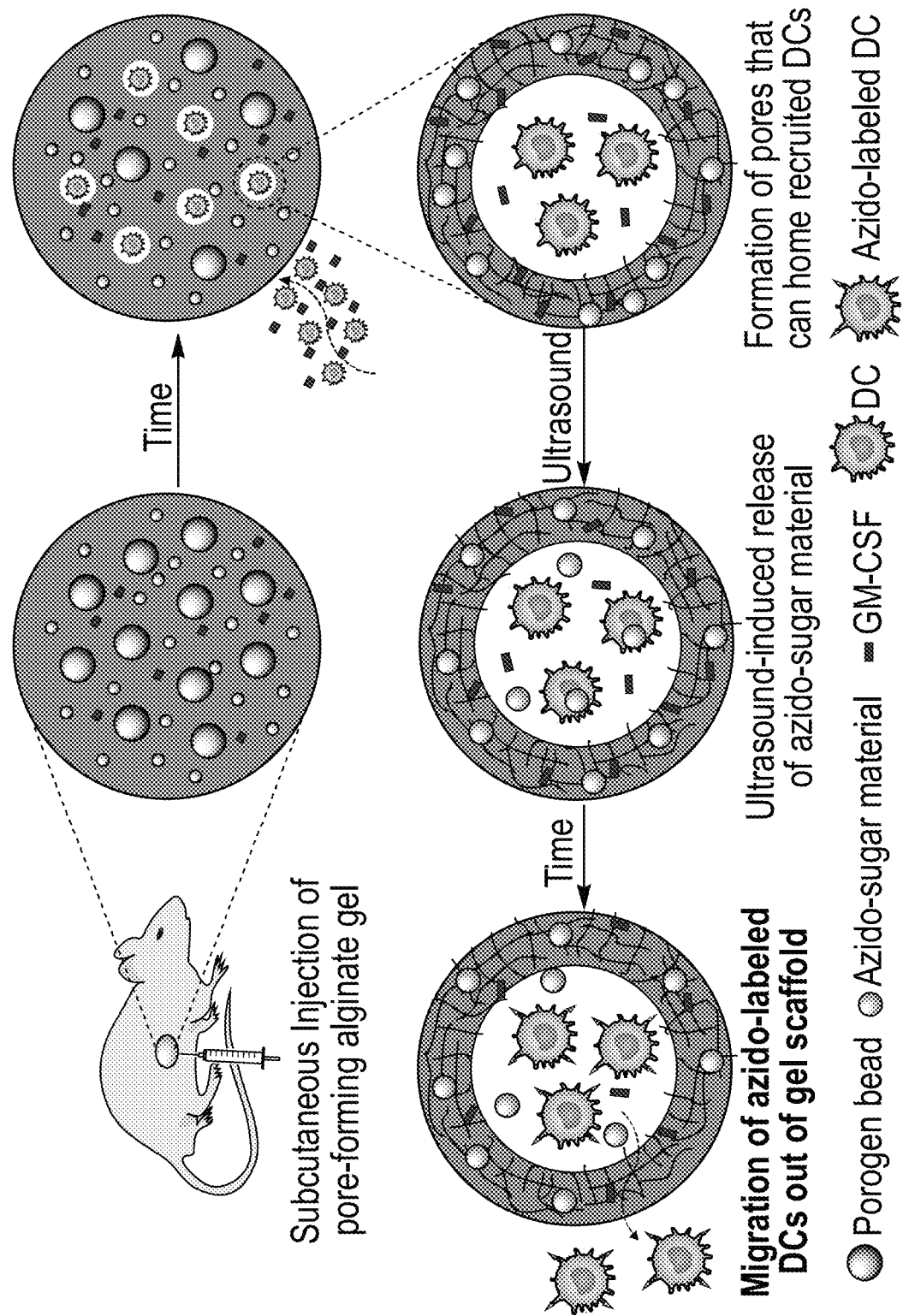
FIGS. 1A and 1B are schematic illustrations of exemplary embodiments of the present invention.
Figure 1B:
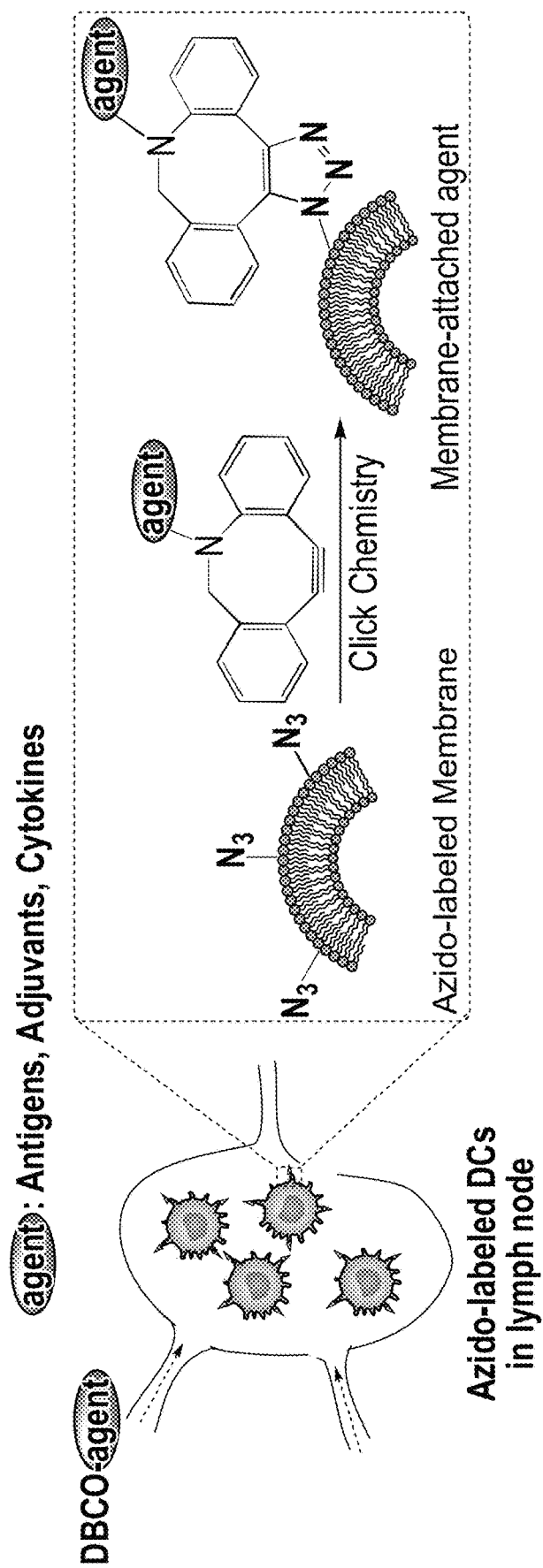
Figure 2D:
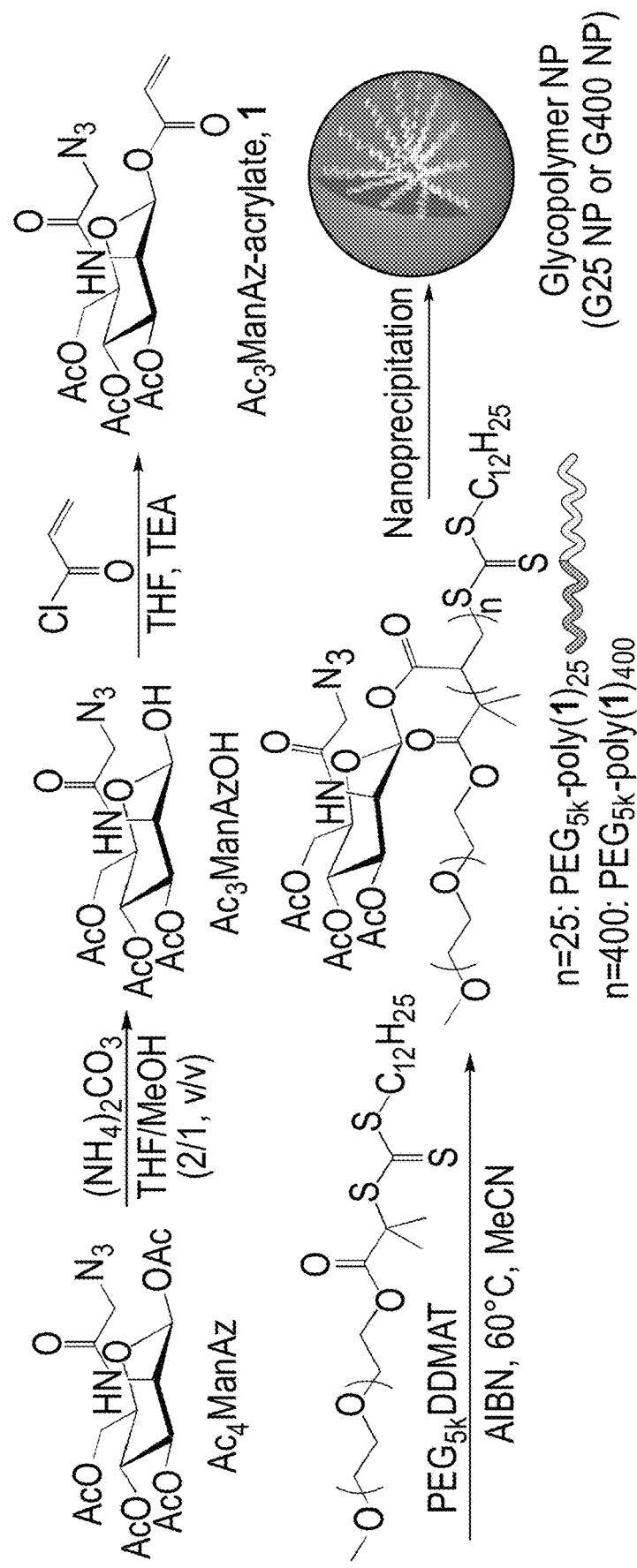
FIG. 2D is a schematic illustration showing the synthetic route of G25 and G400NP.
Figure 2E:
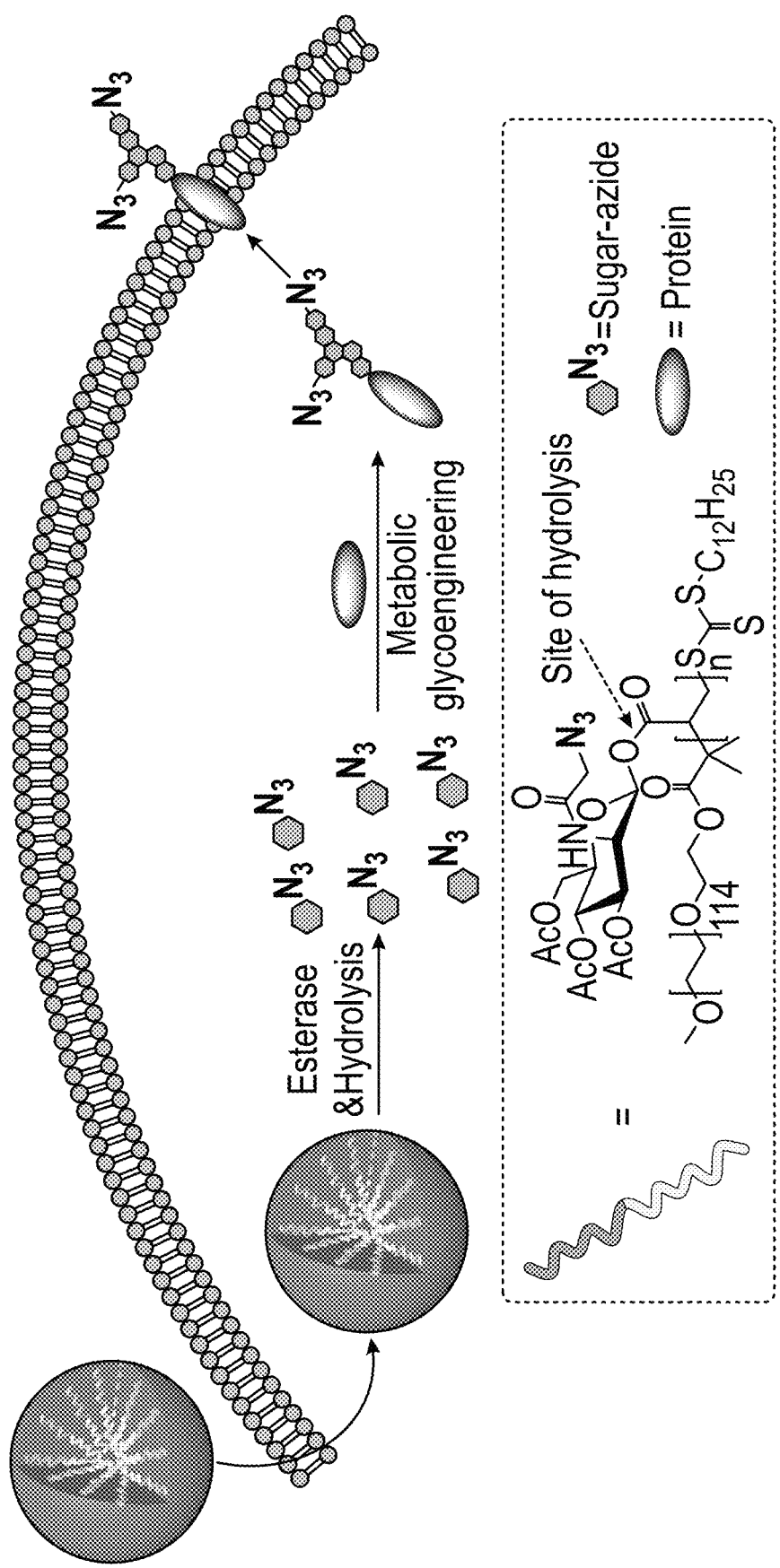
FIGS. 2E and 2F are schematic illustrations of metabolic labeling of DCs with azido-sugar NPs. Azido-sugar NPs enter cells through endocytosis, disassemble and degrade into sugar-azide via hydrolysis or enzymatic degradation, and the released sugar-azide is metabolically presented to cell surface in the form of glycoproteins. The metabolic labeling of cells with azido-sugar NPs is a covalent labeling and stable over weeks. Accordingly, the labeling is suitable for cell tracking, such as DCs tracking. The sugar-azides of dying cells could be re-metabolized by neighboring cells, which can be utilized to understand the fate of the labeled cells, such as DCs. The labeling with azido-sugar NPs also allows click chemistry-based lymph nodes (LN) targeting for modulation of cell function, such as DCs' function.

As illustrated in FIG. 2E, when a polymer of the present invention is introduced into a cell, e.g., as a part of a nanoparticle, the polymer is subjected to hydrolysis, resulting in release inside the cell of individual saccharide monomers attached to a click-reagent. The individual saccharide monomers attached to a click reagent are then subjected to metabolic glycoengineering inside the cell, resulting in incorporation of the saccharide monomers attached to a click reagent into post-translational modifications of, inter alia, proteins of the plasma membrane. The click reagents are then displayed on the cell surface as the proteins span the plasma membrane. As a result, the cell surface becomes labeled with a click reagent.

Any saccharide molecule amenable to metabolic glycoengineering inside a cell may be used to prepare saccharide monomers for preparing click functionalized polymers of the invention. In certain embodiments, the saccharide molecule may be selected from the group consisting of mannose, galactose, fucose and sialic acid. In one specific embodiment, the saccharide molecule may be mannose.

In some examples, in the saccharide monomers, the click reagent may be attached to the saccharide molecule at the C2 position of the sugar moiety. For example, the click reagent may be an azide, and the saccharide molecule may be a mannose, e.g., an acetylated mannose. As illustrated below, an azide may be attached at the C2 position of an acetylated mannose:

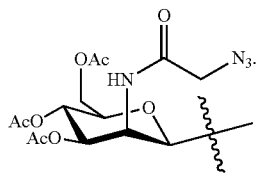

The term "click reagent", which may be used herein interchangeably with the term "click chemistry reagent" and "click moiety", refers to a reagent that can rapidly and selectively react ("click") with its counterpart click reagent under mild conditions in aqueous solution. The mild conditions may include any one of neutral pH, aqueous solution and ambient temperature, with low reactant concentrations. Any suitable click reagent may be used in the context of the present invention. Exemplary click pair reagents are well known to one of skill in the art and include, but are not limited to, moieties that comprise azide and dibenzocyclooctyne (DBCO), tetrazine and transcyclooctene, and tetrazine and norbornene, with the structures illustrated below.

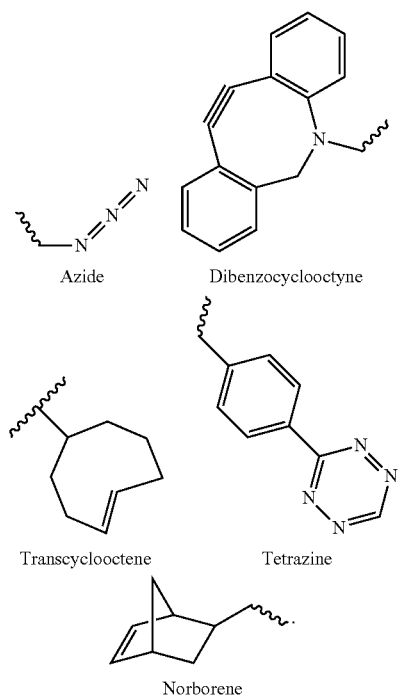

In some embodiments, the click reagent may be an azide. The term "azide" or "azide moiety", as used herein, includes molecules that comprise an azide moiety as shown above. In some examples, azide may be attached to the saccharide molecule with a suitable spacer moiety. In a specific example, the spacer moiety comprises an aminocarbonyl linkage. The term "aminocarbonyl" or "amide", as used herein, includes compounds or moieties which contain a nitrogen atom which is bonded to the carbon of a carbonyl or a thiocarbonyl group. This term includes "alkaminocarbonyl" or "alkylaminocarbonyl", groups wherein alkyl, alkenyl aryl or alkynyl groups are bound to an amino group bound to a carbonyl group. In one specific example, the azide moiety and the spacer moiety may be represented by the following structure:

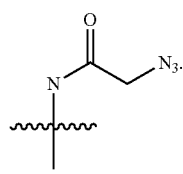 [SMILES: *NC(=O)CN=[N+]=[N-]]

A counterpart click reagent for an azide is dibenzocyclooctyne (DBCO). In some embodiments, the click reagent may be DBCO. As used herein, the term "DBCO" or "DBCO moiety" includes molecules that may comprise a DBCO moiety as shown above. In some examples, DBCO is attached to the saccharide molecule with a suitable spacer moiety, e.g., comprising an aminocarbonyl or an alkylamino linkage. The term "alkylamino", as used herein, includes moieties wherein a nitrogen atom is covalently bonded to at least one carbon or heteroatom and to at least one alkyl group. This term also includes "dialkylamino", wherein the nitrogen atom is bound to at least two alkyl groups.

In some embodiments, the click reagent may be tetrazine. As used herein, the term "tetrazine" or "tetrazine moiety" includes molecules that may comprise a tetrazine moiety as shown above. In some examples, transcyclooctene is attached to the saccharide molecule with a suitable spacer moiety, e.g., comprising an aminocarbonyl or an alkylamino linkage. Exemplary tetrazine moieties suitable within the context of the present invention include, but are not limited to, the structures shown below (see, e.g., Karver et al., (2011) *Bioconjugate Chem.* 22:2263-2270, and WO 2014/065860, the entire contents of each of which are hereby incorporated herein by reference):

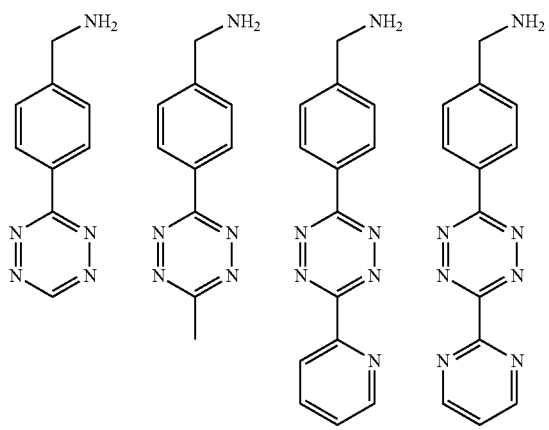

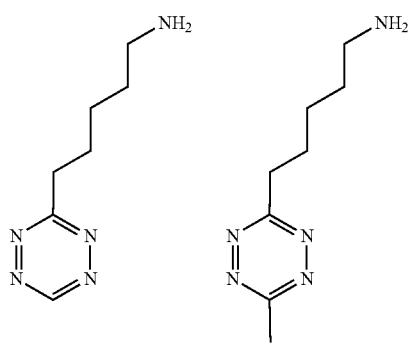

-continued

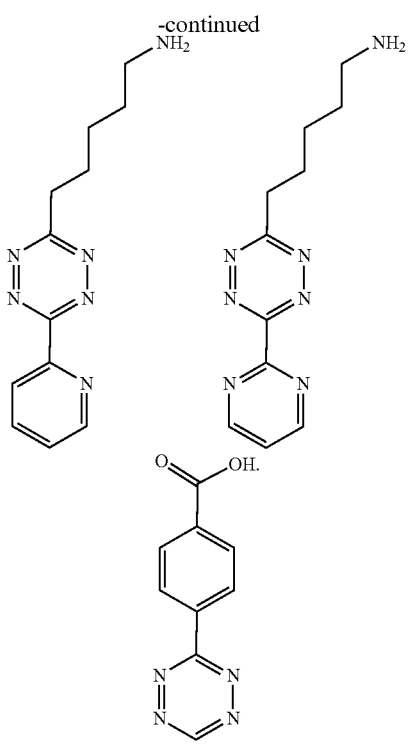

In other examples, exemplary tetrazines that may be used in the context of the present invention are described in U.S. Pat. No. 8,236,949, the entire contents of which are hereby incorporated herein by reference.

One of the counterpart click reagent for a tetrazine is transcyclooctyne. In some embodiments, the click reagent in the context of the present invention may be transcyclooctene. As used herein, the term "transcyclooctene" or "transcyclooctene moiety" includes molecules that may comprise a transcyclooctene moiety as shown above. In some examples, transcyclooctene is attached to the saccharide molecule with a suitable spacer moiety, e.g., comprising an aminocarbonyl or an alkylamino linkage. Exemplary transcyclooctenes that may be used in the context of the present invention include the transyclooctynes described, e.g., in U.S. Pat. No. 8,236,949, the entire contents of which are hereby incorporated herein by reference.

Another counterpart reagents for tetrazine is norbornene (Nb). In some embodiments, the click reagent in the context of the present invention may be norbornene. As used herein, the terms "norbornene" and "norbornene moieties" include but are not limited to the norbornene moiety as shown above, including a moiety comprising norbornadiene and norbornene groups. In some examples, norbornene is attached to the saccharide molecule with a suitable spacer moiety, e.g., comprising an aminocarbonyl or an alkylamino linkage.

In addition to the click reagent, the saccharide monomer may also comprise a moiety comprising a functional group amenable to radical polymerization. The presence of such a moiety in the saccharide monomer provides the means to polymerize the saccharide moieties, thereby forming a click functionalized polymer of the invention. The moiety comprising a functional group amenable to radical polymerization may comprise a double bond. For example, the moiety comprising a functional group amenable to radical polymerization may comprise an acrylate or a methacrylate. In one specific example, the moiety comprising a functional group amenable to radical polymerization comprises an acrylate. In another specific example, the moiety comprising a functional group amenable to radical polymerization comprises a methacrylate.

The moiety comprising a functional group amenable to radical polymerization may be attached to the saccharide molecule, e.g., mannose, galactose, fucose or sialic acid, at the C1 position, the C3 position, the C4 position or the C5 position of the saccharide molecule. In one specific embodiment, the moiety comprising a functional group amenable to radical polymerization is attached to the saccharide molecule at the C1 position.

Illustrated below is an exemplary saccharide monomer comprising mannose as the saccharide molecule, an azide as the click reagent attached at the C2 position of the mannose and the acrylate as the moiety comprising a functional group amenable to radical polymerization attached at the C1 position. The exemplary saccharide monomer is further acetylated at the C3, C4 and C5 positions of the mannose:

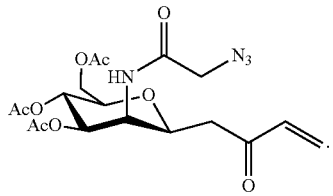

The saccharide monomer used in the radical-catalyzed polymerization to produce the polymers of the present invention may further comprise one or more hydrolysable substituents at any position that is not occupied by the click reagent or moiety comprising a functional group amenable to radical polymerization. For example, a hydrolysable substituent may be present at the C1 position, the C3 position, the C4 position or C5 position of the saccharide monomer. In some examples, the hydrolysable substituent contributes to the hydrophobicity of the polymer, but, once inside the cell, may be hydrolyzed and converted to a hydroxyl group. In some example, the hydrolysable substituent is represented by formula (1):

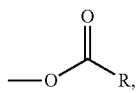

wherein R is alkyl. In a specific example, R is methyl.

The term "alkyl" as used herein, includes saturated aliphatic groups, including straight-chain alkyl groups (e.g., methyl, ethyl, propyl, butyl, pentyl, hexyl, heptyl, octyl nonyl, decyl, etc.), branched-chain alkyl groups (e.g. isopropyl, tert-butyl, isobutyl, etc.). The term alkyl also includes alkyl groups which can further include oxygen, nitrogen, sulfur or phosphorous atoms replacing one or more carbons of the hydrocarbon backbone. In some examples, a straight chain or branched chain alkyl may have 6 or fewer carbon atoms in its backbone (e.g., $C_1$-$C_6$ for straight chain, $C_3$-$C_6$ for branched chain), and more preferably 4 or fewer. The term "$C_1$-$C_6$" includes alkyl groups containing 1 to 6 carbon atoms.

In some examples, the click functionalized polysaccharide polymers of the present invention may comprise 10 to 1000 saccharide units, i.e., 10 to 1000 saccharide monomers attached together to form the click functionalized polysaccharide polymer. For example, the polymers of the invention may comprise 20 to 500, 100 to 500 or 200 to 600 saccharide units. In one specific example, the polymer of the invention may comprise 10-50 saccharide units, e.g., 25 saccharide units. In another specific example, the polymer of the invention may comprise 300-500 saccharide units, e.g., 400 saccharide units. In one specific embodiment, the polymer of the invention may comprise the structure of formula (2):

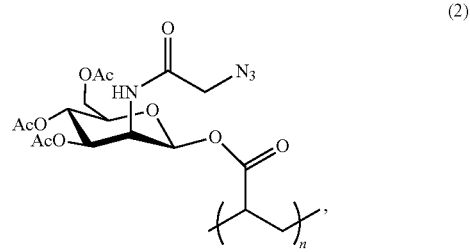

wherein n is a number between 10 and 1000.

In some examples, the click functionalized polysaccharide polymer of the present invention may further comprise a hydrophilic portion. The hydrophilic portion may be attached to the repeating saccharide units in which each saccharide unit is attached, e.g., covalently attached, to a click reagent. The hydrophilic portion may comprise a hydrophilic polymer, such as polyethylene oxide (PEG). In some examples, the PEG may comprise between 20 and 450 PEG units, e.g., about 100 to about 150 PEG units. In some examples, the PEG may have an average molecular weight of about 500 to about 20,000 Daltons, e.g., about 2,000 and about 10,000 Dalton. In one example, the PEG has an average molecular weight of about 5,000 Daltons.

In some examples, the click functionalized polysaccharide polymer of the invention comprising a hydrophilic portion may comprise the structure of formula (3):

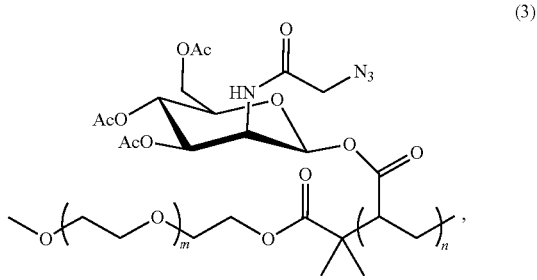

wherein n is a number between 10 and 1000; and m is a number between 45 and 200.

The polymers of the invention are produced by subjecting saccharide monomers as described above and, optionally, the hydrophilic portion, to a radical-catalyzed polymerization. In some examples, the radical-catalyzed polymerization may be reversible addition-fragmentation chain transfer (RAFT) polymerization. The RAFT polymerization involves conventional free radical polymerization of a substituted monomer in the presence of a suitable chain transfer agent (RAFT agent or CTA), which mediate the polymerization via a reversible chain-transfer process.

Any suitable RAFT reagent may be used in the context of the present invention. Exemplary RAFT agents may be found, e.g., in the SIGMA-ALDRICH catalog and may comprise a thiocarbonate moiety, a dithiocarbamate moiety or a dithiobenzoate moiety. In one specific example, the RAFT agent may comprise a thiocarbonate moiety, e.g., 2-(dodecylthiocarbonothioylthio)-2-methylpropionate.

In another specific example, the RAFT agent may comprise poly(ethylene glycol) methyl ether 2-(dodecylthiocarbonothioylthio)-2-methylpropionate. In this example, when the RAFT agent participates in the radical-catalyzed polymerization, the poly(ethylene glycol) portion of the RAFT agent becomes attached to the resulting click functionalized polysaccharide polymer and becomes the hydrophilic portion of the polymer. An exemplary product of the RAFT polymerization that comprises the use of poly(ethylene glycol) methyl ether 2-(dodecylthiocarbonothioylthio)-2-methylpropionate as the RAFT agent is the structure of formula (4):

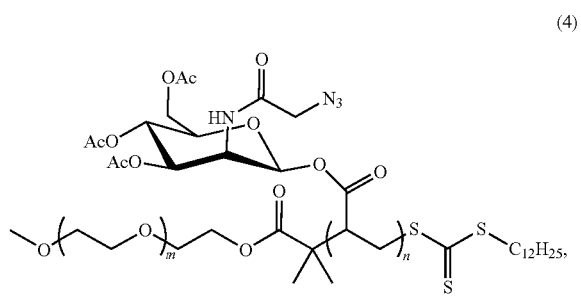

(4)

wherein n is a number between 10 and 1000; and m is a number between 45 and 200.

Nanoparticles

The present invention also provides nanoparticles for labeling cells with a click reagent. The nanoparticles may comprise the click functionalized polysaccharide polymer of the invention as described above.

In some examples, the nanoparticle may be self-assembling, i.e., may spontaneously form when click functionalized polysaccharide polymer of the invention, once prepared, is exposed to certain conditions, such as an aqueous solvent or a physiological pH, or when the click functionalized polysaccharide polymer of the invention is subjected to nanoprecipitation. Scheme 1 below illustrates preparation of an exemplary nanoparticle of the invention starting from synthesis of a click functionalized polysaccharide polymer using RAFT polymerization. The RAFT reagent used in the RAFT polymerization is poly(ethylene glycol) methyl ether 2-(dodecylthiocarbonothioylthio)-2-methylpropionate. The saccharide monomer used in the RAFT polymerization to produce the click functionalized polysaccharide polymer is $Ac_3ManAz$-acrylate. The $Ac_3ManAz$-acrylate comprises mannose as the saccharide molecule which is functionalized at the C1 position with an azide as the click reagent and at the C2 positon with an acrylate as the moiety comprising a functional group amenable to radical polymerization. The $Ac_3ManAz$-acrylate further comprises acetyl groups at the C3, C4 and C5 positions as the hydrolysable substituents. The resulting polymer also comprises PEG5k (or PEG having an average molecular weight of about 5000 Daltons) as the hydrophilic portion. In the last step, a nanoparticle is produced by subjecting the click functionalized polysaccharide polymer of the invention to nanoprecipitation.

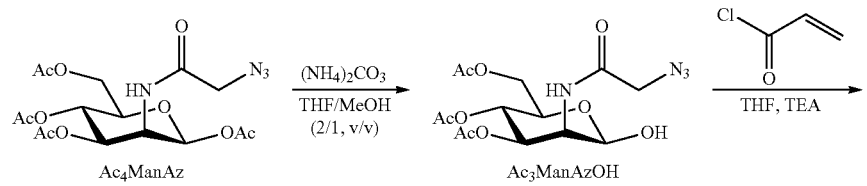

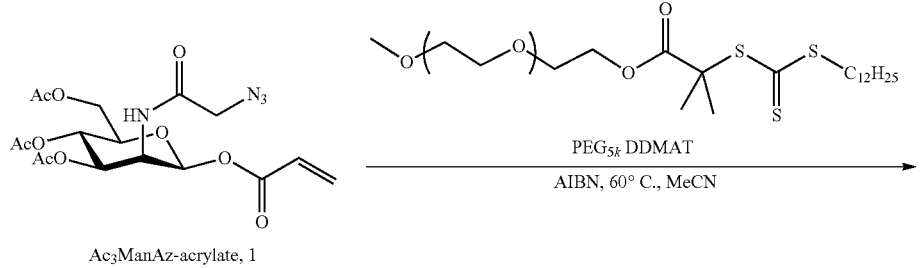

$Ac_3ManAz$-acrylate, 1

-continued

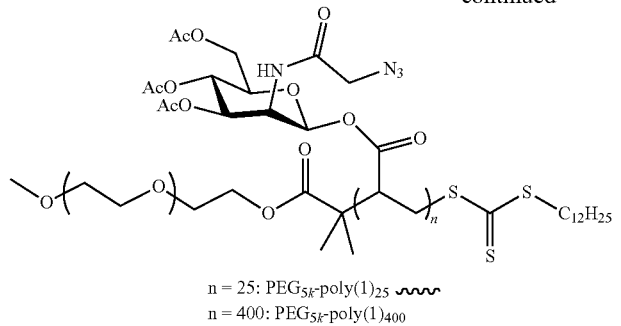

n = 25: PEG$_{5k}$-poly(1)$_{25}$
n = 400: PEG$_{5k}$-poly(1)$_{400}$

→ Nanoprecipitation

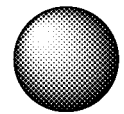

Glycopolymer NP
(G25 NP or G400 NP)

In other examples, the nanoparticle of the invention does not comprise a click functionalized polysaccharide polymer. Rather, the nanoparticle of the invention may comprise a saccharide molecule, e.g., a monomeric saccharide molecule, attached to a click reagent. For example, the saccharide molecule may be selected from the group consisting of mannose, galactose, fucose and sialic acid. In one specific example, the saccharide molecule is mannose.

The click reagent may be attached to the saccharide molecule at the C2 position and may comprise any of the click reagents as described above for saccharide monomers. The saccharide molecule may also comprise one or more hydrolysable substituents at the C1, C3, C4 and/or C5 positions of the saccharide molecule as described above for saccharide monomers.

The nanoparticle useful in the context of the present invention may be selected from the group consisting of a carbon-based nanoparticle, a ceramic nanoparticle, a metal nanoparticle, a semiconductor nanoparticle, a polymeric nanoparticle and a lipid-based nanoparticle. In one specific example, the nanoparticle may be a lipid-based nanoparticle, e.g., a liposome or a micelle. In another specific example, the nanoparticle useful in the context of the present invention may be a semiconductor nanoparticle, e.g., a silica nanoparticle.

III. Compositions and Methods for Labeling and Targeted Modulation of Cells

In some embodiments, the present invention also provides a method for labeling a cell with a click reagent that comprises contacting the cell with the click functionalized polysaccharide polymer of the invention as described above. In other embodiments, the present invention also provides a method for labeling a cell with a click reagent that comprises contacting the cell with a nanoparticle of the invention as described above. Contacting the cell with the polymers or nanoparticles of the invention can take place in vitro, ex vivo, or in vivo.

The foregoing polymer and nanoparticle compositions can be used to metabolically label the surface of cells with click chemistry reagents. Click chemistry reagents coupled to sugar moieties, and nanoparticles comprising the click chemistry reagents as described herein, can enter cells by endocytosis, and subsequently disassemble and degrade by hydrolysis or enzymatic degradation. The released sugar-click reagent is metabolically processed, and is presented on the surface of the cell in the form of a glycoprotein. This process is illustrated schematically for the exemplary embodiment of azido-sugar nanoparticles in FIG. 2E and FIG. 2F.

Preferably, cells are contacted with an effective amount of the click chemistry reagent. In some embodiments, the effective amount is an amount sufficient to metabolically label cell surface glycoproteins with a click moiety, e.g., an azide moiety, a DBCO moiety, a transcyclooctene moiety, a tetrazine moiety, or a norbornene moiety. The amount of a click chemistry reagent needed to metabolically label cells can readily be determined for each reagent and each cell type. In exemplary embodiments, the click reagent is provided to cells at a concentration of 1 nM to 1 µM. In other exemplary embodiments, the click reagent is provided to cells at a concentration of 1 µM to 1 mM. In other exemplary embodiments, the click reagent is provided to cells at a concentration of 1 mM to 1 M.

Virtually any cell type can be labeled with a click reagent in this manner. For example, this method can be used to label an epithelial cell, a fibroblast cell, a neuronal cell, an endothelial cell, and/or an immune cell with a click reagent. In an exemplary embodiment, the method is used to label immune cells, for example, dendritic cells, T cells, macrophages, B cells, or neutrophils. In one embodiment, the cells are CAR-T cells. In another embodiment, the cells are Sipuleucel-T, a mixture of antigen presenting cells used as an immunotherapy agent. In other exemplary embodiments, the click chemistry reagents disclosed herein can be used to label leukocytes, e.g. peripheral blood leukocytes, spleen leukocytes, lymph node leukocytes, hybridoma cells, T cells (cytotoxic/suppressor, helper, memory, naive, and primed), B cells (memory and naive), monocytes, macrophages, granulocytes (basophils, eosinophils, and neutrophils), natural killer cells, natural suppressor cells, thymocytes, and dendritic cells; cells of the hematopoietic system, e.g. hematopoietic stem cells (CD34+), proerythroblasts, normoblasts, promyelocytes, reticulocytes, erythrocytes, pre-erythrocytes, myeloblasts, erythroblasts, megakaryocytes, B cell progenitors, T cell progenitors, thymocytes, macrophages, mast cells, and thrombocytes; stromal cells, e.g. adipocytes, fibroblasts, adventitial reticular cells, endothelial cells, undifferentiated mesenchymal cells, epithelial cells including squamous, cuboid, columnar, squamous keratinized, and squamous non-keratinized cells, and pericytes; cells of the skeleton and musculature, e.g. myocytes (heart, striated, and smooth), osteoblasts, osteoclasts, osteocytes, synoviocytes, chondroblasts, chondrocytes, endochondral fibroblasts, and perichonondrial fibroblasts; cells of the neural system, e.g. astrocytes (protoplasmic and fibrous), microglia, oligodendrocytes, and neurons; cells of the digestive tract, e.g. parietal, zymogenic, argentaffin cells of the duodenum, polypeptide-producing endocrine cells (APUD), islets of langerhans (alpha, beta, and delta), hepatocytes, and kupfer cells; cells of the skin, e.g. keratinocytes, langerhans, and melanocytes; cells of the pituitary and hypothalamus, e.g. somatotropic, mammotropic, gonadotropic, thyrotropic, corticotropin, and melanotropic cells; cells of the adrenals and other endocrine glands, e.g. thyroid cells (C cells and epithelial cells); adrenal cells; cells of the reproductive system, e.g. oocytes, spermatozoa, leydig cells, embryonic stem cells, amniocytes, blastocysts, morulas, and zygotes; and tumor cells. In one embodiment, the click chemistry reagents disclosed herein are used to label immune cells, e.g., dendritic cells, T cells, CAR-T cells, B cells, NK cells, monocytes, and macrophages.

In an exemplary embodiment, the cells are contacted with the reagent for a period of time sufficient for cells to take up the reagent by endocytosis. The period of time sufficient for the cell to take up the click chemistry reagent can be determined empirically, for example, by microscopy, flow cytometry, and other standard techniques. In exemplary embodiments, the period of time sufficient for the cell to take up the click chemistry reagent is about 24 hours, about 48 hours, about 72 hours, about 96 hours, about 120 hours, or more. In other embodiments, the period of time sufficient for the cell to take up the click chemistry reagent is about 24-120 hours, about 48-96 hours, or about 48-72 hours.

Metabolic processing of the click chemistry reagent occurs inside the cell, whereby the sugar moiety is partially degraded and incorporated into glycoproteins, which are then displayed on the cell surface. After processing, the cells contain cell surface proteins which comprise carbohydrate molecules labeled with the click moiety.

Accordingly, in another aspect, the invention provides a cell comprising a cell surface glycoprotein, wherein the glycoprotein comprising a carbohydrate covalently linked to a click reagent. In exemplary embodiments, the click reagent comprises azide, dibenzocyclooctyne (DBCO), transcyclooctene, tetrazine and/or norbornene, or variants thereof. In some embodiments, the cell is an isolated cell. In some embodiments, the cell is an epithelial cell, a fibroblast cell, a neuronal cell, an endothelial cell, or an immune cell. In exemplary embodiments, the cell is an immune cells, for example, a dendritic cell, a T cell, a macrophage, a B cell, or a neutrophil. In one embodiment, the cell is a CAR-T cell. In another embodiment, the cell is Sipuleucel-T, a mixture of antigen presenting cells used as an immunotherapy agent. In other exemplary embodiments, the cell is a cell type selected from leukocytes, e.g. peripheral blood leukocytes, spleen leukocytes, lymph node leukocytes, hybridoma cells, T cells (cytotoxic/suppressor, helper, memory, naive, and primed), B cells (memory and naive), monocytes, macrophages, granulocytes (basophils, eosinophils, and neutrophils), natural killer cells, natural suppressor cells, thymocytes, and dendritic cells; cells of the hematopoietic system, e.g. hematopoietic stem cells (CD34+), proerythroblasts, normoblasts, promyelocytes, reticulocytes, erythrocytes, pre-erythrocytes, myeloblasts, erythroblasts, megakaryocytes, B cell progenitors, T cell progenitors, thymocytes, macrophages, mast cells, and thrombocytes; stromal cells, e.g. adipocytes, fibroblasts, adventitial reticular cells, endothelial cells, undifferentiated mesenchymal cells, epithelial cells including squamous, cuboid, columnar, squamous keratinized, and squamous non-keratinized cells, and pericytes; cells of the skeleton and musculature, e.g. myocytes (heart, striated, and smooth), osteoblasts, osteoclasts, osteocytes, synoviocytes, chondroblasts, chondrocytes, endochondral fibroblasts, and perichonondrial fibroblasts; cells of the neural system, e.g. astrocytes (protoplasmic and fibrous), microglia, oligodendrocytes, and neurons; cells of the digestive tract, e.g. parietal, zymogenic, argentaffin cells of the duodenum, polypeptide-producing endocrine cells (APUD), islets of langerhans (alpha, beta, and delta), hepatocytes, and kupfer cells; cells of the skin, e.g. keratinocytes, langerhans, and melanocytes; cells of the pituitary and hypothalamus, e.g. somatotropic, mammotropic, gonadotropic, thyrotropic, corticotropin, and melanotropic cells; cells of the adrenals and other endocrine glands, e.g. thyroid cells (C cells and epithelial cells); adrenal cells; cells of the reproductive system, e.g. oocytes, spermatozoa, leydig cells, embryonic stem cells, amniocytes, blastocysts, morulas, and zygotes; and tumor cells.

In an exemplary embodiment, the invention provides an isolated immune cell comprising a cell surface glycoprotein, wherein the glycoprotein comprising a carbohydrate covalently linked to an azide.

The click-labeled cells disclosed herein can, in some embodiments, be administered to a subject, e.g., a mammalian subject, such as a murine subject, a primate subject, or a human subject. In some embodiments, click-labeled cells are administered to a subject as part of a treatment regimen. For example, in some embodiments, click-labeled immune cells can be administered to a subject to promote an immune response to an antigen. In other embodiments, click-labeled immune cells can be administered to a subject in method of treating a disease or disorder. For example, click-labeled immune cells can be administered to a subject in a method of treating cancer, or in a method of eliciting an immune response to a cancer antigen. Following administration, the click-labeled cells can be targeted with an agent of interest coupled to a counterpart click reagent, as described herein.

In some embodiments, the click-labeled cells are administered to a subject embedded in a device, e.g., a polymer scaffold device. Accordingly, in one aspect, the invention provides a device comprising a polymer scaffold, and cells comprising a cell surface glycoprotein, wherein the glycoprotein comprises a carbohydrate covalently linked to a click reagent. Exemplary polymer scaffolds suitable for delivery of click-labeled cells to a subject include hydrogel scaffolds and cryogel scaffolds. In one embodiment, cells are delivered in an alginate scaffold. The scaffold can be porous or non-porous. In some embodiments, the scaffold is initially non-porous, but forms pores in situ after administration to a subject. Non-limiting examples of scaffolds that can be used to deliver cells are described in US 2014/0079752 A1, published Apr. 12, 2012; US 2016/0271298 A1, published Sep. 22, 2016; and WO 2018/026884 A1, published Feb. 8, 2018. The entire contents of each of the foregoing publications are incorporated herein by reference. Additional features of devices and scaffolds that can be used to deliver cells to a subject are described herein.

In some aspects, the invention provides compositions and methods for labeling cells with a click reagent of the invention in vivo. In some embodiments, the invention provides a method of labeling cells with a click reagent in vivo, comprising administering a click reagent disclosed herein to a subject. In exemplary embodiments, the click reagent is provided as a polymer, or as a nanoparticle, as described herein. In some embodiments, the click reagent, polymer, or nanoparticle can be incorporated into a polymer scaffold device. Devices suitable for the incorporation of click reagents are disclosed herein. Such devices can be used to label cells that contact the scaffold with click reagents. In some embodiments, the devices described herein can be used to label immune cells, e.g., dendritic cells, with click reagents.

Accordingly, in one aspect, the invention provides a device comprising a polymer scaffold and a click reagent. A number of biomaterial scaffolds are available that allow the migration of cells into an out of the scaffold in vivo. Incorporation of the click reagents of the invention into such scaffolds provides a platform for contacting cells in vivo with the click reagents, thereby allowing metabolic labeling of cells that contact the scaffold in vivo. Labeling of specific cell types in vivo can be achieved by modifying the device to promote recruitment of the desired cells to the scaffold. For example, the device can contain chemoattractants that promote recruitment of specific cell types to the scaffold in vivo. In some embodiments, the click reagents of the invention are formatted as a polymer, e.g., a click functionalized polysaccharide polymer, or as a nanoparticle, as described herein.

Exemplary features of the devices of the present disclosure are provided below.

Device Scaffold

The devices of the present disclosure can comprise a scaffold, e.g., a polymer scaffold. The scaffold can comprise one or more biomaterials. Preferably, the biomaterial is a biocompatible material that is non-toxic and/or non-immunogenic.

The scaffold can comprise biomaterials that are non-biodegradable or biodegradable. In certain embodiments, the biomaterial can be a non-biodegradable material. Exemplary non-biodegradable materials include, but are not limited to, metal, plastic polymer, or silk polymer. In certain embodiments, the polymer scaffold comprises a biodegradable material. The biodegradable material may be degraded by physical or chemical action, e.g., level of hydration, heat, oxidation, or ion exchange or by cellular action, e.g., elaboration of enzyme, peptides, or other compounds by nearby or resident cells. In certain embodiments, the polymer scaffold comprises both non-degradable and degradable materials.

In some embodiments, the scaffold composition can degrade at a predetermined rate based on a physical parameter selected from the group consisting of temperature, pH, hydration status, and porosity, the cross-link density, type, and chemistry or the susceptibility of main chain linkages to degradation or it degrades at a predetermined rate based on a ratio of chemical polymers. For example, a high molecular weight polymer comprised of solely lactide degrades over a period of years, e.g., 1-2 years, while a low molecular weight polymer comprised of a 50:50 mixture of lactide and glycolide degrades in a matter of weeks, e.g., 1, 2, 3, 4, 6, 10 weeks. A calcium cross-linked gels composed of high molecular weight, high guluronic acid alginate degrade over several months (1, 2, 4, 6, 8, 10, 12 months) to years (1, 2, 5 years) in vivo, while a gel comprised of low molecular weight alginate, and/or alginate that has been partially oxidized, will degrade in a matter of weeks.

In certain embodiments, one or more compounds disclosed herein are covalently or non-covalently linked or attached to the scaffold composition. In various embodiments, one or more compounds disclosed herein is incorporated on, into, or present within the structure or pores of, the scaffold composition.

In some embodiments, the scaffolds comprise biomaterials that are modified, e.g., oxidized or reduced. The degree of modification, such as oxidation, can be varied from about 1% to about 100%. As used herein, the degree of modification means the molar percentage of the sites on the biomaterial that are modified with a functional group. For example, the degree of modification can be about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%4, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. It is intended that values and ranges intermediate to the recited values are also intended to be part of this invention. Exemplary modified biomaterials, e.g., hydrogels, include, but not limited to, reduced-alginate, oxidized alginate, MA-alginate (methacrylated alginate) or MA-gelatin.

Exemplary biomaterials suitable for use as scaffolds in the present invention include glycosaminoglycan, silk, fibrin, MATRIGEL®, poly-ethyleneglycol (PEG), polyhydroxy ethyl methacrylate, polyacrylamide, poly (N-vinyl pyrolidone), (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof. In certain embodiments, the biomaterial is selected from the group consisting of alginate, fully or partially oxidized alginate, and combinations thereof.

The scaffolds of the present invention may comprise an external surface. Alternatively, or in addition, the scaffolds may comprise an internal surface. External or internal surfaces of the scaffolds of the present invention may be solid or porous. Pore size of the scaffolds can be less than about 10 nm, between about 100 nm-20 µm, or greater than about 20 µm, e.g., up to and including 1000 µm in diameter. For example, the pores may be nanoporous, microporous, or macroporous. For example, the diameter of nanopores are less than about 10 nm; micropore are in the range of about 100 nm-20 µm in diameter; and, macropores are greater than about 20 µm, e.g., greater than about 100 µm, e.g., greater than about 400 µm, e.g., greater than 600 µm or greater than 800 µm.

In some embodiments, the scaffolds of the present invention are organized in a variety of geometric shapes (e.g., discs, beads, pellets), niches, planar layers (e.g., thin sheets). For example, discs of about 0.1-200 millimeters in diameter, e.g., 5, 10, 20, 40, 50 millimeters may be implanted subcutaneously. The disc may have a thickness of 0.1 to 10 millimeters, e.g., 1, 2, 5 millimeters. The discs are readily compressed or lyophilized for administration to a patient. An exemplary disc for subcutaneous administration has the following dimensions: 8 millimeters in diameter and 1 millimeter in thickness.

In some embodiments, the scaffolds may comprise multiple components and/or compartments. In certain embodiments, a multiple compartment device is assembled in vivo by applying sequential layers of similarly or differentially doped gel or other scaffold material to the target site. For example, the device is formed by sequentially injecting the next, inner layer into the center of the previously injected material using a needle, forming concentric spheroids. In certain embodiments, non-concentric compartments are formed by injecting material into different locations in a previously injected layer. A multi-headed injection device extrudes compartments in parallel and simultaneously. The layers are made of similar or different biomaterials differentially doped with pharmaceutical compositions. Alternatively, compartments self-organize based on their hydrophilic/phobic characteristics or on secondary interactions within each compartment. In certain embodiments, multi-component scaffolds are optionally constructed in concentric layers each of which is characterized by different physical qualities such as the percentage of polymer, the percentage of crosslinking of polymer, chemical composition of the hydrogel, pore size, porosity, and pore architecture, stiffness, toughness, ductility, viscoelasticity, and/or composition of bioactive substances such as growth factors, homing/migration factors, differentiation factors.

In an exemplary embodiment, the device of the present disclosure comprises a polymer scaffold, a click reagent of the invention, and one or more (i.e., one or more, two or more, three or more, or four) of the following: (i) a chemoattractant; (ii) an adjuvant; (iii) an antigen; and (iv) porogen hydrogel microbeads. Additional embodiments and features of the device are described below.

Hydrogel and Cryogel Scaffolds

In certain embodiments, the scaffolds of present invention comprises one or more hydrogels. A hydrogel is a polymer gel comprising a network of crosslinked polymer chains. A hydrogel is usually a composition comprising polymer chains that are hydrophilic. The network structure of hydrogels allows them to absorb significant amounts of water. Some hydrogels are highly stretchable and elastic; others are viscoelastic. Hydrogel are sometimes found as a colloidal gel in which water is the dispersion medium. In certain embodiments, hydrogels are highly absorbent (they can contain over 99% water) natural or synthetic polymers that possess a degree of flexibility very similar to natural tissue, due to their significant water content. In certain embodiments, a hydrogel may have a property that, when an appropriate shear stress is applied, the deformable hydrogel is dramatically and reversibly compressed (up to 95% of its volume), resulting in injectable macroporous preformed scaffolds. Hydrogels have been used for therapeutic applications, e.g., as vehicles for in vivo delivery of therapeutic agents, such as small molecules, cells and biologics. Hydrogels are commonly produced from polysaccharides, such as alginates. The polysaccharides may be chemically manipulated to modulate their properties and properties of the resulting hydrogels.

The hydrogels of the present invention are porous or non-porous. For example, the hydrogels are nanoporous having a diameter of less than about 10 nm; microporous wherein the diameter of the pores are preferably in the range of about 100 nm-20 μm; or macroporous wherein the diameter of the pores are greater than about 20 μm, more preferably greater than about 100 μm and even more preferably greater than about 400 μm. In certain embodiments, the hydrogel is macroporous with aligned pores of about 400-500 μm in diameter. Methods of preparing porous hydrogel products are known in the art. (See, e.g., U.S. Pat. No. 6,511,650, incorporated herein by reference).

The hydrogel may be constructed out of a number of different rigid, semi-rigid, flexible, gel, self-assembling, liquid crystalline, or fluid compositions such as peptide polymers, polysaccharides, synthetic polymers, hydrogel materials, ceramics (e.g., calcium phosphate or hydroxyapatite), proteins, glycoproteins, proteoglycans, metals and metal alloys. The compositions are assembled into hydrogels using methods known in the art, e.g., injection molding, lyophillization of preformed structures, printing, self-assembly, phase inversion, solvent casting, melt processing, gas foaming, fiber forming/processing, particulate leaching or a combination thereof. The assembled devices are then implanted or administered to the body of an individual to be treated.

The device comprising a hydrogel may be assembled in vivo in several ways. The hydrogel is made from a gelling material, which is introduced into the body in its ungelled form where it gels in situ. Exemplary methods of delivering device components to a site at which assembly occurs include injection through a needle or other extrusion tool, spraying, painting, or methods of deposit at a tissue site, e.g., delivery using an application device inserted through a cannula. In some embodiments, the ungelled or unformed hydrogel material is mixed with pharmaceutical compositions prior to introduction into the body or while it is introduced. The resultant in vivo in situ assembled device, e.g., hydrogel, contains a mixture of these pharmaceutical composition(s).

In situ assembly of the hydrogel may occur as a result of spontaneous association of polymers or from synergistically or chemically catalyzed polymerization. Synergistic or chemical catalysis is initiated by a number of endogenous factors or conditions at or near the assembly site, e.g., body temperature, ions or pH in the body, or by exogenous factors or conditions supplied by the operator to the assembly site, e.g., photons, heat, electrical, sound, or other radiation directed at the ungelled material after it has been introduced. The energy is directed at the hydrogel material by a radiation beam or through a heat or light conductor, such as a wire or fiber optic cable or an ultrasonic transducer. Alternatively, a shear-thinning material, such as an ampliphile, is used which re-cross links after the shear force exerted upon it, for example by its passage through a needle, has been relieved.

In some embodiments, the hydrogel may be assembled ex vivo. In some embodiments, the hydrogel is injectable. For example, the hydrogels are created outside of the body as macroporous scaffolds. The hydrogels can be injected into the body because the pores collapse and the gel becomes very small and can fit through a needle. See, e.g., WO 12/149358; and Bencherif et al. Proc. Natl. Acad. Sci. USA 109.48(2012):19590-5, the content of which are incorporated herein by reference).

Suitable hydrogels for both in vivo and ex vivo assembly of hydrogel devices are well known in the art and described, e.g., in Lee et al., 2001, Chem. Rev. 7:1869-1879. The peptide amphiphile approach to self-assembly assembly is described, e.g., in Hartgerink et al., 2002, Proc. Natl. Acad. Sci. U.S.A 99:5133-5138. A method for reversible gellation following shear thinning is exemplified in Lee et al., 2003, Adv. Mat. 15:1828-1832.

In certain embodiments, exemplary hydrogels are comprised of materials that are compatible with encapsulation of materials including polymers, nanoparticles, polypeptides, and cells. Exemplary hydrogels are fabricated from as alginate, polyethylene glycol (PEG), PEG-acrylate, agarose, or synthetic protein (e.g., collagen or engineered proteins (i.e., self-assembly peptide-based hydrogels)). For example, a commercially available hydrogel includes BD™ PuraMatrix™. BD™ PuraMatrix™ Peptide Hydrogel is a synthetic matrix that is used to create defined three dimensional (3D) micro-environments for cell culture.

In some embodiments, the hydrogel is a biocompatible polymer matrix that is biodegradable in whole or in part. Examples of materials which can form hydrogels include alginates and alginate derivatives, polylactic acid, polyglycolic acid, poly(lactic-co-glycolic acid) (PLGA) polymers, gelatin, collagen, agarose, natural and synthetic polysaccharides, polyamino acids such as polypeptides particularly poly(lysine), polyesters such as polyhydroxybutyrate and poly-epsilon.-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone), and copolymers of the above, including graft copolymers. Synthetic polymers and naturally-occurring polymers such as, but not limited to, collagen, fibrin, hyaluronic acid, agarose, and laminin-rich gels may also be used.

The implantable device can have virtually any regular or irregular shape including, but not limited to, spheroid, cubic, polyhedron, prism, cylinder, rod, disc, or other geometric shape. Accordingly, in some embodiments, the implant is of cylindrical form from about 0.5 to about 10 mm in diameter and from about 0.5 to about 10 cm in length. Preferably, its diameter is from about 1 to about 5 mm and length from about 1 to about 5 cm.

In some embodiments, the devices of the invention are of spherical form. When the implantable device is in a spherical form, its diameter can range, in some embodiments, from about 0.5 to about 50 mm in diameter. In some embodiments, a spherical implant's diameter is from about 5 to about 30 mm. In an exemplary embodiment, the diameter is from about 10 to about 25 mm.

In certain embodiments, the scaffold comprises click-hydrogels and/or click-cryogels. A click hydrogel or cryogel is a gel in which cross-linking between hydrogel or cryogel polymers is facilitated by click reactions between the polymers. Each polymer may contain one of more functional groups useful in a click reaction. Given the high level of specificity of the functional group pairs in a click reaction, active compounds can be added to the preformed device prior to or contemporaneously with formation of the hydrogel device by click chemistry. Non-limiting examples of click reactions that may be used to form click-hydrogels include Copper I catalyzed azide-alkyne cycloaddition, strain-promoted assize-alkyne cycloaddition, thiol-ene photocoupling, Diels-Alder reactions, inverse electron demand Diels-Alder reactions, tetrazole-alkene photo-click reactions, oxime reactions, thiol-Michael addition, and aldehyde-hydrazide coupling. Non-limiting aspects of click hydrogels are described in Jiang et al. (2014) Biomaterials, 35:4969-4985, the entire content of which is incorporated herein by reference. Preferably, the click reagent of the present invention for metabolic labeling of cells infiltrating the scaffold is not reactive with the click hydrogel or cryogel.

In various embodiments, a click alginate is utilized (see, e.g., PCT International Patent Application Publication No. WO 2015/154078 published Oct. 8, 2015, hereby incorporated by reference in its entirety).

Exemplary click-hydrogel devices and scaffold materials include a hydrogel comprising a first polymer and a second polymer, where the first polymer is connected to the second polymer by linkers of formula (A):

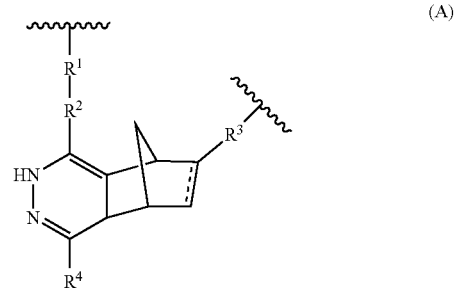

(A)

wherein bond ⊐⊐⊐ is single or a double bond:

$R^1$ is —$C_0$-$C_6$alkyl-$NR^{2N}$—, —$C_0$-$C_6$alkyl-O—, or —$C_0$-$C_3$alkyl-C(O)—;

$R^2$ is a bond, aryl, or heteroaryl, wherein aryl and heteroaryl are optionally substituted with halogen, hydroxy, $C_1$-$C_6$alkyl, $C_1$-$C_6$alkoxy, ($C_1$-$C_6$alkyl)amino, or di($C_1$-$C_6$alkyl)amino;

$R^3$ is —$C_0$-$C_6$alkyl-$NR^{2N}$—, —$C_0$-$C_6$alkyl-O—, or —$C_0$-$C_3$alkyl-C(O)—; and $R^4$ is hydrogen, $C_1$-$C_6$alkyl, aryl, or heteroaryl, wherein aryl and heteroaryl are optionally substituted with halogen, hydroxy, $C_1$-$C_6$alkyl, $C_1$-$C_6$alkoxy, ($C_1$-$C_6$alkyl)amino, or di($C_1$-$C_6$alkyl) amino.

$R^{2N}$ is independently hydrogen, $C_1$-$C_6$ alkyl, aryl, heteroaryl, $R^2N$, or $R^2$, wherein $C^1$-$C^6$ alkyl, aryl and heteroaryl are optionally substituted with halogen, hydroxy, $C_1$-$C_6$ alkyl, $C_1$-$C_6$ alkoxy, ($C_1$-$C_6$ alkyl)amino, or di($C_1$-$C_6$ alkyl)amino. In one embodiment, the hydrogel of the disclosure is wherein the linkers of formula (A) are of the form of formula (I):

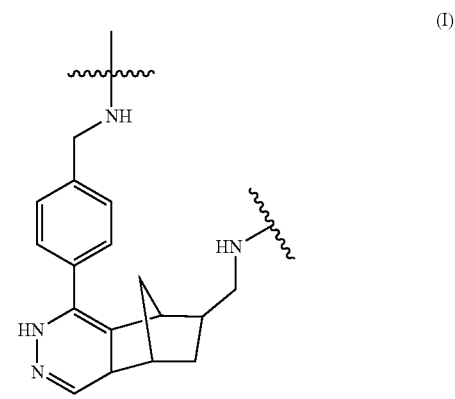 [SMILES: *NCc1ccc(C2=C3C(C=NN2)C2CC(CN*)C3C2)cc1]

(I)

or by formula (II):

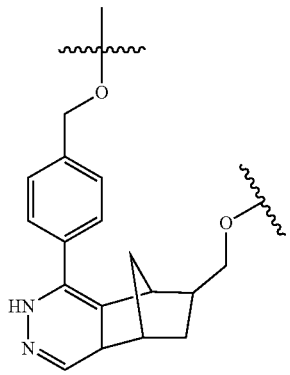

or by formula (III):

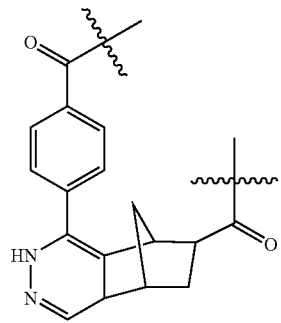

wherein the linkers of formula (I), (II), or (III) are optionally substituted at any suitable position.

Another embodiment provides the linkers of formula (A) according to any preceding embodiment, wherein $R^1$ is:
a. —$NR^{2N}$—, —$C_1$-$C_6$ alkyl-$NR^{2N}$—, —O—, —$C_1$-$C_6$alkyl-O—, —C(O)—, or —$C_1$-$C_3$alkyl-C(O)—;
b. —$C_0$-$C_6$alkyl-$NR^{2N}$—.
c. —$C_1$-$C_6$ alkyl-$NR^{2N}$—.
d. —$C_1$-$C_3$ alkyl-$NR^{2N}$—.
e. -methyl-NH— or -pentyl-NH—;
f. —$C_0$-$C_6$ alkyl-O—;
g. —$C_1$-$C_6$ alkyl-O—;
h. —$C_1$-$C_3$ alkyl-O—;
i. -methyl-O— or -pentyl-O—;
j. —$C_0$-$C_3$ alkyl-C(O)—;
k. —C(O)—;
l. -methyl-C(O)—;
m. the same as $R^3$.

$NR^{2N}$ is independently hydrogen, $C_1$-$C_6$ alkyl, aryl, heteroaryl, $R^2N$, or $R^2$, wherein $C_1$-$C_6$ alkyl, aryl and heteroaryl are optionally substituted with halogen, hydroxy, $C_1$-$C_6$ alkyl, $C_1$-$C_6$ alkoxy, ($C_1$-$C_6$ alkyl)amino, or di($C_1$-$C_6$ alkyl)amino.

Another embodiment provides the linkers of formula (A) according to any preceding embodiment, wherein $R^2$ is a bond.

In one embodiment, the linkers of formula (A) according to any preceding embodiment are those wherein $R^2$ is
a. aryl or heteroaryl, each optionally substituted;
b. optionally substituted aryl;
c. phenyl;
d. optionally substituted heteroaryl; or
e. pyridyl, pyrimidyl, or pyrazinyl.

Another embodiment provides the linkers of formula (A) according to any preceding embodiment, wherein $R^3$ is
a. —$NR^{2N}$—, —$C_1$-$C_6$ alkyl-NR2N—, —O—, —$C_1$-$C_6$ alkyl —O—, —C(O)—, or —$C_1$-$C_3$alkyl-C(O)—;
b. —$C_0$-$C_6$ alkyl-$NR^{2N}$—;
c. —$C_1$-$C_6$ alkyl-$NR^{2N}$—.
d. —$C_1$-$C_3$ alkyl-$NR^{2N}$—.
e. -methyl-NH— or -pentyl-NH—;
f. —$C_0$-$C_6$ alkyl-O—;
g. —$C_1$-$C_6$ alkyl-O—;
h. —$C_1$-$C_3$ alkyl-O—;
i. -methyl-O— or -pentyl-O—;
j. —$C_0$-$C_3$ alkyl-C(O)—;
k. —C(O)—;
l. -methyl-C(O)—; or
m. the same as $R^1$.

$R^{2N}$ is independently hydrogen, $C_1$-$C_6$ alkyl, aryl, heteroaryl, $R^2N$, or $R^2$, wherein $C_1$-$C_6$ alkyl, aryl and heteroaryl are optionally substituted with halogen, hydroxy, $C_1$-$C_6$ alkyl, $C_1$-$C_6$ alkoxy, ($C_1$-$C_6$ alkyl)amino, or di($C_1$-$C_6$ alkyl) amino. In one embodiment, the linkers of formula (A) according to any preceding embodiment are those wherein $R^4$ is hydrogen.

In one embodiment, the linkers of formula (A) according to any preceding embodiment are those wherein $R^4$ is
a. $C_1$-$C_6$alkyl, aryl, or heteroaryl, wherein aryl and heteroaryl are optionally substituted;
b. aryl or heteroaryl, wherein aryl and heteroaryl are optionally substituted;
c. optionally substituted aryl;
d. phenyl;
e. optionally substituted heteroaryl; or
f. pyridyl, pyrimidyl, or pyrazinyl.

Another embodiment provides the linkers of formula (A) according to any preceding embodiment, wherein $R^4$ is $C_1$-$C_6$ alkyl, $C_1$-$C_3$ alkyl, or methyl.

In some embodiments, the hydrogel comprises a plurality of linkers of formula (A); or formula (I), formula (II), or formula (III).

The invention also includes a hydrogel comprising an interconnected network of a plurality of polymers, e.g., including a first polymer and a second polymer. For example, the polymers are connected via a plurality of linkers of formula (A), or of formula (I), formula (II), or formula (III).

Some embodiments of the disclosure provide hydrogels wherein the first polymer and the second polymer are independently soluble polymers. In other embodiments, the first polymer and the second polymer are independently water-soluble polymers.

In some embodiments, the concentration of crosslinks per hydrogel (e.g., where each crosslink comprises formula I) is at least about 10% (w/w), e.g., at least about 10%, about 15%, about 20%, about 30%, about 40%, about 50%, about 60%, about 70%, about 80%, about 90%, about 95%, about 97%, about 99%, or about 100% (w/w).

The first polymer and the second polymer can be the same or different. In some embodiments, the first polymer and the second polymer are the same type of polymer. In other embodiments, the first polymer and/or the second polymer comprise a polysaccharide. For example, the first polymer and the second polymer can both comprise a polysaccharide. In some embodiments, the first polymer and/or the second polymer are independently selected from the group consisting of alginate, chitosan, polyethylene glycol (PEG), gelatin, hyaluronic acid, collagen, chondroitin, agarose, polyacrylamide, and heparin. In some embodiments, the first polymer and the second polymer are the same polymer independently selected from the group consisting of alginate, chitosan, polyethylene glycol (PEG), gelatin, hyaluronic acid, collagen, chondroitin, agarose, polyacrylamide, and heparin.

Such scaffolds and scaffold materials, as well as methods for producing such scaffolds, are described in PCT International Patent Application Publication No. WO 2015/154078 published Oct. 8, 2015, the entire content of which is incorporated herein by reference. For example, a click hydrogel may be prepared in a process: a) providing a first polymer comprising a first click reaction moiety and a second polymer comprising a second click reaction moiety. In non-limiting examples, the first click reaction moiety and the second click reaction moiety may be react with each other in a copper I catalyzed azide-alkyne cycloaddition, strain-promoted assize-alkyne cycloaddition, thiol-ene photo coupling, a Diels-Alder reaction, an inverse electron demand Diels-Alder reaction, a tetrazole-alkene photo-click reaction, a oxime reaction, a thiol-Michael addition, or via aldehyde-hydrazide coupling. In an embodiment, the first click reaction moiety is a diene moiety and the second click reaction moiety is a dienophile moiety. In an embodiment, the first click reaction moiety is a tetrazine moiety and the second click reaction moiety is a norbornene moiety. As used herein, the terms "tetrazine" and "tetrazine moiety" include molecules that comprise 1,2,4,5-tetrazine substituted with suitable spacer for linking to the polymer (e.g., alkylamines like methylamine or pentylamine), and optionally further substituted with one or more substituents at any available position. Exemplary tetrazine moieties suitable for the compositions and methods of the disclosure are described in Karver et al. Bioconjugate Chem. 22(2011):2263-2270, and WO 2014/065860, both incorporated herein by reference). As used herein, the terms "norbornene" and "norbornene moieties" include but are not limited to norbomadiene and norbornene groups further comprising suitable spacer for linking to the polymer (e.g., alkylamines like methylamine or pentylamine), and optionally further substituted with one or more substituents at any available position. Such moieties include, for example, norbornene-S-methylamine and norbomadienemethylamine.

Accordingly, some embodiments feature a cell-compatible and optionally, cell-adhesive, highly crosslinked hydrogel (e.g., cryogel) polymer composition comprising open interconnected pores, wherein the hydrogel (e.g., cryogel) is characterized by shape memory following deformation by compression or dehydration. The device has a high density of open interconnected pores. Also, the hydrogel (e.g., cryogel) comprises a crosslinked gelatin polymer or a crosslinked alginate polymer.

In certain embodiments, a hydrogel (e.g., cryogel) system can deliver one or more agent (e.g., a chemoattractant such as GM-CSF, and/or an adjuvant, such as a specific TLR agonist (such as CpG-ODN), while creating a space for cells (e.g., immune cells such as dendritic cells (DCs)) infiltration and trafficking. In some embodiments, the hydrogel system according the present invention deliver GM-CSF that acts as a DC enhancement/recruitment factor, and CpG ODN as an adjuvant that is a specific TLR agonist (DC activation factor).

In some embodiment, cryogel devices, such as MA-alginate, can function as a labeling platform by creating a local niche, such as immunogenic niche. In some embodiments, the cryogel creates a local niche in which the encounter of cells, such as immune cells, and various exemplary agent of the invention, such as the click functionalized polysaccharide polymer can be controlled. In certain embodiments, the cells and the exemplary agents of the present invention are localized into a small volume, and the labeling of the cells can be quantitatively controlled in space and time.

In non-limiting example, the hydrogel (e.g., cryogel) can be engineered to coordinate the delivery of both adjuvant and antigen in space and time, potentially enhancing overall anti-tumor performance by adjusting the activation and/or maturing of recruited immune cells, such as DCs. In certain embodiments, the cells and immunomodulatory agents are localized into a small volume, and the delivery of factors in space and time can be quantitatively controlled. As the immunomodulatory factors are released locally, few systemic effects are anticipated, in contrast to systemically delivered agents, such as immune checkpoint blocking antibodies.

Examples of polymer compositions from which the cryogel or hydrogel is fabricated are described throughout the present disclosure, and include alginate, hyaluronic acid, gelatin, heparin, dextran, carob gum, PEG, PEG derivatives including PEG-co-PGA and PEG-peptide conjugates. The techniques can be applied to any biocompatible polymers, e.g. collagen, chitosan, carboxymethylcellulose, pullulan, polyvinyl alcohol (PV A), Poly(2-hydroxyethyl methacrylate) (PHEMA), Poly(N-isopropylacrylamide) (PNIPAAm), or Poly(acrylic acid) (PAAc). For example, the composition comprises an alginate-based hydrogel/cryogel. In another example, the scaffold comprises a gelatin-based hydrogel/cryogel.

Cryogels are a class of materials with a highly porous interconnected structure that are produced using a cryotropic gelation (or cryogelation) technique. Cryogels also have a highly porous structure. Typically, active compounds are added to the cryogel device after the freeze formation of the pore/wall structure of the cryogel. Cryogels are characterized by high porosity, e.g., at least about 50, 55, 60, 65, 70, 75, 80, 85, 90, or 95% pores with thin pore walls that are characterized by high density of polymer crosslinking. The walls of cryogels are typically dense and highly crosslinked, enabling them to be compressed through a needle into a subject without permanent deformation or substantial structural damage.

In various embodiments, the pore walls comprise at least about 10, 15, 20, 25, 30, 35, 40, 10-40% or more polymer. In some embodiments, a polymer concentration of about 0.5-4% (before the cryogelation) is used, and the concentration increases substantially by the completion of cryogelation. Non-limiting aspects of cryogel gelation and the increase of polymer concentration after cryogelation are discussed in Beduer et al. (2015) Advanced Healthcare Materials Volume 4, Issue 2, pages 301-312, the entire content of which is incorporated herein by reference.

In certain embodiments, cryogelation comprises a technique in which polymerization-crosslinking reactions are conducted in quasi-frozen reaction solution. Non-limiting examples of cryogelation techniques are described in U.S. Patent Application Publication No. 201410227327, published Aug. 14, 2014, the entire content of which is incorporated herein by reference. An advantage of cryogels compared to conventional macroporous hydrogels obtained by phase separation is their high reversible deformability. Cryogels may be extremely soft but can be deformed and reform their shape. In certain embodiments, cyrogels can be very tough, and can withstand high levels of deformations, such as elongation and torsion and can also be squeezed under mechanical force to drain out their solvent content. In certain embodiments, improved deformability properties of alginate cryogels originate from the high crosslinking density of the unfrozen liquid channels of the reaction system.

In some embodiments, the invention also features gelatin scaffolds, e.g., gelatinhydrogels such as gelatin cryogels, which are a cell-responsive platform for biomaterial-based therapy. Gelatin is a mixture of polypeptides that is derived from collagen by partial hydrolysis. These gelatin scaffolds have distinct advantages over other types of scaffolds and hydrogels/cryogels. For example, the gelatin scaffolds of the invention support attachment, proliferation, and survival of cells and are degraded by cells, e.g., by the action of enzymes such as matrix metalloproteinases (MMPs) (e.g., recombinant matrix metalloproteinase-2 and -9).

In certain embodiments, prefabricated gelatin cryogels rapidly reassume their original shape ("shape memory") when injected subcutaneously into a subject (e.g., a mammal such as a human, dog, cat, pig, or horse) and elicit little or no harmful host immune response (e.g., immune rejection) following injection.

In some embodiments, the hydrogel (e.g., cryogel) comprises polymers that are modified, e.g., sites on the polymer molecule are modified with a methacrylic acid group (methacrylate (MA)) or an acrylic acid group (acrylate). Exemplary modified hydrogels/cryogels are MA-alginate (methacrylated alginate) or MA-gelatin. In the case of MA-alginate or MA-gelatin, 50% corresponds to the degree of methacrylation of alginate or gelatin. This means that every other repeat unit contains a methacrylated group. The degree of methacrylation can be varied from about 1% to about 100%. Preferably, the degree of methacrylation varies from about 1% to about 90%.

In certain embodiments, polymers can also be modified with acrylated groups instead of methacrylated groups. The product would then be referred to as an acrylated-polymer. The degree of methacrylation (or acrylation) can be varied for most polymers. However, some polymers (e.g. PEG) maintain their water-solubility properties even at 100% chemical modification. After crosslinking, polymers normally reach near complete methacrylate group conversion indicating approximately 100% of cross-linking efficiency. For example, the polymers in the hydrogel are 50-100% crosslinked (covalent bonds). The extent of crosslinking correlates with the durability of the hydrogel. Thus, a high level of crosslinking (90-100%) of the modified polymers is desirable.

For example, the highly crosslinked hydrogel/cryogel polymer composition is characterized by at least about 50% polymer crosslinking (e.g., about 75%, 80%, 85%, 90%, 95%, 98%, 99%, 100%). The high level of crosslinking confers mechanical robustness to the structure. Preferably, the percentage of crosslinking is less than about 100%. The composition is formed using a free radical polymerization process and a cryogelation process. For example, the cryogel is formed by cryopolymerization of methacrylated gelatin or methacrylated alginate. In some embodiments, the cryogel comprises a methacrylated gelatin macro monomer or a methacrylated alginate macromonomer at concentration of about 1.5% (w/v) or less (e.g., about, 1.5%, 1.4%, 1.3%, 1.2%, 1.1%, 1%, 0.9%, 0.8%, 0.7%, 0.6%, 0.5%, 0.4%, 0.3%, 0.2% or less). In some embodiments, the methacrylated gelatin or alginate macromonomer concentration is about 1% (w/v).

In certain embodiments, the cryogel comprises at least about 75% pores, e.g., about 80%, 85%, 90%, 91%, 92%, 93%, 94%, 95%, 96%, 97%, 98%, or 99% or more pores. In some embodiments, the pores are interconnected. Interconnectivity is important to the function of the hydrogel and/or cryogel, as without interconnectivity, water would become trapped within the gel. Interconnectivity of the pores permits passage of water (and other compositions such as cells and compounds) in and out of the structure. In certain embodiments, in a fully hydrated state, the hydrogel (e.g., cryogel) comprises at least about 90% water (e.g., between about 90-99%, at least about 92%, 95%, 97%, 99%, or more) water. For example, at least about 90% (e.g., at least about 92%, 95%, 97%, 99%, or more) of the volume of the cryogel is made of liquid (e.g., water) contained in the pores. In certain embodiments, in a compressed or dehydrated hydrogel, up to about 50%, 60%, 70% of that water is absent, e.g., the cryogel comprises less than about 25% (e.g., about 20%, 15%, 10%, 5%, or less) water.

In certain embodiments, the cryogels of the invention comprises pores large enough for a cell to travel through. For example, the cryogel contains pores of about 20-500 μm in diameter, e.g., about 20-30 μm, about 30-150 μm, about 50-500 μm, about 50-450 μm, about 100-400 μm, about 200-500 μm. In some embodiments, the hydrated pore size is about 1-500 μm (e.g., about 10-400 μm, about 20-300 μm, about 50-250 μm).

In some embodiments, injectable hydrogels or cryogels are further functionalized by addition of a functional group chosen from the group consisting of: amino, vinyl, aldehyde, thiol, silane, carboxyl, azide, alkyne. Alternatively or in addition, the cryogel is further functionalized by the addition of a further cross-linker agent (e.g. multiple arms polymers, salts, aldehydes, etc.). The solvent can be aqueous, and in particular acidic or alkaline. The aqueous solvent can comprise a water-miscible solvent (e.g. methanol, ethanol, DMF, DMSO, acetone, dioxane, etc).

For cryogels, the cryo-crosslinking may take place in a mold and the cryogels (which may be injected) can be degradable. The pore size can be controlled by the selection of the main solvent used, the incorporation of a porogen, the freezing temperature and rate applied, the crosslinking conditions (e.g. polymer concentration), and also the type and molecule weight of the polymer used. The shape of the cryogel may be dictated by a mold and can thus take on any shape desired by the fabricator, e.g., various sizes and shapes (disc, cylinders, squares, strings, etc.) are prepared by cryogenic polymerization.

Injectable cryogels can be prepared in the micrometer-scale to millimeter-scale. Exemplary volumes vary from a few hundred $\rho m^3$ (e.g., about 100-500 $\mu m^3$)) to over 100 $mm^3$. In certain embodiment, an exemplary scaffold composition is between about 100 $\mu m^3$ to 100 $mm^3$ in size (e.g., between about 1 $mm^3$ and 10 $mm^3$ in size).

In some embodiments, the cryogels are hydrated, loaded with compounds and loaded into a syringe or other delivery apparatus. For example, the syringes are prefilled and refrigerated until use. In another example, the cryogel is dehydrated, e.g., lyophilized, optionally with a compound (such as a chemoattractant) loaded in the gel and stored dry or refrigerated. Prior to administration, a cryogel-loaded syringe or apparatus may be contacted with a solution containing compounds to be delivered. For example, the barrel of the cryogel pre-loaded syringe is filled with a physiologically-compatible solution, e.g., phosphate-buffered saline (PBS). In some embodiments, the cryogel may be administered to a desired anatomical site followed by the volume of solution, optionally containing other ingredients, e.g., a chemoattractant alone or together with one or more compounds disclosed herein. The cryogel is then rehydrated and regains its shape integrity in situ. In certain embodiments, the volume of PBS or other physiologic solution administered following cryogel placement is generally about 10 times the volume of the cryogel itself.

The cryogel also has the advantage that, upon compression, the cryogel composition maintains structural integrity and shape memory properties. For example, the cryogel is injectable through a hollow needle. For example, the cryogel returns to its original geometry after traveling through a needle (e.g., a 16 gauge (G) needle, e.g., having a 1.65 mm inner diameter). Other exemplary needle sizes are 16-gauge, an IS-gauge, a 20-gauge, a 22-gauge, a 24-gauge, a 26-gauge, a 2S-gauge, a 30-gauge, a 32-gauge, or a 34-gauge needle. Injectable cryogels have been designed to pass through a hollow structure, e.g., very fine needles, such as 18-30 G needles.

The injectable cryogels may be molded to a desired shape, in the form of rods, square, disc, spheres, cubes, fibers, foams. In some cases, the cryogel comprises the shape of a disc, cylinder, square, rectangle, or string. For example, the cryogel composition is between about 100 $\mu m^3$ to 100 $mm^3$ in size, e.g., between 1 $mm^3$ to 50 $mm^3$ in size. For example, the cryogel composition is between about 1 mm in diameter to about 50 mm in diameter (e.g., about 5 mm). Optionally, the thickness of the cryogel is between about 0.2 mm to about 50 mm (e.g., about 2 mm).

In some examples, the scaffold composition comprises a cell adhesion composition chemically linked, e.g., covalently attached, to a polymer. For example, the cell adhesion composition comprises a peptide comprising an RGD amino acid sequence. In non-limiting examples, the hydrogel or cryogel composition (e.g., gelatin) has cell-adhesive properties. In some embodiments, the scaffold composition is not modified with a cell adhesive molecule, such as arginine-glycine-aspartate (RGD).

Three exemplary cryogel materials systems are described below.
  a) Methacrylated gelatin cryogel (CryoGelMA)—An exemplary cryogel utilized methacrylated gelatin and the results are described in detail in U.S. Patent Application Publication No. 2014-0227327, published Aug. 14, 2014, the entire contents of which are incorporated herein by reference.
  b) Methacrylated alginate cryogel (CryoMAAlginate)—An exemplary cryogel utilized methacrylated alginate and the results are described in detail in U.S. Patent Application Publication No. 2014-0227327, published Aug. 14, 2014, the entire contents of which are incorporated herein by reference.
  c) Click Alginate cryogel with Laponite nanoplatelets (CryoClick)—The base material is click alginate (PCT International Patent Application Publication No. WO 2015/154078 published Oct. 8, 2015, hereby incorporated by reference in its entirety). In some examples, the base material contains laponite (commercially available silicate clay used in many consumer products such as cosmetics). Laponite has a large surface area and highly negative charge density which allows it to adsorb positively charged moieties on a variety of proteins and other biologically active molecules by an electrostatic interaction, allowing drug loading. When placed in an environment with a low concentration of drug, adsorbed drug releases from the laponite in a sustained manner. This system allows release of a more flexible array of immunomodulators compared to the base material alone.

Various embodiments of the present subject matter include delivery vehicles comprising a pore-forming scaffold composition. For example, pores (such as macropores) are formed in situ within a hydrogel following hydrogel injection into a subject. Pores that are formed in situ via degradation of a sacrificial porogen hydrogel within the surrounding hydrogel (bulk hydrogel) facilitate recruitment and trafficking of cells, as well as the release of any composition or agent of the present invention, for example, compounds, such as an immunostimulatory compound; a compound that attracts an immune cell to or into the delivery vehicle, or an antigen, or any combination thereof. In some embodiments, the sacrificial porogen hydrogel, the bulk hydrogel, or both the sacrificial porogen hydrogel and the bulk hydrogel may comprise any composition or agent of the present invention, for example, an immunostimulatory compound, a compound that attracts an immune cell to or into the delivery vehicle, a compound that inhibits an immuneinhibitory protein, and/or an antigen, or any combination thereof.

In various embodiments, the pore-forming composition becomes macroporous over time when resident in the body of a recipient animal such as a mammalian subject. For example, the pore-forming composition may comprise a sacrificial porogen hydrogel and a bulk hydrogel, wherein the sacrificial porogen hydrogel degrades at least about 10% faster (e.g., at least about 15%, at least about 20%, at least about 25%, at least about 30%, at least about 35%, at least about 40%, at least about 45%, or at least about 50% faster) than the bulk hydrogel. The sacrificial porogen hydrogel may degrade leaving macropores in its place. In certain embodiments, the macropores are open interconnected macropores. In some embodiments, the sacrificial porogen hydrogel may degrade more rapidly than the bulk hydrogel, because the sacrificial porogen hydrogel (i) is more soluble in water (comprises a lower solubility index), (ii) is crosslinked to protease-mediated degradation motifs as described in U.S. Patent Application Publication No. 2005-0119762, published Jun. 2, 2005 (incorporated herein by reference), (iii) comprises a shorter polymer that degrades more quickly compared to that of a longer bulk hydrogel polymer, (iv) is modified to render it more hydrolytically degradable than the bulk hydrogel (e.g., by oxidation), and/or (v) is more enzymatically degradable compared to the bulk hydrogel.

In various embodiments, a device or scaffold is loaded (e.g., soaked with) with one or more active compounds after polymerization. In certain embodiments, device or scaffold polymer forming material is mixed with one or more active compounds before polymerization. In some embodiments, a device or scaffold polymer forming material is mixed with one or more active compounds before polymerization, and hen is loaded with more of the same or one or more additional active compounds after polymerization.

In some embodiments, pore size or total pore volume of a device or scaffold is selected to influence the release of compounds from the device or scaffold. Exemplary porosities (e.g., nanoporous, microporous, and macroporous scaffolds and devices) and total pore volumes (e.g., about 5, 10, 15, 20, 25, 30, 35, 40, 45, 50, 55, 60, 65, 70, 75, 80, 85, 90, 95% or more) are described herein. Increased pore size and total pore volume increases the amount of compounds that can be delivered into or near a tissue, such as tumor tissue. In some embodiments, a pore size or total pore volume is selected to increase the speed at which active ingredients exit the device or scaffold. In various embodiments, an active ingredient may be incorporated into the scaffold material of a hydrogel or cryogel, e.g., to achieve continuous release of the active ingredient from the scaffold or device over a longer period of time compared to active ingredient that may diffuse from a pore cavity.

Porosity influences recruitment the cells into devices and scaffolds and the release of substances from devices and scaffolds. Pores may be, e.g., nanoporous, microporous, or macroporous. For example, the diameter of nanopores is less than about 10 nm. Micropores are in the range of about 100 nm to about 20 µm in diameter. Macropores are greater than about 20 µm (e.g., greater than about 100 µm or greater than about 400 µm). Exemplary macropore sizes include about 50 µm, about 100 µm, about 150 µm, about 200 µm, about 250 µm, about 300 µm, about 350 µm, about 400 µm, about 450 µm, about 500 µm, about 550 µm, and about 600 µm. Macropores are those of a size that permit a eukaryotic cell to traverse into or out of the composition. In one example, a macroporous composition has pores of about 400 µm to about 500 µm in diameter. The preferred pore size depends on the application.

In various embodiments, the device is manufactured in one stage in which one layer or compartment is made and infused or coated with one or more compounds. Exemplary bioactive compositions comprise polypeptides or polynucleotides. In certain embodiments, the device is manufactured in two or more (3, 4, 5, 6, . . . . 10 or more) stages in which one layer or compartment is made and infused or coated with one or more compounds followed by the construction of a second, third, fourth or more layers, which are in turn infused or coated with one or more compounds in sequence. In some embodiments, each layer or compartment is identical to the others or distinguished from one another by the number or mixture of bioactive compositions as well as distinct chemical, physical and biological properties. Polymers that may be formulated for specific applications by controlling the molecular weight, rate of degradation, and method of scaffold formation. Coupling reactions can be used to covalently attach bioactive epitopes, such as the cell adhesion sequence RGD to the polymer backbone.

In some embodiments, one or more compounds is added to the scaffold compositions using a known method including surface absorption, physical immobilization, e.g., using a phase change to entrap the substance in the scaffold material. For example, an immunostimulatory compound is mixed with the scaffold composition while it is in an aqueous or liquid phase, and after a change in environmental conditions (e.g., pH, temperature, ion concentration), the liquid gels or solidifies thereby entrapping the bioactive substance. In some embodiments, covalent coupling, e.g., using alkylating or acylating agents, is used to provide a stable, long term presentation of a compound on the scaffold in a defined conformation. Exemplary reagents for covalent coupling of such substances are provided in the table below.

TABLE 1

Methods to Covalently Couple Peptides/Proteins to Polymers

| Functional Group of Polymer | Coupling Reagents and Cross-Liner | Reacting Groups on Proteins/Peptides |
| --- | --- | --- |
| —OH | Cyanogen bromide (CNBr) Cyanuric chloride 4-(4,6-Dimethoxy-1,3,5-triazin-2-yl)-4-methylmorpholinium chloride (DMT-MM) | —NH$_2$ |
| —NH$_2$ | Diisocyanate compounds Diisothoncyanate compounds Glutaraldehyde Succinic anhydride | —NH$_2$ —OH |

TABLE 1-continued

Methods to Covalently Couple Peptides/Proteins to Polymers

| Functional Group of Polymer | Coupling Reagents and Cross-Liner | Reacting Groups on Proteins/Peptides |
| --- | --- | --- |
| —NH$_2$ | Nitrous Acid Hydrazine + nitrous acid | —NH$_2$ —SH —Ph-OH |
| —NH$_2$ | Carbodiimide compounds (e.g., EDC, DCC)[a] DMT-MM | —COOH |
| —COOH | Thiony I chloride N-hydroxysuccinimide N-hydroxysulfosuccinimide + EDC | —NH$_2$ |
| —SH | Disulfide compound | —SH |

[a]EDC: 1-ethyl-3-(3-dimethylaminopropyl) carbodiimide hydrochloride; DCC: dicyclohexy lcarbodiimide Alginate Scaffolds In certain embodiments, the device of the invention comprises an alginate hydrogel. Alginates are versatile polysaccharide based polymers that may be formulated for specific applications by controlling the molecular weight, rate of degradation and method of scaffold formation. Alginate polymers are comprised of two different monomeric units, (1-4)-linked β-D-mannuronic acid (M units) and a L-guluronic acid (G units) monomers, which can vary in proportion and sequential distribution along the polymer chain. Alginate polymers are polyelectrolyte systems which have a strong affinity for divalent cations (e.g., $Ca^{+2}$, $Mg^{+2}$ $Ba^{+2}$) and form stable hydrogels when exposed to these molecules. See Martinsen A., et al., Biotech. & Bioeng., 33 (1989) 79-89). For example, calcium cross-linked alginate hydrogels are useful for dental applications, wound dressings chondrocyte transplantation and as a matrix for other cell types. Without wishing to be bound by theory, it is believed that G units are preferentially crosslinked using calcium crosslinking, whereas click reaction based crosslinking is more indiscriminate with respect to G units or M units (i.e., both G and M units can be crosslinked by click chemistry). Alginate scaffolds and the methods for making them are known in the art. See, e.g., International Patent Application Publication No. WO2017/075055 A1, published on May 4, 2017, the entire contents of which are incorporated herein by reference.

The alginate polymers useful in the context of the present invention can have an average molecular weight from about 20 kDa to about 500 kDa, e.g., from about 20 kDa to about 40 kDa, from about 30 kDa to about 70 kDa, from about 50 kDa to about 150 kDa, from about 130 kDa to about 300 kDa, from about 230 kDa to about 400 kDa, from about 300 kDa to about 450 kDa, or from about 320 kDa to about 500 kDa. In one example, the alginate polymers useful in the present invention may have an average molecular weight of about 32 kDa. In another example, the alginate polymers useful in the present invention may have an average molecular weight of about 265 kDa. In some embodiments, the alginate polymer has a molecular weight of less than about 1000 kDa, e.g., less than about 900 Kda, less than about 800 kDa, less than about 700 kDa, less than about 600 kDa, less than about 500 kDa, less than about 400 kDa, less than about 300 kDa, less than about 200 kDa, less than about 100 kDa, less than about 50 kDa, less than about 40 kDa, less than about 30 kDa or less than about 25 kDa. In some embodiments, the alginate polymer has a molecular weight of about 1000 kDa, e.g., about 900 Kda, about 800 kDa, about 700 kDa, about 600 kDa, about 500 kDa, about 400 kDa, about 300 kDa, about 200 kDa, about 100 kDa, about 50 kDa, about 40 kDa, about 30 kDa or about 25 kDa. In one embodiment, the molecular weight of the alginate polymers is about 20 kDa.

Coupling reactions can be used to covalently attach bioactive agent, such as an atom, a chemical group, a nucleoside, a nucleotide, a nucleobase, a sugar, a nucleic acid, an amino acid, a peptide, a polypeptide, a protein, a protein complex, to the polymer backbone.

The term "alginate", used interchangeably with the term "alginate polymers", includes unmodified alginate or modified alginate. Modified alginate includes, but not limited to, oxidized alginate (e.g., comprising one or more algoxalate monomer units) and/or reduced alginate (e.g., comprising one or more algoxinol monomer units). In some embodiments, oxidized alginate comprises alginate comprising one or more aldehyde groups, or alginate comprising one or more carboxylate groups. In other embodiments, oxidized alginate comprises highly oxidized alginate, e.g., comprising one or more algoxalate units. Oxidized alginate may also comprise a relatively small number of aldehyde groups (e.g., less than 15%, e.g., 14,%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2% 0.1% or less aldehyde groups or oxidation on a molar basis). The term "alginate" or "alginate polymers" may also include alginate, e.g., unmodified alginate, oxidized alginate or reduced alginate.

Porous and Pore-Forming Scaffolds

The scaffolds of the present invention may be nonporous or porous. In certain embodiments, the scaffolds of the present invention are porous. Porosity of the scaffold composition influences migration of the cells through the device. Pores may be nanoporous, microporous, or macroporous. For example, the diameter of nanopores is less than about 10 nm. Micropores are in the range of about 100 nm to about 20 µm in diameter. Macropores are greater than about 20 µm (e.g., greater than about 100 µm or greater than about 400 µm). Exemplary macropore sizes include about 50 µm, 100 µm, 150 µm, 200 µm, 250 µm, 300 µm, 350 µm, 400 µm, 450 µm, 500 µm, 550 µm, and 600 µm. Macropores are those of a size that permit a eukaryotic cell to traverse into or out of the composition. In certain embodiments, a macroporous composition has pores of about 400 µm to 500 µm in diameter. The size of pores may be adjusted for different purpose. For example, for cell deployment and cell release, the pore diameter may be greater than 50 µm.

In some embodiments, the scaffolds contains pores before the administration into a subject. In some embodiments, the scaffolds comprises pore-forming scaffold composition. Pore-forming scaffolds and the methods for making pore-forming scaffolds are known in the art. See, e.g., U.S. Patent Publication US2014/0079752A1, the content of which is incorporated herein by reference. In certain embodiments, the pore-forming scaffolds is not initially porous, but which becomes macroporous over time resident in the body of a recipient animal such as a mammalian subject. In certain embodiments, the pore-forming scaffolds are hydrogel scaffolds. The pore may be formed at different time, e.g., after about 12 hours, or 1, 3, 5, 7, or 10 days or more after administration, i.e. resident in the body of the subject.

In certain embodiments, the pore-forming scaffolds comprise a first hydrogel and a second hydrogel, wherein the first hydrogel degrades at least about 10% faster (e.g., at least about 15%, at least about 20%, at least about 25%, at least about 30%, at least about 35%, at least about 40%, at least about 45%, at least about 50% faster, at least about 2 times faster, or at least about 5 times faster) than the second hydrogel. In certain embodiments, the first hydrogel comprises a porogen that degrades leaving a pore in its place. For example, the first hydrogel is a porogen and the resulting pore after degradation in situ is within 25% of the size of the initial porogen, e.g., within 20%, within 15%, or within 10% of the size of the initial porogen. Preferably, the resulting pore is within 5% of the size of the initial porogen. The first hydrogel may degrade faster than the second hydrogel due to the difference in their physical, chemical, and/or biological properties. In certain embodiments, the first hydrogel degrades more rapidly than the second hydrogel, because the first hydrogel is more soluble in water (comprises a lower solubility index). In certain embodiments, the first hydrogel degrades more rapidly because it is cross-linked to protease-mediated degradation motifs as described in U.S. Patent Publication US2005/0119762A1, the content of which is incorporated herein by reference).

In certain embodiments, the molecular mass of the polymers used to form the first hydrogel composition (a porogen) are approximately 50 kilodaltons (kDa), and the molecular mass of the polymers used to form the second hydrogel composition (bulk) comprises approximately 250 kDa. A shorter polymer (e.g. that of a porogen) degrades more quickly compared to that of a longer polymer (e.g., that of the bulk composition). In certain embodiments, a composition is modified to render it more hydrolytically degradable by virtue of the presence of sugar groups (e.g., approximately 3-10% sugar of an alginate composition). In certain embodiments, the porogen hydrogel is chemically modified, such as oxidized, to render it more susceptible to degradation. In some embodiments, the porogen hydrogel is more enzymatically degradable compared to the bulk hydrogel. The composite (first and second hydrogel) composition is permeable to bodily fluids, e.g., such as enzyme which gain access to the composition to degrade the porogen hydrogel. In some embodiments, the second hydrogel is cross-linked around the first hydrogel, i.e., the porogens (first hydrogel) are completely physically entrapped in the bulk (second) hydrogel.

The click reagents disclosed herein can be provided in the bulk hydrogel or the porogen hydrogel. In exemplary embodiments, the click reagents, e.g., polymers or nanoparticles, are provided in the bulk hydrogel.

In certain embodiments, hydrogel micro-beads ("porogens") are formed. Porogens are encapsulated into a "bulk" hydrogel that is either non-degradable or which degrades at a slower rate compared to the porogens. Immediately after hydrogel formation, or injection into the desired site in vivo, the composite material lacks pores. Subsequently, porogen degradation causes pores to form in situ. The size and distribution of pores are controlled during porogen formation, and mixing with the polymers which form the bulk hydrogel.

In some embodiments, the polymer utilized in the pore-forming scaffolds are naturally-occurring or synthetically made. In one example, both the porogens and bulk hydrogels are formed from alginate. "Alginate" as that term is used here, refers to any number of derivatives of alginic acid (e.g., calcium, sodium or potassium salts, or propylene glycol alginate). See, e.g., WO1998012228A1, hereby incorporated by reference.

In certain embodiments, the alginate polymers suitable for porogen formation have a molecular weight from 5,000 to 500,000 Daltons. The polymers are optionally further modified (e.g., by oxidation with sodium periodate, (Bouhadir et al., 2001, Biotech. Prog. 17:945-950, hereby incorporated by reference), to facilitate rapid degradation. In the certain embodiments, the polymers were crosslinked by extrusion through a nebulizer with co-axial airflow into a bath of divalent cation (for example, Ca2+ or Ba2+) to form hydrogel micro-beads. The higher the airflow rate, the lower the porogen diameter.

In some embodiments, the porogen hydrogel microbeads contain oxidized alginate. For example, the porogen hydrogel can contain 1%-50% oxidized alginate. In exemplary embodiments, the porogen hydrogel can contain 1-10% oxidized alginate. In one embodiment, the porogen hydrogel contains 7.5% oxidized alginate.

In certain embodiments, the concentration of divalent ions used to form porogens may vary from 5 to 500 mM, and the concentration of polymer from 1% to 5% by weight. However, any method which produces porogens that are significantly smaller than the bulk phase is suitable. Porogen chemistry can further be manipulated to produce porogens that have a some interaction with host proteins and cells, or to inhibit this interaction.

The alginate polymers suitable for formation of the bulk hydrogel have a Dalton molecular weight from 5,000 to 500,000 Da. The polymers may be further modified (for example, by oxidation with sodium periodate), to facilitate degradation, as long as the bulk hydrogel degrades more slowly than the porogen. The polymers may also be modified to present biological cues to control cell responses (e.g., integrin binding adhesion peptides such as RGD). Either the porogens or the bulk hydrogel may also encapsulate bioactive factors such as oligonucleotides, growth factors or drugs to further control cell responses. The concentration of divalent ions used to form the bulk hydrogel may vary from 5 to 500 mM, and the concentration of polymer from 1% to 5% by weight. The elastic modulus of the bulk polymer is tailored for its purpose, e.g., to recruit immune cells.

Methods relevant to generating the hydrogels described herein include the following. Bouhadir et al. Polymer 1999; 40: 3575-84 (incorporated herein by reference) describes the oxidation of alginate with sodium periodate, and characterizes the reaction. Bouhadir et al. Biotechnol. Prog. 2001; 17: 945-50 (incorporated herein by reference) describes oxidation of high molecular weight alginate to form alginate dialdehyde (alginate dialdehyde is high $M_w$ alginate in which a certain percent, (e.g., 5%), of sugars in alginate are oxidized to form aldehydes), and application to make hydrogels degrade rapidly. Kong et al. Polymer 2002; 43: 6239-46 (incorporated herein by reference) describes the use of gamma-irradiation to reduce the weight-averaged molecular weight ($M_w$) of guluronic acid (GA) rich alginates without substantially reducing GA content (e.g., the gamma irradiation selectively attacks mannuronic acid, MA blocks of alginate). Alginate is comprised of GA blocks and MA blocks, and it is the GA blocks that give alginate its rigidity (elastic modulus). Kong et al. Polymer 2002; 43: 6239-46 (incorporated herein by reference) shows that binary combinations of high $M_w$, GA rich alginate with irradiated, low $M_w$, high GA alginate crosslinks with calcium to form rigid hydrogels, but which degrade more rapidly and also have lower solution viscosity than hydrogels made from the same overall weight concentration of only high $M_w$, GA rich alginate. Alsberg et al. J Dent Res 2003; 82(11): 903-8 (incorporated herein by reference) describes degradation profiles of hydrogels made from irradiated, low $M_w$, GA-rich alginate, with application in bone tissue engineering. Kong et al. Adv. Mater 2004; 16(21): 1917-21 (incorporated herein by reference) describes control of hydrogel degradation profile by combining gamma irradiation procedure with oxidation reaction, and application to cartilage engineering.

Techniques to control degradation of hydrogen biomaterials are well known in the art. For example, Lutolf M P et al. Nat Biotechnol. 2003; 21: 513-8 (incorporated herein by reference) describes poly(ethylene glycol) based materials engineered to degrade via mammalian enzymes (MMPs). Bryant S J et al. Biomaterials 2007; 28(19): 2978-86 (U.S. Pat. No. 7,192,693 B2; incorporated herein by reference) describes a method to produce hydrogels with macro-scale pores. A pore template (e.g., poly-methylmethacrylate beads) is encapsulated within a bulk hydrogel, and then acetone and methanol are used to extract the porogen while leaving the bulk hydrogel intact. Silva et al. Proc. Natl. Acad. Sci USA 2008; 105(38): 14347-52 (incorporated herein by reference; US 2008/0044900) describes deployment of endothelial progenitor cells from alginate sponges. The sponges are made by forming alginate hydrogels and then freeze-drying them (ice crystals form the pores). Ali et al. Nat Mater 2009 (incorporated herein by reference) describes the use of porous scaffolds to recruit dendritic cells and program them to elicit anti-tumor responses. Huebsch et al. Nat Mater 2010; 9: 518-26 (incorporated herein by reference) describes the use of hydrogel elastic modulus to control the differentiation of encapsulated mesenchymal stem cells.

In some embodiments, the scaffold composition comprises open interconnected macropores. Alternatively or in addition, the scaffold composition comprises a pore-forming scaffold composition. In certain embodiments, the pore-forming scaffold composition may comprise a sacrificial porogen hydrogel and a bulk hydrogel, wherein the pore-forming scaffold composition lacks macropores. For example, the sacrificial porogen hydrogel may degrade at least 10% faster than the bulk hydrogel leaving macropores in its place following administration of said pore-forming scaffold into a subject. In some embodiments, the sacrificial porogen hydrogel is in the form of porogens that degrade to form said macropores. For example, the macropores may comprise pores having a diameter of, e.g., about 10-400 µm.

Mesoporous Silica Rods

In some embodiments, the scaffold device comprises mesoporous silica rods. Injectable mesoporous silica rods randomly self-assemble to form a 3D scaffold structure in vivo. The 3D scaffold structure comprises micro spaces that allow for immune cell (e.g., dendritic cell) infiltration and/or trafficking. As with other scaffold compositions disclosed herein, the mesoporous silica rods may comprise, e.g., a click chemistry reagent of the invention alone or together with an immunostimulatory compound; a compound that attracts an immune cell to or into the delivery vehicle; a compound that induces immunogenic cell death of a tumor cell; a compound that inhibits T-cell or dendritic cell suppression; a compound that inhibits an immune-inhibitory protein; or an antigen, or any combination thereof. In some embodiments, the mesoporous silica rod itself serves as an immunostimulatory compound.

In some embodiments, the rods comprise pores of between 1-50 nm in diameter, e.g.; pores comprising within the range about 1-50, 2-50, 3-50, 4-50, 5-50, 6-50, 7-50, 8-50, 9-10, 10-50, 15-50, 25-50, 1-25, 2-25, 3-25, 4-25, 5-25, 6-25, 7-25, 8-25, 9-25, 10-25, or 15-25 nm. In various embodiments, the length of the mesoporous silica rods ranges from 5 µm to 500 µm. In one example, the rods comprise a length of 5-25 µm, e.g., 10-20 µm. In other examples, the rods comprise length of 50 µm to 250 µm or 80 µm to 120 µm. In certain embodiments, the mesoporous silica rods comprise a length of about 25-100, 25-250, 25-500, 50-250, or 50-500 µm, or a length of at least about 5, 10, 15, 20, 25, 30, 35, 40, 45, 50, 75, or 100 µm but no more than about 500 µm.

In some embodiments, the mesoporous silica rods comprise a length of about 100 nm, 150 nm, 200 nm, 250 nm, 300 nm, 350 nm, 400 nm, 450 nm, 500 nm, 600 nm, 700 nm, 800 nm, 900 nm, 100-250 nm, 250-500 nm, 500-750 nm, 750-1000 nm, 1 µm, 2 µm, 3 µm, 4 µm, 5 µm, 6 µm, 7 µm, 8 µm, 9 µm, 10 µm, 15 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 150 µm, 200 µm, 250 µm, 300 µm, 350 µm, 400 µm, 450 µm, 500 µm, 1-5 µm, 1-500 µm, 5-500 µm, 25-50 µm, 25-100 µm, 50-100 µm, 25-500 µm, or 50-500 µm. In certain embodiments, the mesoporous silica rods comprise of length from 100 nm, 150 nm, 200 nm, 250 nm, 300 nm, 350 nm, 400 nm, 450 nm, 500 nm, 600 nm, 700 nm, 800 nm, 900 nm, 100-250 nm, 250-500 nm, 500-750 nm, 750-1000 nm, 1 µm, 2 µm, 3 µm, 4 µm, 5 µm, 6 µm, 7 µm, 8 µm, 9 µm, 10 µm, 15 µm, 25 µm, 30 µm, 35 µm, 40 µm, 45 m, or 50 m to 55 µm, 60 m, 65 m, 70 m, 75 m, 80 m, 85 m, 90 m, 95 m, 100 m, 150 µm, 200 µm, 250 µm, 300 µm, 350 µm, 400 µm, 450 µm, or 500 µm. In various embodiments, the mesoporous silica rods comprise a length of about or at least about any of 100 nm, 150 nm, 200 nm, 250 nm, 300 nm, 350 nm, 400 nm, 450 nm, 500 nm, 600 nm, 700 nm, 800 nm, 900 nm, 100-250 nm, 250-500 nm, 500-750 nm, 750-1000 nm, 1 µm, 2 µm, 3 µm, 4 µm, 5 µm, 6 µm, 7 µm, 8 µm, 9 µm, 10 µm, 15 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 150 µm, 200 µm, 250 µm, 1-500 µm, 5-500 µm, 25-50 µm, 25-100 µm, 50-100 µm, 25-500 µm, or 50-500 µm but less than 550 µm. In some embodiments, the mesoporous silica rods comprise a diameter of about or at least about any of 75 nm, 100 nm, 150 nm, 200 nm, 250 nm, 300 nm, 350 nm, 400 nm, 450 nm, 500 nm, 600 nm, 700 nm, 800 nm, 900 nm, 100-1000 nm, 100-500 nm, 100-250 nm, 250-500 nm, 500-750 nm, or 750-1000 nm, with the proviso that mesoporous silica rods comprise a length that is at least 10% greater than the diameter thereof. In certain embodiments, the mesoporous silica rods comprise a diameter from 75 nm, 100 nm, 150 nm, 200 nm, 250 nm, 300 nm, 350 nm, 400 nm, 450 nm, or 500 nm to 600 nm, 700 nm, 800 nm, 900 nm, or 1000 nm. In some embodiments, the mesoporous silica rods comprise a length that is at least about 10, 20, 25, 30, 35, 40, 45, 50, 55, 60, 65, 70, 75, 80, 85, 90, 95, 100, or 150% greater than the diameter of the mesoporous silica rods. In some embodiments, the mesoporous silica rods comprise a length that is at least about 2, 3, 4, 5, 6, 7, 8, 9, 10, 20, 30, 40, 50, 60, 70, 80, 90, 100, 150, 200, 250, 300, 400, or 500 times the diameter of the mesoporous silica rods. In certain embodiments, the mesoporous silica rods comprise pores having a diameter of about or at least about 1, 2, 3, 4, 5, 6, 7, 8, 9, 10, 15, 20, 25, 30, 35, 40, 45, or 50 nm, or about 1-10, 1-15, 1-5, 2-5, 2-10, 3-10, 4-10, 5-10, 5-15, or 10-25 nm. In certain embodiments, the mesoporous silica rods are 80 to 120 µm in length. For example, the mesoporous silica rods may comprise (a) pores having a diameter of between 2-50 nm, 3-50 nm, 5-50 nm, 5-25 nm, 5-10 nm; and/or (b) a length of about 5-25 µm, 80 to 120 µm. In some embodiments, the mesoporous silica rods may comprise a combination of rods with different lengths and/or rods with range of different sizes (e.g., within one of the ranges disclosed above or 1, 2, 3, 4, 5 or more of the ranges disclosed above). In some embodiments, rods with a length of about 100 nm, 150 nm, 200 nm, 250 nm, 300 nm, 350 nm, 400 nm, 450 nm, 500 nm, 600 nm, 700 nm, 800 nm, 900 nm, 100-250 nm, 250-500 nm, 500-750 nm, or 750-1000 nm are combined with rods having a length of about 5 µm, 6 µm, 7 µm, 8 µm, 9 µm, 10 µm, 15 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 150 µm, 200 µm, 250 µm, 300 µm, 350 µm, 400 µm, 450 µm, 500 µm, 5-500 µm, 25-50 µm, 25-100 µm, 50-100 µm, 25-500 µm, or 50-500 µm. In certain embodiments, the rods have a width of about 0.5 µm, 1 µm, 1.5 µm, 2 µm, 2.5 µm, 3 µm, 3.5 µm, 4 µm, 4.5 µm, 5 µm, 5.5 µm, 6 µm, 6.5 µm, 7 µm, 7.5 µm, 8 µm, 8.5 µm, 9 µm, 9.5 µm, 10 µm, 11 µm, 12 µm, 13 µm, 14 µm, 15 µm, 16 µm, 17 µm, 18 µm, 19 µm, 20 µm, 1-20 µm, 1-10 µm, 5-10 µm, 1-5 µm, 0.5-20 µm, 7.5-12.5 µm, or 5-15 µm.

In some embodiments, one set of rods is small enough to be phagocytosed by immune cells such as dendritic cells or macrophages, and another set of rods is too big to be phagocytosed by the immune cells. In various embodiments, rods having different antigens or other compounds disclosed herein are mixed. Thus, provided herein are mixtures of 1, 2, 3, 4, 5, 6, 7, 8, 9, 10 or more classes of mesoporous silica rods, with each class of rods having a different antigen (e.g., antigenic peptide, such as a purified peptide). For example, a mixture may comprise a first class of rods comprising a first antigen, a second class of rods comprising a second antigen, a third class of rods comprising a third antigen, and so on. A mixture of rods may have the same or similar sizes or range of sizes, or may include one or more rods with a particular antigen or antigens (e.g., rods small enough to be phagocytosed) and another one or more rods with another antigen or antigens (e.g., rods too big to be phagocytosed). In certain embodiments, the rods that are too big to be phagocytosed form scaffolds upon administration (e.g., injection) into a subject. Injectable mesoporous silica rods randomly self-assemble to form a 3 dimensional (3D) scaffold in vivo. This system is designed such that it recruits and transiently houses immune cells (such as dendritic cells), and contact them with a click chemistry reagent of the invention. After recruitment and temporary housing or presence of the cells in the structure, these immune cells migrate out of the device structure and homed to a lymph node. Thus, the composition is one in which cells traffic/circulate in and out of, their status of immune activation being altered/modulated as a result of the trafficking through the device. In various embodiments, the mesoporous silica rods are suspended in an aqueous solution, such as a buffer [e.g., phosphate buffered saline (PBS), Hank's balanced salt solution (HBSS), or another physiologically (e.g., pharmaceutically acceptable) buffer] for injection. In some embodiments, the mesoporous silica rods are injected in water. Mesoporous silica rods may be injected in a variety of concentrations. In some embodiments, the rods are injected at a concentration of about 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 30 mg/ml, 35 mg/ml, 40 mg/ml, 45 mg/ml, 50 mg/ml, 55 mg/ml, 60 mg/ml, 10-40 mg/ml, 20-35 mg/ml, 20-40 mg/ml, 25-35 mg/ml, 25-50 mg/ml, 25-45 mg/ml, 25-30 mg/ml, 30-50 mg/ml, 1-30 mg/ml, 1-40 mg/ml, 1-50 mg/ml, 1-60 mg/ml, 5-50 mg/ml, or 5-60 mg/ml.

Chemoattractants

The device of the present invention can comprise a chemoattractant for cells. The term "chemoattractant," as used herein, refers to any agent that attracts a motile cell, such as immune cells. To enable sustained release from the scaffold, the chemoattractant can, in some embodiments, be coupled to nanoparticles, e.g., gold nanoparticles.

In certain embodiments, the chemoattractant for immune cells is a growth factor or cytokine. In some embodiments, the chemoattractant is a chemokine. Exemplary chemokines include, but are not limited to, CC chemokines, CXC chemokines, C chemokines, CX3C chemokines. Exemplary cytokines include, but are not limited to, interleukin, lymphokines, monokines, interferons, and colony stimulating factors. All known growth factors are encompassed by the compositions, methods, and devices of the present invention. Exemplary growth factors include, but are not limited to, transforming growth factor beta (TGF-β), granulocyte-colony stimulating factor (G-CSF), granulocyte-macrophage colony stimulating factor (GM-CSF), nerve growth factor (NGF), neurotrophins, Platelet-derived growth factor (PDGF), erythropoietin (EPO), thrombopoietin (TPO), myostatin (GDF-8), growth differentiation factor-9 (GDF9), acidic fibroblast growth factor (aFGF or FGF-1), basic fibroblast growth factor (bFGF or FGF-2), epidermal growth factor (EGF), hepatocyte growth factor (HGF). In some embodiments, the device includes a chemoattractant for immune cells. In some embodiments, the device comprises a compound that attracts an immune cell to or into the device, wherein the immune cell comprises a macrophage, T-cell, B-cell, natural killer (NK) cell, or dendritic cell. Non-limiting examples of compounds useful for attracting an immune cell to or into the device comprises granulocyte-macrophage colony stimulating factor (GM-CSF), an FMS-like tyrosine kinase 3 ligand (Flt3L), chemokine (C—C motif) ligand 19 (CCL-19), chemokine (C—C motif) ligand 20 (CCL20), chemokine (C—C motif) ligand 21 (CCL-21), a N-formyl peptide, fractalkine, monocyte chemotactic protein-1, and macrophage inflammatory protein-3 (MIP-3a). The present invention encompasses cytokines as well as growth factors for stimulating dendritic cell activation. Exemplary cytokines include, but are not limited to, IL-1, IL-2, IL-3, IL-4, IL-5, IL-6, IL-8, IL-10, IL-12 IL-15, IL-17, IL-18, TNF-α, IFN-γ, and IFN-α.

In certain embodiments, the chemoattractant for immune cells is Granulocyte-macrophage colony-stimulating factor (GM-CSF). Granulocyte-macrophage colony-stimulating factor (GM-CSF) is a protein secreted by macrophages, T cells, mast cells, endothelial cells and fibroblasts. Specifically, GM-CSF is a cytokine that functions as a white blood cell growth factor. GM-CSF stimulates stem cells to produce granulocytes and monocytes. Monocytes exit the blood stream, migrate into tissue, and subsequently mature into macrophages.

In some embodiments, the device can comprise and release GM-CSF polypeptides to attract host DCs to the device. Contemplated GM-CSF polypeptides are isolated from endogenous sources or synthesized in vivo or in vitro. Endogenous GM-CSF polypeptides may be isolated from healthy human tissue. Synthetic GM-CSF polypeptides are synthesized in vivo following transfection or transformation of template DNA into a host organism or cell, e.g., a mammalian or human cell line. Alternatively, synthetic GM-CSF polypeptides are synthesized in vitro by polymerase chain reaction (PCR) or other art-recognized methods Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

In certain embodiments, GM-CSF polypeptides may be recombinant. In some embodiments, GM-CSF polypeptides are humanized derivatives of mammalian GM-CSF polypeptides. Exemplary mammalian species from which GM-CSF polypeptides are derived include, but are not limited to, mouse, rat, hamster, guinea pig, ferret, cat, dog, monkey, or primate. In some embodiments, GM-CSF is a recombinant human protein (PeproTech, Catalog #300-03). In some embodiments, GM-CSF is a recombinant murine (mouse) protein (PeproTech, Catalog #315-03). In some embodiments, GM-CSF is a humanized derivative of a recombinant mouse protein.

In certain embodiments, GM-CSF polypeptides may be modified to increase protein stability in vivo. In certain embodiments, GM-CSF polypeptides may be engineered to be more or less immunogenic. Endogenous mature human GM-CSF polypeptides are glycosylated, reportedly, at amino acid residues 23 (leucine), 27 (asparagine), and 39 (glutamic acid) (see U.S. Pat. No. 5,073,627). In certain embodiments, GM-CSF polypeptides of the present invention may be modified at one or more of these amino acid residues with respect to glycosylation state.

The chemoattractant for immune cells may recruit immune cells to the scaffolds of the present invention. Immune cells include cells of the immune system that are involved in immune response. Exemplary immune cells includes, but not limited to, T cells, B cells, leucocytes, lymphocytes, antigen presenting cells, dendritic cells, neutrophils, eosinophils, basophils, monocytes, macrophages, histiocytes, mast cells, and microglia.

In certain embodiments, the chemoattractant for immune cells recruits dendritic cells (DCs) to the scaffold of the present invention. Dendritic cells (DCs) are immune cells within the mammalian immune system and are derived from hematopoietic bone marrow progenitor cells. More specifically, dendritic cells can be categorized into lymphoid (or plasmacytoid) dendritic cell (pDC) and myeloid dendritic cell (mDC) subdivisions having arisen from a lymphoid (or plasmacytoid) or myeloid precursor cell, respectively. From the progenitor cell, regardless of the progenitor cell type, an immature dendritic cell is born. Immature dendritic cells are characterized by high endocytic activity and low T-cell activation potential. Thus, immature dendritic cells constitutively sample their immediate surrounding environment for pathogens. Exemplary pathogens include, but are not limited to, a virus or a bacteria. Sampling is accomplished by pattern recognition receptors (PRRs) such as the toll-like receptors (TLRs). Dendritic cells activate and mature once a pathogen is recognized by a pattern recognition receptor, such as a toll-like receptor.

Mature dendritic cells not only phagocytose pathogens and break them down, but also, degrade their proteins, and present pieces of these proteins, also referred to as antigens, on their cell surfaces using MHC (Major Histocompatibility Complex) molecules (Classes I, II, and III). Mature dendritic cells also upregulate cell-surface receptors that serve as co-receptors for T-cell activation. Exemplary co-receptors include, but are not limited to, CD80, CD86, and CD40. Simultaneously, mature dendritic cells upregulate chemotactic receptors, such as CCR7, that allows the cell to migrate through the blood stream or the lymphatic system to the spleen or lymph node, respectively.

Dendritic cells are present in external tissues that are in contact with the external environment such as the skin (dendritic cells residing in skin are also referred to as Langerhans cells). Alternatively, dendritic cells are present in internal tissues that are in contact with the external environment such as linings of the nose, lungs, stomach, and intestines. Finally, immature dendritic cells reside in the blood stream. Once activated, dendritic cells from all off these tissues migrate to lymphoid tissues where they present antigens and interact with T cells and B cells to initiate an immune response. One signaling system of particular importance for the present invention involves the chemokine receptor CCR7 expressed on the surface of dendritic cells and the chemokine receptor ligand CCL19 secreted by lymph node structures to attract migrating mature dendritic cells toward high concentrations of immune cells. Exemplary immune cells activated by contact with mature dendritic cells include, but are not limited to, helper T cells, killer T cells, and B cells. Although multiple cell types within the immune system present antigens, including macrophages and B lymphocytes, dendritic cells are the most potent activators of all antigen-presenting cells.

Dendritic cells earned their name from the characteristic cell shape comprising multiple dendrites extending from the cell body. The functional benefit of this cell shape is a significantly increased cell surface and contact area to the surroundings compared to the cell volume. Immature dendritic cells sometimes lack the characteristic dendrite formations and are referred to as veiled cells. Veiled cells possess large cytoplasmic veils rather than dendrites.

Adjuvants

In certain embodiments, the device of the present invention comprises an adjuvant. The term "adjuvant", as used herein, refers to compounds that can be added to vaccines to stimulate immune responses against antigens. Adjuvants may enhance the immunogenicity of highly purified or recombinant antigens. Adjuvants may reduce the amount of antigen or the number of immunizations needed to protective immunity. For example, adjuvants may activate antibody-secreting B cells to produce a higher amount of antibodies. Alternatively, adjuvants can act as a depot for an antigen, present the antigen over a longer period of time, which could help maximize the immune response and provide a longer-lasting protection. Adjuvants may also be used to enhance the efficacy of a vaccine by helping to modify the immune response to particular types of immune system cells, for example, by activating T cells instead of antibody-secreting B cells depending on the purpose of the vaccine. Adjuvants are also used in the production of antibodies from immunized animals (Petrovskyl et al, 2002, Immunology and Cell Biology 82: 488-496).

Adjuvants can be classified according to their source, mechanism of action or physicochemical properties. For example, adjuvants can be classified into three groups: (i) active immunostimulants, being substances that increase the immune response to the antigen; (ii) carriers, being immunogenic proteins that provide T-cell help; and (iii) vehicle adjuvants, being oil emulsions or liposomes that serve as a matrix for antigens as well as stimulating the immune response (Edelman R. 1992, AIDS Res. Hum. Retroviruses 8: 1409-11). An alternative adjuvant classification divides adjuvants according to administration route, namely mucosal or parenteral. A third classification divides adjuvants into alum salts and other mineral adjuvants; tensoactive agents; bacterial derivatives; vehicles and slow release materials or cytokines (Byars et al., 1990, Laboratory Methods in Immunology: 39-51). A fourth classification divides adjuvants into the following groups: gel-based adjuvants, tensoactive agents, bacterial products, oil emulsions, particulated adjuvants, fusion proteins or lipopeptides (Jennings R et al., 1998, Dev. Biol. Stand, 92: 19-28).

The device of the present invention may comprise one or more adjuvants. Adjuvants suitable for use in the present invention include, but are not limited to, mineral salt-based adjuvants such as alum-based adjuvants, calcium-based adjuvants, iron-based adjuvants, zirconium-based adjuvants; particulate adjuvants; mucosal adjuvants; tensoactive adjuvants; bacteria-derived adjuvants; oil-based adjuvants; cytokines, liposome adjuvants, polymeric microsphere adjuvants, carbohydrate adjuvants.

Exemplary adjuvants include, but are not limited to, aluminium hydroxide, aluminum phosphate, calcium phosphate, Quil A, Quil A derived saponin QS-21, or other types of saponins, Detox, ISCOMs, cell wall peptidoglycan or lipopolysaccharide of Gram-negative bacteria, trehalose dimycolate, bacterial nucleic acids such as DNA containing CpG motifs, FIA, Montanide, Adjuvant 65, Freund's complete adjuvant, Freund's incomplete adjuvant, Lipovant, interferon, granulocyte-macrophage colony stimulating factor (GM-CSF), AS03, AS04, IL-1, IL-2, IL-3, IL-4, IL-5, IL-6, IL-7, IL-8, IL-10, IL-12, IL-15, IL-17, IL-18, STING, Toll-like receptor ligand, CD40L, ovalbumin (OVA), monophosphoryl lipid A (MPL), polyinosinic:poly cytidylic acid (poly(I:C)), a combination of LPS (or MPLA) and OxPAPC, MF59, N-acetyl muramyl-L-alanyl-D-isoglutamine (MDP), poly (DL-lactide-coglycolide) microspheres, paraffin oil, squalene, virosome, gamma inulin, glucans, dextrans, lentinans, glucomannans and galactomannans, pathogen-associated molecular patterns (PAMPs), damage-associated molecular pattern molecules (DAMPs), antibodies against immune suppressive molecules (e.g., antibody or antagonist against transforming growth factor (TGF)-beta, A2aR antagonists), Freund's complete adjuvant, Freund's incomplete adjuvant, lipopolysaccharides (LPS), Fas ligand, Trail, lymphotactin, Mannan (M-FP), APG-2, Hsp70 and Hsp90.

In certain embodiments, the device of the present invention comprises an agent that activates and matures recruited immune cells. In some embodiments, the agent is a toll-like receptor (TLR) ligand.

TLRs are a class of single transmembrane domain, non-catalytic, receptors that recognize structurally conserved molecules referred to as pathogen-associated molecular patterns (PAMPs). PAMPs are present on microbes and are distinguishable from host molecules. TLRs are present in all vertebrates. Thirteen TLRs (referred to as TLRs1-13, consecutively) have been identified in humans and mice. Human TLRs comprise TLRs 1-10.

TLRs and interleukin-1 (IL-1) receptors comprise a receptor superfamily the members of which all share a TIR domain (Toll-IL-1 receptor). TIR domains exist in three varieties with three distinct functions. TIR domains of subgroup 1 are present in receptors for interleukins produced by macrophages, monocytes, and dendritic cells. TIR domains of subgroup 2 are present in classical TLRs which bind directly or indirectly to molecules of microbial origin. TIR domains of subgroup 3 are present in cytosolic adaptor proteins that mediate signaling between proteins comprising TIR domains of subgroups 1 and 2.

TLR ligands comprise molecules that are constantly associated with and highly specific for a threat to the host's survival such as a pathogen or cellular stress. TLR ligands are highly specific for pathogens and not the host. Exemplary pathogenic molecules include, but are not limited to, lipopolysaccharides (LPS), lipoproteins, lipoarabinomannan, flagellin, double-stranded RNA, and unmethylated CpG islands of DNA.

All known TLR ligands found either on a cell surface or an internal cellular compartment are encompassed by the compositions, methods, and devices of the present invention. Exemplary TLR ligands include, but are not limited to, triacyl lipoproteins (TLR1); lipoproteins, gram positive peptidoglycan, lipteichoic acids, fungi, and viral glycoproteins (TLR2); double-stranded RNA, poly I:C (TLR 3); lipopolysaccaride, viral glycoproteins (TLR 4); flagellin (TLR5); diacyl lipoproteins (TLR6); small synthetic compounds, single-stranded RNA (TLR7 and TLR 8); unmethylated CpG DNA (TLR9); Profilin (TLR11). Also included as TRL ligands are host molecules like fibronectin and heat shock proteins (HSPs). Host TLR ligands are also encompassed by the present invention. The role of TLRs in innate immunity and the signaling molecules used to activate and inhibit them are known in the art (for a review, see Holger K. Frank B., Hessel E., and Coffman R L. Therapeutic targeting of innate immunity with Toll-like receptor agonists and antagonists. Nature Medicine 13, 552-559 (2007), the content of which is herein incorporated by reference).

CpG sites are regions of deoxyribonucleic acid (DNA) where a cysteine nucleotide occurs next to a guanine nucleotide in the linear sequence of bases along its length (the "p" represents the phosphate linkage between them and distinguishes them from a cytosine-guanine complementary base pairing). CpG sites play a pivotal role in DNA methylation, which is one of several endogenous mechanisms cells use to silence gene expression. Methylation of CpG sites within promoter elements can lead to gene silencing. In the case of cancer, it is known that tumor suppressor genes are often silences while oncogenes, or cancer-inducing genes, are expressed. Importantly, CpG sites in the promoter regions of tumor suppressor genes (which prevent cancer formation) have been shown to be methylated while CpG sites in the promoter regions of oncogenes are hypomethylated or unmethylated in certain cancers. The TLR-9 receptor binds unmethylated CpG sites in DNA.

In certain embodiments, the device of present invention comprises a cytosine-guanosine dinucleotides and oligonucleotides (CpG-ODN). Contemplated CpG oligonucleotides may be isolated from endogenous sources or synthesized in vivo or in vitro. Exemplary sources of endogenous CpG oligonucleotides include, but are not limited to, microorganisms, bacteria, fungi, protozoa, viruses, molds, or parasites. In some embodiments, endogenous CpG oligonucleotides are isolated from mammalian benign or malignant neoplastic tumors. In some embodiments, synthetic CpG oligonucleotides are synthesized in vivo following transfection or transformation of template DNA into a host organism. In certain embodiments, Synthetic CpG oligonucleotides are synthesized in vitro by polymerase chain reaction (PCR) or other art-recognized methods (Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

CpG oligonucleotides are presented for cellular uptake by dendritic cells. In some embodiments, naked CpG oligonucleotides are used. The term "naked" is used to describe an isolated endogenous or synthetic polynucleotide (or oligonucleotide) that is free of additional substituents. In some embodiments, CpG oligonucleotides are bound to one or more compounds to increase the efficiency of cellular uptake. In some embodiments, CpG oligonucleotides are bound to one or more compounds to increase the stability of the oligonucleotide within the scaffold and/or dendritic cell.

In certain embodiments, CpG oligonucleotides are condensed prior to cellular uptake. In some embodiments, CpG oligonucleotides are condensed using polyethylimine (PEI), a cationic polymer that increases the efficiency of cellular uptake into dendritic cells.

CpG oligonucleotides can be divided into multiple classes. For example, exemplary CpG-ODNs encompassed by compositions, methods and devices of the present invention are stimulatory, neutral, or suppressive. The term "stimulatory" used herein is meant to describe a class of CpG-ODN sequences that activate TLR9. The term "neutral" used herein is meant to describe a class of CpG-ODN sequences that do not activate TLR9. The term "suppressive" used herein is meant to describe a class of CpG-ODN sequences that inhibit TLR9. The term "activate TLR9" describes a process by which TLR9 initiates intracellular signaling.

Simulatory CpG-ODNs can further be divided into three types A, B and C, which differ in their immune-stimulatory activities. Type A stimulatory CpG ODNs are characterized by a phosphodiester central CpG-containing palindromic motif and a phosphorothioate 3' poly-G string. Following activation of TLR9, these CpG ODNs induce high IFN-α production from plasmacytoid dendritic cells (pDC). Type A CpG ODNs weakly stimulate TLR9-dependent NF-κB signaling.

Type B stimulatory CpG ODNs contain a full phosphorothioate backbone with one or more CpG dinucleotides. Following TLR9 activation, these CpG-ODNs strongly activate B cells. In contrast to Type A Cpg-ODNs, Type B CpG-ODNs weakly stimulate IFN-α secretion.

Type C stimulatory CpG ODNs comprise features of Types A and B. Type C CpG-ODNs contain a complete phosphorothioate backbone and a CpG containing palindromic motif. Similar to Type A CpG ODNs, Type C CpG ODNs induce strong IFN-α production from pDC. Similar to Type B CpG ODNs, Type C CpG ODNs induce strong B cell stimulation.

Exemplary stimulatory CpG ODNs comprise, but are not limited to, ODN 1585, ODN 1668, ODN 1826, ODN 2006, ODN 2006-G5, ODN 2216, ODN 2336, ODN 2395, ODN M362 (all InvivoGen). The present invention also encompasses any humanized version of the preceding CpG ODNs. In one preferred embodiment, compositions, methods, and devices of the present invention comprise ODN 1826 (the sequence of which from 5' to 3' is tccatgacgttcctgacgtt, wherein CpG elements are bolded, SEQ ID NO: 10).

Neutral, or control, CpG ODNs that do not stimulate TLR9 are encompassed by the present invention. These ODNs comprise the same sequence as their stimulatory counterparts but contain GpC dinucleotides in place of CpG dinucleotides.

Exemplary neutral, or control, CpG ODNs encompassed by the present invention comprise, but are not limited to, ODN 1585 control, ODN 1668 control, ODN 1826 control, ODN 2006 control, ODN 2216 control, ODN 2336 control, ODN 2395 control, ODN M362 control (all InvivoGen). The present invention also encompasses any humanized version of the preceding CpG ODNs.

Suppressive CpG ODNs that inhibit TLR9 are encompassed by the present invention. Exemplary potent inhibitory sequences are (TTAGGG)$_4$ (ODN TTAGGG, InvivoGen, SEQ ID NO:11), found in mammalian telomeres and ODN 2088 (InvivoGen), derived from a murine stimulatory CpG ODN by replacement of 3 bases. Suppressive ODNs disrupt the colocalization of CpG ODNs with TLR9 in endosomal vesicles without affecting cellular binding and uptake. Suppressive CpG ODNs encompassed by the present invention are used to fine-tune, attenuate, reverse, or oppose the action of a stimulatory CpG-ODN. Alternatively, or in addition, compositions, methods, or devices of the present invention comprising suppressive CpG ODNs are used to treat autoimmune conditions or prevent immune responses following transplant procedures.

Antigens

In certain embodiments, the device of the present invention comprises an antigen. The antigen can be a cancer antigen or a non-cancer antigen (e.g., a microbial antigen or a viral antigen). In one embodiment, the antigen is a polypeptide. In one embodiment, the polypeptide antigen comprises a stretch of at least 10 consecutive amino acids identical to a stretch of at least 10 consecutive amino acids of a cancer antigen, a microbial antigen, or a viral antigen. In some embodiments, the antigen is a cancer antigen. The device comprising a cancer antigen can be used to vaccinate and/or provide protective immunity to a subject to whom such a device was administered. In some embodiments, a cancer/tumor antigen is from a subject who is administered a device provided herein. In certain embodiments, a cancer/tumor antigen is from a different subject. In various embodiments, a cancer antigen is present in a cancer cell lysate. For example, the tumor cell lysate may comprise one or more lysed cells from a biopsy. In some embodiments, the cancer antigen is present on an attenuated live cancer cell. For example, the attenuated live cancer cell may be an irradiated cancer cell. Antigens may be used alone or in combination with GM-CSF, CpG-ODN sequences, or immunomodulators. Moreover, antigens can be provided simultaneously or sequentially with GM-CSF, CpG-ODN sequences, or immunomodulators.

One or more antigens may be selected based on an antigenic profile of a subject's cancer or of a pathogen. In certain embodiments, the device lacks a cancer antigen prior to administration to a subject. In some embodiments, the device comprises an immunoconjugate, wherein the immunoconjugate comprises an immunostimulatory compound covalently linked to an antigen. In various embodiments, the antigen comprises a cancer antigen, such as a central nervous system (CNS) cancer antigen, CNS germ cell tumor antigen, lung cancer antigen, leukemia antigen, acute myeloid leukemia antigen, multiple myeloma antigen, renal cancer antigen, malignant glioma antigen, medulloblastoma antigen, breast cancer antigen, prostate cancer antigen, Kaposi's sarcoma antigen, ovarian cancer antigen, adenocarcinoma antigen, or melanoma antigen. In some embodiments, treating the subject comprises reducing metastasis in the subject.

Exemplary cancer antigens encompassed by the compositions, methods, and devices of the present invention include, but are not limited to, tumor lysates extracted from biopsies, and irradiated tumor cells. Exemplary polypeptide cancer antigens include one or more of the following proteins, or fragments thereof. MAGE series of antigens (MAGE-1 is an example), MART-1/melana, tyrosinase, ganglioside, gp100, GD-2, O-acetylated GD-3, GM-2, MUC-1, Sos1, Protein kinase C-binding protein, Reverse transcriptase protein, AKAP protein, VRK1, KIAA1735, T7-1, T11-3, T11-9, Homo Sapiens telomerase ferment (hTRT), Cytokeratin-19 (CYFRA21-1), SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3), CTCL tumor antigen sel-1, CTCL tumor antigen sel4-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B1 ANTIGEN (MAGE-XP ANTIGEN) (DAM10), MAGE-B2 ANTIGEN (DAM6), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A; parathyroid secretory protein 1, DUPAN-2, CA 19-9, CA 72-4, CA 195, Carcinoembryonic antigen (CEA), Trp2, ovalbumin, M27, and M30. In embodiments, the antigen comprises a fragment of one or more of the following proteins. In exemplary embodiments, the fragment can comprise 10 or more consecutive amino acids identical in sequence to one or more of the foregoing proteins. In some embodiments, the fragment can comprise 10, 20, 30, 40, 50, 60, 70, 80, 90, 100, 150, 200, 250, 300, 350, 400, 450, 500, 600, 700, 800, 900, 1000 or more amino acids. In one embodiment, the fragment can comprise 10-500 amino acids.

In one embodiment, the antigen is a melanoma antigen. Exemplary melanoma antigens include, but are not limited to, tyrosinase, gp75 (tyrosinase related protein-1 (TRP-1)), gp100 (Pmel17), Melan A/MART-1, TRP-2, MAGE family, BAGE family, GAGE family, NY-ESO-1, CDK4, β-catenin, mutated introns, N-acetylglucosaminyltransferase V gene product, MUM-1, p15, gangliosides (e.g., GM2, GD2, GM3, GD3), high molecular weight chondroitin sulfate proteoglycan, p97 melanotransferrin, and SEREX antigens (e.g., D-1, SSX-2) (Hodi F S, Clin Cancer Res, Feb. 1, 2006, 12: 673-678), or fragments thereof.

In certain embodiments, the antigen comprises a non-tumor antigen such as a microbial antigen. For example, the microbial antigen may comprise a bacterial antigen, a fungal antigen, an archaean antigen, or a protozoan antigen. In some embodiments, the microbial antigen is a viral antigen, e.g., an HIV antigen or influenza antigen. In some embodiments, the antigen is from a microbe such as a bacterium, virus, protozoan, archaean, or fungus. Various embodiments relate to vaccinating against or treating a bacterial, viral, or fungal infection. In various embodiments, a delivery vehicle comprising an antigen from a pathogen. For example, a pathogen includes but is not limited to a fungus, a bacterium (e.g., Staphylococcus species, Staphylococcus aureus, Streptococcus species, Streptococcus pyogenes, Pseudomonas aeruginosa, Burkholderia cenocepacia, Mycobacterium species, Mycobacterium tuberculosis, Mycobacterium avium, Salmonella species, Salmonella typhi, Salmonella typhimurium, Neisseria species, Brucella species, Bordetella species, Borrelia species, Campylobacter species, Chlamydia species, Chlamydophila species, Clostrium species, Clostrium botulinum, Clostridium difficile, Clostridium tetani, Helicobacter species, Helicobacter pylon, Mycoplasma pneumonia, Corynebacterium species, Neisseria gonorrhoeae, Neisseria meningitidis, Enterococcus species, Escherichia species, Escherichia coli, Listeria species,

*Francisella* species, *Vibrio* species, *Vibrio cholera*, *Legionella* species, or *Yersinia pestis*), a virus (e.g., adenovirus, Epstein-Barr virus, Hepatitis A virus, Hepatitis B virus, Hepatitis C virus, Herpes simplex virus type 1, 2, or 8, human immunodeficiency virus, influenza virus, measles, Mumps, human papillomavirus, poliovirus, rabies, respiratory syncytial virus, rubella virus, or varicella-zoster virus), a parasite or a protozoa (e.g., *Entamoeba histolytica*, *Plasmodium*, *Giardia lamblia*, *Trypanosoma brucei*, or a parasitic protozoa such as malaria-causing *Plasmodium*). In one embodiment, a pathogen antigen can be derived from a pathogen cell or particle described herein.

IV. Labeling Cells with Click Reagents In Vivo

In one embodiment, the invention provides an in vivo method of labeling a cell, e.g., an immune cell, e.g., a dendritic cell, with a click reagent. The method can comprise administering to a subject a device comprising a polymer scaffold and a click reagent, as disclosed herein, and maintaining the device in the subject for a period of time sufficient for recruitment of the cell to the device. Devices comprising click reagents are disclosed herein. Any of the devices disclosed herein are suitable for use in in vivo methods of cell labeling. In an exemplary embodiment, the click chemistry reagent is formulated in a nanoparticle. In exemplary embodiments, the device comprises a hydrogel scaffold containing nanoparticles comprising click chemistry reagents embedded therein.

Following administration, the device can be maintained in the subject for a period of time sufficient for recruitment of cells to the device. The period of time sufficient for recruitment of cells can be determined by methods including, for example, administering the device to one or more test subjects, removing the device after predetermined intervals of time, and quantifying the number of cells present in the device. In an exemplary embodiment, the cells are immune cells, e.g., dendritic cells. In one embodiment, the period of time sufficient for recruitment of cells is 2-21 days. In another embodiment, the period of time sufficient for recruitment of cells is 2-14 days. In another embodiment, the period of time sufficient for recruitment of cells is 2-10 days. In another embodiment, the period of time sufficient for recruitment of cells is 3-7 days. In another embodiment, the period of time sufficient for recruitment of cells is 3-5 days. In exemplary embodiments, the period of time sufficient for recruitment of cells is about 2, 3, 4, 5, 6, 7, 8, 9, 10, 11, 12, 13, 14, 15, 16, 17, 18, 19, 20, or 21 days, or more. In another exemplary embodiment, the period of time sufficient for recruitment of cells is about 3 days. In another exemplary embodiment, the period of time sufficient for recruitment of cells is at least 2 days, at least 3 days, at least 4 days, at least 5 days, at least 6 days, at least 7 days, at least 8 days, at least 9 days, at least 10 days, at least 14 days, at least 21 days, or more. In some embodiments, the period of time sufficient for recruitment of cells is at least about 24 hours, 48 hours, 72 hours, 96 hours, or 120 hours. In some embodiments, the period of time sufficient for recruitment of cells is about 48-96 hours. In some embodiments, the period of time sufficient for recruitment of cells is about 48-72 hours. In some embodiments, the period of time sufficient for recruitment of cells is about 72 hours.

In embodiments in which the device is a hydrogel, the hydrogel scaffold can, in some embodiments, be disrupted by application of ultrasound to the device, e.g., by application of ultrasound to the subject in the vicinity of the device. Ultrasound treatment can induce the burst release of reagents, e.g., polymers or nanoparticles, embedded in the hydrogel, by temporarily disrupting the ionic crosslinks of the gel. Accordingly, ultrasound can be applied after infiltration of cells, e.g., immune cells, into the device, to increase the availability of nanoparticles for uptake by the cells. In one embodiment, ultrasound is applied to the hydrogel after a period of time sufficient for recruitment of cells to the device. For example, ultrasound can be applied to the scaffold about 2-21 days after administration of the scaffold to a subject. In another embodiment, ultrasound is applied to the hydrogel scaffold about 2-14 days after administration of the scaffold to a subject. In another embodiment, ultrasound is applied to the hydrogel scaffold about 2-10 days after administration of the scaffold to a subject. In another embodiment, ultrasound is applied to the hydrogel scaffold about 3-7 days after administration of the scaffold to a subject. In another embodiment, ultrasound is applied to the hydrogel scaffold about 3-5 days after administration of the scaffold to a subject. In another embodiment, ultrasound is applied to the hydrogel scaffold about 2, 3, 4, 5, 6, 7, 8, 9, 10, 11, 12, 13, 14, 15, 16, 17, 18, 19, 20, or 21 days, or more, after administration of the scaffold to a subject. In another embodiment, ultrasound is applied to the hydrogel scaffold about 3 days after administration of the scaffold to a subject. In another exemplary embodiment, ultrasound is applied to the hydrogel scaffold at least 2 days, at least 3 days, at least 4 days, at least 5 days, at least 6 days, at least 7 days, at least 8 days, at least 9 days, at least 10 days, at least 14 days, at least 21 days, or more after administration of the scaffold to a subject. In some embodiments, ultrasound is applied to the hydrogel scaffold at least about 24 hours, 48 hours, 72 hours, 96 hours, or 120 hours after administration of the scaffold to a subject. In some embodiments, ultrasound is applied to the hydrogel scaffold about 48-96 hours after administration of the scaffold to a subject. In some embodiments, ultrasound is applied to the hydrogel scaffold about 48-72 hours after administration of the scaffold to a subject. In some embodiments, ultrasound is applied to the hydrogel scaffold about 72 hours after administration of the scaffold to a subject.

Ultrasound parameters, including the amplitude and duration of treatment, can be selected using standard methods. In one embodiment, the ultrasound treatment is applied at about 10%, 20%, 30%, 40%, 50%, 60%, 70%, 80%, or 90% amplitude. In an exemplary embodiment, the ultrasound treatment is applied at 20-40% amplitude. In another exemplary embodiment, the ultrasound treatment is applied at about 30% amplitude. In one embodiment, the ultrasound treatment is applied for a duration of about 1-30 minutes. For example, the ultrasound treatment can be applied for about 1, 2, 3, 4, 5, 6, 7, 8, 9, 10, 12, 15, 20, 25, or 30 minutes. In an exemplary embodiment, the ultrasound treatment is applied for about 1-5 minutes, e.g., 2-3 minutes. In one embodiment, the ultrasound treatment is applied for about 2.5 minutes.

Administration of the polymer scaffold device to a subject can be performed using standard techniques. As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by injection, e.g., subcutaneous injection or intratumoral injection, or by intravenous infusion.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

In some embodiments, administration includes implanting or injecting a device, e.g., a hydrogel, described herein in a subject.

In one embodiment, the site of administration is at or near the site of a tumor in a subject. For example, the device can be administered within 5 cm of a tumor, e.g., within 4 cm, within 3 cm, within 2 cm, or within 1 cm of a tumor in the subject. In other embodiments, the device can be administered within 10 mm of tumor, e.g., within 9 mm, within 8 mm, within 7 mm, within 6 mm, within 5 mm, within 4 mm, within 3 mm, within 2 mm, or within 1 mm of a tumor in a subject. In other embodiments, the device can be administered intratumorally.

In another embodiment, the site of administration is distal from the site of a tumor in a subject. For example, the device can be administered more than 5 cm from the site of a tumor. In one embodiment, the device is administered to a limb of a subject, e.g., to an arm or leg of a subject.

The term "therapeutically effective amount", as used herein, means that amount of a compound, material, or composition comprising a compound described herein which is effective for producing some desired therapeutic effect in at least a sub-population of cells in a subject at a reasonable benefit/risk ratio applicable to any medical treatment. Thus, "therapeutically effective amount" means that amount which, when administered to a subject for treating a disease, is sufficient to effect such treatment for the disease.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

V. Targeting Agents to Cells Using Click Chemistry Pairs

Cells labeled with click reagents in vitro, ex vivo, or in vivo can be covalently coupled to a moiety of interest using click chemistry. For example, the cell can be contacted with a counterpart click reagent that is, in turn, attached to a moiety, thereby conjugating the moiety to the cell. The contacting can occur in vitro, ex vivo, or in vivo. Accordingly, in one embodiment, cells are labeled with a click reagent in vitro or ex vivo, and are contacted in vitro or ex vivo with a counterpart click reagent that is attached to a moiety for conjugation to the cells. In another embodiment, cells are labeled with a click reagent in vitro or ex vivo, and are contacted in vivo with a counterpart click reagent that is attached to a moiety for conjugation to the cells. In this embodiment, the contacting can be performed by administration of the counterpart click reagent attached to the moiety to a subject who comprises the click-labeled cells. In another embodiment, cells are labeled with a click reagent in vivo, and are contacted in vivo with a counterpart click reagent that is attached to a moiety for conjugation to the cells. Exemplary moieties that can be conjugated to cells in this manner are described below.

In some embodiments, the click reagent presented on the surface of a cell, e.g., coupled to a cell surface glycoprotein, may react with its counterpart click reagent that is, in turn, attached to a moiety, thereby conjugating the moiety to the cell. Any moiety may be conjugated to the click labeled cells of the invention using the click reagents. The moiety should be coupled to a click reagent that can rapidly and selectively react ("click") with its counterpart click reagent, i.e., the click reagent presented on the surface of a cell to be targeted, under mild conditions in aqueous solution. The mild conditions include neutral pH, aqueous solution and ambient temperature, with low reactant concentrations. In embodiments in which cells are labeled with a click reagent by recruitment and infiltration of a polymer scaffold device comprising the click reagent, as described herein, the click reagent presented on the surface of a cell to be targeted is also the click reagent present in the device. Exemplary click reagent pairs are well known to one of skill in the art and include, but are not limited to, azide and dibenzocyclooctyne (DBCO), tetrazine and transcyclooctene, and tetrazine and norbornene. Accordingly, a cell labeled with azide can be conjugated to a moiety that is coupled to DBCO. In other embodiments, a cell labeled with DBCO can be conjugated to a moiety that is coupled to azide. In other embodiments, a cell labeled with tetrazine can be conjugated to a moiety that is coupled to transcyclooctene or norbornene. In other embodiments, a cell labeled with transcyclooctene or norbornene can be conjugated to a moiety that is coupled to tetrazine. In embodiments of in which cells are labeled in vivo by recruitment to a device comprising one or more of the click reagents described herein, the moiety to be conjugated to a cell is coupled to a click reagent that can selectively react with the click reagent present in the device.

For example, in embodiments in which a subject comprises a device comprising a click reagent that comprises azide, a moiety coupled to DBCO can be conjugated to click-labeled cells in the subject. Likewise, in another embodiment in which a subject comprises a device comprising a click reagent that comprises DBCO, a moiety coupled to azide can be conjugated to click-labeled cells in the subject. In another embodiment in which a subject comprises a device comprising a click reagent that comprises tetrazine, a moiety coupled to transcyclooctene or norbornene can be conjugated to click-labeled cells in the subject. In another embodiment in which a subject comprises a device comprising a click reagent that comprises transcyclooctene or norbornene, a moiety coupled to tetrazine can be conjugated to click-labeled cells in the subject.

Non-limiting examples of moieties that can be targeted to click-labeled cells include a small organic molecule, a small inorganic molecule; a saccharine; a monosaccharide; a disaccharide; a trisaccharide; an oligosaccharide; a polysaccharide; a peptide; a protein, a peptide analog, a peptide derivative; a peptidomimetic; an antibody (polyclonal or monoclonal); an antigen binding fragment of an antibody; a nucleic acid, e.g., an oligonucleotide, an antisense oligonucleotide, siRNAs, shRNAs, a ribozyme, an aptamer, microRNAs, pre-microRNAs, iRNAs, plasmid DNA (e.g. a condensed plasmid DNA), a modified RNA, and a nucleic acid analog or derivative. In some embodiments, the moiety is a therapeutic agent. In other embodiments, the moiety is a detection agent.

This strategy allows cells in vivo, ex vivo, or in vitro to be covalently coupled to virtually any agent.

In an exemplary embodiment, the click-coupled moieties are targeted to click-labeled immune cells, e.g., click-labeled dendritic cells.

In one embodiment, the click-coupled moiety is a protein, a peptide, a nucleic acid, or a small molecule. In an exemplary embodiment, the click-coupled moiety is a protein or a peptide.

Using this approach, cells can be covalently coupled to a detectable label. For example, click-labeled cells can be contacted with a detectable label coupled to a second click reagent, which selectively reacts with the click reagent on the click-labeled cells. In embodiments where cells are covalently coupled to a detectable label in vivo, this can be accomplished by administering the detectable label coupled to the second click reagent to a subject. The detectable label can be a fluorescent label. Exemplary fluorescent labels include, but are not limited to, Alexa Fluor (e.g., Alexa Fluor 405, Alexa Fluor 488, Alexa Fluor 700, Alexa Fluor 750, etc.), GFP, FITC, CFSE, DyLight 488, phycoerythrin (PE), propidium iodide (PI), PerCP, Cy5, Cy5.5, Cy7, APC-eFluor 780, Draq-5, APC, amine aqua, pacific orange, pacific blue, DAPI, eFluor 450, eFluor 605, eFluor 625, and eFluor 650. In other embodiments, the detectable label can be a radiolabel. Exemplary radiolabels include, but are not limited to, $^3$H, $^{14}$C, $^{13}$N, $^{15}$O, $^{18}$F, $^{32}$P, $^{35}$S, $^{99m}$Tc, $^{123}$I, $^{125}$I, and $^{67}$Ga.

In other embodiments, cells can be covalently coupled to an antigen. For example, click-labeled cells can be contacted with an antigen coupled to a second click reagent, which selectively reacts with the click reagent on the click-labeled cells. In embodiments where cells are covalently coupled to an antigen in vivo, this can be accomplished by administering the antigen coupled to the second click reagent to a subject. In one embodiment, the antigen is an undesirable antigen. For example, the antigen can be the desired target of an immune response. In one embodiment, the antigen is a cancer antigen, also referred to herein as a cancer antigen.

A cancer antigen is an antigen that is selectively or semi-selectively expressed by cancer cells, and that is generally not expressed under normal conditions by non-cancerous cells. In some embodiments, the cancer antigen is a central nervous system (CNS) cancer antigen, CNS germ cell tumor antigen, lung cancer antigen, leukemia antigen, acute myeloid leukemia antigen, multiple myeloma antigen, renal cancer antigen, malignant glioma antigen, medulloblastoma antigen, breast cancer antigen, prostate cancer antigen, Kaposi's sarcoma antigen, ovarian cancer antigen, adenocarcinoma antigen, or melanoma antigen. In an exemplary embodiment, the cancer antigen is a melanoma antigen, for example, tyrosinase, gp75 (tyrosinase related protein-1 (TRP-1)), gp100 (Pmel17), Melan A/MART-1, TRP-2, MAGE family, BAGE family, GAGE family, NY-ESO-1, CDK4, β-catenin, mutated introns, N-acetylglucosaminyl-transferase V gene product, MUM-1, p15, gangliosides (e.g., GM2, GD2, GM3, GD3), high molecular weight chondroitin sulfate proteoglycan, p97 melanotransferrin, and SEREX antigens (e.g., D-1, SSX-2) (Hodi F S, Clin Cancer Res, Feb. 1, 2006, 12: 673-678). In some embodiments, the antigen is a non-tumor antigen. For example, the antigen can be a viral antigen or a microbial antigen. In embodiments in which the click-labeled cells are immune cells, e.g., dendritic cells, conjugation of an antigen to the cells through the reaction of counterpart click reagents can promote an immune response against the antigen in the subject. For example, delivery of an antigen to DCs via click chemistry can significantly augment or enhance an antigen-specific T cell response against the antigen.

In some embodiments, cells can be covalently coupled to an adjuvant. For example, click-labeled cells can be contacted with an adjuvant coupled to a second click reagent, which selectively reacts with the click reagent on the click-labeled cells. In embodiments where cells are covalently coupled to an adjuvant in vivo, this can be accomplished by administering the adjuvant coupled to the second click reagent to the subject. An adjuvant, as used herein, is an agent that improves or enhances a subject's immune response to an antigen. Exemplary adjuvants include, but are not limited to, toll-like receptor (TLR) agonists, poly(I:C), monophosphoryl lipid A (MPLA), pathogen associated molecular patterns (PAMPs), and cytokines, and combinations thereof. In one embodiment, the adjuvant is a TLR agonist. For example, the TLR agonist can, in some embodiments, be a TLR3 agonist. Exemplary TLR3 agonists include, but are not limited to, polyinosine-polycytidylic acid (poly I:C), PEI-poly (I:C), polyadenylic-polyuridylic acid (poly (A:U)), PEI-poly (A:U), or double stranded ribonucleic acid (RNA). In another embodiment, the TLR agonist can be a TLR9 agonist. Exemplary TLR9 agonists include, but are not limited to, a cytosine-guanosine oligonucleotide (CpG-ODN), a poly(ethylenimine) (PEI)-condensed oligonucleotide (ODN) such as PEI-CpG-ODN, or double stranded deoxyribonucleic acid (DNA). In an exemplary embodiment, the adjuvant is CpG-ODN. In some embodiments, cells are covalently coupled to a combination of adjuvants, e.g., a TLR3 agonist and a TLR9 agonist. In some embodiments, cells are covalently coupled to an antigen (e.g., one or more antigens) and an adjuvant (e.g., one or more adjuvants). For example, a subject comprising click-labeled target cells, e.g. click-labeled immune cells, can be administered an adjuvant coupled to a second click reagent, and an antigen coupled to a second click reagent, wherein the second click reagent selectively reacts with the click reagent on the click-labeled cells. In one embodiment, the click-labeled cells are dendritic cells.

In some embodiments, cells can be covalently coupled to a cytokine. For example, click-labeled cells can be contacted with a cytokine coupled to a second click reagent, which selectively reacts with the click reagent on the click-labeled cells. In embodiments where cells are covalently coupled to a cytokine in vivo, this can be accomplished by administering the cytokine coupled to the second click reagent to the subject. Exemplary cytokines include, but are not limited to, interleukin 15 (IL-15), interleukin 10 (IL-10), IL-2, interleukin 12 (IL-12), interleukin 15 (IL-15), interleukin 18 (IL-18), tumor necrosis factor alpha (TNFα), interferon gamma (IFNγ), granulocyte-macrophage colony-stimulating factor (GM-CSF), or a combination thereof. In one embodiment, the cytokine receptor is IL-15.

In some embodiments, cells can be covalently coupled to a cytokine receptor. For example, click-labeled cells can be contacted with a cytokine receptor coupled to a second click reagent, which selectively reacts with the click reagent on the click-labeled cells. In embodiments where cells are covalently coupled to a cytokine receptor in vivo, this can be accomplished by administering the cytokine receptor coupled to the second click reagent to the subject. Cytokine receptors include, but are not limited to, growth hormone receptors, Type I interleukin receptors, type II interleukin receptors, GM-CSF receptor, interferon alpha/beta receptor, interferon gamma receptor, CD27, CD30, CD40, CD120IL-15 receptor, and IL-12 receptor. In one embodiment, the cytokine receptor is IL-15 receptor.

In one embodiment, cells can be covalently coupled to a cytokine/cytokine receptor fusion protein. For example, click-labeled cells can be contacted with a cytokine/cytokine receptor fusion protein that is coupled to a second click reagent, which selectively reacts with the click reagent on the click-labeled cells. In embodiments where cells are covalently coupled to a cytokine/cytokine receptor fusion protein in vivo, this can be accomplished by administering the cytokine/cytokine receptor fusion protein that is coupled to the second click reagent to the subject. In one embodiment, the fusion protein is an IL-15/IL-15 receptor alpha (IL-15/ILRα) fusion protein. IL-15 is a cytokine that can bind to IL-15Rα on the surface of antigen presenting cells to induce proliferation of $CD8^+$ T cells and natural killer cells. The IL-15/IL-15Rα complex enables prolonged and more persistent activation of T cells and natural killer cells. Accordingly, in one embodiment, a subject comprising click-labeled antigen presenting cells, e.g., click-labeled dendritic cells, can be administered an IL-15/IL-15Rα fusion protein coupled to a second click reagent.

A moiety coupled to a click reagent can be administered to a subject, e.g., a subject comprising click-coupled cells, by any suitable method. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by injection, e.g., subcutaneous injection or intratumoral injection, or by intravenous infusion.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives.

Transmucosal administration can be accomplished through the use of nasal sprays or suppositories. For transdermal administration, the compounds are formulated into ointments, salves, gels, or creams as generally known in the art.

In some embodiments, the administration is by subcutaneous injection.

In one embodiment, the site of administration is at or near the site of a tumor in a subject. For example, a moiety coupled to a click reagent can be administered within 5 cm of a tumor, e.g., within 4 cm, within 3 cm, within 2 cm, or within 1 cm of a tumor in the subject.

In other embodiments, a moiety coupled to a click reagent can be administered within 10 mm of tumor, e.g., within 9 mm, within 8 mm, within 7 mm, within 6 mm, within 5 mm, within 4 mm, within 3 mm, within 2 mm, or within 1 mm of a tumor in a subject. In other embodiments, a moiety coupled to a click reagent can be administered intratumorally.

In another embodiment, the site of administration is distal from the site of a tumor in a subject. For example, a moiety coupled to a click reagent can be administered more than 5 cm from the site of a tumor.

In one embodiment, the site of administration is at or near the site of a polymer scaffold device of the invention. For example, a moiety coupled to a click reagent can be administered within 5 cm of the device, e.g., within 4 cm, within 3 cm, within 2 cm, or within 1 cm of the device in the subject. In other embodiments, a moiety coupled to a click reagent can be administered within 10 mm the device, e.g., within 9 mm, within 8 mm, within 7 mm, within 6 mm, within 5 mm, within 4 mm, within 3 mm, within 2 mm, or within 1 mm of the device in a subject. In other embodiments, a moiety coupled to a click reagent is administered at the site of the device in a subject.

In another embodiment, the site of administration is distal from the site of the device in a subject. For example, a moiety coupled to a click reagent can be administered more than 5 cm from the site of the device.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject. In one embodiment, the amount is a therapeutically effective amount. In another embodiment, the amount is an immunogenic amount.

The term "therapeutically effective amount", as used herein, means that amount of a compound, material, or composition comprising a compound described herein which is effective for producing some desired therapeutic effect in at least a sub-population of cells in a subject at a reasonable benefit/risk ratio applicable to any medical treatment. Thus, "therapeutically effective amount" means that amount which, when administered to a subject for treating a disease, is sufficient to effect such treatment for the disease.

The term "immunogenic amount" of an antigen and/or adjuvant refers to an amount of antigen and/or adjuvant sufficient to stimulate a useful immune response. The amount of antigen and/or adjuvant necessary to provide an immunogenic amount is readily determined by one of ordinary skill in the art, e.g., by preparing a series of vaccines of the invention with varying concentrations of antigen and/or adjuvant, administering the vaccines to suitable laboratory animals (e.g., mice, rats, guinea pigs, etc.), and assaying the resulting immune response by measuring serum antibody titer, antigen-induced swelling in the skin, and the like.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

In one embodiment, the dosage is a weight-based dose. In exemplary embodiments, the weight-based dose is 0.001-100 mg/kg. For example, in some embodiments, the dosage is 0.001-0.1 mg/kg. In other embodiments, the dosage is 0.01-1 mg/kg. In other embodiments, the dosage is 0.1-10 mg/kg. In other embodiments, the dosage is 1-100 mg/kg.

In other embodiments, the dosage is about 1 mg/kg, 2 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, or 100 mg/kg.

The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

In embodiments in which cells are labeled with a click reagent in vivo by recruitment of cells to a polymer scaffold device of the invention comprising the click reagent, a moiety for conjugation to the cell is preferably administered to the subject after a period of time sufficient for labeling of cells in the subject with the click reagent present in the device. The average time for cells in a subject to become labeled with a click reagent following administration of the device can be determined empirically, for example, by detecting the presence of click-labeled cells in a test subject using a click reagent coupled to a detectable label. In exemplary embodiments, the moiety for conjugation to click-labeled cells is administered to a subject at least 2 days, at least 3 days, at least 4 days, at least 5 days, at least 6 days, at least 7 days, at 8 days, at least 9 days, at least 10 days, at least 12 days, at least 14 days, or at least 21 days after administration of the device to the subject. For example, in some embodiments, the moiety is administered about 2-21 days after administration of the device. In some embodiments, the moiety is administered about 4-21 days after administration of the device. In some embodiments, the moiety is administered about 4-14 days after administration of the device. In some embodiments, the moiety is administered about 4-10 days after administration of the device. In some embodiments, the moiety is administered about 6-10 days after administration of the device.

VI. Methods of Enhancing an Immune Response and Preventing or Treating a Disease The compositions and methods disclosed herein can be used, in some embodiments, to promote, augment, or enhance a subject's immune response to an antigen. The methods allow targeted delivery of agents such as antigens and/or adjuvants directly to immune cells localized at biologically relevant sites in the body, such as the lymph nodes. In exemplary embodiments, the methods allow targeted delivery of an IL-15/IL-15Rα fusion protein to immune cells, e.g., dendritic cells.

In one embodiment, the invention provides a method of promoting an immune response to an antigen in a subject, by targeted delivery of the antigen to immune cells in the subject. The method comprises administering to the subject a device comprising a polymer scaffold comprising a click reagent of the invention, maintaining the device in the subject for a period of time sufficient for recruitment of immune cells, and administering to the subject a second click chemistry reagent coupled to the antigen, wherein the second click chemistry reagent can selectively react with the click reagent present in the device. Upon administration of the device to the subject, immune cells, e.g., dendritic cells, infiltrate the device, and take up the click reagent. The click reagent is metabolically processed inside the cells, as described herein, and is displayed on the surface of the cells by incorporation into cell surface glycoproteins. As immune cells can migrate into and out of the polymer scaffold devices described herein, the immune cells can leave the device and localize to other sites in the body, e.g., lymph nodes. Administration of the antigen coupled to a second click chemistry reagent specifically targets the antigen to the click-labeled immune cells. Accordingly, in one embodiment, an antigen can be specifically targeted to immune cells localized to the appropriate niche in vivo. For example, antigen can be targeted to immune cells localized to lymph nodes in a subject. The antigen is covalently attached to the surface of the immune cells, e.g., dendritic cells, through reaction of the click reagents, thereby potentiating the downstream immune response to the antigen in the subject.

In another embodiment, the invention provides a method of promoting an immune response to an antigen in a subject, by targeted delivery of an adjuvant to immune cells in the subject. The method comprises administering to the subject a device comprising a polymer scaffold comprising a click reagent of the invention, maintaining the device in the subject for a period of time sufficient for recruitment of immune cells, and administering to the subject a second click chemistry reagent coupled to the adjuvant, wherein the second click chemistry reagent can selectively react with the click reagent present in the device. The adjuvant is covalently attached to the surface of the immune cells, e.g., dendritic cells, through reaction of the click reagents, thereby potentiating a downstream immune response to an antigen by providing an adjuvant directly to immune cells. Suitable adjuvants are described herein. Exemplary adjuvants include TLR agonists, e.g., CpG-ODN, and/or poly (I.C). Immune cells recruited to the device can be primed to mount an immune response against a particular antigen of interest, by inclusion of the antigen in the device. Upon infiltration of the device, the immune cells can take up and process antigen from the device, in addition to the click reagent. Accordingly, in one embodiment, the device comprises an antigen. For use as a cancer vaccine, the device can contain a cancer antigen. In one embodiment, the cancer antigen is a melanoma antigen.

In another embodiment, the invention provides a method of promoting an immune response to an antigen in a subject, by targeted delivery of an IL-15/IL-15Rα fusion protein to immune cells, e.g., dendritic cells in the subject. IL-15 is a cytokine that can bind to IL-15 receptor a (IL-15Rα) on the surface of antigen presenting cells to induce the proliferation of $CD8^+$ T cells and natural killer (NK) cells. The IL-15/IL-15Rα complex enables prolonged and more persistent activation of target T cells and NK cells. The invention provides an IL-15/IL-15Rα fusion protein coupled to a click chemistry reagent, e.g., azide, DBCO, transcyclooctene, tetrazine, norbomene, and variants thereof.

In one aspect, the invention provides a method of promoting an immune response to an antigen in a subject, comprising administering to the subject a device comprising a polymer scaffold comprising a click reagent of the invention, maintaining the device in the subject for a period of time sufficient for recruitment of immune cells, and administering to the subject a second click chemistry reagent coupled to an IL-15/IL-15Rα fusion protein, wherein the second click chemistry reagent can selectively react with the click reagent present in the device. The IL-15/IL-15Rα fusion protein is covalently attached to the surface of the immune cells, e.g., dendritic cells, through reaction of the click reagents, thereby potentiating a downstream immune response to an antigen by activating T cells and NK cells. As described above, immune cells recruited to the device can be primed to mount an immune response against a particular antigen of interest, by inclusion of the antigen in the device. Upon infiltration of the device, the immune cells can take up and process antigen from the device, in addition to the click reagent. Accordingly, in one embodiment, the device comprises an antigen. For use as a cancer vaccine, the device can contain a cancer antigen. In one embodiment, the cancer antigen is a melanoma antigen.

Recruitment of immune cells to the device can be enhanced by inclusion of a chemoattractant for immune cells in the device. Accordingly, in some embodiments, the device used in the foregoing methods contains GM-CSF, which promotes the recruitment of immune cells including dendritic cells to the device.

In some embodiments, the device can comprise a hydrogel polymer scaffold, as described herein. The hydrogel scaffold can contain the click reagents of the invention. The click reagents can be formatted as polymers or nanoparticles. In embodiments in which the device comprises a hydrogel, the method can, in some embodiments, further comprise applying ultrasound to the device in the subject, to facilitate metabolic labeling of recruited immune cells by inducing burst release of the click reagents from the hydrogel, increasing their availability to cells in the device.

In some embodiments, the device can comprise a hydrogel polymer scaffold, as described herein, which contains porogen hydrogel microbeads. Such a scaffold can form pores in situ, following administration of the device to a subject. Cells can infiltrate the device after the formation of pores in the hydrogel.

In some embodiments, the click reagent is a polymer comprising repeating saccharide units, wherein each saccharide unit is attached to a click reagent. In one embodiment, the saccharide is mannose, and the click reagent is azide. In an exemplary embodiment, the click reagent comprises the structure of formula (2), wherein n is a number between 10 and 1000:

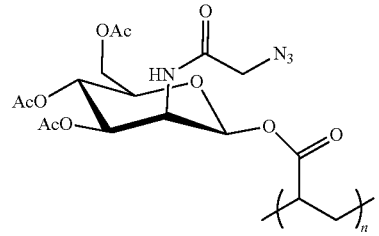

(2)

In another exemplary embodiment, the click reagent comprises the structure of formula (3), wherein n is a number between 10 and 1000, and m is a number between 45 and 200.

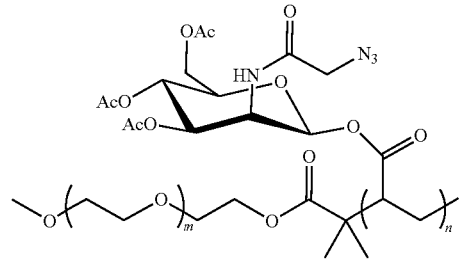

(3)

In another exemplary embodiment, the click reagent comprises the structure of formula (4), wherein n is a number between 10 and 1000, and m is a number between 45 and 200.

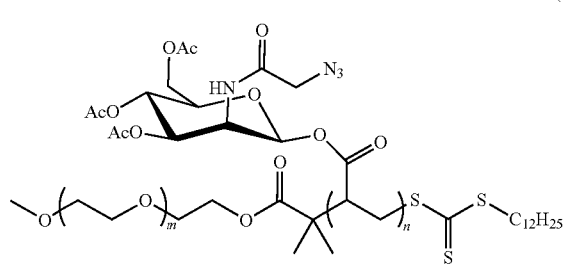

(4)

In some embodiments, the click reagent is formatted as a nanoparticle.

In some embodiments, foregoing compositions and methods can be used as a cancer vaccine. In such embodiments, the antigen comprises a cancer antigen. In exemplary embodiments, the cancer antigen is a melanoma antigen. Additional cancer antigens are disclosed herein. Accordingly, in some embodiments, the foregoing compositions and methods can be used in methods of preventing or treating cancer in a subject, by promoting an immune response to the cancer in the subject.

In some embodiments, the invention provides a method of preventing or treating cancer in a subject, comprising administering to the subject a device comprising a polymer scaffold comprising a click reagent of the invention, maintaining the device in the subject for a period of time sufficient for recruitment of immune cells, and administering to the subject a second click chemistry reagent coupled to a cancer antigen, wherein the second click chemistry reagent can selectively react with the click reagent present in the device.

In other embodiments, the invention provides a method of preventing or treating a subject having cancer, comprising administering to the subject a device comprising a polymer scaffold comprising a click reagent of the invention and a cancer antigen, maintaining the device in the subject for a period of time sufficient for recruitment of immune cells, and administering to the subject a second click chemistry reagent coupled to the adjuvant, wherein the second click chemistry reagent can selectively react with the click reagent present in the device.

In other embodiments, the invention provides a method of preventing or treating a subject having cancer, comprising administering to the subject a device comprising a polymer scaffold comprising a click reagent of the invention and a cancer antigen, maintaining the device in the subject for a period of time sufficient for recruitment of immune cells, and administering to the subject a second click chemistry reagent coupled to an IL-15/IL-15Rα fusion protein, wherein the second click chemistry reagent can selectively react with the click reagent present in the device.

VII. Pharmaceutical Compositions

For administration to a subject, the polymers, nanoparticles, devices, scaffolds, hydrogels and agents coupled to click chemistry reagents described herein can be provided as pharmaceutically acceptable (e.g., sterile) compositions. Accordingly, in one aspect, the invention provides a pharmaceutical composition comprising a polymer or nanoparticle comprising a click reagent. In another aspect, the invention provides a pharmaceutical composition comprising a device that comprises polymer scaffold comprising a click reagent. In one embodiment, the polymer scaffold is a hydrogel.

These pharmaceutically acceptable compositions can be formulated together with one or more pharmaceutically acceptable carriers (additives) and/or diluents. As described in detail below, the pharmaceutical compositions of the present disclosure can be specifically formulated for administration in solid or liquid form, including those adapted for the following: (1) parenteral administration, for example, by subcutaneous, intramuscular, intravenous (e.g., bolus or infusion) or epidural injection as, for example, a sterile solution or suspension, or sustained-release formulation; (2) oral administration, for example, drenches (aqueous or non-aqueous solutions or suspensions), lozenges, dragees, capsules, pills, tablets (e.g., those targeted for buccal, sublingual, and/or systemic absorption), boluses, powders, granules, pastes for application to the tongue; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., *Ann. Rev. Pharmacol. Toxicol.* 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960, content of all of which is herein incorporated by reference.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by FDA Office of Biological Standards.

As used herein, the term "pharmaceutically acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable carrier" or the like are used interchangeably herein.

The pharmaceutical compositions of the invention comprising a click reagent can be delivered to an in vivo locus in a subject. Exemplary in vivo loci include, but are not limited to site of a wound, trauma or disease. The composition can be delivered to the in vivo locus by, for example, implanting the compositions into a subject. The composition can optionally include one or more additives. Additives can include, but are not limited to, resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidones, polyethylene glycols, carboxymethyl celluloses, methyl celluloses, starch or their mixtures.

VIII. Kits

Any of the compositions described herein may be comprised in a kit. In a non-limiting example, the kit comprises a click functionalized polysaccharide polymer which is a product of radical-catalyzed polymerization. In certain embodiments, the kit includes nanoparticles for labeling cells with a click reagent comprising the click functionalized polysaccharide polymer. In some embodiments, the kit includes the device and/or scaffold described elsewhere herein. In a non-limiting example, the kit includes a device including a polymer scaffold, a click reagent, and a chemoattractant for immune cells. In certain embodiments, the kit comprises a click functionalized polysaccharide polymer which is a product of radical-catalyzed polymerization and a second click chemistry reagent coupled to an agent targeted to the immune cell, wherein the second click chemistry reagent can selectively react with the click reagent present in the functionalized polysaccharide polymer. In some embodiments, the kit includes nanoparticles for labeling cells with a click reagent comprising the click functionalized polysaccharide polymer and a second click chemistry reagent coupled to an agent targeted to the immune cell, wherein the second click chemistry reagent can selectively react with the click reagent present in the nanoparticle. In certain embodiments, the kits includes a device comprising polymer scaffold, a click reagent, and a chemoattractant for immune cells, and a second click chemistry reagent coupled to an agent targeted to the immune cell, wherein the second click chemistry reagent can selectively react with the click reagent present in the device.

The kit may further include reagents or instructions for in vivo labeling a cell in a subject and/or in vitro labeling a cell with a click chemistry reagent described elsewhere herein. It may also include one or more buffers. Other kits of the invention may include components for assays to detect the labeling of the cell. In certain embodiments, the kits of the invention comprise the reagents for detecting a detectable label that is targeted to a cell.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (labeling reagent and label may be packaged together), the kit also will generally contain a second, third or other additional container into which the additional components may be separately placed. The kits may also comprise a second container means for containing a sterile, pharmaceutically acceptable buffer and/or other diluent. However, various combinations of components may be comprised in a vial. The kits of the present invention also will typically include a means for containing the compositions of the invention, e.g., the click functionalized polysaccharide polymer, and any other reagent containers in close confinement for commercial sale.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The present invention is further illustrated by the following examples, which should not be construed as limiting. The entire contents of all of the references cited throughout this application are hereby expressly incorporated herein by reference.

EXAMPLES

Example 1: Poly(Azido-Sugar) for Metabolic Labeling of DCs

It was first tested whether tetraacetyl-N-azidoacetylmannosamine ($Ac_4ManAz$), a commonly used metabolic labeling agent, can label DC2.4 cell line with azido groups (FIG. 2A). $Ac_4ManAz$ was synthesized following the reported procedure (Wang, H. et al. Selective in vivo metabolic cell-labeling-mediated cancer targeting. *Nature Chemical Biology* 13, 415-424 (2017)). To label After incubation with $Ac_4ManAz$ for three days and staining with DBCO-Cy5 for 30 min, DC2.4 cells showed significantly enhanced Cy5 signal compared to control cells without $Ac_4ManAz$ pre-treatment, but nonspecific cellular uptake of DBCO-Cy5 was high (FIG. 2B). In comparison, a DBCO- and efluor660-conjugated rat lgG2a isotype control antibody (DBCO/efluor660-antibody) showed minimal background uptake by DC2.4 cells and could well detect cell-surface azido groups (FIG. 2C). For flow cytometry analysis of azido-labeled cells, cells were seeded in a 24-well plate at a density of $1\times10^4$ cells per well and allowed to attach for 12 hours. Azido-sugar was added and incubated with cells for 72 hours. After washing with PBS, cells were incubated with DBCO/efluor660-antibody for 40 minutes along with other antibody stains on ice. Cells were then collected via a cell scraper, re-suspended in FACS buffer, and analyzed by flow cytometry.

As one objective of the present invention is to develop a pore-forming alginate gel with on-demand release of azido-sugars for DC labeling in vivo, $Ac_4ManAz$ with poor water-solubility, uncontrolled encapsulation, and burst release kinetics was disqualified. To solve these issues, the C1 site of $Ac_4ManAz$ was functionalized with an acrylate bond, followed by reversible addition-fragmentation chain transfer (RAFT) polymerization using poly(ethylene glycol) methyl ether 2-(dodecylthiocarbonothioylthio)-2-methylpropionate as the RAFT agent and azobisisobutyronitrile as the initiator to yield poly(azido-sugar)$_n$ (n=25 (G25) or 400 (G400)) (FIG. 2D). Briefly, $Ac_4ManAz$ (1 mmol) was dissolved in methanol/tetrahydrofuran (½, v/v), followed by the addition of ammonium carbonate (1.2 mmol). The reaction mixture was stirred at room temperature for 24 hours. After removal of the solvent under reduced pressure, the crude product was purified by silica gel column chromatography to yield $Ac_3ManAzOH$. $Ac_3ManAzOH$ (1.0 mmol) was then dissolved in dry dichloromethane, followed by the addition of acryloyl chloride (3.0 mmol) and triethylamine (1.0 mmol). The reaction mixture was stirred at room temperature for 24 hours. After removal of the solvent and residual acryloyl chloride, the crude product was redissolved in dichloromethane, washed with deionized water for three times, and dried to yield $Ac_3ManAzAL$. $Ac_3ManAzAL$ (1.0 mmol), azobisisobutyronitrile (AIBN, 0.008 or 0.0005 mmol), and poly(ethylene glycol) methyl ether 2-(dodecylthiocarbonothioylthio)-2-methylpropionate (PEG DDMAT, 0.04 or 0.0025 mmol) were dissolved in anhydrous DMF, followed by three freeze-thaw cycles and stirring at 65° C. for 48 hours. Poly(azido-sugar) (G25 or G400) was obtained via precipitation in cold diethyl ether, washed with diethyl ether for three times, and dried under reduced pressure. Fluorescently labeled G25 and G400 were prepared via conjugation of DBCO-dyes to G25 and G400, respectively (1 mg).

Figure 2F:
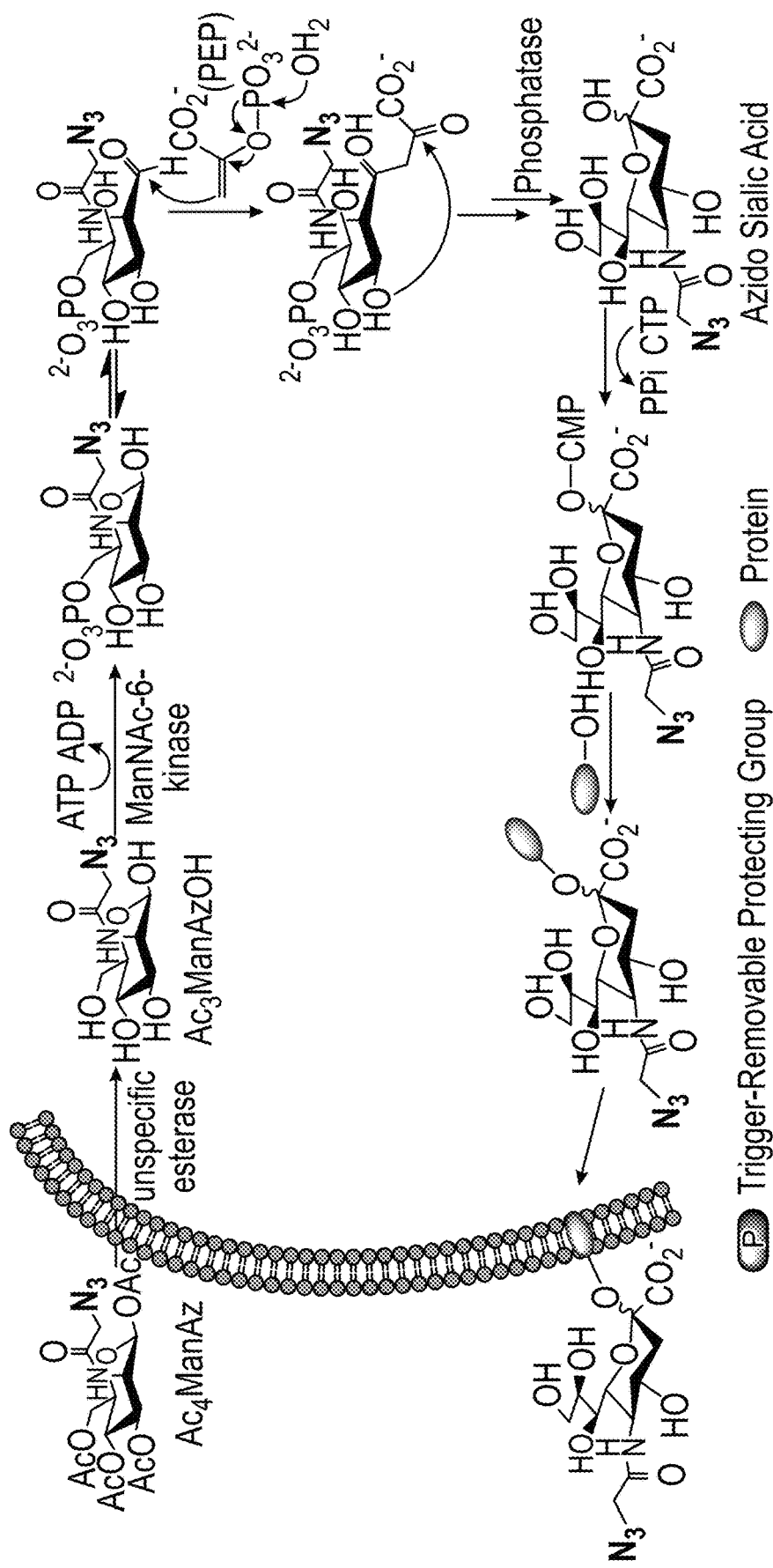
Figure 2G:
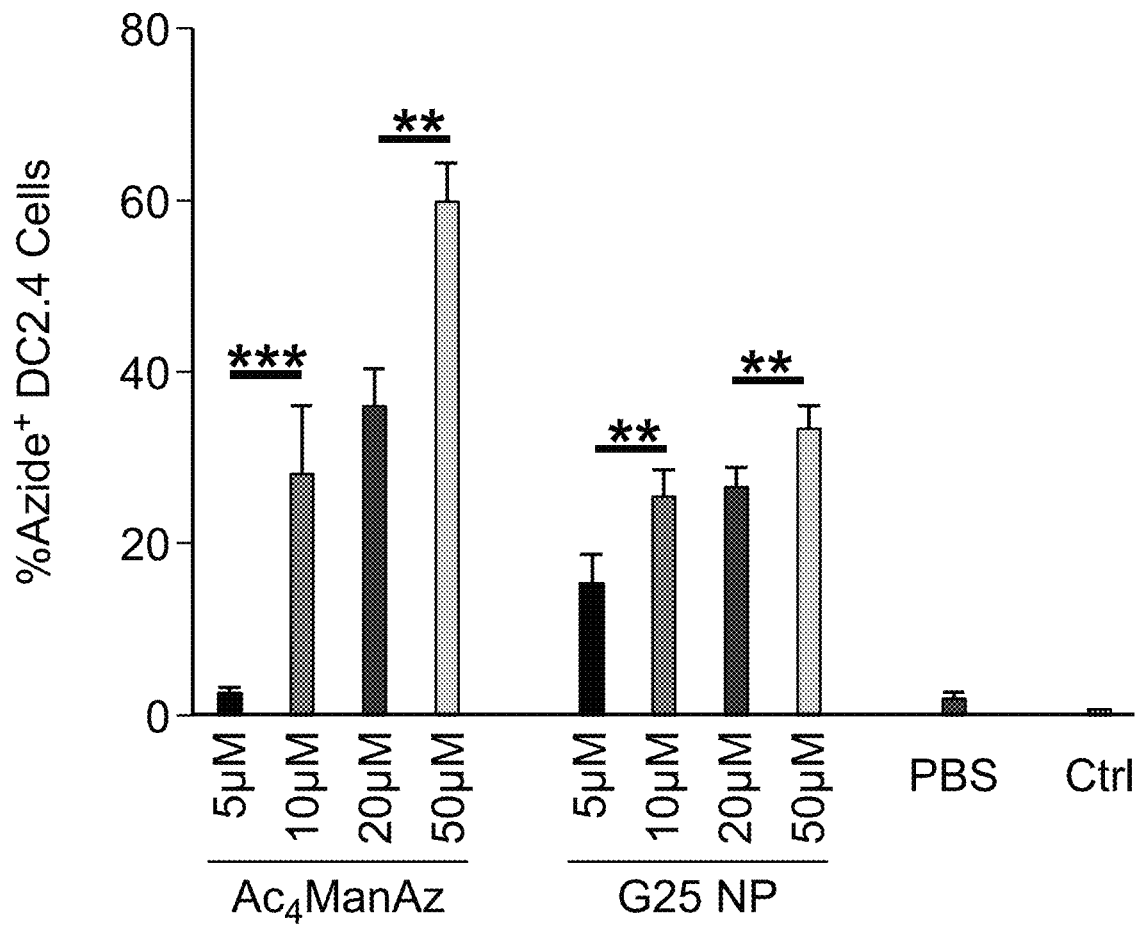
FIG. 2G is a graph showing the percentage of $azide^+$ DC2.4 cells after 3-d incubation with $Ac_4ManAz$ or G25 NP (n=6). Cell-surface azido groups were detected by DBCO/efluor660-antibody.
Figure 2H:
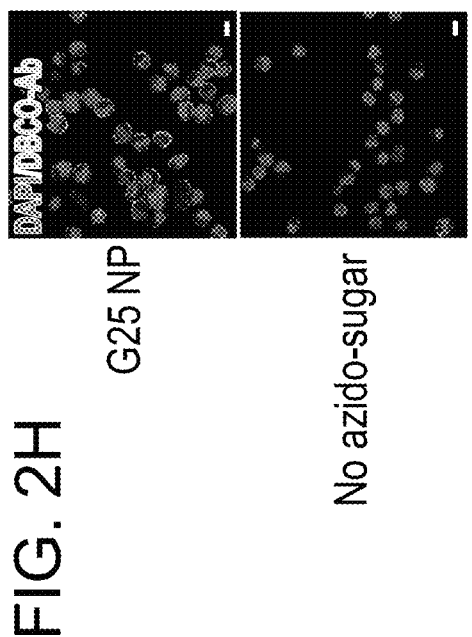
FIG. 2H provides confocal images of DC2.4 cells after 3 days incubation with G25 NP and 30-min staining with DBCO/efluor660-antibody.
Figure 2I:
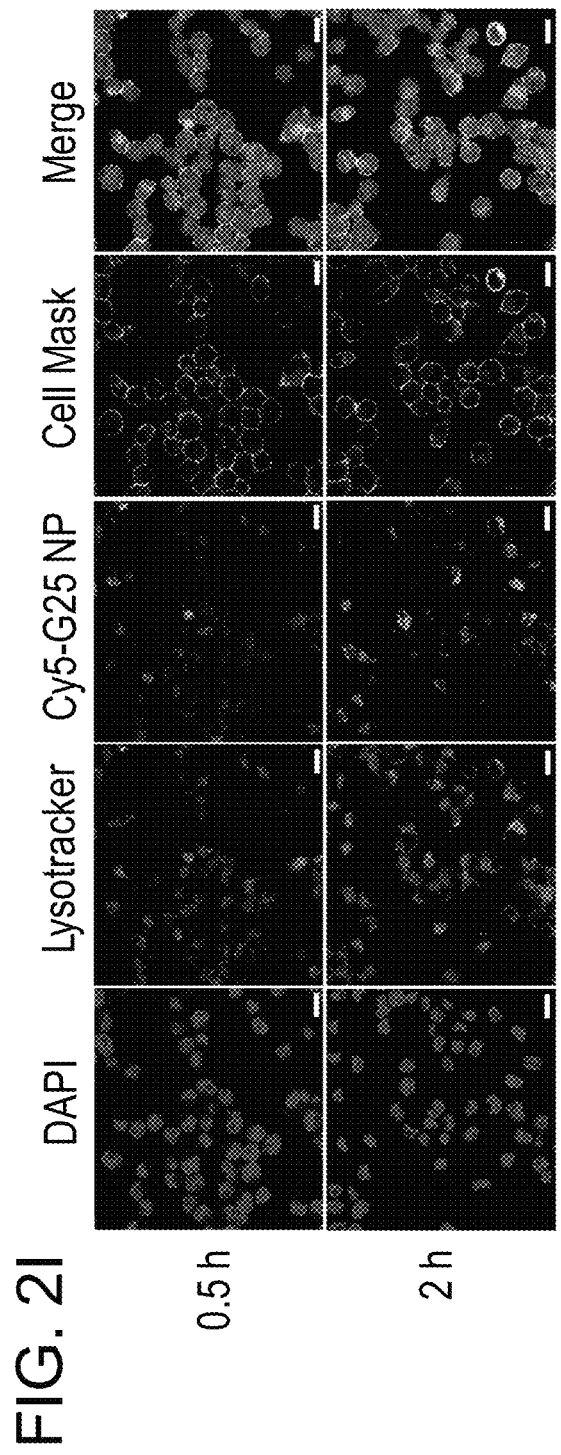
Figure 2J:
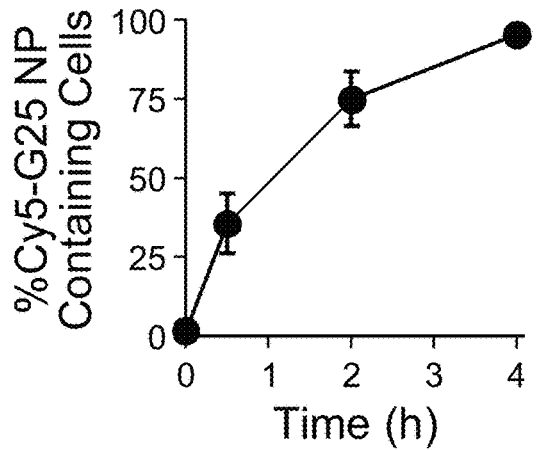
Figure 2K:
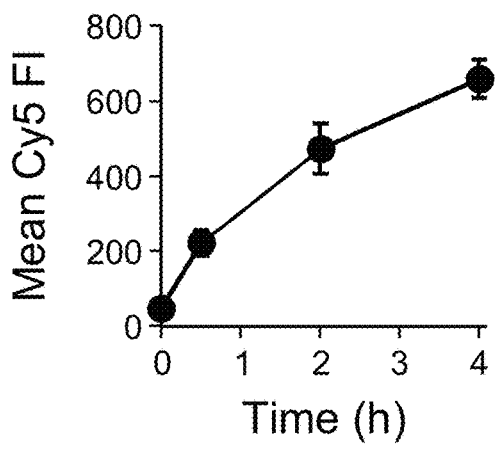

G25 and G400 NP were then prepared via nanoprecipitation of G25 and G400, respectively (FIGS. 2D-2F). Briefly, G25 or G400 polymer was dissolved in DMF at a concentration of 40 mg/mL, and dropwise added to ultrapure water (20-fold volume) upon vigorous stirring. After stirring for 4 hours, G25 NP or G400 NP solution was dialyzed against deionized water for 48 hours, sterilized, and then stored at 4° C. for use. Dye-labeled G25 NP and G400 NP were prepared similarly using dye-labeled G25 and G400, respectively.

G25 NP was able to enter and metabolically label DC2.4 cells and bone marrow-derived DCs (BMDCs) with azido groups in a concentration-dependent manner (FIGS. 2G-2K and 2S). For metabolic labeling of BMDCs, bone marrow cells were extracted from the tibia and femur of C57BL/6 mice and cultured in RPMI medium containing GM-CSF. On Day 6 or 7, suspended DCs were collected and seeded into 24 well plates at a cell density of $1 \times 10^5$ per well, followed by the addition of azido-sugar materials. The cells were incubated at 37° C. for 72 hours. After washing with PBS, cells were incubated with DBCO/efluor660-antibody and other antibody stains on ice for 40 min. Cells were then collected, re-suspended in FACS buffer, and analyzed by flow cytometry.

Figure 2L:
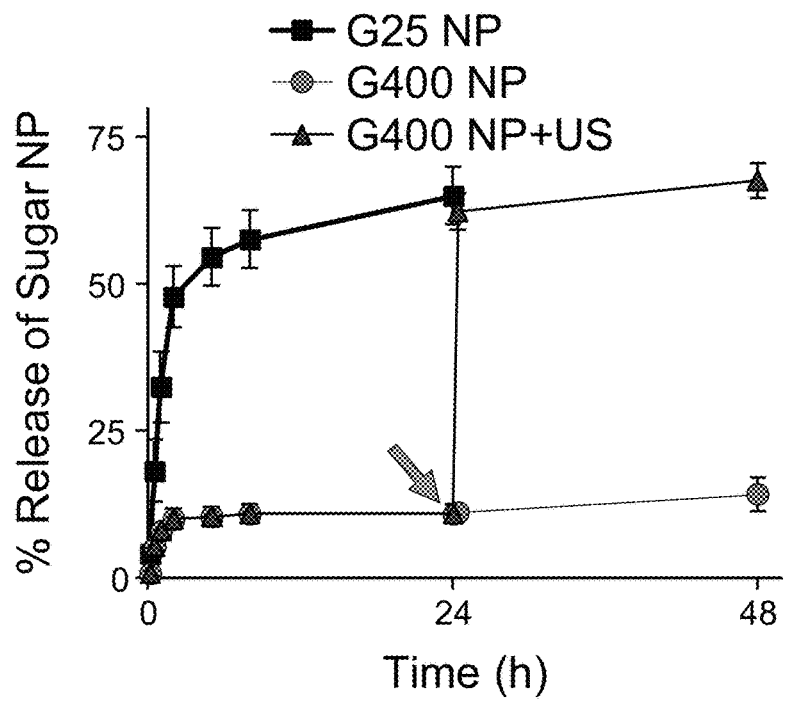
FIG. 2L is a graph showing the release profiles of G25 NP and G400 NP from pore-forming alginate gels (n=4). Green arrows indicate the time of ultrasound treatment.
Figure 2M:
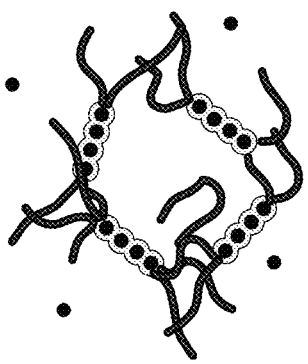
FIG. 2M is a schematic illustration showing temporary disruption of the ionic crosslinks of alginate gels following ultrasound.
Figure 2M:
Figure 2M:
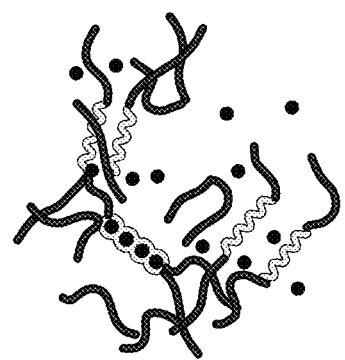
Figure 2M:
Figure 2M:
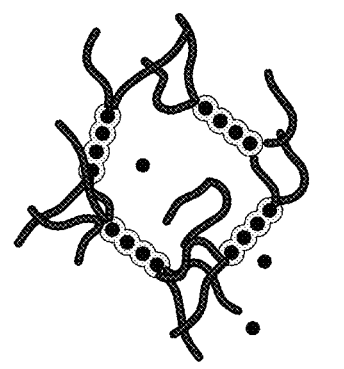
Figures 2N, 2O:
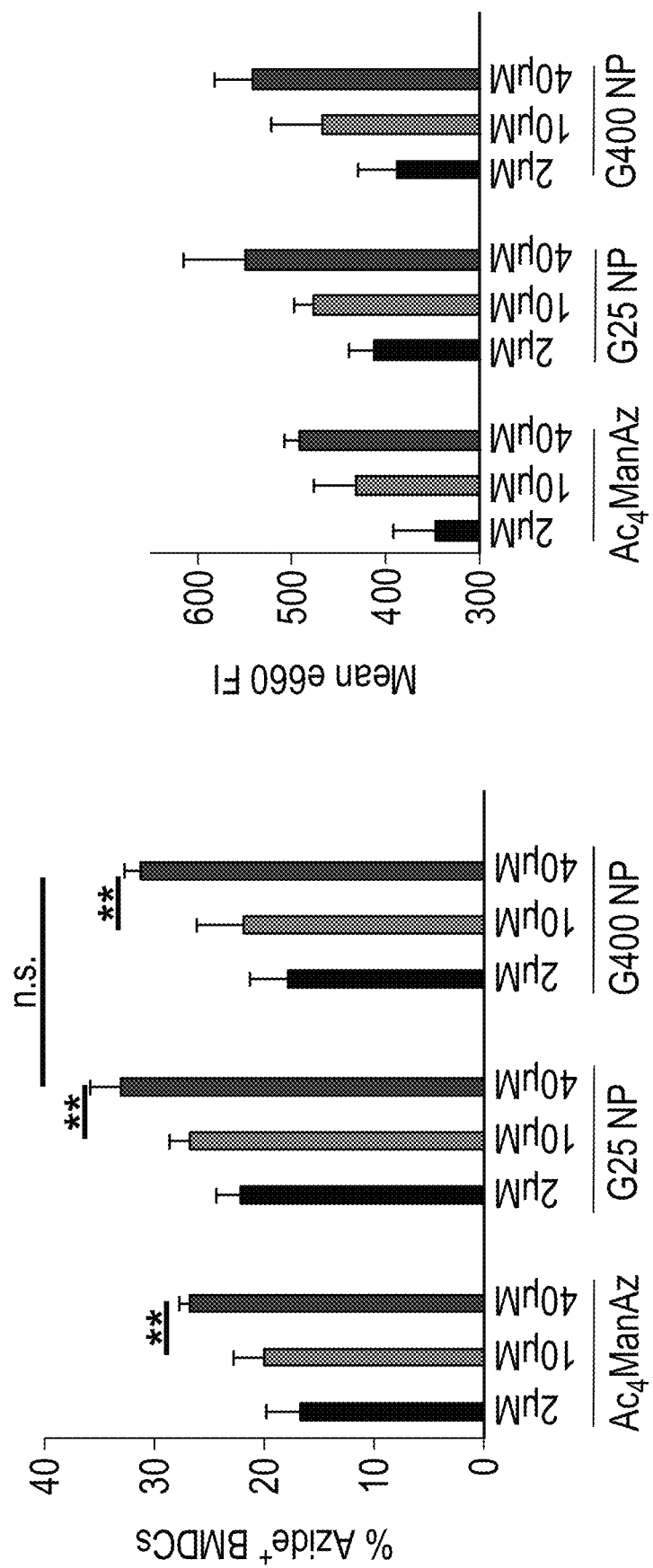

However, G25 NP that was encapsulated into the bulk phase of pore-forming alginate gels showed significantly higher premature release (>50%) than G400 NP (~10%) within 24 hours incubation at 37° C. (FIG. 2L). Upon ultrasound treatment, G400 NP showed a burst release (~40%) (FIG. 2L), presumably due to temporary disruption of the ionic crosslinks of alginate gels (Kearney, C. J. et al. Switchable release of entrapped nanoparticles from alginate hydrogels. *Advanced healthcare materials* 4, 1634-1639 (2015)) (FIG. 2M). Considering the comparable labeling efficiency of G400 NP and G25 NP (FIGS. 2N, 2O and 3I) while less premature release of G400 NP from alginate gels, G400 NP was used for the rest of studies.

For the preparation of pore-forming alginate gels used in the studies described above and elsewhere herein, GM-CSF loaded Au NPs and porogen beads were prepared following the reported method (Verbeke, C. S. & Mooney, D. J. Injectable, Pore-Forming Hydrogels for In Vivo Enrichment of Immature Dendritic Cells. *Advanced Healthcare Materials* 4, 2677-2687, doi:10.1002/adhm.201500618 (2015)). A solution of MVG alginate in DMEM was reconstituted while stirring at 4° C. overnight. The 3% w/v alginate solution was mixed with G400 NP and GM-CSF (antigens and adjuvants were incorporated in some studies), resulting in a final concentration of 2% w/v alginate. This mixture, which constituted the bulk phase of the gels, was then mixed with porogen beads. Finally, the bulk phase alginates were cross-linked by mixing with a sterile $CaSO_4$ slurry (0.2 g/mL). For in vitro studies, the gels were immediately cast between two silanized glass plates separated by 2 mm spacers. After allowing the gels to cross-link for 40 min, gel disks were punched out using a sterile 8 mm biopsy punch. For in vivo studies, gels (100 µL) containing 3 µg of GM-CSF were freshly prepared and subcutaneously injected via an 18 G needle.

For the analysis of in vitro release of G25 NP and G400 NP from gels as described above and elsewhere herein, gel disks containing Cy3-labeled G25 NP or G400 NP (n=6) were incubated in DMEM at 37° C. At different time points, medium was collected for measurement of Cy3 fluorescence intensity via a plate reader. Fresh medium was added to keep the total volume of incubation medium constant. The culture medium of gels was subject to ultrasound treatment (30% amplitude) for 2.5 min at certain time points.

Next, the in vivo release of Cy5-conjugated G400 NP from subcutaneously injected pore-forming gels was studied by monitoring the fluorescence signals over time. Mice were subcutaneously injected with gels containing GM-CSF and Cy5-labeled G400 NP, and imaged via the IVIS imaging system at 1, 3, 24, 48, and 72 hours post gel injection. Mice were then treated with ultrasound (30% amplitude) for 2.5 min, and imaged again at 1, 9, 24, 48, and 72 hour post ultrasound treatment. After the last in vivo imaging, mice were euthanized, and gels and lymph nodes were imaged ex vivo. After ex vivo imaging, gels and lymph nodes were disrupted, and cells were collected for subsequent antibody staining and FACS analyses.

Figure 2P:
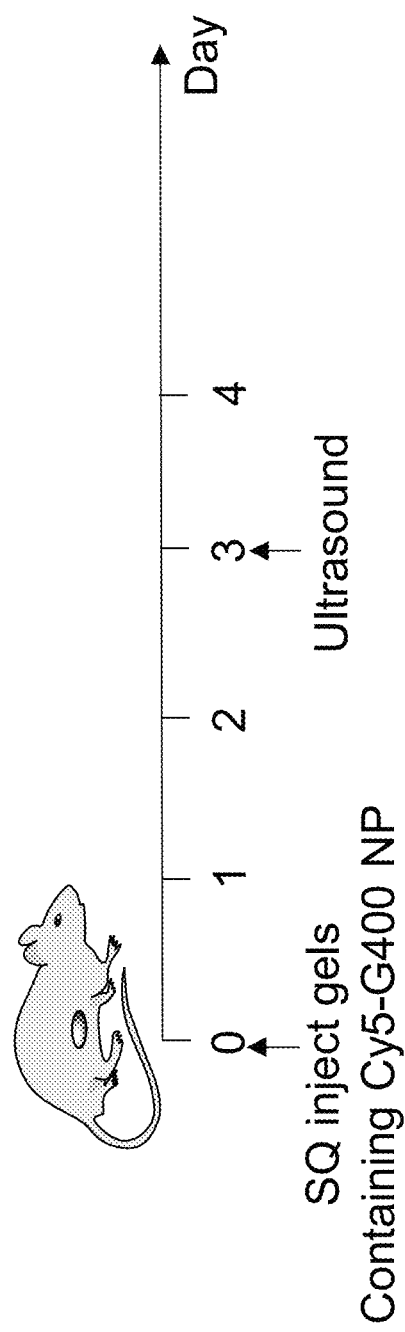
FIG. 2P is a schematic illustration showing the time frame study of in vivo release of G400NP. Mice were injected subcutaneously (SQ) at day 0 with gels containing Cy5-labeled G400 NP. Ultrasound was applied at 72 hours post gel injection.
Figure 2Q:
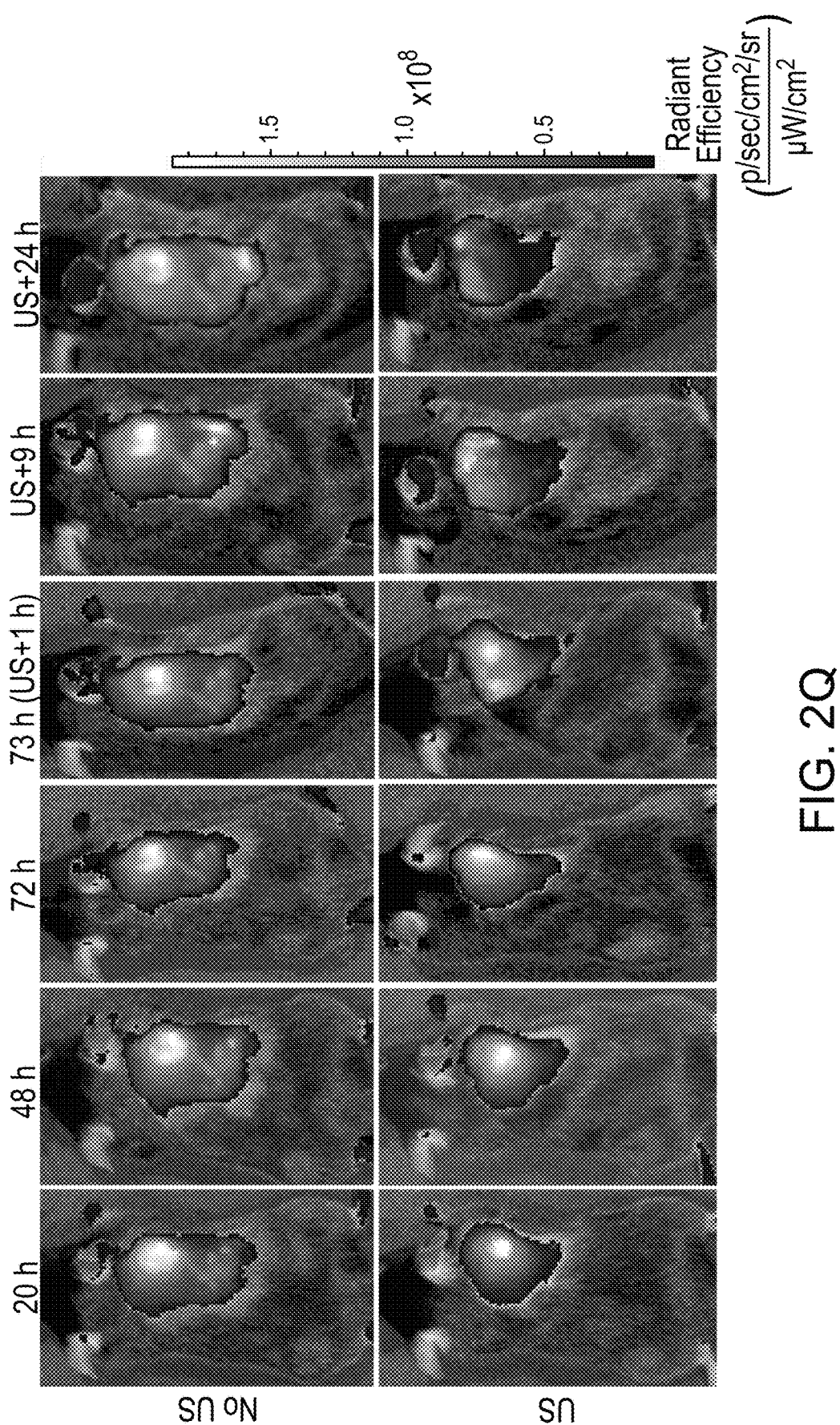
FIG. 2Q provides representative IVIS images of C57BL/6 mice showing the release of Cy5-labeled G400 NP from pore-forming gels in vivo in the absence or presence of ultrasound treatment. G400 NP-loaded pore-forming alginate gels were subcutaneously injected through an 18G needle, and mice were imaged at designated time points. Ultrasound was applied at 72 hours post gel injection.
Figure 2R:
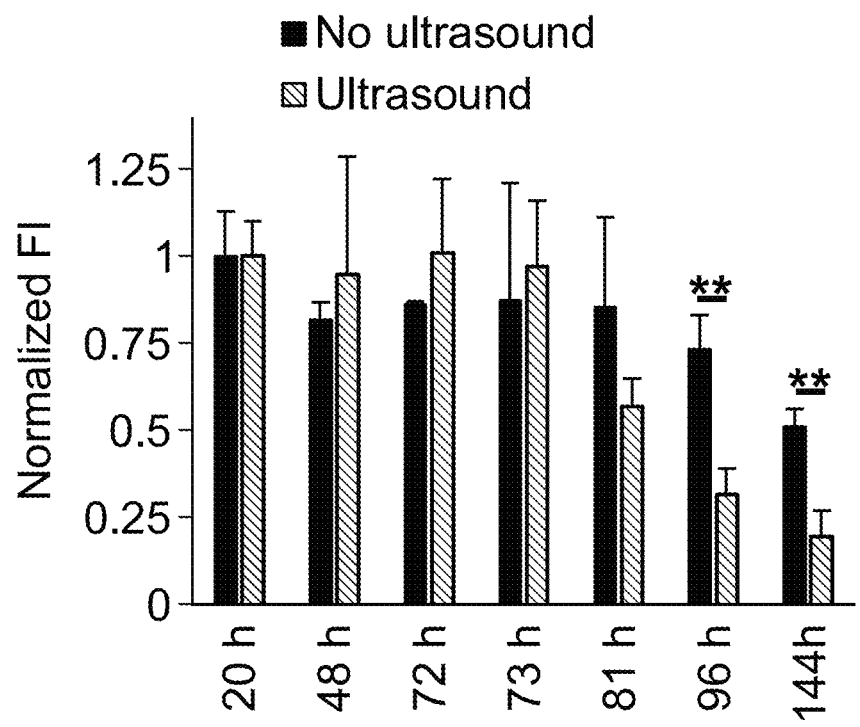
Figure 2S:
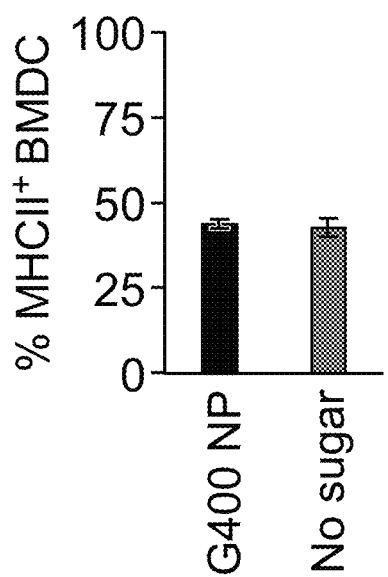
FIG. 2S is a graph showing the percentage of $MHCII^+$ BMDCs after incubating with G400 NP or PBS for 4 h.
Figure 2T:
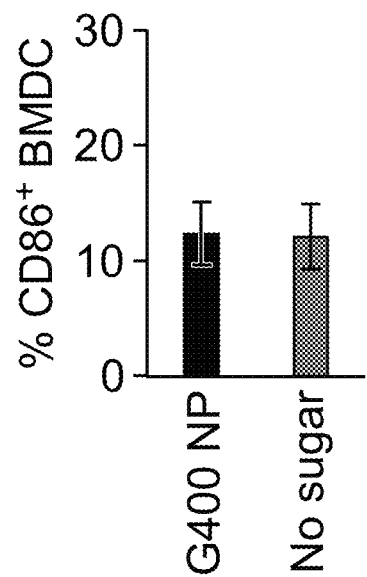
FIG. 2T is a graph showing the percentage of $CD86^+$ BMDCs after incubating with G400 NP or PBS for 4 h.

As a result, Cy5-labeled G400 NP were retained in the gels within 72 hours after gel injection, while the localized Cy5 signal decreased dramatically within 9 hour after ultrasound treatment (FIGS. 2P and 2Q). In comparison, gels without ultrasound treatment showed a significantly higher retention of Cy5 signal after 72 hours (FIGS. 2P and 2Q), substantiating ultrasound-triggered release of G400 NP from pore-forming alginate gels and subsequent uptake by surrounding cells including DCs prior to their migration out of the gels.

Example 2: In Vivo Labeling and Tracking of DCs

It was next investigated whether G400 NP-loaded pore-forming alginate gels are able to metabolically label the recruited DCs with azido groups with the assistance of ultrasound.

For in vivo DC labeling study, C57BL/6 mice were divided into five groups: gels containing G400 NP and GM-CSF+ultrasound treatment, gels containing G400 NP and GM-CSF, gels containing G400 NP, gels containing GM-CSF, and blank gels. Gels were freshly prepared and subcutaneously injected into the right flank of mice on day 0. On day 3, the hair around the gel was removed and a layer of transmission gel was added, followed by ultrasound treatment (30% amplitude) for 2.5 min. On day 6, lymph nodes (LNs) and gel scaffolds were excised for analyses: (1) For FACS analyses, gel scaffolds were treated with EDTA for 15 min on ice and disrupted to release the encapsulated cells. LNs were disrupted via mechanical force to release cells. Cells were strained using a 70-um cell strainer, centrifuged at 350 g for 5 min, re-suspended in FACS buffer, and counted. Cells were then seeded into 96-well plates at a cell density of $1 \times 10^5$ cells per well, incubated with DBCO/efluo660-antibody for 20 min on ice, and further incubated together with other antibody stains of cell surface markers for another 20 min on ice. After washing with FACS for twice, cells were re-suspended in FACS buffer and analyzed by flow cytometry. (2) For confocal imaging, LNs and gel scaffolds were directly frozen in optimal cutting temperature (O.C.T.) compound and sectioned with a thickness of 8 µm. Tissue sections were rehydrated, incubated with blocking buffer (5% goat serum) for 2 hours, and then stained with DBCO/efluor660-antibody and primary antibodies overnight at 4° C. For the study of DC labeling kinetics in vivo, mice were subcutaneously injected with gels containing G400 NP and GM-CSF on day 0, followed by ultrasound treatment (30% amplitude, 2.5 min) on day 3. Gel scaffolds and LNs were harvested and analyzed on day 6, 10, and 14, respectively or day 6, 13, and 20, respectively, following the abovementioned procedures.

Figure 3A:
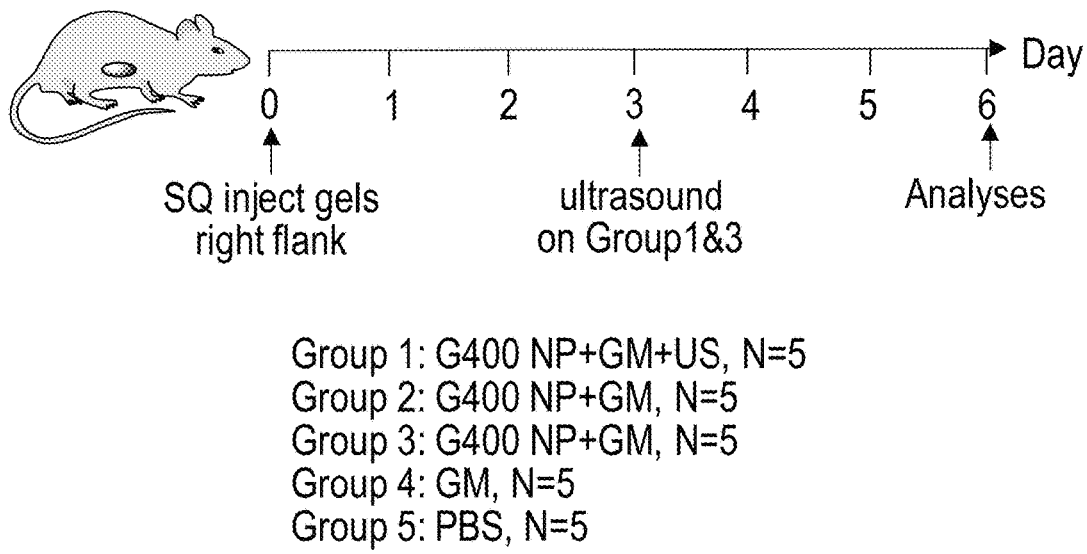
FIGS. 3A-3S illustrate that G400 NP-containing pore-forming alginate gels recruit and metabolically label DCs with azido groups in vivo. Unless otherwise indicated, these figures reflect the analysis on day 6 after injection of pore-forming alginate gel.
Figures 3B, 3C:
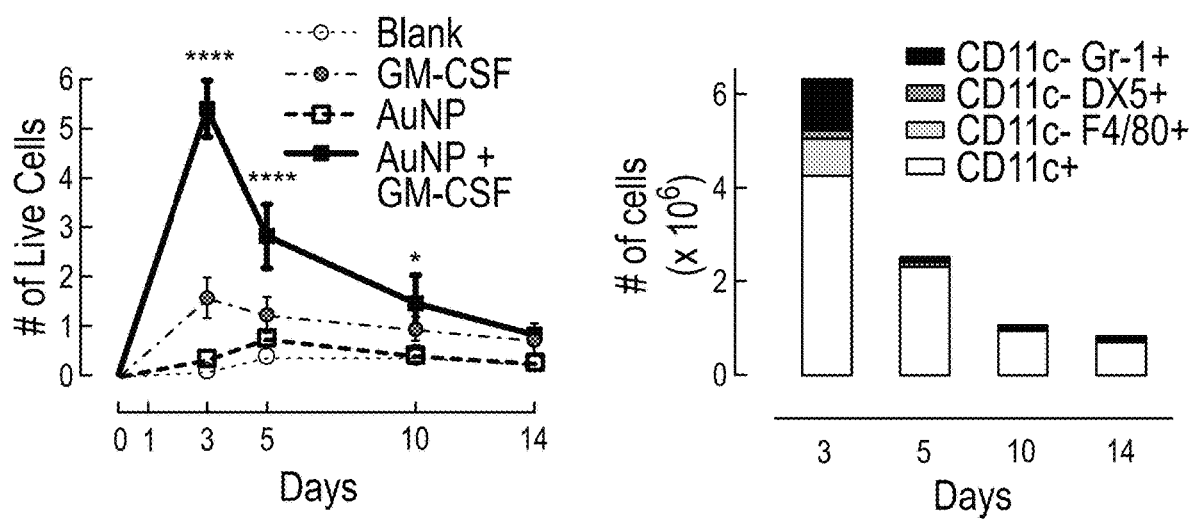
FIG. 3B is a graph showing that a pore-forming alginate gel loaded with GM-CSF recruited the maximum number of cells at day 3 after injection.
FIG. 3C is a graph showing that a pore-forming alginate gel loaded with GM-CSF recruited the maximum number of $CD11c^+$ cells at day 3 after injection.
Figure 3D:
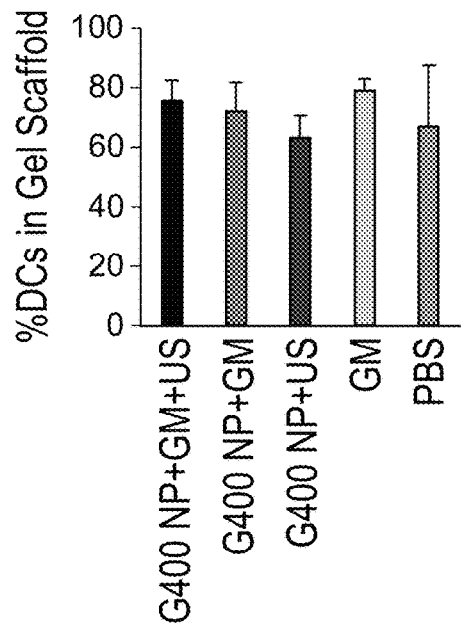
FIGS. 3D and 3E are graphs showing the percentage (FIG. 3D) and total number (FIG. 3E) of DCs in gel scaffolds on day 6.
Figure 3E:
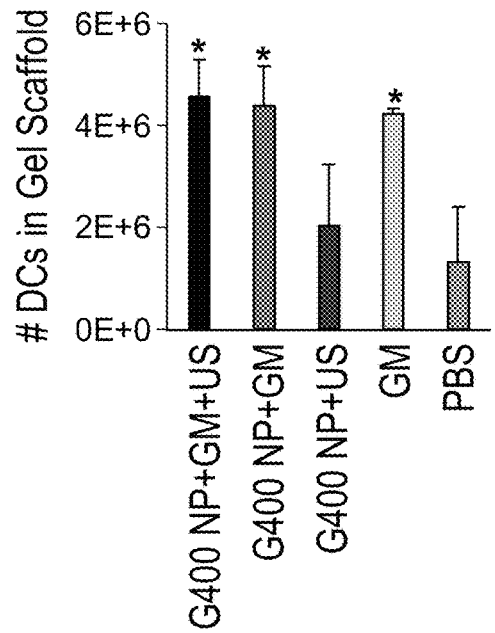
Figure 3F:
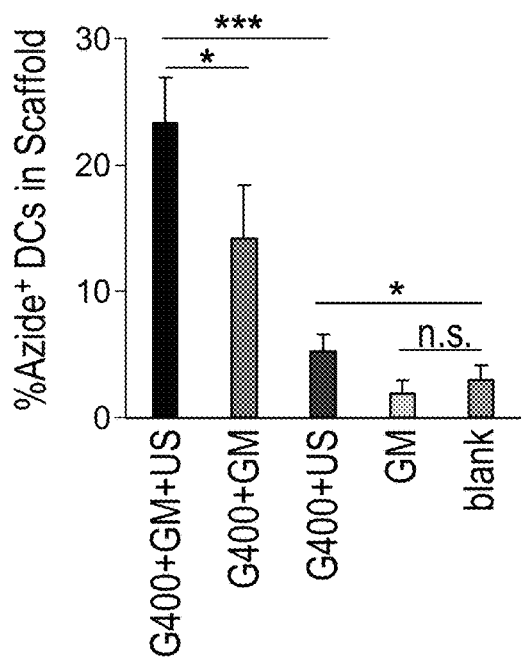
FIG. 3F is a graph showing percentage of azido-labeled DCs in gel scaffolds on day 6, as determined by FACS analyses and live cell counting.
Figure 3G:
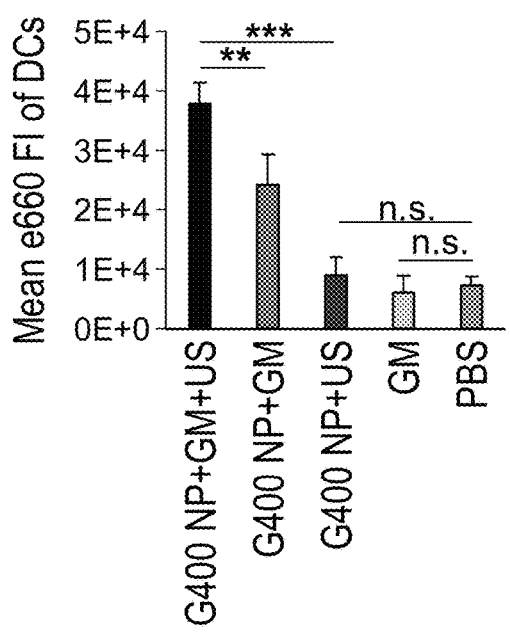
FIG. 3G is a graph showing mean e660 fluorescence intensity (FI) of DCs in gel scaffolds after staining with e660/DBCO-antibody for 30 min.
Figure 3H:
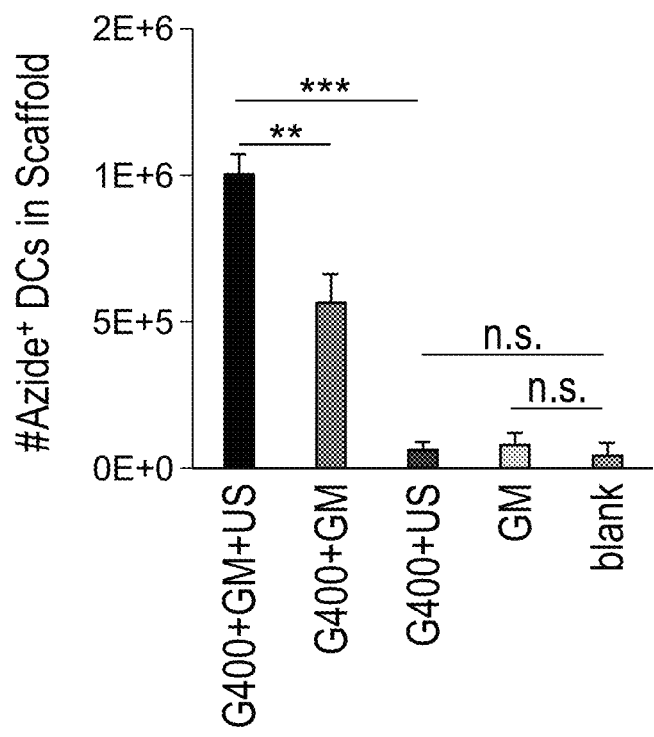
FIG. 3H is a graph showing the total number of $azide^+$ DCs in gel scaffolds on day 6.
Figure 3I:
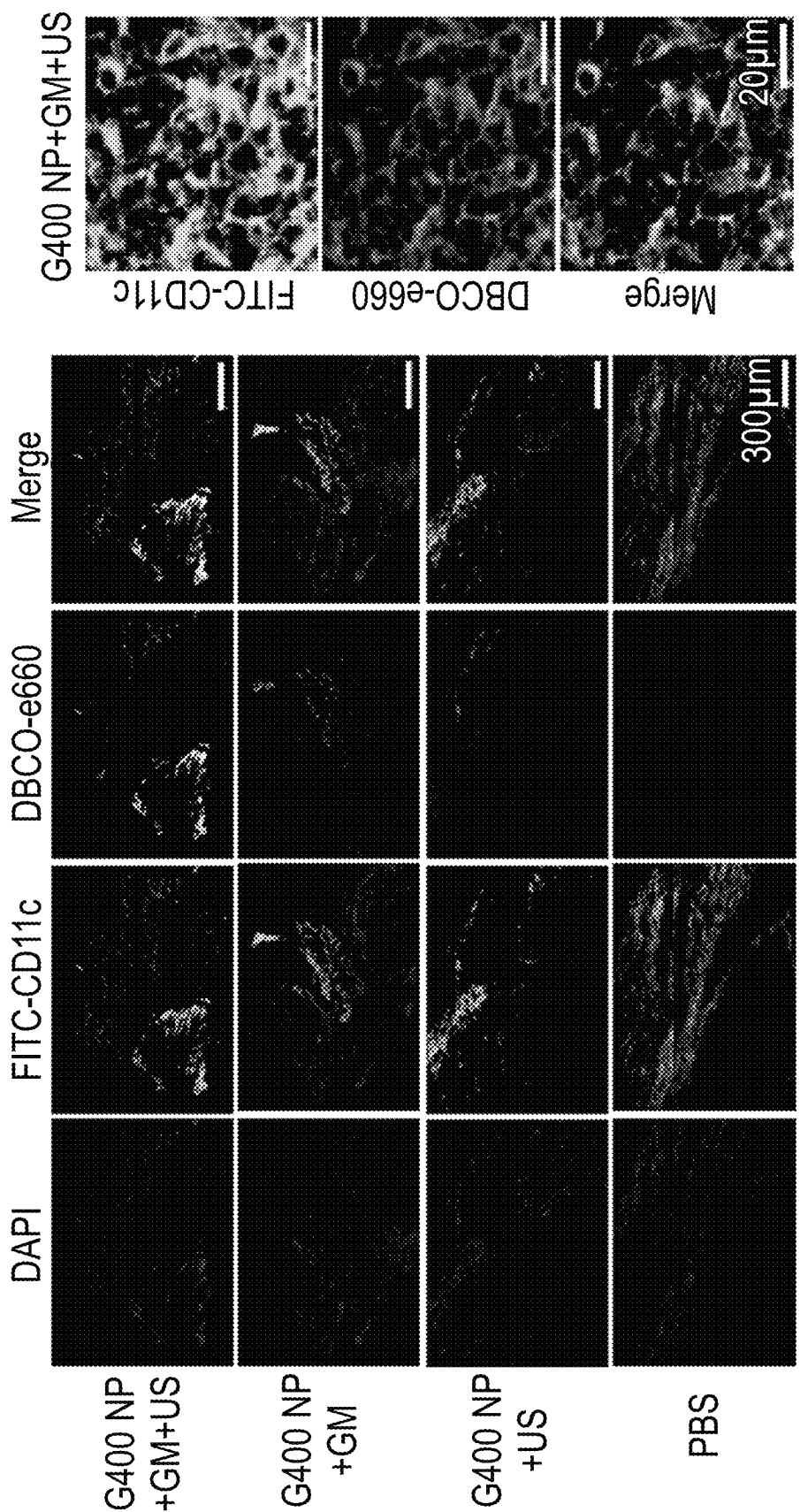
FIG. 3I provides representative confocal images of gel scaffold sections (left panel) and dLN sections (right panel) which were stained with e660/DBCO-antibody, FITC-conjugated anti-CD11c, and DAPI.

Mice were subcutaneously injected with pore-forming gels containing G400 NP and GM-CSF on day 0, followed by ultrasound treatment on day 3 when the number of recruited DCs approached a maximum (Verbeke, C. S. et al, 2015; Verbeke, C. S. et al. Multicomponent Injectable Hydrogels for Antigen-Specific Tolerogenic Immune Modulation. *Advanced Healthcare Materials* 6, 1600773-n/a, doi: 10.1002/adhm.201600773 (2017)) (FIGS. 3A-3C). GM-CSF was conjugated to gold NPs to enable sustained release and better recruitment of DCs (Verbeke, C. S. et al, 2015). On day 6, over 70% of cells recruited into the gel scaffold were $CD11b^+CD11c^+$ DCs, with significantly more cells being recruited to gel scaffolds containing GM-CSF (FIGS. 3D and 3E). About 23% of DCs in the gels containing G400 NP and GM-CSF in the presence of ultrasound treatment were azide-positive (FIG. 3F), indicating the successful metabolic labeling of DCs in the gels. In comparison, only about 14.2% of DCs in the same gels without ultrasound treatment were azide-positive (FIGS. 3F and 3G), validating the importance of ultrasound to facilitate the release of G400 NP for cell labeling. Gels without GM-CSF but with ultrasound treatment also contained a much lower percentage (5.3%) of azide-positive DCs (FIGS. 3F and 3G), presumably due to the inefficient uptake and metabolism of released G400 NPs by the smaller number of DCs. The total number of azide-positive DCs ($1.0 \times 10^6$) in gels containing G400 NP and GM-CSF, and treated with ultrasound was also much higher than gels without ultrasound treatment ($5.6 \times 10^5$) and gels without GM-CSF ($6.4 \times 10^4$) (FIG. 3H). Confocal images also showed increased azide density in gels containing G400 NP and GM-CSF, and treated with ultrasound, in comparison to other groups (FIG. 3I).

Figure 3J:
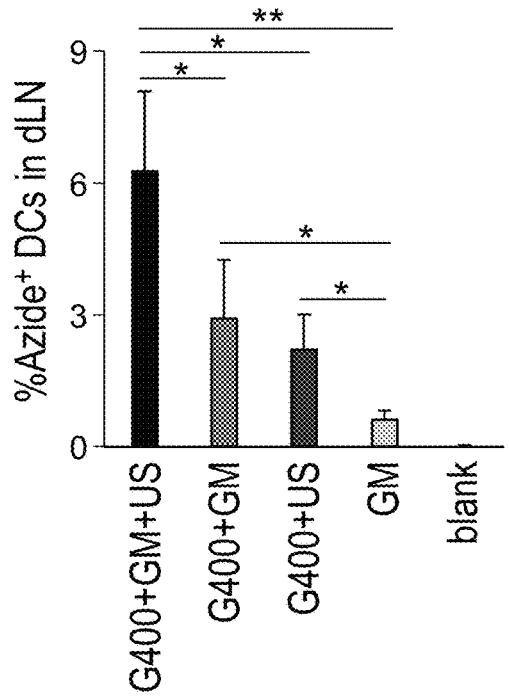
FIGS. 3J and 3K are graphs showing percentage (FIG. 3J) and total number (FIG. 3K) of azide+ DCs in draining lymph nodes (dLNs).
Figure 3K:
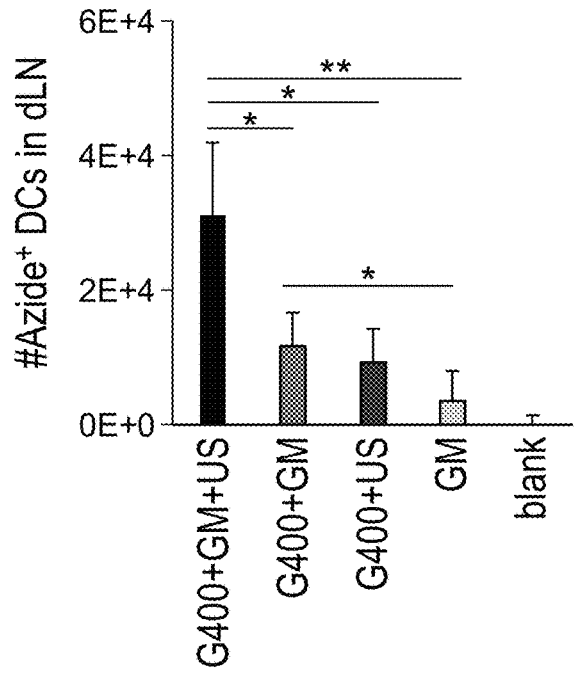
Figure 3L:
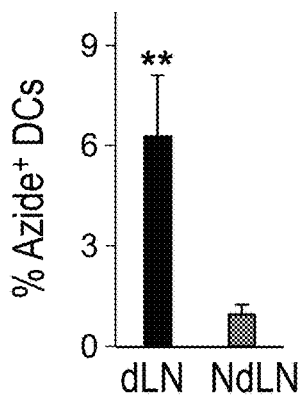
FIGS. 3L and 3M are graphs showing percentage (FIG. 3L) and total number (FIG. 3M) of azide+ DCs in dLNs and NdLNs of mice treated with gels containing GM-CSF and G400 NP and ultrasound.
Figure 3M:
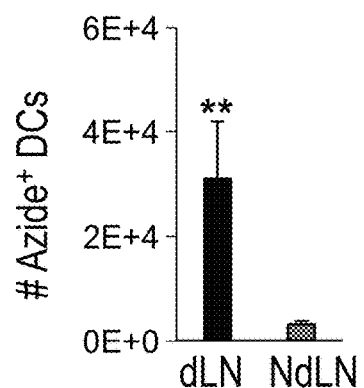

To study whether azido-labeled DCs in the gel scaffold migrated into LNs, DCs in the gel-draining lymph nodes (dLNs) and non-draining lymph nodes (NdLNs) were analyzed. G400 NP treatment groups showed a statistically higher number of $azide^+$ DCs in dLNs than the control groups without G400 NP treatment (FIGS. 3J and 3K). Gels with G400 NP, GM-CSF and ultrasound treatment resulted in the highest number of $azide^+$ DCs in dLNs among all groups (FIGS. 3J and 3K). Within this group, a significantly lower number of $azide^+$ DCs were observed in the NdLNs compared to dLNs (FIGS. 3L and 3M). Confocal images also showed increased azide density in dLNs of mice injected with gels containing G400 NP and GM-CSF, and treated with ultrasound, in comparison to other groups (FIG. 3N). Also, overlay of DBCO/efluor660-antibody and FITC-conjugated anti-CD11c signals were observed, substantiating the existence of azido-labeled DCs (FIG. 3N). These experiments demonstrated that G400 NP can metabolically label recruited DCs in the gels with azido groups and that the azido-labeled DCs successfully migrated into dLNs.

Figure 3O:
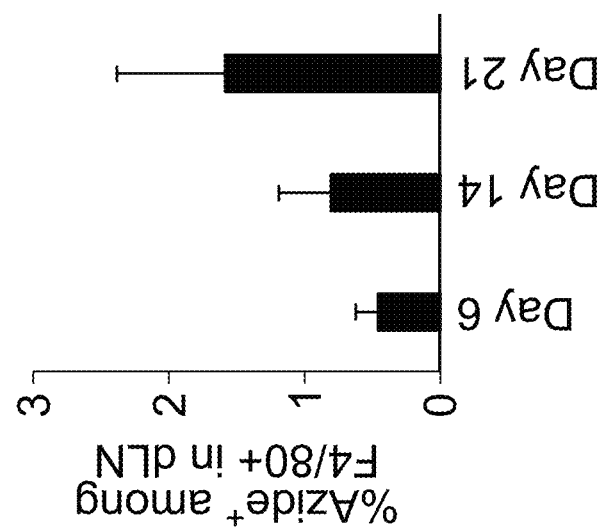
FIGS. 3O-3Q reflect analyses for the change of azide+ DCs over time. After injection of pore-forming alginate gels containing GM-CSF and G400 NP on day 0 and ultrasound treatment on day 3, LNs and gels were excised and analyzed on day 6, 10, and 14, respectively, or on day 6, 14, and 21, respectively (n=4).
Figure 3P:
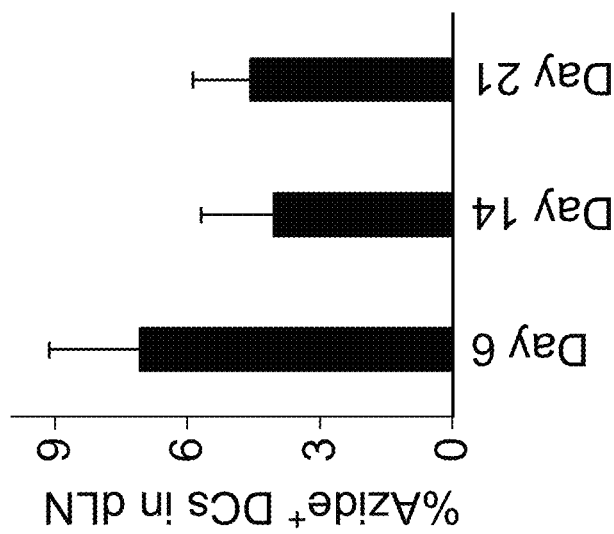
Figure 3Q:
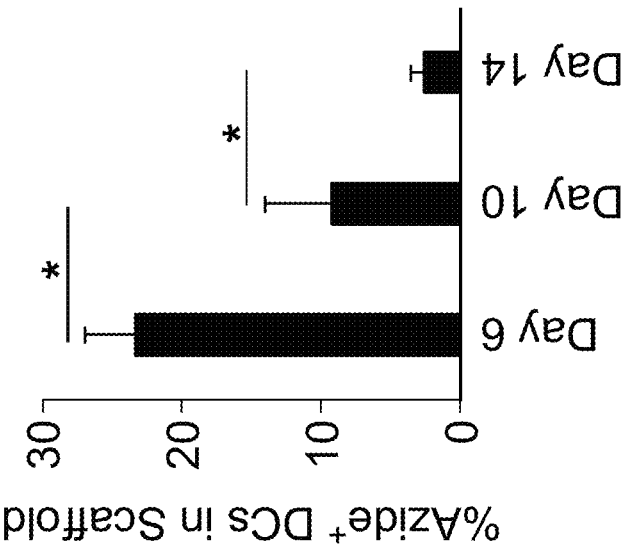
Figure 3R:
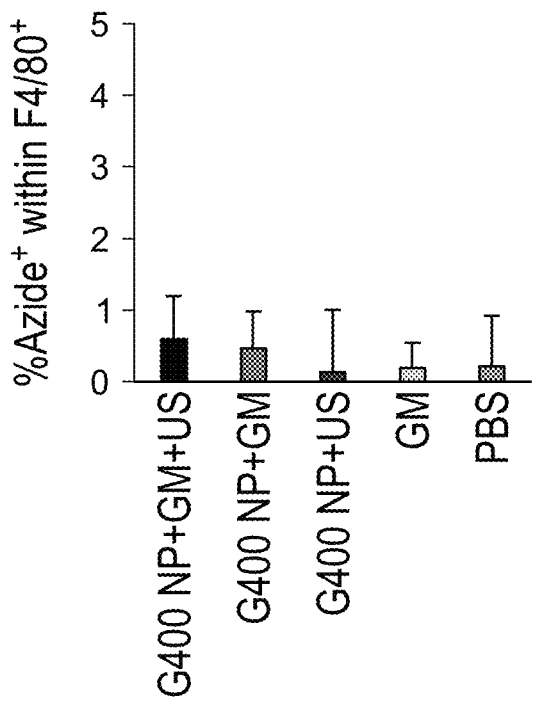
FIG. 3R is a graph showing percentage of azide+ macrophagocytes in dLNs on day 6.
Figure 3S:
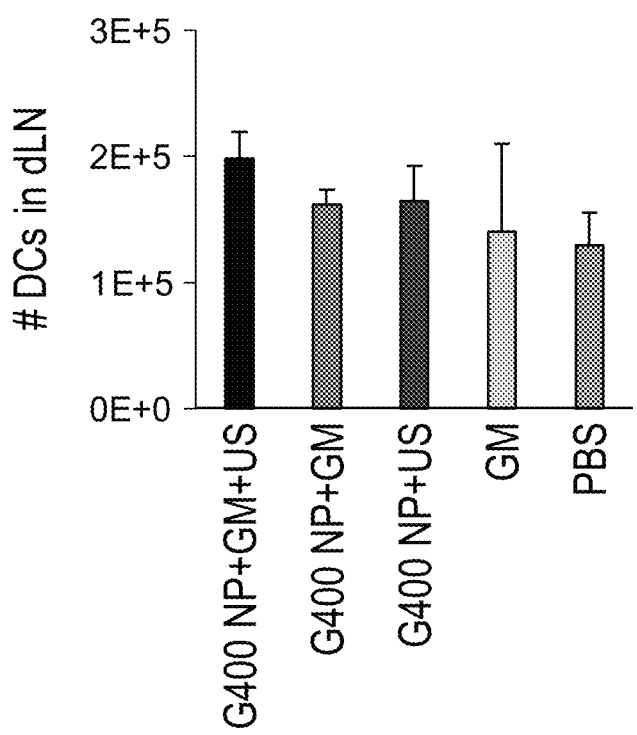

To potentially understand the cellular fate of these azido-labeled DCs, azido-labeled immune cells in LNs were monitored over a longer period. The percentage of azido-labeled DCs in gel scaffolds significantly decreased from day 6 to day 10 and then to day 14 (FIG. 3O), indicating the continuous migration of azido-labeled DCs out of the gel scaffold and the complete consumption of G400 NP in the gel scaffold over time. The percentage of azido-labeled DCs in dLNs decreased from day 6 to 14 (FIG. 3P), presumably because of the apoptosis of azido-labeled DCs in dLNs and proliferation-mediated dilution of cell-surface azido groups. The percentage of azido-labeled DCs remained unchanged from day 14 to day 21, likely due to the continuous migration of azido-labeled DCs from the gel scaffold and re-metabolism of sugar-azides by resident DCs. In comparison, the percentage of azido-labeled macrophages slightly increased over time (FIGS. 3Q and 3R), indicating that microphages may phagocytose apoptotic azido-labeled DCs and re-metabolize the azido-sugars.

Example 3: In Vivo LN Targeting Via Click Chemistry

After demonstrating that azido-labeled DCs can migrate to dLNs and that a number of azido-labeled DCs still exist in dLNs after three weeks of gel injection, it was next studied whether these azido-labeled cells can be utilized for LN-targeted delivery of DBCO-modified agents via Click chemistry.

For in vivo LN-targeted delivery of DBCO-Cy5 study, C57BL/6 mice were subcutaneously injected with gels containing G400 NP and GM-CSF or control gels containing GM-CSF alone on day 0, followed by ultrasound treatment (30% amplitude, 2.5 min) on day 3. DBCO-Cy5 was intravenously injected via tail vein on day 8 or 15. At 24 hours post injection of DBCO-Cy5, gels and LNs were harvested and imaged ex vivo. Cells were then isolated from gels and LNs for FACS analyses.

Mice were subcutaneously injected with gels containing G400 NP and GM-CSF on day 0, treated with ultrasound on day 3, and intravenously injected with DBCO-Cy5 on day 8 (FIG. 4A). At 24 hours post injection of DBCO-Cy5, dLNs showed significantly enhanced Cy5 fluorescence intensity than NdLNs, with a fluorescence intensity ratio of 2.67±0.79 (FIGS. 4B-4D). In comparison, negligible difference of Cy5 fluorescence intensity between dLNs and NdLNs was observed in mice treated with G400 NP solution or control gels without G400 NP.

To study whether the LN-targeting effect still exists over a longer period, another experiment was performed similarly except that DBCO-Cy5 was i.v. injected at 12 days after ultrasound treatment, and ex vivo imaging of LNs was taken at 24 hours post injection of DBCO-Cy5. Similarly, dLNs showed a significantly greater accumulation of DBCO-Cy5 than NdLNs in mice treated with G400 NP-loaded gels, with a fluorescence intensity ratio of 2.34±0.84 (FIGS. 4E-4G). In comparison, no difference in Cy5 fluorescence intensity between dLNs and NdLNs of mice treated with G400 NP solution or control gels was observed. FACS analyses of LN cells showed that the majority of DBCO-Cy5 accumulated in DCs and macrophages (FIG. 4H), and dLNs contained a significantly increased number of $azide^+$ DCs compared to NdLNs in mice treated with G400 NP-loaded gels (FIGS. 4H-J). All these experiments demonstrated that azido-labeled DCs in dLNs could mediate targeted delivery of DBCO-Cy5 via efficient Click chemistry.

Another objective of this invention was to utilize azido-labeled DCs, as achieved above, for LN-targeted delivery of DBCO-bearing antigens and adjuvants. It was first studied whether azido-labeled DCs could covalently capture DBCO-ovalbumin (OVA) and DBCO-CpG in vitro. BMDCs were labeled with G400 NP for three days and incubated with DBCO/FITC-OVA or FITC-OVA for 30 min. DBCO/FITC-OVA showed improved cellular uptake by azido-labeled BMDCs in comparison to FITC-OVA (FIGS. 5A and 5B), indicating Click chemistry-mediated targeting of DBCO/FITC-OVA. Similarly, BMDCs pretreated with G400 NP were able to capture more DBCO/Cy5-CpG than control BMDCs (FIGS. 5C and 5D).

It was next studied whether the azido-labeled DCs in dLNs can mediate targeted delivery of DBCO-OVA via Click chemistry. C57BL/6 mice were subcutaneously injected with gels containing G400 NP and GM-GSF on day 0, followed by ultrasound treatment on day 3 and tail base subcutaneous injection of DBCO/Alexa fluor 647 (A647)-OVA or A647-OVA on day 6. At 6 h post injection, compared to A647-OVA, DBCO-A647-OVA showed significantly enhanced A647 fluorescent signal in dLNs (FIGS. 5F-5H), indicating the existence of azido-labeled cells which captured DBCO/A647-OVA via Click chemistry. FACS analyses showed the existence of ~43% of A647-OVA$^+$ DCs in the dLNs of DBCO/A647-OVA group, which is significantly higher than dLNs of A647-OVA group and NdLNs of both groups (FIGS. 5I and 5J). At 24 h post injection, DBCO/A647-OVA still showed significantly improved accumulation in dLNs than A647-OVA (FIGS. 5K and 5L). At 48 h post injection, the A647 signal of LNs dramatically decreased (FIG. 5G), presumably because of the intracellular processing of DBCO-A647-OVA or A647-OVA and the clearance of A647 derivatives from LNs. These experiments demonstrated that azido-labeled DCs in LNs enable targeted delivery of DBCO-antigens and adjuvants via Click chemistry.

Example 4: LN-Targeted Cancer Vaccines

After demonstrating that azido-labeled DCs in LNs can mediate targeted delivery of DBCO-agents, it was next studied whether DBCO-OVA/DBCO-CpG with DC-targeting capability would impart a stronger SIINFEKL-specific CD8$^+$ T cell response than OVA/CpG. For the vaccination study of DBCO-OVA/DBCO-CpG, mice were divided into 4 groups (n=8 per group): gel containing G400 NP and GM-CSF+ultrasound+DBCO-OVA/DBCO-CpG; gel containing G400 NP and GM-CSF+ultrasound+OVA/CpG; control gels containing GM-GN+ultrasound+DBCO-OVA/DBCO-CpG; untreated. Gels were subcutaneously injected on day 0, followed by ultrasound treatment (30% amplitude, 2.5 min) on day 3 and tail base subcutaneous injection of DBCO-OVA/DBCO-CpG or OVA/CpG on day 6. On day 10, 14, and 20, respectively, blood was drawn via retroorbital bleeding and PBMCs were isolated for H2Kb-SIINFEKL tetramer staining and SIINFEKL-stimulated IFN-$\gamma$ generation. For tetramer staining, PBMCs were stained with PE/Cy7-conjugated anti-mouse CD3, FITC-conjugated anti-mouse CD8, pacific blue-conjugated anti-mouse CD4, and APC-conjugated anti-mouse SIINFEKL peptide bound to H-2Kb for 20 min on ice. For in vitro peptide re-stimulation, PBMCs were pulsed with 2 µg/mL SIINFEKL and OVA323-339 CD4 epitope for 1.5 hours, incubated with GolgiPlug for 4 hours, and stained with APC-conjugated anti-mouse IFN-$\gamma$, PE/Cy7-conjugated anti-mouse CD3, FITC-conjugated anti-mouse CD8, and pacific blue-conjugated anti-mouse CD4. Cells were washed and assessed by flow cytometry.

Gels containing G400 NP and GM-CSF (G400 gel) were subcutaneously injected on day 0, followed by ultrasound treatment on day 3 and tail base subcutaneous injection of DBCO-OVA/DBCO-CpG or OVA/CpG on day 6 (FIG. 6A). Mice treated with gels containing GM-CSF alone (control gel) and DBCO-OVA/DBCO-CpG were used as controls. On day 14 and 20, a significantly higher percentage of H-2Kb SIINFEKL tetramer$^+$ CD8$^+$ T cells was observed in PBMCs of mice treated with G400 gel and DBCO-OVA/DBCO-CpG in comparison to other groups (FIGS. 6B-6E), presumably as a result of the targeted delivery of DBCO-OVA/DBCO-CpG to azido-labeled DCs. Upon in vitro SIINFEKL re-stimulation, PBMCs in mice treated with G400 gel and DBCO-OVA/DBCO-CpG also showed a significantly higher percentage of IFN-$\gamma^+$ CD8$^+$ T cells than other groups (FIGS. 6B, 6D, 6F, and 6G).

A prohpylactic tumor study was also performed. For this study, mice were subcutaneously injected with pore-forming gels containing G400 NP and GM-CSF on day 0, treated with ultrasound on day 3, and subcutaneously injected with DBCO-OVA/DBCO-CpG or OVA/CpG at tail base on day 6. On day 26, mice were challenged with a subcutaneous injection of $1\times10^6$ EG7.OVA lymphoma cells in the back of the neck. Tumor growth and body weight of animals were closely monitored. The tumor volume was calculated using the formula (length)×(width)$^2$/2, where the long axis diameter was regarded as the length and the short axis diameter was regarded as the width. Animals were euthanized for humane reasons when tumors grew to 20 mm in longest diameter. For the neoantigen studies, mice were subcutaneously injected with pore-forming gels containing G400 NP, GM-CSF, M27, M30, and CpG on day 0, treated with ultrasound on day 3, and subcutaneously injected with DBCO-IL-15/IL-15R$\alpha$ or IL-15/IL-15R$\alpha$ at tail base on day 6, mice were challenged with a subcutaneous injection of $1\times10^5$ B16F10 melanoma cells in the back of the neck.

In the prophylactic E.G7-OVA tumor study, all three vaccination groups showed significantly slower tumor growth and longer median survival than untreated group (FIGS. 6H and 6I). Mice treated with G400 gel and DBCO-OVA/DBCO-CpG exhibited significantly slower tumor growth and longer median survival, in comparison to mice treated with G400 gel and OVA/CpG or mice treated with control gel and DBCO-OVA/DBCO-CpG. These experiments demonstrated that the targeted delivery of antigens and adjuvants to azido-labeled DCs could significantly improve antigen-specific T cell responses.

To demonstrate the generality of this DC/LN-targeted cancer vaccine system, the system's capability to amplify E7-specific CD8$^+$ T cell responses is also studied. Mice were divided into 4 groups (n=8 per group): gel containing G400 NP (1 mg) and GM-CSF (3 µg)+ultrasound+DBCO-E7 (100 µg)/DBCO-CpG (50 µg); gel containing G400 NP and GM-CSF+ultrasound+E7/CpG; control gels containing GM-GN+ultrasound+DBCO-E7/DBCO-CpG; untreated. Gels were subcutaneously injected on day 0, followed by ultrasound treatment (30% amplitude, 2.5 min) on day 3 and tail base subcutaneous injection of DBCO-E7/DBCO-CpG or E7/CpG on day 6, 8, and 10. On day 12 and 16, blood was collected and PBMCs were isolated for E7 tetramer staining and IFN-$\gamma$ re-stimulation. For in vitro peptide re-stimulation, PBMCs were pulsed with 5 µg/mL E7 for 1.5 h and incubated with GolgiPlug for 4 h, prior to antibody staining and flow cytometry analyses. For prophylactic tumor study, mice were challenged with a subcutaneous injection of $2.5\times10^5$ TC-1 cells on day 19. Mice with azido-labeled DCs in the dLN were subjected to subcutaneous injection of DBCO-E7/DBCO-CpG. The DC-targeted cancer vaccine was again able to generate significantly higher numbers of E7 tetramer$^+$ CD8$^+$ T cells and IFN-$\gamma^+$ CD8$^+$ T cells, as compared to non-targeting groups (FIGS. 6J-6M).

This potent T cell response translated to full protection from TC-1 tumor challenge in the subsequent prophylactic study (FIGS. 6N and 6O).

For TC-1 tumor therapeutic study, TC-1 tumors ($1\times10^6$ per mouse) were inoculated on day 0, followed by subcutaneous injection of gels loaded with G400 NP (1 mg) and GM-CSF (3 µg) on day 4, ultrasound treatment on day 7, and subcutaneous injection of DBCO-E7 (100 µg) and DBCO-CpG (50 µg) on day 10, 12, and 14. In this therapeutic TC-1 tumor study, DC-targeted vaccine was able to eradicate established TC-1 tumors, and resulted in the slowest tumor growth and highest tumor-free survival (FIGS. 6P and 6Q). Altogether, these experiments demonstrated the potency and broad applicability of this DC-targeted cancer vaccine strategy.

Example 5: IL-15/IL-15Rα-Conjugated DCs Improved CD8$^+$ T Cell Proliferation In Vitro Considering that DBCO-agents, once covalently captured by azido-labeled cells, can stay on the cell surface for up to 12 hours (Wang, H. et al. Selective in vivo metabolic cell-labeling-mediated cancer targeting. *Nature Chemical Biology* 13, 415-424 (2017)), it was hypothesized that DBCO-cytokines can be conjugated to azido-labeled DCs to regulate subsequent priming of T cells (FIG. 7A). While cytokine therapies can be potent, treating patients with these pleiotropic agents in a non-targeted manner typically leads to severe complications (Dranoff, G. Cytokines in cancer pathogenesis and cancer therapy. *Nat. Rev. Cancer* 4, 11 (2004); Motzer, R. J. et al. Effect of cytokine therapy on survival for patients with advanced renal cell carcinoma. *J. Clin. Oncol.* 18, 1928-1935 (2000); Waldmann, T. A. The biology of interleukin-2 and interleukin-15: implications for cancer therapy and vaccine design. *Nat. Rev. Immunol.* 6, 595 (2006)). The conjugation of DBCO-modified cytokines, including IL-2, IFN-γ, and IL-15/IL-15Rα, onto azido-labeled DCs in vitro was demonstrated first (FIGS. 7C-7J, 7Q, 7R and 8M-8O). IL-15 is a cytokine that can bind to IL-15 receptor a on the surface of antigen presenting cells to induce the proliferation of CD8$^+$ T cells and natural killer cells (Sato, N., et al. The IL-15/IL-15Rα on cell surfaces enables sustained IL-15 activity and contributes to the long survival of CD8 memory T cells. *Proceedings of the National Academy of Sciences of the United States of America* 104, 588-593, doi:10.1073/pnas.0610115104 (2007); Stoklasek, T. A., et al. Combined IL-15/IL-15Rα Immunotherapy Maximizes IL-15 Activity In Vivo. *Journal of immunology* (Baltimore, Md.: 1950) 177, 6072-6080 (2006)) (FIG. 7B). Compared to soluble IL-15, the IL-15/IL-15Rα complex enables prolonged and more persistent activation of target T cells or natural killer cells (Sato, N et al. 2007). It was first studied whether azido-labeled BMDCs could covalently capture DBCO-IL-15/IL-15Rα in vitro. For in vitro display of IL-15/IL-15Rα on azido-labeled DCs, IL-15/IL-15Rα with a pending cysteine group was synthesized and purified. DBCO-IL-15/IL-15Rα was obtained via conjugation of DBCO-sulfo-maleimide to IL-15/IL-15Rα. BMDCs were incubated with different concentrations of G400 NP (2, 10, 50, and 200 µM, respectively) for three days, washed, and incubated with DBCO-IL-15/IL-15Rα or IL-15/IL-15Rα for 30 min. For quantification purposes, DBCO/Cy5-IL-15/IL-15Rα and Cy5-IL-15/IL-15Rα were used, and cells were harvested for flow cytometry analyses.

IL-15/IL-15Rα with a pending cysteine was synthesized (FIGS. 7C-7E), and reacted with DBCO-sulfo-maleimide to yield DBCO-IL-15/IL-15Rα (FIGS. 7F and 7G). Cy5-labeled DBCO-IL-15/IL-15Rα was also synthesized for quantification needs (FIGS. 7H and 7I). BMDCs that were pretreated with G400 NP for three days showed significantly improved binding of Cy5/DBCO-IL-15/IL-15Rα compared to control BMDCs without azido-sugar treatment (FIGS. 7J-7P). In the presence of a competing agent, DBCO-sulfo-maleimide, the binding of Cy5/DBCO-IL-15/IL-15Rα was significantly reduced, further demonstrating Click chemistry-mediated conjugation of Cy5/DBCO-IL-15/IL-15Rα by azido-labeled DCs (FIGS. 7K-7P).

It was next studied whether IL-15/IL-15Rα-displayed DCs would improve the activation and proliferation of antigen-specific CD8$^+$ T cells. For DCs and T cells co-culture, BMDCs were pretreated with different concentrations of G400 NP (2, 10, 50, and 200 µM, respectively) for three days and incubated with DBCO-IL-15/IL-15Rα or IL-15/IL-15Rα or PBS for 30 minutes. For pSTAT5 analyses, these DCs were cocultured with OT1 cells for 1.5 hours and fixed with cold methanol (90%, v/v) overnight, prior to anti-mouse pSTAT5 staining and FACS analyses. For OT1 proliferation analyses, these DCs were cocultured with CFSE-labeled OT1 cells (1/1 or 3/1 T cell/DC ratio) in the presence of SIINFEKL peptide. Co-cultures with the continuous presence of IL-15/IL-15Rα were used as controls. FACS analyses were conducted 3 days later. For some studies, BMDCs were labeled with G400 NP for three days and pulsed with SIINFEKL peptide and CpG for 24 hours, prior to the conjugation of DBCO-IL-15. IL-15/IL-15Rα-displayed DCs obtained by incubating azido-labeled DCs with DBCO-IL-15/IL-15Rα for 30 min were co-cultured with OT1 cells in the presence of SIINFEKL peptide. Compared to DCs without surface conjugation of cytokines, IL-15/IL-15Rα-displayed DCs induced a significantly higher level of pSTAT5 in OT1 cells within 1 hour (FIGS. 8A-8E).

The proliferation of CFSE-stained OT1 cells was then examined in the presence of BMDCs and SIINFEKL peptide. BMDCs with or without G400 NP pretreatment were incubated with DBCO-IL-15/IL-15Rα or IL-15/IL-15Rα or PBS for 30 min. At 20 ng/mL DBCO-IL-15/IL-15Rα and 5 nM SIINFEKL, IL-15/IL-15Rα-displayed BMDCs, that is, azido-labeled BMDCs incubated with DBCO-IL-15/IL-15Rα, induced significantly better OT1 proliferation, in comparison to BMDCs without IL-15/IL-15Rα conjugation (FIGS. 8A-8C, 8F, 8G, and 8J). Notably, IL-15/IL-15Rα-displayed BMDCs also outperformed continuous IL-15/IL-15Rα (present throughout the co-culture period) in inducing OT1 proliferation (FIGS. 8F and 8G). The proliferation index of OT1 cells also increased with the concentration of G400 NP that was used to metabolically label BMDCs (FIGS. 8H and 8I). In the absence of azido-sugar labeling, however, negligible differences in OT1 proliferation were observed among all groups (FIGS. 8H-8J). These experiments demonstrated that the display of IL-15/IL-15Rα on the surface of DCs could significantly improve the activation and proliferation of antigen-specific CD8$^+$ T cells. This T cell activation benefit was dependent on the concentration of IL-15/IL-15Rα and antigen. At 5 nM SIINFEKL, DC surface-displayed IL-15/IL-15Rα resulted in a T cell proliferation benefit within the concentration range of 6-60 ng/mL (FIG. 8K). At 20 ng/mL IL-15/IL-15Rα, IL-15/IL-15Rα-displayed DCs resulted in better OT1 proliferation than control DCs at low SIINFEKL concentrations, in the range of 1-20 nM (FIG. 8L).

Example 6: Conjugation of IL-15/IL-15Rα to DCs Potentiates Neoantigen Vaccination It was next studied whether targeted modulation of DCs with IL-15/IL-15Rα in vivo would improve neoantigen-specific CD8$^+$ T cell responses and antitumor efficacy. For in vivo DC targeting of DBCO-IL-15/IL-15Rα study, pore forming gels containing GM-CSF and G400 NP were subcutaneously injected on day 0, followed by ultrasound treatment on day 3 and tail base subcutaneous injection of DBCO/Cy5-IL-15/IL-15Rα or Cy5-IL-15/IL-15Rα on day 6. Gel scaffolds and lymph nodes were excised for cell isolation and FACS analyses 16 hours later. In addition to G400 NP and GM-CSF, CpG and two B16F10 neoantigens, M27 and M30, were also incorporated into the pore-forming alginate gel to compose a cancer vaccine.

It was first studied whether G400 NP in the full cancer vaccine could still label recruited DCs with azido groups. Pore-forming alginate gel vaccines were subcutaneously injected into C57BL/6 mice on day 0, followed by ultrasound treatment on day 3 (FIG. 9A). On day 6, about 20% of DCs in the gel scaffolds were labeled with azido groups (FIG. 9B), and azido-labeled DCs were detected in dLNs (FIGS. 9C and 9D). It was next studied whether these azido-labeled DCs could be used for targeted conjugation of DBCO-IL-15/IL-15Rα in vivo. After subcutaneous injection of gel vaccines loaded with G400 NP, GM-CSF, CpG, M27, and M30 on day 0, and ultrasound treatment on day 3, Cy5/DBCO-IL-15/IL-15Rα or Cy5-IL-15/IL-15Rα was subcutaneously injected at tail base on day 6 (FIG. 9E). After 16 hours, ~13% of DCs in the gels captured Cy5/DBCO-IL-15/IL-15Rα, as compared to 4% that captured Cy5-IL-15/IL-15Rα (FIGS. 9E, 9F-91), indicating successful Click chemistry-mediated conjugation of Cy5/DBCO-IL-15/IL-15Rα to azido-labeled DCs. Among the Cy5$^+$ DCs in LNs, a significantly higher mean Cy5 fluorescence intensity was observed in Cy5/DBCO-IL-15/IL-15Rα group compared to Cy5-IL-15/IL-15Rα group (FIG. 9I). These experiments demonstrated that the full gel vaccine can metabolically label the recruited DCs with azido groups and that the azido-labeled DCs allow for targeted conjugation of DBCO-IL-15/IL-15Rα via Click chemistry. Also, the gel vaccine was able to generate M27-specific CD8$^+$ T cells and M30-specific CD4$^+$ T cells (FIGS. 10A-10E), and significantly slower the growth of B16F10 tumors compared to untreated group (FIG. 10F).

It was next studied whether the conjugation of DBCO-IL-15/IL-15Rα to azido-labeled DCs in vivo would improve the neoantigen-specific CD8$^+$ T cell responses and antitumor efficacy of gel vaccines. In this study, a co-culture of splenic CD8+ T cells and CD11c+ DCs was used. For the co-culture, C57BL/6 mice were subcutaneously injected with pore-forming gels containing G400 NP, GM-CSF, M27, M30, and CpG on day 0, treated with ultrasound on day 3, and subcutaneously injected with DBCO-IL-15/IL-15Rα or IL-15/IL-15Rα or PBS at tail base on day 6. Spleens were harvested and disrupted on day 12. CD8$^+$ T cells were isolated from splenocytes, stained with CFSE, and co-cultured with pre-isolated CD11c$^+$ DCs (10:1 T:DC ratio) from spleens of naïve mice. After three days, cells were stained with anti-CD3, anti-CD8, live/dead stain, anti-IFN-γ, and anti-TNF-α, followed by FACS analyses.

At first, prophylactic tumor studies were conducted to compare different doses (1, 10, 50 μg/kg) of DBCO-IL-15/IL-15Rα (FIGS. 10G and 10H), and it was decided on 1 μg/kg for the subsequent studies. Following gel vaccination on day 0, ultrasound treatment on day 3, and DBCO-IL-15/IL-15Rα injection on day 6, splenocytes were collected on day 11 and CD8$^+$ T cells isolated and cultured with M27-pulsed DCs ex vivo. All vaccination groups showed increased M27-specific CD8$^+$ T cell proliferation compared to untreated group (FIG. 10I). Compared to IL-15/IL-15Rα, DBCO-IL-15/IL-15Rα resulted in a higher M27-specific CD8$^+$ T cell proliferation, along with a higher percentage of IFN-γ$^+$TNF-α$^+$ CD8$^+$ T cells (FIGS. 10I and 10J). In another experiment, splenocytes were directly restimulated with M27 and M30, and a significantly higher number ratio of IFN-γ$^+$ CD8$^+$ T cells to IFN-γ$^+$ CD4$^+$ T cells was observed in DBCO-IL-15/IL-15Rα group, in comparison to IL-15/IL-15Rα or vaccine alone group (FIG. 10K). In a prophylactic B16F10 tumor study, DBCO-IL-15/IL-15Rα also resulted in significantly slower tumor growth in comparison to IL-15/IL-15Rα (FIGS. 10H and 10L). In a therapeutic setting, DBCO-IL-15/IL-15Rα treatment also resulted in more persistent tumor control and longer survival than other groups (FIGS. 10O-10Q). By administering multiple doses of DBCO-IL-15/IL-15Rα, the antitumor efficacy against B16F10 tumors was further improved, with complete tumor regression in 25% of mice and a 57% increase in median survival compared to the vaccine only group (FIGS. 10M and 10N). These experiments demonstrated that the conjugation of DBCO-IL-15/IL-15Rα to azido-labeled, neoantigen-presenting DCs could improve neoantigen-specific CD8$^+$ T cell responses in vivo.

It was next studied whether targeted modulation of DCs with IL-15/IL-15Rα in vivo would improve cancer therapy. For this study, B16F10 tumor cells were subcutaneously injected on day 0. On day 5, pore-forming gels containing G400 NP, GM-CSF, M27, M30, gp100 (glycoprotein 100), trp2 (tyrosinase-related protein-2) and CpG were injected subcutaneously on day 5, treated with ultrasound on day 8, and subcutaneously injected with DBCO-IL-15/IL-15Rα or IL-15/IL-15Rα or PBS at tail base on day 11 (FIG. 11A). All three vaccination groups showed showed significantly slower tumor growth and longer median survival than untreated group (FIGS. 11B and 11C). Mice treated with DBCO-IL15-L/IL-15Rα exhibited significantly slower tumor growth and longer median survival, in comparison to mice treated with G400 gel and PBS or mice treated with G400 gel and IL-15/IL-15Rα. These experiments demonstrated that the conjugation of IL-15/IL-15Rα could significantly improve cancer therapy by augmenting the immune response to cancer cells.

Biomaterial scaffolds with controlled release of GM-CSF can gradually recruit DCs, and in the presence of TAAs and adjuvants, can program these DCs before they migrate out of the scaffold. The migration of DCs from scaffolds to LNs dictates the effectiveness of elicited immune responses but is poorly understood. Previous attempts have been made to incorporate fluorescent dyes in biomaterial scaffolds and detect dye-containing DCs in LNs (Ali, O. A., et al., Infection-mimicking materials to program dendritic cells in situ. *Nature materials* 8, 151-158 (2009); Kim, J. et al. Injectable, spontaneously assembling, inorganic scaffolds modulate immune cells in vivo and increase vaccine efficacy. *Nature biotechnology* 33, 64-72 (2015)). However, encapsulated dyes may diffuse out of the scaffold rapidly prior to the recruitment of DCs, and may light up DCs in LNs by themselves and provide false-positive signals. In comparison, G400 NP encapsulated in pore-forming alginate gels show minimal background release and can metabolically label recruited DCs with azido groups, which are stable for weeks if normalized for the proliferation-induced dilution effect and allow for detection by DBCO-bearing agents. Azido-labeled DCs in LNs will eventually undergo apoptosis and potential phagocytosis by macrophages, in which azido-conjugated glycoproteins may degrade into small-molecule azido-sugars. We were able to detect a slightly increasing amount of azido-labeled macrophages over time, which might indicate the re-metabolism of azido-sugars and cell-surface expression of azido groups by macrophages.

Azido-labeled DCs still exist in dLNs three weeks after gel injection, and enable targeted capture of DBCO-bearing molecules via Click chemistry. Targeted delivery of antigens and adjuvants to DCs, especially DCs in LNs, has long been a goal of therapeutic cancer vaccines. Nanomaterial vaccines that encapsulate antigens and adjuvants can passively accumulate in LNs and release them slowly for DC uptake. Antigens and adjuvants were also modified with albumin-binding lipids to take advantage of the LN-trafficking property of albumin (Liu, H. et al. Structure-based programming of lymph-node targeting in molecular vaccines. *Nature* 507, 519-522 (2014)). However, these strategies cannot directly target DCs in LNs. Modification of antigens and adjuvants with targeting ligands such as anti-CD11c and anti-Dec205 that can specifically bind to DC receptors has also been attempted (Caminschi, I., et al., Targeting dendritic cells in vivo for cancer therapy. *Frontiers in immunology* 3 (2012)), but minimal in vivo targeting benefits has been achieved. The azido-labeled DCs, as achieved in our approach, enable targeted delivery of DBCO-antigens and DBCO-adjuvants for improved antigen-specific CD8$^+$ T cell responses and antitumor efficacy. Antigens and adjuvants can be readily modified with DBCO without impairing their biological functions, and the Click chemistry-mediated targeting strategy avoids occupying cell-surface protein receptors.

The modulation of DC-T cell interaction in vivo could be impactful to regulate antigen-specific CTL responses. Our approach provides an unprecedented strategy to conjugate cytokines onto antigen-presenting DCs in vivo for subsequent regulation of T cell priming. Subcutaneously injected gel vaccines containing GM-CSF, neoantigens, adjuvants, and G400 NP were able to generate a number of azido-labeled, antigen-presenting DCs in situ and in LNs. Subsequently administered DBCO-IL-15/IL-15Rα was able to conjugate to DC surface and contribute to the priming of neoantigen-specific CD8$^+$ T cells. More efforts will be needed to decipher the timeframe of antigen presentation in the gel scaffolds and DC-mediated T cell priming in LNs, in order to optimize the timing of DBCO-IL-15/IL-15Rα administration. This IL-15/IL-15Rα-displaying approach might also change the phenotype of effector T cells including the generation of more memory T cells, which will be further explored in future studies. Besides IL-15/IL-15Rα, a variety of other cytokines can benefit from this DC surface-displaying strategy to modulate the activation, priming, and differentiation of T cells in lymphoid tissues. In principle, any molecule of interest, after simple DBCO modification, can be targeted to azido-labeled DCs via efficient Click chemistry to manipulate the interaction between DCs and other types of immune cells.

Example 7: Statistical Analysis

Statistical analysis was performed by one-way analysis of variance (ANOVA) with post hoc Fisher's LSD test (OriginPro 8.5), and P-values <0.05 were considered statistically significant. The results were deemed significant at $0.01<*P\leq0.05$, highly significant at $0.001<P\leq0.01$, and extremely significant at $*P\leq0.001$. Sample size was empirically set at n=3-6 for in vitro cell experiments, n=3-4 for in vivo biodistribution and imaging studies, n=5-6 for xenograft tumor studies, and n=7-8 for metastatic tumor studies.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the present invention described herein. Such equivalents are intended to be encompassed by the following claims.

The invention claimed is:

1. A click functionalized polysaccharide polymer which is a product of radical-catalyzed polymerization;
   wherein said radical-catalyzed polymerization involves a reaction between one or more saccharide monomers;
   wherein each saccharide monomer comprises a saccharide molecule; a click reagent attached to said saccharide molecule; and a moiety comprising a functional group amenable to radical polymerization attached to said saccharide molecule; and
   wherein:
   (i) said saccharide molecule further comprises one or more hydrolysable substituents at the C1 position, the C3 position, the C4 position or C5 position, and wherein at least one of said hydrolysable substituent is represented by formula (1):

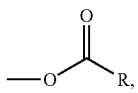
(1)

wherein R is alkyl;
(ii) said moiety comprising a functional group amenable to radical polymerization is attached to said saccharide molecule at the C1 position;
(iii) said moiety comprising a functional group amenable to radical polymerization comprises an acrylate or methacrylate; and/or
(iv) said radical-catalyzed polymerization is reversible addition-fragmentation chain transfer (RAFT) polymerization involving the use of a RAFT agent; and wherein said RAFT agent comprises a thiocarbonate moiety, a dithiocarbamate moiety or a dithiobenzoate moiety.

2. The polymer of claim 1, wherein:
(i) said saccharide molecule is selected from the group consisting of mannose, galactose, fucose and sialic acid;
(ii) said click reagent is attached to said saccharide molecule at the C2 position; and/or
(iii) said polymer comprises 10 to 1000 saccharide units.

3. The polymer of claim 2, wherein said saccharide molecule is mannose.

4. The polymer of claim 2, wherein said click reagent is selected from the group consisting of azide, dibenzocyclooctyne (DBCO), transcyclooctene, tetrazine and norbornene and variants thereof.

5. The polymer of claim 4, wherein said click reagent is azide.

6. The polymer of claim 1, wherein:
(i) said moiety comprising a functional group amenable to radical polymerization is attached to said saccharide molecule at the C1 position; and/or
(ii) said moiety comprising a functional group amenable to radical polymerization comprises an acrylate or methacrylate.

7. The polymer of claim 1, wherein said saccharide molecule further comprises one or more hydrolysable substituents at the C1 position, the C3 position, the C4 position or C5 position, and wherein said hydrolysable substituent is represented by formula (1):

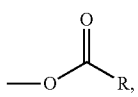
(1)

wherein R is alkyl.

8. The polymer of claim 7, wherein R is methyl.

9. The polymer of claim 1, wherein said radical-catalyzed polymerization is reversible addition-fragmentation chain transfer (RAFT) polymerization involving the use of a RAFT agent; and wherein said RAFT agent comprises a thiocarbonate moiety, a dithiocarbamate moiety or a dithiobenzoate moiety.

10. The polymer of claim 9, wherein said RAFT agent comprises a thiocarbonate moiety.

11. The polymer of claim 10, wherein said RAFT agent comprises 2-(dodecylthiocarbonothioylthio)-2-methylpropionate or poly(ethylene glycol)methyl ether 2-(dodecylthiocarbonothioylthio)-2-methylpropionate.

12. The polymer of claim 1 comprising 20 to 500, 100 to 500 or 200 to 600 saccharide units.

13. The polymer of claim 1 comprising:
(i) the structure of formula (2):

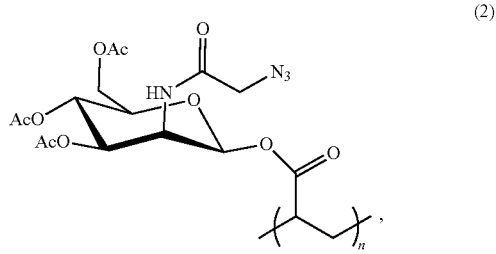
(2)

wherein n is a number between 10 and 1000;
(ii) the structure of formula (3):

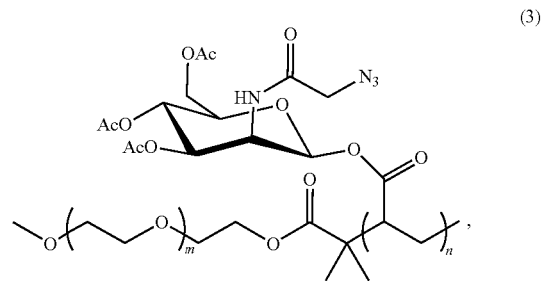
(3)

wherein n is a number between 10 and 1000; and m is a number between 45 and 200; or
(iii) the structure of formula (4):

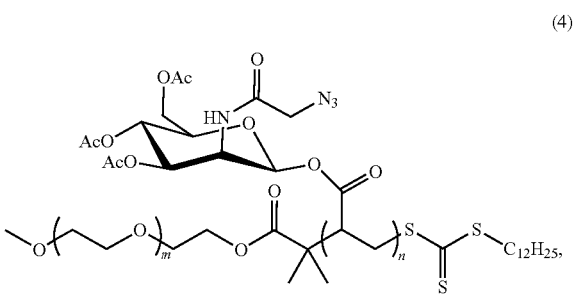
(4)

wherein n is a number between 10 and 1000; and m is a number between 45 and 200.

14. A click-functionalized amphiphilic polymer which is a product of radical-catalyzed polymerization;
wherein said radical-catalyzed polymerization involves a reaction between a reagent comprising a hydrophilic portion and one or more saccharide monomers;
wherein each saccharide monomer comprises a saccharide molecule; a click reagent attached to said saccharide molecule; and a moiety comprising a functional group amenable to radical polymerization attached to said saccharide molecule; and
wherein:
(i) said saccharide molecule further comprises one or more hydrolysable substituents at the C1 position, the C3 position, the C4 position or C5 position, and wherein at least one of said hydrolysable substituent is represented by formula (1);

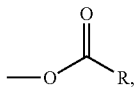

(1)

wherein R is alkyl;
(ii) said moiety comprising a functional group amenable to radical polymerization is attached to said saccharide molecule at the C1 position;
(iii) said moiety comprising a functional group amenable to radical polymerization comprises an acrylate or methacrylate;
(iv) said radical-catalyzed polymerization is reversible addition-fragmentation chain transfer (RAFT) polymerization involving the use of a RAFT agent; and wherein said RAFT agent comprises a thiocarbonate moiety, a dithiocarbamate moiety or a dithiobenzoate moiety; and/or
(v) said hydrophilic portion comprises a hydrophilic polymer comprising polyethylene oxide (PEG), and wherein said PEG comprises between 20 and 450 PEG units.

15. The polymer of claim 14, wherein said hydrophilic polymer is polyethylene oxide (PEG).

16. The polymer of claim 15, wherein said PEG comprises between 20 and 450 PEG units.

17. A nanoparticle for labeling cells with a click reagent comprising the polymer of claim 1.

18. An in vitro method of labeling a cell with a click chemistry reagent, comprising contacting the cell with the polymer of claim 1.

* * * * *